(12) United States Patent
Yurieva et al.

(10) Patent No.: US 7,556,958 B1
(45) Date of Patent: Jul. 7, 2009

(54) ENZYME DERIVED FROM THERMOPHILIC ORGANISMS THAT FUNCTIONS AS A CHROMOSOMAL REPLICASE, AND PREPARATION AND USES THEREOF

(75) Inventors: Olga Yurieva, New York, NY (US); John Kuriyan, Riverdale, NY (US); Michael E. O'Donnell, Hastings-on-Hudson, NY (US); David Jeruzalmi, New York, NY (US)

(73) Assignee: The Rockefeller University, New York, NY (US)

( * ) Notice: Subject to any disclaimer, the term of this patent is extended or adjusted under 35 U.S.C. 154(b) by 430 days.

(21) Appl. No.: 09/642,218

(22) Filed: Aug. 18, 2000

Related U.S. Application Data

(63) Continuation of application No. 09/057,416, filed on Apr. 8, 1998, now abandoned.

(51) Int. Cl.
 *C12N 1/20* (2006.01)
 *C12N 9/12* (2006.01)
 *C07H 21/04* (2006.01)

(52) U.S. Cl. ............... 435/252.3; 435/194; 435/183; 435/6; 435/320.1; 536/23.1; 536/23.2; 536/23.7

(58) Field of Classification Search ............... 435/194, 435/183, 252.3, 320.1, 254.11, 325; 536/23.1, 536/23.3, 23.7
See application file for complete search history.

(56) References Cited

U.S. PATENT DOCUMENTS

| | | |
|---|---|---|
| 5,192,674 A | 3/1993 | Oshima et al. ............ 435/194 |
| 5,242,818 A | 9/1993 | Oshima et al. |
| 5,322,785 A | 6/1994 | Comb et al. ............ 435/194 |
| 5,352,778 A | 10/1994 | Comb et al. ............ 536/23.2 |
| 5,374,553 A | 12/1994 | Gelfand et al. |
| 5,413,926 A | 5/1995 | Oshima et al. |
| 5,500,363 A | 3/1996 | Comb et al. |
| 5,545,552 A | 8/1996 | Mathur ............ 435/252.3 |
| 5,583,026 A | 12/1996 | O'Donnell ............ 435/194 |
| 5,618,711 A | 4/1997 | Gelfand et al. |
| 5,624,833 A | 4/1997 | Gelfand et al. |
| 5,633,159 A | 5/1997 | Pearson et al. ............ 435/194 |
| 5,736,373 A | 4/1998 | Hamilton |
| 5,744,312 A | 4/1998 | Mamone et al. |
| 5,789,224 A | 8/1998 | Gelfand et al. |
| 5,830,714 A | 11/1998 | Swaminathan et al. |
| 5,834,285 A | 11/1998 | Comb et al. |
| 6,066,483 A | 5/2000 | Riggs et al. |
| 6,100,078 A | 8/2000 | Riggs et al. |
| 6,238,905 B1 | 5/2001 | McHenry et al. |
| 6,395,526 B1 | 5/2002 | Uemori et al. |
| 6,677,146 B1 | 1/2004 | Janjic et al. |
| 6,897,053 B1 | 5/2005 | O'Donnell et al. |
| 2004/0038289 A1 | 2/2004 | O'Donnell et al. |
| 2004/0038290 A1 | 2/2004 | O'Donnell et al. |
| 2004/0043414 A1 | 3/2004 | O'Donnell et al. |
| 2004/0043415 A1 | 3/2004 | O'Donnell et al. |
| 2004/0048309 A1 | 3/2004 | O'Donnell et al. |
| 2004/0077012 A1 | 4/2004 | O'Donnell et al. |
| 2004/0081995 A1 | 4/2004 | O'Donnell et al. |
| 2004/0106137 A1 | 6/2004 | O'Donnell et al. |
| 2004/0110210 A1 | 6/2004 | O'Donnell et al. |
| 2004/0197796 A1 | 10/2004 | O'Donnell et al. |
| 2005/0048510 A1 | 3/2005 | O'Donnell et al. |
| 2005/0100920 A1 | 5/2005 | O'Donnell et al. |
| 2005/0112580 A1 | 5/2005 | O'Donnell et al. |
| 2005/0153299 A1 | 7/2005 | O'Donnell et al. |

FOREIGN PATENT DOCUMENTS

| | | |
|---|---|---|
| WO | WO 91/09950 | 7/1991 |
| WO | WO 9109950 | 7/1991 |
| WO | WO 93/15115 | 8/1993 |
| WO | WO 9315115 | 8/1993 |
| WO | WO 99/13060 | 3/1999 |
| WO | WO 01/73052 | 10/2001 |

OTHER PUBLICATIONS

Alonso et al, 1990, Nuc Acids Res, 18:6771-7.
Blinkowa et al., 1990, Nucleic Acids Res, 18:1725-9.
Carter et al, 1993, J Bacteriol, 175:3812-22.
Chen et al, 1992, Proc Natl Acad Sci USA, 5211-5.
Cullman et al, 1995, Mol Cell Biol, 150:4661-71.
Dong et al., 1993, J Biol Chem, 11758-66.
Flower et al, 1990, Proc Natl Acad Sci USA, 87:3713-7.
Guibus et al, 1996, Cell, 87:297-306.
Jack et al, 1988, Cell, 55:447-58.
Kelman et al, 1994, Curr Opin Gen & Dev, 4:185-95.
Kong et al, 1992, Cell, 69:425-37.
Kornberg et al, 1992, DNA Replication, $2^{nd}$ ed. New York: W H Freeman com, pp. 165-194.
Krishna et al, 1994, Cell, 79:1233-43.
Kuriyan et al, 1993, J Mol Biol, 234:915-25.
Larsen et al, 1994, J Bact, 176:6842-51.
Lee et al, 1987, Proc Natl Acad Sci USA, 84:2713-7.
Maki et al, 1988, J Biol Chem, 263:6570-8.
Mchenry et al., 1982, J Biol Chem, 257:1657-63.
Mchenry et al., 1997, J Mol Biol, 272:178-9.
O'Donnell et al, 1992, Mol Cell Biol, 3:953-7.

(Continued)

*Primary Examiner*—Richard G Hutson
(74) *Attorney, Agent, or Firm*—Nixon Peabody LLP

(57) ABSTRACT

A DNA Polymerase has been identified in a thermophile that functions as a chromosomal replicase. The specific enzyme is a holoenzyme III that has been identified in *Thermus thermophilus*, and corresponds to Polymerase III in *E. coli*. The genes and the polypeptides corresponding to T.th. γ, τ, ε, α and β subunits that they encode are disclosed, as are probes, vectors, methods of preparation and the methods of use. The enzymes of the present invention and their components are particularly well suited for use in procedures for the preparation of DNA, such as PCR, because of the speed and accuracy that they are able to achieve.

8 Claims, 31 Drawing Sheets

OTHER PUBLICATIONS

O'Donnell et al, 1993, Nucl Acids Res, 21:1-3.
Onrust et al, 1995, J Biol Chem, 270:13366-77.
Onrust et al, 1991, J Biol Chem, 266:21681-6.
Perrino et al., 1990, Biochemistry, 29:5226-31.
Studwell-Vaughan, 1991, J Biol Chem, 266:19833-41.
Stukenberg et al, 1991, J Biol Chem, 266:11328-34.
Tsuchihashi et al, 1990, Proc Natl Acad Sci USA, 87:2516-20.
Tsuchihashi et al, 1992, Gen & Dev, 6:511-9.
Tsuchihashi et al, 1989, J Biol Chem, 264:17790-5.
Weiss et al, 1987, Slippery runs, shift stops, backward steps, and forward hops:−2,−1,+5 and +6 rebosomal frameshifting, in Cold Spring Harbor Symposia on Quantitative Biology, 52:687-93.
Yin et al, 1986, Nuc Acids Res, 14:6541-49.
Yurieva et al., 1997, J Biol Chem, 272:27131-9.
Yuzhakov et al, 1996, Cell, 86:877-86.
Rudinger, "Characteristics of the Amino Acids as Components of a Peptide Hormone Sequence," In: Peptide Hormones, Ed. J.A. Parsons. University Park Press, Baltimore, MD, pp. 1-7 (1976).
Ngo et al., "Computational Complexity, Protein Structure Prediction, and the Ilevinthal Paradox," In: The Protein Folding Problem and Tertiary Structure Prediction, Eds. Merz et al., Birkhauser et al., Boston, MA, pp. 491-495 (1994).
Thornton et al., "Protein Engineering: Editorial Overview," *Current Opinion in Biotechnology* 6(4):367-369 (1995).
Wallace, "Understanding Cytochrome C Function: Engineering Protein Structure by Semisynthesis," *The FASEB Journal* 7:505-515 (1993).
McHenry et al., "A DNA polymerase III Holoenzynme-Like Subassembly from an Extreme Thermophilic Eubacterium," *J. Mol. Biol.* 272:178-189 (1997).
Yurieva et al., *J. Biol. Chem.* 272(43):27131-27139 (1997).
Bukhrashvili et al., "Comparison of Initiating Abilities of Primers of Different Length in Polymerization Reactions Catalyzed by DNA Polymerases from Thermoacidophilic Archaebacteria," *Biochimica et Biophysica Acta* 1008:102-107 (1989).
Elie et al., "A DNA Polymerase from a Thermoacidophilic Archaebacterium: Evolutionary and Technological Interests," *Biochimica et Biophysica Acta* 951:261-267 (1988).
Pluthero, "Rapid Purification of High-Activity Taq DNA Polymerase," *Nucleic Acids Research* 21(20):4850-4851 (1993).
Alonso et al., *Nucl. Acids Res.* 18:6771-6777 (1990).
Blinkowa et al., *Nucleic Acids Research* 18:1725-1729 (1990).
Carter et al., *J. Bacteriol* 175:3812-22 (1993).
Chen et al., *Proc. Natl. Acad. Sci USA* 5211-5 (1992).
Cullman et al., *Mol. Cell Biol.* 150:4661-71 (1995).
Dong et al., *J. Biol. Chem.* 11758-66 (1993).
Flower et al., *Proc. Natl. Acad. Sci. USA* 87:3713-7 (1990).
Guibus et al., *Cell* 87:297-306 (1996).
Jack et al., *Cell* 55:447-58 (1988).
Kelman et al., *Curr Opin Gen & Dev* 4:185-95 (1994).
Kong et al., *Cell* 69:425-37 (1992).
Kornberg et al., *DNA Replication*, $2^{nd}$ ed. New York: W.H. Freeman com, pp. 165-194 (1992).
Krishna et al., *Cell* 79:1233-43 (1994).
Kuriyan et al., *J. Mol. Biol.* 234:915-25 (1993).
Larsen et al., *J. Bact.* 176:6842-51 (1994).
Lee et al., *Proc. Natl. Acad. Sci. USA* 84:2713-7 (1987).
Maki et al., *J. Biol. Chem.* 263:6570-78 (1988).
McHenry et al., *J. Biol. Chem.* 257:1657-63 (1982).
O'Donnell et al., *Mol. Cell Biol.* 3:953-7 (1992).
O'Donnell et al., *Nucl. Acids Res.* 21:1-3 (1993).
Onrust et al., *J. Biol. Chem.* 270:13366-77 (1995).
Onrust et al., *J. Biol. Chem.* 266:21681-6 (1991).
Perrino et al., *Biochemistry* 29:5226-31 (1990).
Studwell-Vaughan, *J. Biol. Chem.* 266:19833-841 (1991).
Stukenberg et al., *J. Biol. Chem.* 266:11328-34 (1991).
Tsuchihashi et al., *Proc. Natl. Acad. Sci. USA* 87:2516-20 (1990).
Tsuchihashi et al., *Gen. & Dev.* 6:511-9 (1992).
Tsuchihashi et al., *J. Biol. Chem.* 264:17790-5 (1989).
Weiss et al., Cold Spring Harbor Symposia on Quantitative Biology, 52:687-93 (1987).
Yin et al., *Nucl. Acids Res.* 14:6541-49 (1986).
Yuzhakov et al., *Cell* 86:877-86 (1996).
Ngo et al., "Computational Complexity, Protein Structure Prediction and the Levinthal Paradox," in The Protein Folding Problem and Tertiary Structure Prediction, Merz et al. (eds.), Birkhauser, Boston, MA, pp. 443 and 492-495 (1994).

E. coli DNA Polymerase III

ATP binding

E. coli
MSYQVLARKWRPQTFADVVGQEHVLTALANGLSLGRIHHAYLFSGTRGVGKTSIARLLAK
B. subtilis
MSYQALYRVFRPQRFEDVVGQEHITKTLQNALLQKKFSHAYLFSGPRGTGKTSAAKIFAK
**** * * *** * *******.  . * *   . ******  ***  .

E. coli
GLNCETGITATPCGVCDNCREIEQGRFVDLIEIDAASRTKVEDTRDLLDNVQYAPARGRF
B. subtilis
AVNCEHAPVDEPCNECAACKGITNGSISDVIEIDAASNNGVDEIRDIRDKVKFAPSAVTY
 .*      . *   *. * .*   *.******* . *.. **. * *...**.   ..

E. coli
KVYLIDEVHMLSRHSFNALLKTLEEPPEHVKFLLATTDPQKLPVTILSRCLQFHLKALDV
B. subtilis
KVYIIDEVHMLSIGAFNALLKTLEEPPEHCIFILATTEPHKIPLTIISRCQRFDFKRITS
*.****  .************* *.****.*.*.*..*  .*   *  .

Figure 2

```
TCCGGGGGTG    GGGTTCCCAG    GTAGACCCCG    GCCCCTCCCG    TGAGCCCCTT    TACCCAGGCC         60

GCCACCTCCT    CCAGGGGGGC    CAAGGCGTGC    AAGGAGAGGA    ACGTCCGCAC    CACGCCCTAT        120
                                                                     S.D.
ACTAGCCTT    GTG AGC GCC CTC TAC CGC CGC TTC CGC CCC CTC ACC TTC CAG GAG GTG GTG       180
             met ser ala leu tyr arg arg phe arg pro leu thr phe gln glu val val       (17)
                                                                            CAC
GGG CAG GAG CAC GTG AAG GAG CCC CTC CTC AAG GCC ATC CGG GAG GGG AGG CTC GCC CAG        240
gly gln glu his val lys glu pro leu leu lys ala ile arg glu gly arg leu ala gln        (37)

GCS TAC CTS TTC TCC GGS AC
GCC TAC CTC TTC TCC GGG CCC AGG GGC GTG GGC AAG ACC ACC ACG GCG AGG CTC CTC GCC        300
ala tyr leu phe ser gly pro arg gly val gly lys thr thr thr ala arg leu leu ala        (57)

ATG GCG GTG GGG TGC CAG GGG GAA GAC CCC CCT TGC GGG GTC TGC CCC CAC TGC CAG GCG        360
met ala val gly cys gln gly glu asp pro pro cys gly val cys pro his cys gln ala        (77)

GtG CAG AGG GGC GCC CAC CCG GAC GTG GTG GAC ATT GAC GCC GCC AGC AAC AAC TCC GTG        420
val gln arg gly ala his pro asp val val asp ile asp ala ala ser asn asn ser val        (97)

GAG GAC GTG CGG GAG CTG AGG GAA AGG ATC CAC CTC GCC CCC CTC TCT GCC CCC AGG AAG        480
glu asp val arg glu leu arg glu arg ile his leu ala pro leu ser ala pro arg lys        (117)
                                                                              C
GTC TTC ATC CTG GAC GAG GCC CAC ATG CTC TCC AAA AGC GCC TTC AAC GCC CTC CTC AAG        540
val phe ile leu asp glu ala his met leu ser lys ser ala phe asn ala leu leu lys        (137)

TGS CTS CTC CTC GGS GGS CTC GTG
ACC CTG GAG GAG CCC CCG CCC CAC GTC CTC TTC GTC TTC GCC ACC ACC GAG CCC GAG AGG        600
thr leu glu glu pro pro pro his val leu phe val phe ala thr thr glu pro glu arg        (157)

ATG CCC CCC ACC ATC CTC TCC CGC ACC CAG CAC TTC CGC TTC CGC CGC CTC ACG GAG GAG        660
met pro pro thr ile leu ser arg thr gln his phe arg phe arg arg leu thr glu glu        (177)

GAG ATC GCC TTT AAG CTC CGG CGC ATC CTG GAG GCC GTG GGG CGG GAG GCG GAG GAG GAG        720
glu ile ala phe lys leu arg arg ile leu glu ala val gly arg glu ala glu glu glu        (197)

GCC CTC CTC CTC CTC GCC CGC CTG GCG GAC GGG GCC CTT AGG GAC GCG GAA AGC CTC CTG        780
ala leu leu leu leu ala arg leu ala asp gly ala leu arg asp ala glu ser leu leu        (217)

GAG CGC TTC CTC CTC CTG GAA GGC CCC CTC ACC CGG AAG GAG GTG GAG CGC GCC CTA GGC        840
glu arg phe leu leu leu glu gly pro leu thr arg lys glu val glu arg ala leu gly        (237)

TCC CCC CCA GGG ACC GGG GTG GCC GAG ATC GCC GCC TCC CTC GCG AGG GGG AAA ACG GCG        900
ser pro pro gly thr gly val ala glu ile ala ala ser leu ala arg gly lys thr ala        (257)

GAG GCC CTG GGC CTC GCC CGG CGC CTC TAC GGG GAA GGG TAC GCC CCG AGG AGC CTG GTC        960
glu ala leu gly leu ala arg arg leu tyr gly glu gly tyr ala pro arg ser leu val        (277)

TCG GGC CTT TTG GAG GTG TTC CGG GAA GGC CTC TAC GCC GCC TTC GGC CTC GCG GGA ACC       1020
ser gly leu leu glu val phe arg glu gly leu tyr ala ala phe gly leu ala gly thr        (297)

CCC CTT CCC GCC CCG CCC CAG GCC CTG ATC GCC GCC ATG ACC GCC CTG GAC GAG GCC ATG       1080
pro leu pro ala pro pro gln ala leu ile ala ala met thr ala leu asp glu ala met        (317)
```

Figure 4A

```
GAG CGC CTC GCC CGC CGC TCC GAC GCC TTA AGC CTG GAG GTG GCC CTC CTG GAG GCG GGA    1140
glu arg leu ala arg arg ser asp ala leu ser leu glu val ala leu leu glu ala gly    (337)

AGG GCC CTG GCC GCC GAG GCC CTA CCC CAG CCC ACG GGC GCT CCT TCC CCA GAG GTC GGC    1200
arg ala leu ala ala glu ala leu pro gln pro thr gly ala pro ser pro glu val gly    (357)

CCC AAG CCG GAA AGC CCC CCG ACC CCG GAA CCC CCA AGG CCC GAG GAG GCG CCC GAC CTG    1260
pro lys pro glu ser pro pro thr pro glu pro pro arg pro glu glu ala pro asp leu    (377)

CGG GAG CGG TGG CGG GCC TTC CTC GAG GCC CTC AGG CCC ACC CTA CGG GCC TTC GTG CGG    1320
arg glu arg trp arg ala phe leu glu ala leu arg pro thr leu arg ala phe val arg    (397)

GAG GCC CGC CCG GAG GTC CGG GAA GGC CAG CTC TGC CTC GCT TTC CCC GAG GAC AAG GCC    1380
glu ala arg pro glu val arg glu gly gln leu cys leu ala phe pro glu asp lys ala    (417)

TTC CAC TAC CGC AAG GCC TCG GAA CAG AAG GTG AGG CTC CTC CCC CTG GCC CAG GCC CAT    1440
phe his tyr arg lys ala ser glu gln lys val arg leu leu pro leu ala gln ala his    (437)
                                                         frameshift site
TTC GGG GTG GAG GAG GTC GTC CTC GTC CTG GAG GGA GAA AAA AAA AGC CTG AGC CCA AGG    1500
phe gly val glu glu val val leu val leu glu gly glu lys lys ser leu ser pro arg    (457)

CCC CGC CCG GCC CCA CCT CCT GAA GCG CCC GCA CCC CCG GGC CCT CCC GAG GAG GAG GTA    1560
pro arg pro ala pro pro pro glu ala pro ala pro pro gly pro pro glu glu glu val    (477)

GAG GCG GAG GAA GCG GCG GAG GAG GCC CCG GAG GAG GCC TTG AGG CGG GTG GTC CGC CTC    1620
glu ala glu glu ala ala glu glu ala pro glu glu ala leu arg arg val val arg leu    (497)

CTG GGG GGG CGG GTG CTC TGG GTG CGG CGG CCC AGG ACC CGG GAG GCG CCG GAG GAG GAA    1680
leu gly gly arg val leu trp val arg arg pro arg thr arg glu ala pro glu glu glu    (517)

CCC CTG AGC CAA GAC GAG ATA GGG GGT ACT GGT ATA TAA    TGGGGCATG    ACGCGGACCAC    1740
pro leu ser gln asp glu ile gly gly thr gly ile  *                                 (529)

CGACCTCGGA    CAAGAGACCG    TGGACAACAT    CCTCAAGCGC    CTCCGCCGTA    TTGAGGCCA    1800

GGTGCGGGGG    CTCCAGAAGA    TGGTGGCCGA    GGGCCGCCCC    TGCGACGAGG    TCCTCACCCA    1860

GATGACCGCC    ACCAAGAAGG    CCATGGAGGC    GGCGGCCACC    CTGATCCTCC    ACGAGTTCCT    1920

GAACGTCTGC    GCCGCCGAGG    TCTCCGAGGG    CAAGGTGAAC    CCCAAGAAGC    CCGAGGAGAT    1980

CGCCACCATG    CTGAAGAACT    TCATCTA                                                2007
```

Figure 4B

```
                GTG AGC GCC CTC TAC CGC CGC TTC CGC CCC CTC ACC TTC CAG GAG GTG GTG    51
GGG CAG GAG CAC GTG AAG GAG CCC CTC CTC AAG GCC ATC CGG GAG GGG AGG CTC GCC CAG   111
GCC TAC CTC TTC TCC GGG CCC AGG GGC GTG GGC AAG ACC ACC ACG GCG AGG CTC CTC GCC   171
ATG GCG GTG GGG TGC AGG GGA GAA GAC CCC CCT TGC GGG GTC TGC CCC CAC TGC CAG GCG   231
GtG CAG AGG GGC GCC CAC CCG GAC GTG GTG GAC ATT GAC GCC GCC AGC AAC AAC TCC GTG   291
GAG GAC GTG CGG GAG CTG AGG GAA AGG ATC CAC CTC GCC CCC CTC TCT GCC CCC AGG AAG   351
GTC TTC ATC CTG GAC GAG GCC CAC ATG CTC TCC AAA AGC GCC TTC AAC GCC CTC CTC AAG   411
ACC CTG GAG GAG CCC CCG CCC CAC GTC CTC TTC GTC TTC GCC ACC ACC GAG CCC GAG AGG   471
ATG CCC CCC ACC ATC CTC TCC CGC ACC CAG CAC TTC CGC TTC CGC CGC CTC ACG GAG GAG   531
GAG ATC GCC TTT AAG CTC GGG CGC ATC CTG GAG GCC GTG GGG CGG GAG GCG GAG GAG GAG   591
GCC CTC CTC CTC CTC GCC CGC CTG GCG GAC GGG GCC CTT AGG GAC GCG GAA AGC CTC CTG   651
GAG CGC TTC CTC CTC CTG GAA GGC CCC CTC ACC AAG GAG GTG GAG CGC GCC CTA GGC   711
TCC CCC CCA GGG ACC GGG GTG GCC GAG ATC GCC GCC TCC CTC GCG AGG GGG AAA ACG GCG   771
GAG GCC CTG GGC CTC GCC CGG CGC CTC TAC GGG GAA GGG TAC GCC CCG AGG AGC CTG GTC   831
TCG GGC CTT TTG GAG GTG TTC CGG GAA GGC CTC TAC GCC GCC TTC GGC CTC GCG GGA ACC   891
CCC CTT CCC GCC CCG CCC CAG GCC CTG ATC GCC GCC ATG ACC GCC CTG GAC GAG GCC ATG   951
GAG CGC CTC GCC CGC CGC TCC GAC GCC TTA AGC CTG GAG GTG GCC CTC CTG GAG GCG GGA  1011
AGG GCC CTG GCC GCC GAG GCC CTA CCC CAG CCC ACG GGC GCT CCT TCC CCA GAG GTC GGC  1071
CCC AAG CCG GAA AGC CCC CCG ACC CCG GAA CCC CCA AGG CCC GAG GAG GCG CCC GAC CTG  1131
CGG GAG CGG TGG CGG GCC TTC CTC GAG GCC CTC AGG CCC ACC CTA CGG GCC TTC GTG CGG  1191
GAG GCC CGC CCG GAG GTC CGG GAA GGC CAG CTC TGC CTC GCT TTC CCC GAG GAC AAG GCC  1251
TTC CAC TAC CGC AAG GCC TCG GAA CAG AAG GTG AGG CTC CTC CCC CTG GCC CAG GCC CAT  1311
TTC GGG GTG GAG GAG GTC GTC CTC GTC CTG GAG GGA GAA AAA AAA AGC CTG AGC CCA AGG  1371
CCC CGC CCG GCC CCA CCT CCT GAA GCG CCC GCA CCC CCG GGC CCT CCC GAG GAG GAG GTA  1431
GAG GCG GAG GAA GCG GCG GAG GAG GCC CCG GAG GAG GCC TTG AGG CGG GTG GTC CGC CTC  1491
CTG GGG GGG CGG GTG CTC TGG GTG CGG CGG CCC AGG ACC GGG GAG GCG CCG GAG GAG GAA  1551
            CCC CTG AGC CAA GAC GAG ATA GGG GGT ACT GGT ATA TAA   (1590)
```

Figure 4C

```
Met ser ala leu tyr arg arg phe arg pro leu thr phe gln glu val val gly gln glu   20
his val lys glu pro leu leu lys ala ile arg glu gly arg leu ala gln ala tyr leu   40
phe ser gly pro arg gly val gly lys thr thr thr ala arg leu leu ala met ala val   60
gly cys gln gly glu asp pro pro cys gly val cys pro his cys gln ala val gln arg   80
gly ala his pro asp val val asp ile asp ala ala ser asn asn ser val glu asp val  100
arg glu leu arg glu arg ile his leu ala pro leu ser ala pro arg lys val phe ile  120
leu asp glu ala his met leu ser lys ser ala phe asn ala leu leu lys thr leu glu  140
glu pro pro his val leu phe val phe ala thr thr glu pro glu arg met pro pro  160
thr ile leu ser arg thr gln his phe arg phe arg arg leu thr glu glu glu ile ala  180
phe lys leu arg arg ile leu glu ala val gly arg glu ala glu glu glu ala leu leu  200
leu leu ala arg leu ala asp gly ala leu arg asp ala glu ser leu leu glu arg phe  220
leu leu leu glu gly pro leu thr arg lys glu val glu arg ala leu gly ser pro pro  240
gly thr gly val ala glu ile ala ala ser leu ala arg gly lys thr ala glu ala leu  260
gly leu ala arg arg leu tyr gly glu gly tyr ala pro arg ser leu val ser gly leu  280
leu glu val phe arg glu gly leu tyr ala ala phe gly leu ala gly thr pro leu pro  300
ala pro pro gln ala leu ile ala ala met thr ala leu asp glu ala met glu arg leu  320
ala arg arg ser asp ala leu ser leu glu val ala leu leu glu ala gly arg ala leu  340
ala ala glu ala leu pro gln pro thr gly ala pro ser pro glu val gly pro lys pro  360
glu ser pro pro thr pro glu pro pro arg pro glu glu ala pro asp leu arg glu arg  380
trp arg ala phe leu glu ala leu arg pro thr leu arg ala phe val arg glu ala arg  400
pro glu val arg glu gly gln leu cys leu ala phe pro glu asp lys ala phe his tyr  420
arg lys ala ser glu gln lys val arg leu leu pro leu ala gln ala his phe gly val  440
gly glu val val leu val leu gly gly leu lys lys ser leu ser pro arg pro arg pro  460
ala pro pro pro glu ala pro ala pro pro gly pro pro glu glu glu val glu ala glu  480
glu ala ala glu glu ala pro glu glu ala leu arg arg val val arg leu leu gly gly  500
arg val leu trp val arg arg pro arg thr arg glu ala pro glu glu glu pro leu ser  520
gln asp glu ile gly gly thr gly ile                                               529
```

Figure 4D

```
Met ser ala leu tyr arg arg phe arg pro leu thr phe gln glu val val gly gln glu  20
his val lys glu pro leu leu lys ala ile arg glu gly arg leu ala gln ala tyr leu  40
phe ser gly pro arg gly val gly lys thr thr thr ala arg leu leu ala met ala val  60
gly cys gln gly glu asp pro pro cys gly val cys pro his cys gln ala val gln arg  80
gly ala his pro asp val val asp ile asp ala ala ser asn asn ser val glu asp val 100
arg glu leu arg glu arg ile his leu ala pro leu ser ala pro arg lys val phe ile 120
leu asp glu ala his met leu ser lys ser ala phe asn ala leu leu lys thr leu glu 140
glu pro pro pro his val leu phe val phe ala thr thr glu pro glu arg met pro pro 160
thr ile leu ser arg thr gln his phe arg phe arg arg leu thr glu glu glu ile ala 180
phe lys leu arg arg ile leu glu ala val gly arg glu ala glu glu glu ala leu leu 200
leu leu ala arg leu ala asp gly ala leu arg glu arg asp ala glu ser leu leu glu arg phe 220
leu leu leu glu gly pro leu thr arg lys glu val glu arg ala leu gly ser pro pro 240
gly thr gly val ala glu ile ala ala ser leu ala arg gly lys thr ala glu ala leu 260
gly leu ala arg arg leu tyr gly glu gly tyr ala pro arg ser leu val ser gly leu 280
leu glu val phe arg glu gly leu tyr ala ala phe gly leu ala gly thr pro leu pro 300
ala pro pro gln ala leu ile ala ala met thr ala leu asp glu ala met glu arg leu 320
ala arg arg ser asp ala leu ser leu glu val ala leu leu glu ala gly arg ala leu 340
ala ala glu ala leu pro gln pro thr gly ala pro ser pro glu val gly pro lys pro 360
glu ser pro pro thr pro glu pro pro arg pro glu glu ala pro asp leu arg glu arg 380
trp arg ala phe leu glu ala leu arg pro thr leu arg ala phe val arg glu ala arg 400
pro glu val arg glu gly gln leu cys leu ala phe pro glu asp lys ala phe his tyr 420
arg lys ala ser glu gln lys val arg leu leu pro leu ala gln ala his phe gly val 440
glu glu val val leu val leu glu gly glu lys lys lys pro asp pro lys ala pro pro 460
gly pro thr ser                                                                  464
```

Figure 4E

```
Met ser ala leu tyr arg arg phe arg pro leu thr phe gln glu val val gly gln glu  20
his val lys glu pro leu leu lys ala ile arg glu gly arg leu ala gln ala tyr leu  40
phe ser gly pro arg gly val gly lys thr thr thr ala arg leu leu ala met ala val  60
gly cys gln gly glu asp pro pro cys gly val cys pro his cys gln ala val gln arg  80
gly ala his pro asp val val asp ile asp ala ala ser asn asn ser val glu asp val 100
arg glu leu arg glu arg ile his leu ala pro leu ser ala pro arg lys val phe ile 120
leu asp glu ala his met leu ser lys ser ala phe asn ala leu leu lys thr leu glu 140
glu pro pro his val leu phe val phe ala thr thr glu pro glu arg met pro pro 160
thr ile leu ser arg thr gln his phe arg phe arg arg leu thr glu glu glu ile ala 180
phe lys leu arg arg ile leu glu ala val gly arg glu ala glu glu glu ala leu leu 200
leu leu ala arg leu ala asp gly ala leu arg asp ala glu ser leu leu glu arg phe 220
leu leu leu glu gly pro leu thr arg lys glu val glu arg ala leu gly ser pro pro 240
gly thr gly val ala glu ile ala ala ser leu ala arg gly lys thr ala glu ala leu 260
gly leu ala arg arg leu tyr gly glu gly tyr ala pro arg ser leu val ser gly leu 280
leu glu val phe arg glu gly leu tyr ala ala phe gly leu ala gly thr pro leu pro 300
ala pro pro gln ala leu ile ala ala met thr ala leu asp glu ala met glu arg leu 320
ala arg arg ser asp ala leu ser leu glu val ala leu leu glu ala gly arg ala leu 340
ala ala glu ala leu pro gln pro thr gly ala pro ser pro glu val gly pro lys pro 360
glu ser pro pro thr pro glu pro pro arg pro glu ala pro asp leu arg glu arg 380
trp arg ala phe leu glu ala leu arg pro thr leu arg ala phe val arg glu ala arg 400
pro glu val arg glu gly gln leu cys leu ala phe pro glu asp lys ala phe his tyr 420
arg lys ala ser glu gln lys val arg leu leu pro leu ala gln ala his phe gly val 440
glu glu val val leu val leu glu gly glu lys lys lys ala                         454
```

Figure 4F

```
                                                          ATP site
E.coli    MSYQVLARKWRPQTFADVVGQEHVLTALANGLSLGRIHHAYLFSGTRGVGKTSIARLLAK   60
H.inf.    ............K..........II.......KDN.L....................F..   60
B.sub.    ....A.Y.VF...R.E.......ITKT.Q.A.LQKKFS.......P..T....A.KIF..   60
C.cres.   DA.T.....Y..R..E.LI...AMVRT...AF.T...A..FMLT.V......TT.....R  113
M.gen.    -MH..FYQ.Y..IN.KQTL...SIRKI.V.AINRDKLPNG.I...E..T...TF.KII..   59
T.th.     --VSA.Y.RF..L..QE.......KEP.LKAIRE...LAQ......P......TT.....M   58

Zn++ finger
              *    *  *  *
E.coli    GLNCET----GITATPCGVCDNCREIEQGRFVDLIEIDAASRTKVEDTRDLLDNVQYAPA  116
H.inf.    ....VH----.V.......E.E..KA....N.I....................E.......K.V  116
B.sub.    AV...H----APVDE..NE.AA..KG.TN.SIS.V.......NNG.DEI..IR.K.KF..S  116
C.cres.   A..Y..DTVK.PSVDLTTEGYH..S.IE..HM.VL.L........DEM.E...G.R...V  173
M.gen.    AI..LN----WDQIDV.NS..V.KS.NTNSAI.IV......KNGIN.I.E.VE..FNH.F  115
T.th      AVG.QG------EDP.....PH.QAVQR.AHP.VVD.....NNS...V.E.RERIHL..L  112

E.coli    RGRFKVYLIDEVHMLSRHSFNALLKTLEEPPEHVKFLLATTDPQKLPVTILSRCLQFHLK  176
H.inf.    V............................Y..............................  176
B.sub.    AVTY...I........IGA..............CI.I.....E.H.I.L..I...QR.DF.  176
C.cres.   EA.Y...I........TAA.........P.A..IF...EIR.V........QR.D.R  233
M.gen.    TFKK...IL..A...TTQ.WGG.......S.PY.L.IFT..EFN.I.L.......QS.FF.  175
T.th.     SAPR..FIL..A....KSA..........P..L.VF...E.ERM.P.....TQH.RFR  172

E.coli    ALDVEQIRHQLEHILNEEHIAHEPRALQLLARAAEGSLRDALSLTDQAIASGDGQ--VST  234
H.inf.    ...ET..SQH.A...TQ.N.PF.DP..VK..K..Q..I..S.........M..R.--.TN  234
B.sub.    RITSQA..VGRMNK.VDA.QLQV.EGS.EII.S..H.GM......L.....SFSGDI--LKV  234
C.cres.   RVEPDVLVKHFDR..SAK.GARI.MD..A.I.......V..G...L....VQTERGQT.TS  293
M.gen.    KITSDL..LER..ND..AKK.K..KI..KD...IKI.DLSQ.....G...L...LAI.LIVKKL.LL  235
T.th.     R.TE.E..AFK..RR...EAVGREA.EE..L....L.D.A....E..LERFLLLEGP---LTR  229

E.coli    QAVSAMLGTLDDDQALSLVEAMVEANGERVMALINEAAARGIEWEALLVEMLGLLHRIAM  294
H.inf.    NV..N...L...NYSVDILY.LHQG...LL.RTLQRV.DAAGD.DK..G.CAEK..Q..L  294
B.sub.    EDALLIT.AVSQLYIGK.AKSLHDK..VSDALETL..LLQQ.KDPAK.IED.IFYFRDMLL  294
C.cres.   TV.RD...LA.RS.TIA.Y.HVMAGKTKDALEGFRALWGF.ADPAVVMLDV.DHC.AS.V  353
M.gen.    MLKKHLISLIEMQNL.L.KQFYQ.I                                    260
T.th.     KE.ERA..SPPGTGVAEIAASLARGKTAEALG.ARRLYGE.YAPRS.VSGL.EVFREGLY  289
```

Figure 5

A) Cell induction    B) Purification    C) Western

A) Alignment of TTH1 with alphas subunits of other organisms.

| | | | |
|---|---|---|---|
| E.coli   | DRYFLELIRTGRPDEESYLHAAVELAEARGLPVV 197 | | (ID#72) |
| V.chol.  | DHFYLELIRTGRADEESYLHFALDVAEQYDLPVV 197 | | (ID#73) |
| H.inf.   | DHFYLALSRTGRPNEERYIQAALKLAERCDLPLV 197 | | (ID#74) |
| R.prow.  | DRFYFEIMRHDLPEEQFIENSYIQIASELSIPIV 195 | | (ID#75) |
| H.pyl.   | DDFYLEIMRHGILDQRFIDEQVIKMSLETGLKII 213 | | (ID#76) |
| S.sp.    | DDYYLEIQDHGSVEDRLVNINLVKIAQELDIKIV 202 | | (ID#77) |
| M.tub.   | DNYFLELMDHGLTIERRVRDGLLEIGRALNIPPL 220 | | (ID#78) |
| T.th.    | FFIEIQNHGLSEQK | | (ID#61) |

B) Alignment of TTH2 with alphas subunits of other organisms.

| | | | |
|---|---|---|---|
| E.coli   | NKRRAKNGEPPLDIAAIPLDDKKSFDMLQRSETTAVFQLESRGMKD 618 | | (ID#79) |
| V.chol.  | NPRLKKAGKPPVRIEAIPLDDARSFRNLQDAKTTAVFQLESRGMKE 618 | | (ID#80) |
| H.inf.   | NVRMVREGKPRVDIAAIPLDDPESFELLKRSETTAVFQLESRGMKD 618 | | (ID#81) |
| R.prow.  | CKKLLKEQGIKIDFDDMTFDDKKTYQMLCKGKGVGVFQFESIGMKD 624 | | (ID#82) |
| H.pyl.   | LKIIKTQHKISVDFLSLDMDDPKVYKTIQSGDTVGIFQIES-GMFQ 648 | | (ID#83) |
| S.sp.    | QERKALQIRARTGSKKLPDDVKKTHKLLEAGDLEGIFQLESQGMKQ 643 | | (ID#84) |
| M.tub.   | IDNVRANRGIDLDLESVPLDDKATYELLGRGDTLGVFQLDGGPMRD 646 | | (ID#85) |
| T.th.    | RVELDYDALTLDD | | (ID#60) |

Start codon
ATGGGCCGGGAGCTCCGCTTCGCCCACCTCCACCAGCACA
CCCAGTTCTCCCTCCTGGACGGGGCGCCGAAGCTTTCCGA
CCTCCTCAAGTGGGTGGAGGAGACGACCCCCGAGGACCCC 120
GCCTTGGCCATGACCGACCACGGCAACCTCTTCGGGGCCG
TAGAGTTCTACAAGAAGGCCGCCGAAATGGGCATCGAGCC
CATCCTGGGTACGAGGCCTTACGTGGCGGCGGAAAGCCCG 240
TTTGACCGCAAGCGGGGAAAGGGCCTAGACGGGGGCTACT
TTCACCTCACCCTCCTCGCCAAGGACTTCACGGGGTACCA
GAACCTGGTGCGCCTGGCGAGCCGGGCTTACCTGGAGGGG 360
TTTTACGAAAAGCCCCGGATTGACCGGGAGATCCTGCGCG
AGCGCCGAGGGCCTCATCGCCTCTCGGGGTGCCTCGGGGC
GGAGATCCCCCAGTTCATCCTCCAGGACCGTCTGGACCTG 480
GCCGAGGCCCGGCTCAACGAGGACCTCTCCATCTTCAAGG
ACCGCTTCTTCATTCACATCCAGAACCACGGCCTCCCCGA
GCAGAAAAAGGTCAACGAGGTCCTCAAGGAGTTCGCCCGA 600
AAGTACGGCCTGGGGATGGTGGCCACCAACGACGGCCATT
ACGGGAGGAAGGAGGCCCGCAGCGCCCACGAGGTTTTCCT
CGCCATCCAGTCCAAGAGCACCCTGGACGACCCCGGGGCC 720
GTTGGCTTTCCCCTGCGGGAGTTCTACGTGAAGACCCCCG
AGGAGACGTGCGGGCCGGTGTTCCCCGAGGAGGAGTGGGG
GGACGAGCCCTTTGACAACACCGTGGAGATCGCCCGCATG 840
TGCAACGTGGAGCTGCCCATCGGGACAAGATGGTCTACCC
GAATCCCCCGCTTCCCCCTCCCCGAGGGACCGGGGACCGA
GGCCAAGTACCTAATGGAGCTAACCTTCAAGGGGCCCCTC 960
CGCCGTTACCCGGACCGAATCACCGAGGGTTTCTACCGGG
AGGTTTTCCGCCTTTTGGGGAAGCTTCCCCCCCACGGGCA
CGGGGAGGCCTTGGCCGAGGCCTTGGCCCAGGTGGAGCGG 1080
GAGGCTTGGGAGAGGCTCATGAAGAGCCTCCCCCCCTTTG
ACCGGGGTCCAAGGAGTTCCA

B)

MGRELRFAHLHQHTQFSLLDGAPKLSDLLKWVEETTPEDP
ALAMTDHGNLFGAVEFYKKAAEMGIEPILGTRPYVAAESP
FDRKRGKGLDGGYFHLTLLAKDFTGYQNLVRLASRAYLEG 120
FYEKPRIDREILRERRGPHRLSGCLGAEIPQFILQDRLDL
FFIEIQNHGLSEQK
AEARLNEDLSIFKDRFFIHIQNHGLPEQKKVNEVLKEFAR
KYGLGMVATNDGHYGRKEARSAHEVFLAIQSKSTLDDPGA 240
VGFPLREFYVKTPEETCGPVFPEEEWGDEPFDNTVEIARM
CNVELPIGTRWSTRIPRFPLPEGPGTEAKYLMELTFKGPL
RRYPDRITEGFYREVFRLLGKLPPHGHGEALAEALAQVER 360
EAWERLMKSLPPFDRGPRSS

Figure 16

```
              Start1          Start2            3'-Exo I
T.th.     VERVVRTLLDGRFLLEEGVGLWEWRYPFPLEGEAVVVLDLETTGLAG------LDEVIEVGLLRLEGG---RRLPF
D.rad.                              PWPQDVVVFDLETTGFSPA-----SAAIVEIGAVRIVGGQIDETLKF
Bac.sub.  HGIKMIYGMEANLVDDGVPIAYNAAHRLLEEETYVVFDVETTGLSAV-----YDTIIELAAVKVKGGE--IIDKF
H.inf.                          MINPNRQIVLDTETTGMNQLGAHYEGHCIIEIGAVELINRR-YTGNNX
E.c.                           MSTAITRQIVLDTETTGMNQIGAHSEGHKIIEIGAVEVVNRR-LTGNNF
H.pyl.    NLEYLKACGLNFIETSENLITLKNLKTPLKDEVFSFIDLETTGSCPI-----KHEILEIGAVQVKGGE--IINRF 3'-Exo II
T.th.     QSLVR-PLPP---AEARSWNLT---GIPREALEEAPSLEEVLEKAYPLRGDATLVIHNAAFDLGFL-RPALEGLG
D.rad.    ETLVR-PTRPDGSMLSIPWQAQRVHGISDEMVRRAPAXKDVLPDFFDFVDGSAVVAHNVSFDGGFM-RAGAERLG
Bac.sub.  EAFAN-PHRP---LSATIIELT---GITDDMLQDAPDVVDVIRDFREWIGDDILVAHNASFDMGFL-NVAYKKLL
H.inf.    HIYIK-PDRP---XDPDAIKVH---GITDEMLADKPEFKEVAQDFLDYINGAELLIHNAPFDVGFM-DYEFRKLN
E.c.      HVYLK-DRLV----DPEAFGVH---GIAVDFLLDKPTFAEVAVEFMDYIRGAELVIHNAAFDIGFM-DYEFSLLK
H.pyl.    ETLVKVKSVP-----DYIAELT---GITYEDTLNAPSAHEALQELRLFLGNSVFVAHNANFDYNFLGRYFVEKLH 3'-Exo IIIC
T.th.     -----YRLENPVVDSLRLARRGLPGLRRYGLDALSEVLELPRRT--CHRALEDVERTLAVVHEVYYMLT-----SG
D.rad.    ----LSWAPERELCTMQLSRRAFPRERTHNLTVLAERLGLEFAPGGRHRSYGDVQVTAQAYLRLLELLG-----ER
Bac.sub.  E---VEKAKNPVIDTLELGRFLYPEFKNHRLNTLCKKFDIELTQ--HHRAIYDTEATAYLLLKMLKDAA-----EK
H.inf.    -LNVKTDDICLVTDTLQMARQMYPGKRN-NLDALCDRLGIDNSKRTLHGALLDAEILADVYLMMTGGQTNLFDEEE
E.c.      RDIAKTNTFCKVTDSLAVARKMFPGKRN-SLDALCARYEIDNSKRTLHGALLDAQILAEVYLAMTGGQTSMAFAME
H.pyl.    -----CPLLNLKLCTLDLSKRAILSMRY-SLSFLKELLGFGIEV--SHRAYADALASYKLFEICLLNLP--SYIKT
```

ATGGTGGAGCGGGTGGTGCGGACCCTTCTGGACGGGAGGT 40
TCCTCCTGGAGGAGGGGGTGGGGCTTTGGGAGTGGCGCTA
CCCCTTTCCCCTGGAGGGGGAGGCGGTGGTGGTCCTGGAC 120
CTGGAGACCACGGGGCTTGCCGGCCTGGACGAGGTGATTG
AGGTGGGCCTCCTCCGCCTGGAGGGGGGAGGCGCCTCCC 200
CTTCCAGAGCCTCGTCCGGCCCTCCCGCCCGCCGAAGCC
CGTTCGTGGAACCTCACCGGCATCCCCGGGAGGCCCTGG 280
AGGAGGCCCCCTCCCTGGAGGAGGTTCTGGAGAAGGCCTA
CCCCCTCCGCGGCGACGCCACCTTGGTGATCCACAACGCC 360
GCCTTTGACCTGGGCTTCCTCCGCCCGGCCTTGGAGGGCC
TGGGCTACCGCCTGGAAAACCCCGTGGTGGACTCCCTGCG 440
CTTGGCCAGACGGGGCTTACCAGGCCTTAGGCGCTACGGC
CTGGACGCCCTCTCCGAGGTCCTGGAGCTTCCCCGAAGGA 520
CCTGCCACCGGGCCCTCGAGGACGTGGAGCGCACCCTCGC
CGTGGTGCACGAGGTATACTATATGCTTACGTCCGGCCGT 600
CCCCGCACGCTTTGGGAACTCGGGAGGTAG

B)

MVERVVRTLLDGRFLLEEGVGLWEWRYPFPLEGEAVVVLD 40
LETTGLAGLDEVIEVGLLRLEGGRRLPFQSLVRPLPPAEA
RSWNLTGIPREALEEAPSLEEVLEKAYPLRGDATLVIHNA 120
AFDLGFLRPALEGLGYRLENPVVDSLRLARRGLPGLRRYG
LDALSEVLELPRRTCHRALEDVERTLAVVHEVYYMLTSGR 200
PRTLWELGRZ

Figure 18

Alignment of dnaA genes.

```
P.mar.    MLEASWEK VQSSL--KQNLSK-- -----------PSYE TWIRPTEFSG--FKN GELTLIAPNSFSSAW LKNNYSQTIQETAE-    65
Syn.sp.   MVSCENLWQQ ALAIL--ATQLTK-- -----------PAFD TWIKASVLIS--LGD GVATIQVENGFVLNH LQKSYGPLLMEVLT-   67
B.sut.    MENILDLWNQ ALAQI--EKKLSK-- -----------PSFE TWMKSTKAHS--LQG DTLTITAPNEFARDW LESRYLHLIADTIY-   67
M.tub.    MTDDPGSGFTTVWNA VVSELNGDPKVDDGP SSDANLSAPLTPQQR AWLNLVQPLT--IVE GFALLSVPSSFVQNE IERHLRAPITDALS-  87
T.th.     MSHEAVWQH VLEHI--RRSITE-- -----------VEFH TWFERIRPLG--IRD GVLELAVPTSFALDW IRRHYAGLIQEGPR-   66
E.coli    MSLSLWQQ CLARL--QDELPA-- -----------TEFS MWIRPLQAE---LSD NTLALYAPNRFVLDW VRDKYLNNINGLLT-    64
T.mar.    MKER ILQEI--KTRVNR-- -----------KSWE LWFSSFDVKS--IEG NKVVFSVGNLFIKEW LEKKYYSVLSKAVK-          61
H.pyl.    MDTNNNIEKE ILALVKQNPKVSL-- -----------IEYE NYFSQLKYNPNASKS DIAFFYAPNQVLCTT ITAKYGALLKEILSQ   72

P.mar.    EIFG---EPVTVHVK VKANAESSDEHYSSA P-------------- ---ITPPLEASPGSV DSSGSSLRLSK---- -KTLPLLNLRYVFNR  130
Syn.sp.   DLTG---QEITVKLI TDGLEPHS---LIGQ E-------------- ---SSLPMETTP--- --------------- -KNATALNGKYTFSR  115
B.sut.    ELTG---EELSIKFV IPQNQDVEDFMPKPQ VKKAVKEDTSDFPQN --------------- --------------- -----MLNPKYTFDT  119
M.tub.    RRLGH-QIQLGVRIA PPATDEADDTTVPPS ENPATTSPDTTTDND EIDDSAAARGDNQHS WPSYFTERPHNTDSA TAGVTSLNRRYTFDT  176
T.th.     LLGAQ-APRFELRVV PGVVVQEDIFQPPPS PPAQAQP-------- --------------- --------------- ---------EDTFKT  108
E.coli    SFCGADAPQLRFEVG TKPVTQTPQAAVTSN VAAPAQVAQTQPQRA APSTRSGWDNVPAPA EP------------- -TYRSNVNVKHTFDN  140
T.mar.    VVLG---NDATFEIT YEAFEPHSSYSEPLV KKRAVLLTP------ --------------- --------------- ------LNPDYTFEN  106
H.pyl.    NKVG-MHLAHSVDVR IEVAPKIQINAQSNI NYKAIKTS------- --------------- --------------- ------VKDSYTFEN  118

P.mar.    FVVGPNSRMAHAAAM AVAESPGREFNPLFI CGGVGLGKTHLMQAI GHYRLEIDPGAKVSY VSTETFTNDLIL--A IRQDRMQAFRDRYR-  217
Syn.sp.   FVVGPTNRMAHAASL AVAESPGREFNPLFL CGGVGLGKTHLMQAI AHYRLEMYPNAKVYY VSTERFTNDLIT--A IRQDNMEDFRSYYR-  202
B.sut.    FVIGSGNRFAHAASL AVAEAPAKAYNPLFI YGGVGLGKTHLMHAI GHYVIDHNPSAKVVY LSSEKFTNEFIN--S IRDNKAVDFRNRYR-  206
M.tub.    FVIGASNRFAHAAAL AIAEAPARAYNPLFI WGESGLGKTHLLHAN GNYAQRLFPGMRVKY VSTEEFTNDFIN--S LRDDRKVAFKRSYR-  263
T th      SWWGPTTPWPHGGAV AVAESPGRAYNPLFI YGGRGLGKTYLMHAV GPLRAKRFPHMRLEY VSTETFTNELINRPS AR-DRMTEFRERYR-  196
E coli    FVEGKSNQLARAAAR QVADNPGGAYNPLFL YGGTGLGKTHLLHAV GNGIMARKPNAKVVY MHSERFVQDMVK--A LQNNAIEEFKRYYR-  227
T.mar.    FVVGPGNSFAYHAAL EVAKHPGR-YNPLFI YGGVGLGKTHLLQSI GNYVVQNEPDLRVMY ITSEKFLNDLVD--S MKEGKLNEFREKYRK  193
H.pyl.    FVVGSCNNTVYEIAK KVAQSDTPPYNPVLF YGGTGLGKTHILNAI GNHALEK--HKKVVL VTSEDFLTDFLK--H LDNKTMDSFKAKYR-  203

P.mar.    AADLILVDDIQFIEG KEYTQEEFFHTFNAL HDAGSQIVLASDRPP SQIPRLQERLMSRFS MGLIADVQAPDLETR MAILQKKAEHERVGL  307
Syn.sp.   SADFLLIDDIQFIKG KEYTQEEFFHTFNSL HEAGKQVVVASDRAP QRIPGLQDRLISRFS WGLITDITPPDLETR MAILQKKAEYDRIRL  292
B.sut.    NVDVLLIDDIQFLAG KEQTQEEFFHTFNTL HEESKQIVISSDRPP KEIPTLEDRLRSRFE WGLITDITPPDLETR IAILRKKAKAEGLDI  296
M.tub.    DVDVLLVDDIQFIEG KEGIQEEFFHTFNTL HNANKQIVISSDRPP KQLATLEDRLRTRFE WGLITDVQPPELETR IAILRKKAQMERLAV  353
T.th.     SVDLLLVDDVQFLAG KERTQEEFFHTFNAL YEAHKQIILSSDRPP KDIILTLEARLRSRFE WGLITDNPAPDLETR IAILKMNAS-SGPED  285
E.coli    SVDALLIDDIQFFAN KERSQEEFFHTFNAL LEGNQQIILTSDRYP KEINGVEDRLKSRFG WGLTVAIEPPELETR VAILMKKADENDIRL  317
T.mar.    KVDILLIDDVQFLIG KTGVQTELFHTFNEL HDSGKQIVICSDREP QKLSEFQDRLVSRFQ MGLVAKLEPPDEETR KSIARKMLEIEHGEL  283
H.pyl.    HCDFFLLDDAQFLQG KPKLEEEFFHTFNEL HANSKQIVLISDRSP KNIAGLEDRLKSRFE WGITAKVMPPDLETK LSIVKQKCQLNQITL  293

P.mar.    PRDLIQFIAGRFTSN IRELEGALTRAIAFA SITGLPMTVDSIAPM LD----PNGQGVEVT PKQVLDKVAEVFKVT PDEMRSASRRR-PVS  392
Syn.sp.   PKEVIEYIASHYTSN IRELEGALIRAIAYT SLSNVAMTVENIAPV LN----PPVEKVAAA PETIITIVAQHYQLK VEELLSNSRRR-EVS  377
B.sut.    PNEVMLYIANQIDSN IRELEGALIRVVAYS SLINKDINADLAAEA LKDII-PSSKPKVIT IKEIQRVVGQQFNIK LEDFKAKKRTK-SVA  384
M.tub.    PDDVLELIASSIERN IRELEGALIRVTAFA SLNKTPIDKALAEIV LRDLI-ADANTMQIS AATIMAATAEYFDTT VEELRGPGKTR-ALA  441
T.th.     PEDALEYIARQVTSN IREWEGALMRASPFA SLNGVELTRAVAAKA LRHLR-P--RELEAD PLEIIRKAAGPVRPE TPGGAHGERRKKEVV  372
E.coli    PGEVAFFIAKRLRSN VRELEGALNRVIANA NFTGRAITIDFVREA LRDLL-A-LQEKLVT IDNIQKTVAEYYKIK VADLLSKRRSR-SVA  404
T.mar.    PEEVLNFVAENVDDN LRRLRGAIIKLLVYK ETTGKEVDLKEAILL LKDFIKPNRVKAMDP IDELIEIVAKVTGVP REEILSNSRNV-KAL  372
H.pyl.    PEEVMEYIAQHISDN IRQMEGAIIKISVNA NLMNASIDLNLAKTV LEDL--QKDHAEGSS LENILLAVAQSLNLK SSEIKVSSRQK-NVA  380

P.mar.    QARQVGMYLMRQGTN LSLPRIGDTFGGKDH TTVMYAIEQVEKKLS S---------DPQIA SQVQKIRDLLQIDSR RKR----           461
Syn.sp.   LARQVGMYLMRQHTD LSLPRIGEAFGGKDH TTVMYSCDKITQLQQ K---------DWETS QTLTSLSHRINIAGQ APES---            447
B.sut.    FPRQIAMYLSREMTD SSLPKIGEEFGGRDH TTVIHAHEKISKLLA D---------DEQLQ QHVKEIKEQLK---- -------            446
M.tub.    QSRQIAMYLCRELTD SSLPKIGQAFG-RDH TTVMYAQRKILSEMA E---------RREVF DHVKELTTRIRQRSK R------            507
T.th.     LPRQLAMYLVRELTP ASLPEIGQLFGGRDH TTVRYAIQKVQELAG KP--------DREVQ GLLRTLREACTDPVD NLWITCG            446
E.coli    RPRQMAMALAKELTN HSLPEIGDAFGGRDH TTVLHACRKIEQLRE E---------SHDIK EDFSNLIRTLSS--- -------            467
T.mar.    TARRIGMYVAKNYLK SSLRTIAEKFN-RSH PVVVDSVKKVKDSLL KG--------NKQLK ALIDEVIGEISRRAL SG-----            440
H.pyl.    LARKLVVYFARLYTP NPTLSLAQFLDLKDH SSISKMYSGVKKMLE EEKSPFVLSLREEIK NRLNELNDKKTAFNS SE-----            457
```

```
GTGTCGCACGAGGCCGTCTGGCAACACGTTCTGGAGCACA
TCCGCCGCAGCATCACCGAGGTGGAGTTCCACACCTGGTT
TGAAAGGATCCGCCCCTTGGGGATCCGGGACGGGGTGCTG  120
GAGCTCGCCGTGCCCACCTCCTTTGCCCTGGACTGGATCC
GGCGCCACTACGCCGGCCTCATCCAGGAGGGCCCTCGGCT
CCTCGGGGCCCAGGCGCCCCGGTTTGAGCTCCGGGTGGTG  240
CCCGGGGTCGTAGTCCAGGAGGACATCTTCCAGCCCCCGC
CGAGCCCCCGGCCCAAGCTCAACCCGAAGATACCTTTAA
AACTTCGTGGTGGGGCCCAACAACTCCATGGCCCCACGGC  360
GGCGCCGTGGCCGTGGCCGAGTCCCCCGGCCGGGCCTACA
ACCCCCTCTTCATCTACGGGGCCGTGGCCTGGGAAAGAC
CTACCTGATGCACGCCGTGGGCCCACTCCGTGCGAAGCGC  480
TTCCCCCACATGAGATTAGAGTACGTTTCCACGGAAACTT
TCACCAACGAGCTCATCAACCGGCCATCCGCGAGGGACCG
GATGACGGAGTTCCGGGAGCGGTACCGCTCCGTGGACCTC  600
CTGCTGGTGGACGACGTCCAGTTCATCGCCGGAAAGGAGC
GCACCCAGGAGGAGTTTTTCCACACCTTCAACGCCCTTTA
CGAGGCCCACAAGCAGATCATCCTCTCCTCCGACCGGCCG  720
CCCAAGGACATCCTCACCCTGGAGGCGCGCCTGCGGAGCC
GCTTTGAGTGGGGCCTGATCACCGACAATCCAGCCCCCGA
CCTGGAAACCCGGATCGCCATCCTGAAGATGAACGCCAGC  840
AGCGGGCCTGAGGATCCCGAGGACGCCCTGGAGTACATCG
CCCGGCAGGTCACCTCCAACATCCGGGAGTGGGAAGGGGC
CCTCATGCGGGCATCGCCTTTCGCCTCCCTCAACGGCGTT  960
GAGCTGACCCGCGCCGTGGCGGCCAAGGCTCTCCGACATC
TTCGCCCCAGGGAGCTGGAGGCGGACCCCTTGGAGATCAT
CCGCAAAGCGGCGGGACCAGTTCGGCCTGAAACCCCGGGA  1080
GGAGCTCACGGGGAGCGCCGCAAGAAGGAGGTGGTCCTCC
CCCGGCAGCTCGCCATGTACCTGGTGCGGGAGCTCACCCC
GGCCTCCCTGCCCGAGATCGACCAGCTCAACGACGACCGG  1200
GACCACACCACGGTCCTCTACGCCATCCAGAAGGTCCAGG
AGCTCGCGGAAAGCGACCGGGAGGTGCAGGGCCTCCTCCG
CACCCTCCGGGAGGCGTGCACATGA
```

B)

```
VSHEAVWQHVLEHIRRSITEVEFHTWFERIRPLGIRDGVL
ELAVPTSFALDWIRRHYAGLIQEGPRLLGAQAPRFELRVV
PGVVVQEDIFQPPPSPPAQAQPEDTFKTSWWGPTTPWPHG  120
GAVAVAESPGRAYNPLFIYGGRGLGKTYLMHAVGPLRAKR
FPHMRLEYVSTETFTNELINRPSARDRMTEFRERYRSVDL
LLVDDVQFIAGKERTQEEFFHTFNALYEAHKQIILSSDRP  240
PKDILTLEARLRSRFEWGLITDNPAPDLETRIAILKMNAS
SGPEDPEDALEYIARQVTSNIREWEGALMRASPFASLNGV
ELTRAVAAKALRHLRPRELEADPLEIIRKAAGPVRPETPG  360
GAHGERRKKEVVLPRQLAMYLVRELTPASLPEIDQLNDDR
DHTTVLYAIQKVQELAESDREVQGLLRTLREACT
```

| | |
|---|---|
| ATGAACATAACGGTTCCCAAAAAACTCCTCTCGGACCAGC | 40 |
| TTTCCCTCCTGGAGCGCATCGTCCCTCTAGAAGCGCCAA | |
| CCCCCTCTACACCTACCTGGGGCTTTACGCCGAGGAAGGG | 120 |
| GCCTTGATCCTCTTCGGGACCAACGGGGAGGTGGACCTCG | |
| AGGTCCGCCTCCCCGCCGAGGCCCAAAGCCTTCCCCGGGT | 200 |
| GCTCGTCCCCGCCCAGCCCTTCTTCCAGCTGGTGCGGAGC | |
| CTTCCTGGGGACCTCGTGGCCCTCGGCCTCGCCTCGGAGC | 280 |
| CGGGCCAGGGGGGGCAGCTGGAGCTCTCCTCCGGGCGTTT | |
| CCGCACCCGGCTCAGCCTGGCCCCTGCCGAGGGCTACCCC | 360 |
| GAGCTTCTGGTGCCCGAGGGGGAGGACAAGGGGGCCTTCC | |
| CCCTCCGGACGCGGATGCCCTCCGGGGAGCTCGTCAAGGC | 440 |
| CTTGACCCACGTGCGCTACGCCGCGAGCAACGAGGAGTAC | |
| CGGGCCATCTTCCGCGGGGTGCAGCTGGAGTTCTCCCCCC | 520 |
| AGGGCTTCCGGGCGGTGGCCTCCGACGGGTACCGCCTCGC | |
| CCTCTACGACCTGCCCCTGCCCCAAGGGTTCCAGGCCAAG | 600 |
| GCCGTGGTCCCCGCCCGGAGCGTGGACGAGATGGTGCGGG | |
| TCCTGAAGGGGGCGGACGGGGCCGAGGCCGTCCTCGCCCT | 680 |
| GGGCGAGGGGGTGTTGGCCCTGGCCCTCGAGGGCGGAAGC | |
| GGGGTCCGGATGGCCCTCCGCCTCATGGAAGGGGAGTTCC | 760 |
| CCGACTACCAGAGGGTCATCCCCCAGGAGTTCGCCCTCAA | |
| GGTCCAGGTGGAGGGGGAGGCCCTCAGGGAGGCGGTGCGC | 840 |
| CGGGTGAGCGTCCTCTCCGACCGGCAGAACCACCGGGTGG | |
| ACCTCCTTTTGGAGGAAGGCCGGATCCTCCTCTCCGCCGA | 920 |
| GGGGGACTACGGCAAGGGGCAGGAGGAGGTGCCCGCCCAG | |
| GTGGAGGGGCCGGACATGGCCGTGGCCTACAACGCCCGCT | 1000 |
| ACCTCCTCGAGGCCCTCGCCCCCGTGGGGGACCGGGCCCA | |
| CCTGGGCATCTCCGGGCCCACGAGCCCGAGCCTCATCTGG | 1080 |
| GGGGACGGGGAGGGGTACCGGGCGGTGGTGGTGCCCCTCA | |
| GGGTCTAG | 1128 |

B)

| | |
|---|---|
| MNITVPKKLLSDQLSLLERIVPSRSANPLYTYLGLYAEEG | 40 |
| ALILFGTNGEVDLEVRLPAEAQSLPRVLVPAQPFFQLVRS | |
| LPGDLVALGLASEPGQGGQLELSSGRFRTRLSLAPAEGYP | 120 |
| ELLVPEGEDKGAFPLRTRMPSGELVKALTHVRYAASNEEY | |
| RAIFRGVQLEFSPQGFRAVASDGYRLALYDLPLPQGFQAK | 200 |
| AVVPARSVDEMVRVLKGADGAEAVLALGEGVLALALEGGS | |
| GVRMALRLMEGEFPDYQRVIPQEFALKVQVEGEALREAVR | 280 |
| RVSVLSDRQNHRVDLLLEEGRILLSAEGDYGKGQEEVPAQ | |
| VEGPDMAVAYNARYLLEALAPVGDRAHLGISGPTSPSLIW | 360 |
| GDGEGYRAVVVPLRVZ | |

Figure 21

```
T.th.beta    MNITVPKKLLSDQLSLLERIVPSRSANPLYTYLGLYAEEGALILFGTNGEVDLEVRLPAE
E.coli.bet   MKFTVEREHLLKPLQQVSGPLGGRPTLPILGNLLLQVADGTLSLTGTDLEMEMVARVALV
P.mirab.be   MKFIIEREQLLKPLQQVSGPLGGRPTLPILGNLLLKVTENTLSLTGTDLEMEMMARVSLS
H.infl.bet   MQFSISRENLLKPLQQVCGVLSNRPNIPVLNNVLLQIEDYRLTITGTDLEVELSSQTQLS
P.put.beta   MHFTIQREALLKPLQLVAGVVERRQTLPVLSNVLLVVQGQQLSLTGTDLEVELVGRVQLE
B.cap.beta   MKFTIQNDILTKNLKKITRVLVKNISFPILENILIQVEDGTLSLTTTNLEIELISKIEII
                 *    *   *       *. .      *.    *  *. *...  .

T.th.beta    AQSLP-RVLVPAQPFFQLVRSLPGDLVALGLASEPGQGGQLELSSGRFRTRLSLAPAEGY
E.coli.bet   QPHEPGATTVPARKFFDICRGLP-EGAEIAVQLE---GERMLVRSGRSRFSLSTLPAADF
P.mirab.be   QSHEIGATTVPARKFFDIWRGLP-EGAEISVELD---GDRLLVRSGRSRFSLSTLPASDF
H.infl.bet   SSSENGTFTIPAKKFLDICRTLS-DDSEITVTFE---QDRALVQSGRSRFTLATQPAEEY
P.put.beta   EPAEPGEITVPARKLMDICKSLP-NDALIDIKVD---EQKLLVKAGRSRFTLSTLPANDF
B.cap.beta   TKYIPGKTTISGRKILNICRTLS-EKSKIKMQLK---NKKMYISSENSNYILSTLSADTF
                  .  . .*      . .   ...         *.  *   .

T.th.beta    PELLVPEGEDKGAFPLRTRMPSGELVKALTHVRYAASNEEYRAIFRGVQLEFSPQGFRAV
E.coli.bet   PNLDD--WQSEVEFTLPQAT----MKRLIEATQFSMAHQDVRYYLNGMLFETEGEELRTV
P.mirab.be   PNLDD--WQSEVEFTLPQAT----LKRLIESTQFSMAHQDVRYYLNGMLFETENTELRTV
H.infl.bet   PNLTD--WQSEVDFELPQNT----LRRLIEATQFSMANQDARYFLNGMKFETEGNLLRTV
P.put.beta   PTVEE--GPGSLTCNLEQSK----LRRLIERTSFAMAQQDVRYYLNGMLLEVSRNTLRAV
B.cap.beta   PNHQN--FDYISKFDISSNI----LKEMIEKTEFSMGKQDVRYYLNGMLLEKKDKFLRSV
             *            .        ..     ..  ..  *  *.  *   *.*

T.th.beta    ASDGYRLALYDLPLPQGFQA--KAVVPARSVDEMVRVLKGADGAEAVLALGEGVLALALE
E.coli.bet   ATDGHRLAVCSMPIGQSLPS-HSVIVPRKGVIELMRMLDG-GDNPLRVQIGSNNIRAHVG
P.mirab.be   ATDGHRLAVCAMDIGQSLPG-HSVIVPRKGVIELMRLLDGSGESLLQLQIGSNNLRAHVG
H.infl.bet   ATDGHRLAVCTISLEQELQN-HSVILPRKGVLELVRLLET-NDEPARLQIGTNNLRVHLK
P.put.beta   STDGHRLALCSMSAPIEQEDRHQVIVPRKGILELARLLTD-PEGMVSIVLGQHHIRATTG
B.cap.beta   ATDGYRLAISYTQLKKDINF-FSIIIPNKAVMELLKLLNT-QPQLLNILIGSNSIRIYTK
             ..**  ***.                ...*..  *....*       ..*    .

T.th.beta    GGSGVRMALRLMEGEFPDYQRVIPQEFALKVQVEGEALREAVRRVSVLSDRQNHRVDLLL
E.coli.bet   ---DFIFTSKLVDGRFPDYRRVLPKNPDKHLEAGCDLLKQAFARAAILSNEKFRGVRLYV
P.mirab.be   ---DFIFTSKLVDGRFPDYRRVLPKNPTKTVIAGCDILKQAFSRAAILSNEKFRGVRINL
H.infl.bet   ---NTVFTSKLIDGRFPDYRRVLPRNATKIVEGNWEMLKQAFARASILSNERARSVRLSL
P.put.beta   ---EFTFTSKLVDGKFPDYERVLPKGGDKLVVGDRQALREAFSRTAILSNEKYRGIRLQL
B.cap.beta   ---NLIFTTQLIEGEYPDYKSVLFKEKKNPIITNSILLKKSLLRVAILAHEKFCGIEIKI
               .*..* .*** *.                  *      .    *  ..*.  .

T.th.beta    EEGRILLSAEGDYGK-GQEEVPAQVEGPDMAVAYNARYLLEALAPVG-DRAHLGISGPTS
E.coli.bet   SENQLKITANNPEQEEAEEIIDVTYSGAEMEIGFNVSYVLDVLNALKCENVRMMLTDSVS
P.mirab.be   TNGQLKITANNPEQEEAEEIVDVQYQGEEMEIGFNVSYLLDVLNTLKCEEVKLLLTDAVS
H.infl.bet   KENQLKITASNTEHEEAEEIVDVNYNGEELEVGFNVTYILDVLNALKCNQVRMCLTDAFS
P.put.beta   AAGQLKIQANNPEQEEAEEEISVDYEGSSLEIGFNVSYLLDVLGVMTTEQVRLILSDSNS
B.cap.beta   ENGKFKVLSDNQEEETAEDLFEIDYFGEKIEISINVYYLLDVINNIKSENIALFLNKSKS
                ..  . . ..       *  . *  *  *.*. .    .       . . . *

T.th.beta    PSLIWGDG-EGYRAVVVPLRVZ    (ID#108)
E.coli.bet   SVQIEDAASQSAAYVVMPMRLZ    (ID#109)
P.mirab.be   SVQVENVASAAAAYVVMPMRL-    (ID#110)
H.infl.bet   SCLIENCEDSSCEYVIMPMRL-    (ID#111)
P.put.beta   SALLQEAGNDDSSYVVMPMRL-    (ID#112)
B.cap.beta   SIQIEAENNSSNAYVVMLLKR-    (ID#113)
                   *..  ..
```

Figure 22

A) Induction
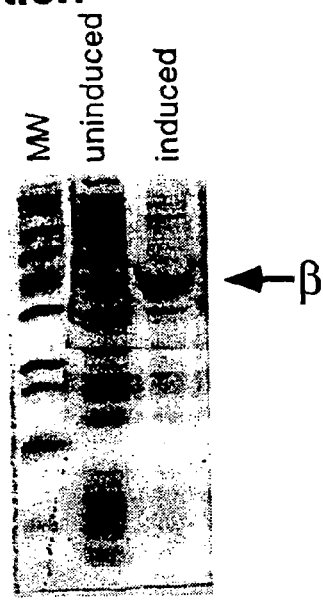
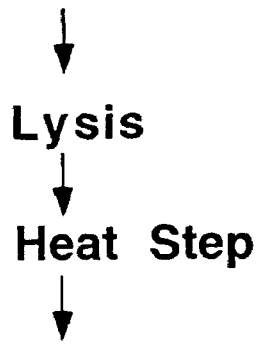
B) MonoQ Column
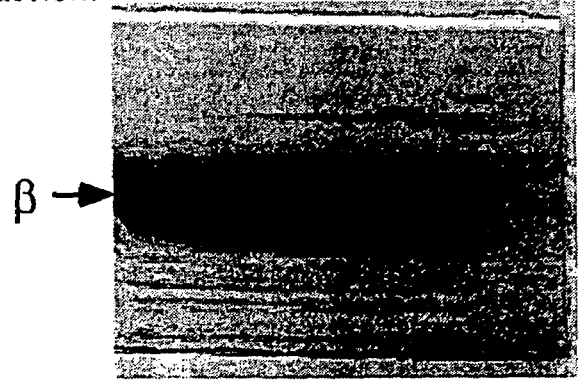
Figure 24

SEQUENCE LISTING

```
<160> NUMBER OF SEQ ID NOS: 117

<210> SEQ ID NO 1
<211> LENGTH: 2007
<212> TYPE: DNA
<213> ORGANISM: Thermus thermophilus

<400> SEQUENCE: 1
tccgggggtg gggttccag gtagacccg gccctcccg tgagcccctt tacccaggcc      60
gccacctcct ccagggggc caaggcgtgc aaggagagga acgtccgcac cacgccctat    120
actagccttg tgacgccct ctaccgccgc ttccgccccc tcaccttcca ggaggtggtg    180
gggcaggagc acgtgaagga gccctcctc aaggccatcc gggaggggag gctcgcccag    240
gcctacctct tctccgggcc caggggcgtg ggcaagacca ccacgcgag gctcctcgcc    300 atggcggtgg ggtgccaggg ggaagacccc ccttgcgggg tctgccccca ctgccaggcg    360
gtgcagaggg gcgcccaccc ggacgtggtg gacattgacg ccgccagcaa caactccgtg    420
gaggacgtgc gggagctgag ggaaaggatc caccctcgcc cctctctgc ccccaggaag    480 gtcttcatcc tggacgaggc ccacatgctc tccaaaagcg ccttcaacgc cctcctcaag    540
accctggagg agccccgcc ccacgtcctc ttcgtcttcg ccaccaccga gcccgagagg    600 atgccccca ccatcctctc ccgcacccag cacttccgct tccgccgcct cacggaggag    660
gagatcgcct ttaagctccg gcgcatcctg gaggccgtgg ggcgggaggc ggaggaggag    720
gccctcctcc tcctcgcccg cctggcggac ggggcccta gggacgcgga aagcctcctg    780
gagcgcttcc tcctcctgga aggcccctc acccggaagg aggtggagcg cgccctaggc    840
tcccccccag ggaccggggt ggccgagatc gccgcctccc tcgcgagggg gaaaacggcg    900 gaggcctgg gcctcgcccg gcgcctctac ggggaaggggt acgcccgag gagcctggtc    960 tcgggccttt tggaggtgtt ccgggaaggc ctctacgccg ccttcggcct cgcgggaacc  1020
ccccttcccg ccccgcccca ggccctgatc gccgccatga ccgccctgga cgaggccatg  1080
gagcgcctcg cccgccgctc cgacgcctta agcctggagg tggccctcct ggaggcggga  1140
agggccctgg ccgccgaggc cctacccag cccacgggcg ctccttcccc agaggtcggc  1200
cccaagccgg aaagcccccc gacccccgaa ccccccaaggc ccgaggaggc gcccgacctg  1260
cgggagcggt ggcgggcctt cctcgaggcc ctcaggccca ccctacgggc cttcgtgcgg  1320
```

```
gaggcccgcc cggaggtccg ggaaggccag ctctgcctcg ctttccccga ggacaaggcc      1380
ttccactacc gcaaggcctc ggaacagaag gtgaggctcc tcccctggc ccaggcccat       1440 ttcggggtgg aggaggtcgt cctcgtcctg gagggagaaa aaaaaagcct gagcccaagg      1500
ccccgcccgg ccccacctcc tgaagcgccc gcaccccgg gccctcccga ggaggaggta       1560
gaggcggagg aagcggcgga ggaggccccg gaggaggcct tgaggcgggt ggtccgcctc      1620
ctgggggggc gggtgctctg ggtgcggcgg cccaggaccc gggaggcgcc ggaggaggaa      1680
cccctgagcc aagacgagat aggggtact ggtatataat gggggcatga cgcggaccac       1740
cgacctcgga caagagaccg tggacaacat cctcaagcgc ctccgccgta ttgagggcca     1800
ggtgcggggg ctccagaaga tggtggccga gggccgcccc tgcgacgagg tcctcaccca     1860
gatgaccgcc accaagaagg ccatggaggc ggcggccacc ctgatcctcc acgagttcct    1920
gaacgtctgc gccgccgagg tctccgaggg caaggtgaac cccaagaagc ccgaggagat    1980
cgccaccatg ctgaagaact tcatcta                                          2007
```

<210> SEQ ID NO 2
<211> LENGTH: 529
<212> TYPE: PRT
<213> ORGANISM: Thermus thermophilus

<400> SEQUENCE: 2

```
Met Ser Ala Leu Tyr Arg Arg Phe Arg Pro Leu Thr Phe Gln Glu Val
 1               5                  10                  15

Val Gly Gln Glu His Val Lys Glu Pro Leu Leu Lys Ala Ile Arg Glu
            20                  25                  30

Gly Arg Leu Ala Gln Ala Tyr Leu Phe Ser Gly Pro Arg Gly Val Gly
        35                  40                  45

Lys Thr Thr Thr Ala Arg Leu Leu Ala Met Ala Val Gly Cys Gln Gly
    50                  55                  60

Glu Asp Pro Pro Cys Gly Val Cys Pro His Cys Gln Ala Val Gln Arg
65                  70                  75                  80

Gly Ala His Pro Asp Val Val Asp Ile Asp Ala Ala Ser Asn Asn Ser
                85                  90                  95

Val Glu Asp Val Arg Glu Leu Arg Glu Arg Ile His Leu Ala Pro Leu
            100                 105                 110

Ser Ala Pro Arg Lys Val Phe Ile Leu Asp Glu Ala His Met Leu Ser
        115                 120                 125

Lys Ser Ala Phe Asn Ala Leu Leu Lys Thr Leu Glu Glu Pro Pro Pro
    130                 135                 140

His Val Leu Phe Val Phe Ala Thr Thr Glu Pro Glu Arg Met Pro Pro
145                 150                 155                 160

Thr Ile Leu Ser Arg Thr Gln His Phe Arg Phe Arg Arg Leu Thr Glu
                165                 170                 175

Glu Glu Ile Ala Phe Lys Leu Arg Arg Ile Leu Glu Ala Val Gly Arg
            180                 185                 190

Glu Ala Glu Glu Glu Ala Leu Leu Leu Ala Arg Leu Ala Asp Gly
        195                 200                 205

Ala Leu Arg Asp Ala Glu Ser Leu Leu Glu Arg Phe Leu Leu Leu Glu
    210                 215                 220

Gly Pro Leu Thr Arg Lys Glu Val Glu Arg Ala Leu Gly Ser Pro Pro
225                 230                 235                 240

Gly Thr Gly Val Ala Glu Ile Ala Ala Ser Leu Ala Arg Gly Lys Thr
                245                 250                 255
```

-continued

```
Ala Glu Ala Leu Gly Leu Ala Arg Arg Leu Tyr Gly Glu Gly Tyr Ala
            260                 265                 270

Pro Arg Ser Leu Val Ser Gly Leu Leu Glu Val Phe Arg Glu Gly Leu
        275                 280                 285

Tyr Ala Ala Phe Gly Leu Ala Gly Thr Pro Leu Pro Ala Pro Pro Gln
    290                 295                 300

Ala Leu Ile Ala Ala Met Thr Ala Leu Asp Glu Ala Met Glu Arg Leu
305                 310                 315                 320

Ala Arg Arg Ser Asp Ala Leu Ser Leu Glu Val Ala Leu Leu Glu Ala
                325                 330                 335

Gly Arg Ala Leu Ala Ala Glu Ala Leu Pro Gln Pro Thr Gly Ala Pro
            340                 345                 350

Ser Pro Glu Val Gly Pro Lys Pro Glu Ser Pro Thr Pro Glu Pro
        355                 360                 365

Pro Arg Pro Glu Glu Ala Pro Asp Leu Arg Glu Arg Trp Arg Ala Phe
    370                 375                 380

Leu Glu Ala Leu Arg Pro Thr Leu Arg Ala Phe Val Arg Glu Ala Arg
385                 390                 395                 400

Pro Glu Val Arg Glu Gly Gln Leu Cys Leu Ala Phe Pro Glu Asp Lys
                405                 410                 415

Ala Phe His Tyr Arg Lys Ala Ser Glu Gln Lys Val Arg Leu Leu Pro
            420                 425                 430

Leu Ala Gln Ala His Phe Gly Val Glu Glu Val Val Leu Val Leu Glu
        435                 440                 445

Gly Glu Lys Lys Ser Leu Ser Pro Arg Pro Arg Pro Ala Pro Pro Pro
    450                 455                 460

Glu Ala Pro Ala Pro Pro Gly Pro Pro Glu Glu Glu Val Glu Ala Glu
465                 470                 475                 480

Glu Ala Ala Glu Glu Ala Pro Glu Glu Ala Leu Arg Arg Val Val Arg
                485                 490                 495

Leu Leu Gly Gly Arg Val Leu Trp Val Arg Arg Pro Arg Thr Arg Glu
            500                 505                 510

Ala Pro Glu Glu Glu Pro Leu Ser Gln Asp Glu Ile Gly Gly Thr Gly
        515                 520                 525

Ile
```

<210> SEQ ID NO 3
<211> LENGTH: 1590
<212> TYPE: DNA
<213> ORGANISM: Thermus thermophilus

<400> SEQUENCE: 3

| | | | | | |
|---|---|---|---|---|---|
| gtgagcgccc | tctaccgccg | cttccgcccc | ctcaccttcc | aggaggtggt | ggggcaggag | 60 |
| cacgtgaagg | agcccctcct | caaggccatc | cgggagggga | ggctcgccca | ggcctacctc | 120 |
| ttctccgggc | ccaggggcgt | gggcaagacc | accacgcga | ggctcctcgc | catggcggtg | 180 |
| gggtgccagg | gggaagaccc | cccttgcggg | gtctgccccc | actgccaggc | ggtgcagagg | 240 |
| ggcgcccacc | cggacgtggt | ggacattgac | gccgccagca | acaactccgt | ggaggacgtg | 300 |
| cgggagctga | gggaaaggat | ccacctcgcc | cccctctctg | ccccaggaa | ggtcttcatc | 360 |
| ctggacgagg | cccacatgct | ctccaaaagc | gccttcaacg | ccctcctcaa | gaccctggag | 420 |
| gagccccgc | cccacgtcct | cttcgtcttc | gccaccaccg | agcccgagag | gatgcccccc | 480 |
| accatcctct | cccgcaccca | gcacttccgc | ttccgccgcc | tcacggagga | ggagatcgcc | 540 |

-continued

```
tttaagctcc ggcgcatcct ggaggccgtg gggcgggagg cggaggagga ggccctcctc    600
ctcctcgccc gcctggcgga cggggccctt agggacgcgg aaagcctcct ggagcgcttc    660
ctcctcctgg aaggccccct cacccggaag gaggtggagc gcgccctagg ctccccccca    720
gggaccgggg tggccgagat cgccgcctcc ctcgcgaggg ggaaaacggc ggaggccctg    780
ggcctcgccc ggcgcctcta cggggaaggg tacgccccga ggagcctggt ctcgggcctt    840
ttggaggtgt tccgggaagg cctctacgcc gccttcggcc tcgcgggaac cccccttccc    900
gccccgcccc aggccctgat cgccgccatg accgccctgg acgaggccat ggagcgcctc    960
gcccgccgct ccgacgcctt aagcctggag gtggccctcc tggaggcggg aagggccctg   1020
gccgccgagg ccctacccca gcccacgggc gctccttccc cagaggtcgg ccccaagccg   1080
gaaagccccc cgaccccgga accccaaggg cccgaggagg cgcccgacct gcgggagcgg   1140
tggcgggcct tcctcgaggc cctcaggccc accctacggg ccttcgtgcg ggaggcccgc   1200
ccggaggtcc gggaaggcca gctctgcctc gctttccccg aggacaaggc cttccactac   1260
cgcaaggcct cggaacagaa ggtgaggctc ctcccctgg cccaggccca tttcggggtg    1320
gaggaggtcg tcctcgtcct ggagggagaa aaaaaaagcc tgagcccaag gccccgcccg   1380
gccccacctc ctgaagcgcc cgcacccccg ggccctcccg aggaggaggt agaggcggag   1440
gaagcggcgg aggaggcccc ggaggaggcc ttgaggcggg tggtccgcct cctgggggggg   1500 cgggtgctct gggtgcggcg gcccaggacc cgggaggcgc cggaggagga accctgagc   1560 caagacgaga taggggtac tggtatataa                                    1590
```

<210> SEQ ID NO 4
<211> LENGTH: 464
<212> TYPE: PRT
<213> ORGANISM: Thermus thermophilus

<400> SEQUENCE: 4

Met Ser Ala Leu Tyr Arg Arg Phe Arg Pro Leu Thr Phe Gln Glu Val
1               5                   10                  15

Val Gly Gln Glu His Val Lys Glu Pro Leu Leu Lys Ala Ile Arg Glu
            20                  25                  30

Gly Arg Leu Ala Gln Ala Tyr Leu Phe Ser Gly Pro Arg Gly Val Gly
        35                  40                  45

Lys Thr Thr Ala Arg Leu Leu Ala Met Ala Val Gly Cys Gln Gly
    50                  55                  60

Glu Asp Pro Pro Cys Gly Val Cys Pro His Cys Gln Ala Val Gln Arg
65                  70                  75                  80

Gly Ala His Pro Asp Val Val Asp Ile Asp Ala Ala Ser Asn Asn Ser
                85                  90                  95

Val Glu Asp Val Arg Glu Leu Arg Glu Arg Ile His Leu Ala Pro Leu
            100                 105                 110

Ser Ala Pro Arg Lys Val Phe Ile Leu Asp Glu Ala His Met Leu Ser
        115                 120                 125

Lys Ser Ala Phe Asn Ala Leu Leu Lys Thr Leu Glu Glu Pro Pro
    130                 135                 140

His Val Leu Phe Val Phe Ala Thr Thr Glu Pro Glu Arg Met Pro Pro
145                 150                 155                 160

Thr Ile Leu Ser Arg Thr Gln His Phe Arg Phe Arg Arg Leu Thr Glu
                165                 170                 175

Glu Glu Ile Ala Phe Lys Leu Arg Arg Ile Leu Glu Ala Val Gly Arg
            180                 185                 190

-continued

```
Glu Ala Glu Glu Ala Leu Leu Leu Ala Arg Leu Ala Asp Gly
        195                 200                 205

Ala Leu Arg Asp Ala Glu Ser Leu Leu Glu Arg Phe Leu Leu Glu
    210                 215                 220

Gly Pro Leu Thr Arg Lys Glu Val Glu Arg Ala Leu Gly Ser Pro Pro
225                 230                 235                 240

Gly Thr Gly Val Ala Glu Ile Ala Ala Ser Leu Ala Arg Gly Lys Thr
                245                 250                 255

Ala Glu Ala Leu Gly Leu Ala Arg Arg Leu Tyr Gly Glu Gly Tyr Ala
            260                 265                 270

Pro Arg Ser Leu Val Ser Gly Leu Glu Val Phe Arg Glu Gly Leu
        275                 280                 285

Tyr Ala Ala Phe Gly Leu Ala Gly Thr Pro Leu Pro Ala Pro Pro Gln
        290                 295                 300

Ala Leu Ile Ala Ala Met Thr Ala Leu Asp Glu Ala Met Glu Arg Leu
305                 310                 315                 320

Ala Arg Arg Ser Asp Ala Leu Ser Leu Glu Val Ala Leu Leu Glu Ala
                325                 330                 335

Gly Arg Ala Leu Ala Ala Glu Ala Leu Pro Gln Pro Thr Gly Ala Pro
            340                 345                 350

Ser Pro Glu Val Gly Pro Lys Pro Glu Ser Pro Thr Pro Glu Pro
        355                 360                 365

Pro Arg Pro Glu Glu Ala Pro Asp Leu Arg Glu Arg Trp Arg Ala Phe
        370                 375                 380

Leu Glu Ala Leu Arg Pro Thr Leu Arg Ala Phe Val Arg Glu Ala Arg
385                 390                 395                 400

Pro Glu Val Arg Glu Gly Gln Leu Cys Leu Ala Phe Pro Glu Asp Lys
                405                 410                 415

Ala Phe His Tyr Arg Lys Ala Ser Glu Gln Lys Val Arg Leu Leu Pro
            420                 425                 430

Leu Ala Gln Ala His Phe Gly Val Glu Glu Val Val Leu Val Leu Glu
        435                 440                 445

Gly Glu Lys Lys Lys Pro Glu Pro Lys Ala Pro Pro Gly Pro Thr Ser
450                 455                 460
```

<210> SEQ ID NO 5
<211> LENGTH: 454
<212> TYPE: PRT
<213> ORGANISM: Thermus thermophilus

<400> SEQUENCE: 5

```
Met Ser Ala Leu Tyr Arg Arg Phe Arg Pro Leu Thr Phe Gln Glu Val
1               5                   10                  15

Val Gly Gln Glu His Val Lys Glu Pro Leu Leu Lys Ala Ile Arg Glu
                20                  25                  30

Gly Arg Leu Ala Gln Ala Tyr Leu Phe Ser Gly Pro Arg Gly Val Gly
            35                  40                  45

Lys Thr Thr Thr Ala Arg Leu Leu Ala Met Ala Val Gly Cys Gln Gly
        50                  55                  60

Glu Asp Pro Pro Cys Gly Val Cys Pro His Cys Gln Ala Val Gln Arg
65                  70                  75                  80

Gly Ala His Pro Asp Val Val Asp Ile Asp Ala Ala Ser Asn Asn Ser
                85                  90                  95

Val Glu Asp Val Arg Glu Leu Arg Glu Arg Ile His Leu Ala Pro Leu
            100                 105                 110
```

```
Ser Ala Pro Arg Lys Val Phe Ile Leu Asp Glu Ala His Met Leu Ser
        115                 120                 125

Lys Ser Ala Phe Asn Ala Leu Leu Lys Thr Leu Glu Glu Pro Pro Pro
130                 135                 140

His Val Leu Phe Val Phe Ala Thr Thr Glu Pro Glu Arg Met Pro Pro
145                 150                 155                 160

Thr Ile Leu Ser Arg Thr Gln His Phe Arg Phe Arg Arg Leu Thr Glu
                165                 170                 175

Glu Glu Ile Ala Phe Lys Leu Arg Arg Ile Leu Glu Ala Val Gly Arg
                180                 185                 190

Glu Ala Glu Glu Ala Leu Leu Leu Ala Arg Leu Ala Asp Gly
                195                 200                 205

Ala Leu Arg Asp Ala Glu Ser Leu Leu Glu Arg Phe Leu Leu Leu Glu
        210                 215                 220

Gly Pro Leu Thr Arg Lys Glu Val Arg Ala Leu Gly Ser Pro Pro
225                 230                 235                 240

Gly Thr Gly Val Ala Glu Ile Ala Ala Ser Leu Ala Arg Gly Lys Thr
                245                 250                 255

Ala Glu Ala Leu Gly Leu Ala Arg Arg Leu Tyr Gly Glu Gly Tyr Ala
            260                 265                 270

Pro Arg Ser Leu Val Ser Gly Leu Leu Glu Val Phe Arg Glu Gly Leu
        275                 280                 285

Tyr Ala Ala Phe Gly Leu Ala Gly Thr Pro Leu Pro Ala Pro Pro Gln
        290                 295                 300

Ala Leu Ile Ala Ala Met Thr Ala Leu Asp Glu Ala Met Glu Arg Leu
305                 310                 315                 320

Ala Arg Arg Ser Asp Ala Leu Ser Leu Glu Val Ala Leu Leu Glu Ala
                325                 330                 335

Gly Arg Ala Leu Ala Ala Glu Ala Leu Pro Gln Pro Thr Gly Ala Pro
            340                 345                 350

Ser Pro Glu Val Gly Pro Lys Pro Glu Ser Pro Pro Thr Pro Glu Pro
        355                 360                 365

Pro Arg Pro Glu Glu Ala Pro Asp Leu Arg Glu Arg Trp Arg Ala Phe
370                 375                 380

Leu Glu Ala Leu Arg Pro Thr Leu Arg Ala Phe Val Arg Glu Ala Arg
385                 390                 395                 400

Pro Glu Val Arg Glu Gly Gln Leu Cys Leu Ala Phe Pro Glu Asp Lys
                405                 410                 415

Ala Phe His Tyr Arg Lys Ala Ser Glu Gln Lys Val Arg Leu Leu Pro
            420                 425                 430

Leu Ala Gln Ala His Phe Gly Val Glu Glu Val Val Leu Val Leu Glu
        435                 440                 445

Gly Glu Lys Lys Lys Ala
    450

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 6
cgcaagcttc acgcstacct sttctccggs ac                                    32
```

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: peptide

<400> SEQUENCE: 7

His Ala Tyr Leu Phe Ser Gly Thr
 1               5

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 8
cgcgaattcg tgctcsggsg gctcctcsag sgtc                              34

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: peptide

<400> SEQUENCE: 9

Lys Thr Leu Glu Glu Pro Pro Glu His
 1               5

<210> SEQ ID NO 10
<211> LENGTH: 38
<212> TYPE: DNA
<213> ORGANISM: Artificial Sequence
<220> FEATURE:
<223> OTHER INFORMATION: Description of Artificial Sequence: primer

<400> SEQUENCE: 10
gcgcggatcc ggagggagaa aaaaaaagcc tcagccca                          38

<210> SEQ ID NO 11
<211> LENGTH: 38
<212> TYPE: DNA
<213> ORGANISM: Artificial Sequence
<220> FEATURE:
<223> OTHER INFORMATION: Description of Artificial Sequence: primer

<400> SEQUENCE: 11
gcgcggatcc ggagggagag aagaaaagcc tcagccca                          38

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 12
gaattaaatt cgcgcttcgg gaggtggg                                     28

<210> SEQ ID NO 13
<211> LENGTH: 27
<212> TYPE: DNA
<213> ORGANISM: Artificial Sequence

```
<220> FEATURE:
<223> OTHER INFORMATION: Description of Artificial Sequence:  primer

<400> SEQUENCE: 13
gcgcgaattc gcgcttcggg aggtggg                                              27

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence:  primer

<400> SEQUENCE: 14
gcgcgaattc gggcgcttca ggaggtggg                                            29

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence:  primer

<400> SEQUENCE: 15
gtggtgcata tggtgagcgc cctctaccgc c                                         31

<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence:  primer

<400> SEQUENCE: 16
gtggtggtcg acccaggagg gccacctcca g                                         31

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence:  peptide
<220> FEATURE:
<221> NAME/KEY: PEPTIDE
<222> LOCATION: (2)
<223> OTHER INFORMATION: X is any aa at position 2
<220> FEATURE:
<221> NAME/KEY: PEPTIDE
<222> LOCATION: (3)
<223> OTHER INFORMATION: X is any aa at position 3
<220> FEATURE:
<221> NAME/KEY: PEPTIDE
<222> LOCATION: (5)
<223> OTHER INFORMATION: X is any aa at position 5

<400> SEQUENCE: 17

Gly Xaa Xaa Gly Xaa Gly Lys Thr
  1               5

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence:  peptide
```

<400> SEQUENCE: 18

Lys Pro Asp Pro Lys Ala Pro Pro Gly Pro Thr Ser
 1               5                  10

<210> SEQ ID NO 19
<211> LENGTH: 180
<212> TYPE: PRT
<213> ORGANISM: Escherichia coli

<400> SEQUENCE: 19

Met Ser Tyr Gln Val Leu Ala Arg Lys Trp Arg Pro Gln Thr Phe Ala
 1               5                  10                  15

Asp Val Val Gly Gln Glu His Val Leu Thr Ala Leu Ala Asn Gly Leu
                20                  25                  30

Ser Leu Gly Arg Ile His His Ala Tyr Leu Phe Ser Gly Thr Arg Gly
            35                  40                  45

Val Gly Lys Thr Ser Ile Ala Arg Leu Leu Ala Lys Gly Leu Asn Cys
        50                  55                  60

Glu Thr Gly Ile Thr Ala Thr Pro Cys Gly Val Cys Asp Asn Cys Arg
 65                  70                  75                  80

Glu Ile Glu Gln Gly Arg Phe Val Asp Leu Ile Glu Ile Asp Ala Ala
                85                  90                  95

Ser Arg Thr Lys Val Glu Asp Thr Arg Asp Leu Leu Asp Asn Val Gln
            100                 105                 110

Tyr Ala Pro Ala Arg Gly Arg Phe Lys Val Tyr Leu Ile Asp Glu Val
        115                 120                 125

His Met Leu Ser Arg His Ser Phe Asn Ala Leu Leu Lys Thr Leu Glu
130                 135                 140

Glu Pro Pro Glu His Val Lys Phe Leu Leu Ala Thr Thr Asp Pro Gln
145                 150                 155                 160

Lys Leu Pro Val Thr Ile Leu Ser Arg Cys Leu Gln Phe His Leu Lys
                165                 170                 175

Ala Leu Asp Val
            180

<210> SEQ ID NO 20
<211> LENGTH: 180
<212> TYPE: PRT
<213> ORGANISM: Bacillus subtilis

<400> SEQUENCE: 20

Met Ser Tyr Gln Ala Leu Tyr Arg Val Phe Arg Pro Gln Arg Phe Glu
 1               5                  10                  15

Asp Val Val Gly Gln Glu His Ile Thr Lys Thr Leu Gln Asn Ala Leu
                20                  25                  30

Leu Gln Lys Lys Phe Ser His Ala Tyr Leu Phe Ser Gly Pro Arg Gly
            35                  40                  45

Thr Gly Lys Thr Ser Ala Ala Lys Ile Phe Ala Lys Ala Val Asn Cys
        50                  55                  60

Glu His Ala Pro Val Asp Glu Pro Cys Asn Glu Cys Ala Ala Cys Lys
 65                  70                  75                  80

Gly Ile Thr Asn Gly Ser Ile Ser Asp Val Ile Glu Ile Asp Ala Ala
                85                  90                  95

Ser Asn Asn Gly Val Asp Glu Ile Arg Asp Ile Arg Asp Lys Val Lys
            100                 105                 110

```
Phe Ala Pro Ser Ala Val Thr Tyr Lys Val Tyr Ile Ile Asp Glu Val
        115                 120                 125

His Met Leu Ser Ile Gly Ala Phe Asn Ala Leu Leu Lys Thr Leu Glu
    130                 135                 140

Glu Pro Pro Glu His Cys Ile Phe Ile Leu Ala Thr Thr Glu Pro His
145                 150                 155                 160

Lys Ile Pro Leu Thr Ile Ile Ser Arg Cys Gln Arg Phe Asp Phe Lys
                165                 170                 175

Arg Ile Thr Ser
            180

<210> SEQ ID NO 21
<211> LENGTH: 294
<212> TYPE: PRT
<213> ORGANISM: Escherichia coli

<400> SEQUENCE: 21

Met Ser Tyr Gln Val Leu Ala Arg Lys Trp Arg Pro Gln Thr Phe Ala
  1               5                  10                  15

Asp Val Val Gly Gln Glu His Val Leu Thr Ala Leu Ala Asn Gly Leu
             20                  25                  30

Ser Leu Gly Arg Ile His His Ala Tyr Leu Phe Ser Gly Thr Arg Gly
         35                  40                  45

Val Gly Lys Thr Ser Ile Ala Arg Leu Leu Ala Lys Gly Leu Asn Cys
     50                  55                  60

Glu Thr Gly Ile Thr Ala Thr Pro Cys Gly Val Cys Asp Asn Cys Arg
 65                  70                  75                  80

Glu Ile Glu Gln Gly Arg Phe Val Asp Leu Ile Glu Ile Asp Ala Ala
                 85                  90                  95

Ser Arg Thr Lys Val Glu Asp Thr Arg Asp Leu Leu Asp Asn Val Gln
            100                 105                 110

Tyr Ala Pro Ala Arg Gly Arg Phe Lys Val Tyr Leu Ile Asp Glu Val
        115                 120                 125

His Met Leu Ser Arg His Ser Phe Asn Ala Leu Leu Lys Thr Leu Glu
    130                 135                 140

Glu Pro Pro Glu His Val Lys Phe Leu Leu Ala Thr Thr Asp Pro Gln
145                 150                 155                 160

Lys Leu Pro Val Thr Ile Leu Ser Arg Cys Leu Gln Phe His Leu Lys
                165                 170                 175

Ala Leu Asp Val Glu Gln Ile Arg His Gln Leu Glu His Ile Leu Asn
            180                 185                 190

Glu Glu His Ile Ala His Glu Pro Arg Ala Leu Gln Leu Leu Ala Arg
        195                 200                 205

Ala Ala Glu Gly Ser Leu Arg Asp Ala Leu Ser Leu Thr Asp Gln Ala
    210                 215                 220

Ile Ala Ser Gly Asp Gly Gln Val Ser Thr Gln Ala Val Ser Ala Met
225                 230                 235                 240

Leu Gly Thr Leu Asp Asp Asp Gln Ala Leu Ser Leu Val Glu Ala Met
                245                 250                 255

Val Glu Ala Asn Gly Glu Arg Val Met Ala Leu Ile Asn Glu Ala Ala
            260                 265                 270

Ala Arg Gly Ile Glu Trp Glu Ala Leu Leu Val Glu Met Leu Gly Leu
        275                 280                 285

Leu His Arg Ile Ala Met
    290
```

<210> SEQ ID NO 22
<211> LENGTH: 294
<212> TYPE: PRT
<213> ORGANISM: Haemophilus influenzae

<400> SEQUENCE: 22

Met Ser Tyr Gln Val Leu Ala Arg Lys Trp Arg Pro Lys Thr Phe Ala
1               5                   10                  15

Asp Val Val Gly Gln Glu His Ile Ile Thr Ala Leu Ala Asn Gly Leu
            20                  25                  30

Lys Asp Asn Arg Leu His His Ala Tyr Leu Phe Ser Gly Thr Arg Gly
        35                  40                  45

Val Gly Lys Thr Ser Ile Ala Arg Leu Phe Ala Lys Gly Leu Asn Cys
    50                  55                  60

Val His Gly Val Thr Ala Thr Pro Cys Gly Glu Cys Glu Asn Cys Lys
65                  70                  75                  80

Ala Ile Glu Gln Gly Asn Phe Ile Asp Leu Ile Glu Ile Asp Ala Ala
                85                  90                  95

Ser Arg Thr Lys Val Glu Asp Thr Arg Glu Leu Leu Asp Asn Val Gln
            100                 105                 110

Tyr Lys Pro Val Val Gly Arg Phe Lys Val Tyr Leu Ile Asp Glu Val
        115                 120                 125

His Met Leu Ser Arg His Ser Phe Asn Ala Leu Leu Lys Thr Leu Glu
    130                 135                 140

Glu Pro Pro Glu Tyr Val Lys Phe Leu Leu Ala Thr Thr Asp Pro Gln
145                 150                 155                 160

Lys Leu Pro Val Thr Ile Leu Ser Arg Cys Leu Gln Phe His Leu Lys
                165                 170                 175

Ala Leu Asp Glu Thr Gln Ile Ser Gln His Leu Ala His Ile Leu Thr
            180                 185                 190

Gln Glu Asn Ile Pro Phe Glu Asp Pro Ala Leu Val Lys Leu Ala Lys
        195                 200                 205

Ala Ala Gln Gly Ser Ile Arg Asp Ser Leu Ser Leu Thr Asp Gln Ala
    210                 215                 220

Ile Ala Met Gly Asp Arg Gln Val Thr Asn Asn Val Val Ser Asn Met
225                 230                 235                 240

Leu Gly Leu Leu Asp Asp Asn Tyr Ser Val Asp Ile Leu Tyr Ala Leu
                245                 250                 255

His Gln Gly Asn Gly Glu Leu Leu Met Arg Thr Leu Gln Arg Val Ala
            260                 265                 270

Asp Ala Ala Gly Asp Trp Asp Lys Leu Leu Gly Glu Cys Ala Glu Lys
        275                 280                 285

Leu His Gln Ile Ala Leu
    290

<210> SEQ ID NO 23
<211> LENGTH: 294
<212> TYPE: PRT
<213> ORGANISM: Bacillus subtilis

<400> SEQUENCE: 23

Met Ser Tyr Gln Ala Leu Tyr Arg Val Phe Arg Pro Gln Arg Phe Glu
1               5                   10                  15

Asp Val Val Gly Gln Glu His Ile Thr Lys Thr Leu Gln Asn Ala Leu
            20                  25                  30

-continued

```
Leu Gln Lys Lys Phe Ser His Ala Tyr Leu Phe Ser Gly Pro Arg Gly
         35                  40                  45

Thr Gly Lys Thr Ser Ala Ala Lys Ile Phe Ala Lys Ala Val Asn Cys
     50                  55                  60

Glu His Ala Pro Val Asp Glu Pro Cys Asn Gly Cys Ala Ala Cys Lys
 65                  70                  75                  80

Gly Ile Thr Asn Gly Ser Ile Ser Asp Val Ile Glu Ile Asp Ala Ala
                 85                  90                  95

Ser Asn Asn Gly Val Asp Glu Ile Arg Asp Ile Arg Asp Lys Val Lys
             100                 105                 110

Phe Ala Pro Ser Ala Val Thr Tyr Lys Val Tyr Ile Ile Asp Glu Val
         115                 120                 125

His Met Leu Ser Ile Gly Ala Phe Asn Ala Leu Leu Lys Thr Leu Glu
     130                 135                 140

Glu Pro Pro Glu His Cys Ile Phe Ile Leu Ala Thr Thr Glu Pro His
145                 150                 155                 160

Lys Ile Pro Leu Thr Ile Ile Ser Arg Cys Gln Arg Phe Asp Phe Lys
                 165                 170                 175

Arg Ile Thr Ser Gln Ala Ile Val Gly Arg Met Asn Lys Ile Val Asp
             180                 185                 190

Ala Glu Gln Leu Gln Val Glu Glu Gly Ser Leu Glu Ile Ile Ala Ser
         195                 200                 205

Ala Ala His Gly Gly Met Arg Asp Ala Leu Ser Leu Leu Asp Gln Ala
     210                 215                 220

Ile Ser Phe Ser Gly Asp Ile Leu Lys Val Glu Asp Ala Leu Leu Ile
225                 230                 235                 240

Thr Gly Ala Val Ser Gln Leu Tyr Ile Gly Lys Leu Ala Lys Ser Leu
                 245                 250                 255

His Asp Lys Asn Val Ser Asp Ala Leu Glu Thr Leu Asn Glu Leu Leu
             260                 265                 270

Gln Gln Gly Lys Asp Pro Ala Lys Leu Ile Glu Asp Met Ile Phe Tyr
         275                 280                 285

Phe Arg Asp Met Leu Leu
     290

<210> SEQ ID NO 24
<211> LENGTH: 300
<212> TYPE: PRT
<213> ORGANISM: Caulobacter crescentus

<400> SEQUENCE: 24

Asp Ala Tyr Thr Val Leu Ala Arg Lys Tyr Arg Pro Arg Thr Phe Glu
  1               5                  10                  15

Asp Leu Ile Gly Gln Glu Ala Met Val Arg Thr Leu Ala Asn Ala Phe
             20                  25                  30

Ser Thr Gly Arg Ile Ala His Ala Phe Met Leu Thr Gly Val Arg Gly
         35                  40                  45

Val Gly Lys Thr Thr Ala Arg Leu Leu Ala Arg Ala Leu Asn Tyr
     50                  55                  60

Glu Thr Asp Thr Val Lys Gly Pro Ser Val Asp Leu Thr Thr Glu Gly
 65                  70                  75                  80

Tyr His Cys Arg Ser Ile Ile Glu Gly Arg His Met Asp Val Leu Glu
                 85                  90                  95

Leu Asp Ala Ala Ser Arg Thr Lys Val Asp Glu Met Arg Glu Leu Leu
             100                 105                 110
```

```
Asp Gly Val Arg Tyr Ala Pro Val Glu Ala Arg Tyr Lys Val Tyr Ile
        115                 120                 125

Ile Asp Glu Val His Met Leu Ser Thr Ala Ala Phe Asn Ala Leu Leu
130                 135                 140

Lys Thr Leu Glu Glu Pro Pro His Ala Lys Phe Ile Phe Ala Thr
145                 150                 155                 160

Thr Glu Ile Arg Lys Val Pro Val Thr Ile Leu Ser Arg Cys Gln Arg
                165                 170                 175

Phe Asp Leu Arg Arg Val Glu Pro Asp Val Leu Val Lys His Phe Asp
            180                 185                 190

Arg Ile Ser Ala Lys Glu Gly Ala Arg Ile Glu Met Asp Ala Leu Ala
        195                 200                 205

Leu Ile Ala Arg Ala Ala Glu Gly Ser Val Arg Asp Gly Leu Ser Leu
    210                 215                 220

Leu Asp Gln Ala Ile Val Gln Thr Glu Arg Gly Gln Thr Val Thr Ser
225                 230                 235                 240

Thr Val Val Arg Asp Met Leu Gly Leu Ala Asp Arg Ser Gln Thr Ile
                245                 250                 255

Ala Leu Tyr Glu His Val Met Ala Gly Lys Thr Lys Asp Ala Leu Glu
            260                 265                 270

Gly Phe Arg Ala Leu Trp Gly Phe Gly Ala Asp Pro Ala Val Val Met
        275                 280                 285

Leu Asp Val Leu Asp His Cys His Ala Ser Ala Val
    290                 295                 300

<210> SEQ ID NO 25
<211> LENGTH: 260
<212> TYPE: PRT
<213> ORGANISM: Mycoplasma genitalium

<400> SEQUENCE: 25

Met His Gln Val Phe Tyr Gln Lys Tyr Arg Pro Ile Asn Phe Lys Gln
  1               5                  10                  15

Thr Leu Gly Gln Glu Ser Ile Arg Lys Ile Leu Val Asn Ala Ile Asn
             20                  25                  30

Arg Asp Lys Leu Pro Asn Gly Tyr Ile Phe Ser Gly Glu Arg Gly Thr
         35                  40                  45

Gly Lys Thr Thr Phe Ala Lys Ile Ile Ala Lys Ala Ile Asn Cys Leu
     50                  55                  60

Asn Trp Asp Gln Ile Asp Val Cys Asn Ser Cys Asp Val Cys Lys Ser
 65                  70                  75                  80

Ile Asn Thr Asn Ser Ala Ile Asp Ile Val Glu Ile Asp Ala Ala Ser
                 85                  90                  95

Lys Asn Gly Ile Asn Asp Ile Arg Glu Leu Val Glu Asn Val Phe Asn
            100                 105                 110

His Pro Phe Thr Phe Lys Lys Val Tyr Ile Leu Asp Glu Ala His
        115                 120                 125

Met Leu Thr Thr Gln Ser Trp Gly Gly Leu Leu Lys Thr Leu Glu Glu
130                 135                 140

Ser Pro Pro Tyr Val Leu Phe Ile Phe Thr Thr Thr Glu Phe Asn Lys
145                 150                 155                 160

Ile Pro Leu Thr Ile Leu Ser Arg Cys Gln Ser Phe Phe Lys Lys
                165                 170                 175

Ile Thr Ser Asp Leu Ile Leu Glu Arg Leu Asn Asp Ile Ala Lys Lys
            180                 185                 190
```

```
Glu Lys Ile Lys Ile Glu Lys Asp Ala Leu Ile Lys Ile Ala Asp Leu
            195                 200                 205

Ser Gln Gly Ser Leu Arg Asp Gly Leu Ser Leu Leu Asp Gln Leu Ala
    210                 215                 220

Ile Ser Leu Ile Val Lys Lys Leu Val Leu Met Leu Lys Lys His
225                 230                 235                 240

Leu Ile Ser Leu Ile Glu Met Gln Asn Leu Leu Leu Lys Gln Phe
            245                 250                 255

Tyr Gln Glu Ile
            260

<210> SEQ ID NO 26
<211> LENGTH: 289
<212> TYPE: PRT
<213> ORGANISM: Thermus thermophilus

<400> SEQUENCE: 26

Val Ser Ala Leu Tyr Arg Arg Phe Arg Pro Leu Thr Phe Gln Glu Val
 1               5                  10                  15

Val Gly Gln Glu His Val Lys Glu Pro Leu Leu Lys Ala Ile Arg Glu
            20                  25                  30

Gly Arg Leu Ala Gln Ala Tyr Leu Phe Ser Gly Pro Arg Gly Val Gly
        35                  40                  45

Lys Thr Thr Thr Ala Arg Leu Leu Ala Met Ala Val Gly Cys Gln Gly
    50                  55                  60

Glu Asp Pro Pro Cys Gly Val Cys Pro His Cys Gln Ala Val Gln Arg
65                  70                  75                  80

Gly Ala His Pro Asp Val Val Asp Ile Asp Ala Ala Ser Asn Asn Ser
                85                  90                  95

Val Glu Asp Val Arg Glu Leu Arg Glu Arg Ile His Leu Ala Pro Leu
            100                 105                 110

Ser Ala Pro Arg Lys Val Phe Ile Leu Asp Glu Ala His Met Leu Ser
        115                 120                 125

Lys Ser Ala Phe Asn Ala Leu Leu Lys Thr Leu Glu Glu Pro Pro Pro
    130                 135                 140

His Val Leu Phe Val Phe Ala Thr Thr Glu Pro Glu Arg Met Pro Pro
145                 150                 155                 160

Thr Ile Leu Ser Arg Thr Gln His Phe Arg Phe Arg Arg Leu Thr Glu
                165                 170                 175

Glu Glu Ile Ala Phe Lys Leu Arg Arg Ile Leu Glu Ala Val Gly Arg
            180                 185                 190

Glu Ala Glu Glu Glu Ala Leu Leu Leu Ala Arg Leu Ala Asp Gly
        195                 200                 205

Ala Leu Arg Asp Ala Glu Ser Leu Leu Glu Arg Phe Leu Leu Leu Glu
    210                 215                 220

Gly Pro Leu Thr Arg Lys Glu Val Glu Arg Ala Leu Gly Ser Pro Pro
225                 230                 235                 240

Gly Thr Gly Val Ala Glu Ile Ala Ala Ser Leu Ala Arg Gly Lys Thr
                245                 250                 255

Ala Glu Ala Leu Gly Leu Ala Arg Arg Leu Tyr Gly Glu Gly Tyr Ala
            260                 265                 270

Pro Arg Ser Leu Val Ser Gly Leu Leu Glu Val Phe Arg Glu Gly Leu
        275                 280                 285

Tyr
```

<210> SEQ ID NO 27
<211> LENGTH: 101
<212> TYPE: RNA
<213> ORGANISM: Thermus thermophilus

<400> SEQUENCE: 27
guccuggagg gagaaaaaaa aagccugagc ccaaggcccc gcccggcccc accuccugaa    60
gcgcccgcac ccccgggccc ucccgaggag gagguagagg c                       101

<210> SEQ ID NO 28
<211> LENGTH: 11
<212> TYPE: PRT
<213> ORGANISM: Thermus thermophilus

<400> SEQUENCE: 28

Val Leu Glu Gly Glu Lys Lys Ser Leu Ser Pro
 1               5                  10

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence:  primer
<220> FEATURE:
<221> NAME/KEY: unsure
<222> LOCATION: (6)
<223> OTHER INFORMATION: N at position 6 is either G or C
<220> FEATURE:
<221> NAME/KEY: unsure
<222> LOCATION: (12)
<223> OTHER INFORMATION: N at position 12 is either G or C
<220> FEATURE:
<221> NAME/KEY: unsure
<222> LOCATION: (21)
<223> OTHER INFORMATION: N at position 21 is either G or C

<400> SEQUENCE: 29
cacgcntacc tnttctccgg nac                                           23

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence:  primer
<220> FEATURE:
<221> NAME/KEY: unsure
<222> LOCATION: (7)
<223> OTHER INFORMATION: N at position 7 is either G or C
<220> FEATURE:
<221> NAME/KEY: unsure
<222> LOCATION: (10)
<223> OTHER INFORMATION: N at position 10 is either G or C
<220> FEATURE:
<221> NAME/KEY: unsure
<222> LOCATION: (19)
<223> OTHER INFORMATION: N at position 19 is either G or C
<220> FEATURE:
<221> NAME/KEY: unsure
<222> LOCATION: (22)
<223> OTHER INFORMATION: N at position 22 is either G or C

<400> SEQUENCE: 30
gtgctcnggn ggctcctcnt cngtc                                         25

<210> SEQ ID NO 31
<211> LENGTH: 33
<212> TYPE: DNA
<213> ORGANISM: Artificial Sequence

```
<220> FEATURE:
<223> OTHER INFORMATION: Description of Artificial Sequence: primer

<400> SEQUENCE: 31
gtgggatccg tggttctgga tctcgatgaa gaa                                33

<210> SEQ ID NO 32
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 32
gtgggatcca cggsctstcs gagcagaag                                    29

<210> SEQ ID NO 33
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 33
gcgggatcct caacgaggac ctctccatct tcaa                              34

<210> SEQ ID NO 34
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 34
gcgggatcct tgtcgtcsag sgtsagsgcg tcgta                             35

<210> SEQ ID NO 35
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 35
gggaaggacc agcgcgtact cccctgctc ctaggtgtg                          39

<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 36
gtgtggatcc ttcttcttsc ccatsgc                                      27

<210> SEQ ID NO 37
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 37
caccgattcc agtggtgcct aggtgtg                                      27
```

```
<210> SEQ ID NO 38
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 38
caacacctgg tgttccagga gcctgtgctt                                          30

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 39
ccagaatcgt ctgctggtcg tag                                                 23

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 40
agcaccctgg aggagcttc                                                      19

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 41
catgtcgtac tgggtgtac                                                      19

<210> SEQ ID NO 42
<211> LENGTH: 27
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: unsure
<222> LOCATION: (7)
<223> OTHER INFORMATION: N at position 7 is A, C, G, or T
<220> FEATURE:
<221> NAME/KEY: unsure
<222> LOCATION: (8)
<223> OTHER INFORMATION: N at position 8 is A, C, G, or T
<220> FEATURE:
<221> NAME/KEY: unsure
<222> LOCATION: (13)
<223> OTHER INFORMATION: N at position 13 is A, C, G, or T
<220> FEATURE:
<221> NAME/KEY: unsure
<222> LOCATION: (14)
<223> OTHER INFORMATION: N at position 14 is A, C, G, or T

<400> SEQUENCE: 42
gtsgtsnnsg acnnsgagac sacsggg                                             27
```

<210> SEQ ID NO 43
<211> LENGTH: 27
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: unsure
<222> LOCATION: (8)
<223> OTHER INFORMATION: N at position 8 is A, C, G, or T
<220> FEATURE:
<221> NAME/KEY: unsure
<222> LOCATION: (9)
<223> OTHER INFORMATION: N at position 9 is A, C, G, or T
<220> FEATURE:
<221> NAME/KEY: unsure
<222> LOCATION: (17)
<223> OTHER INFORMATION: N at position 17 is A, C, G, or T
<220> FEATURE:
<221> NAME/KEY: unsure
<222> LOCATION: (18)
<223> OTHER INFORMATION: N at position 18 is A, C, G, or T

<400> SEQUENCE: 43
gaasccsnng tcgaasnngg cgttgtg                               27

<210> SEQ ID NO 44
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 44
cggggatcca cctcaatcac ctcgtgg                               27

<210> SEQ ID NO 45
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 45
cggggatccg ccaccttgcg gctccgggtg                            30

<210> SEQ ID NO 46
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 46
gcgctctaga cgagttccca aagcgtgcgg t                          31

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 47
cgcgtctaga tcacctgtat ccaga                                 25

```
<210> SEQ ID NO 48
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 48
gcggcgcata tggtggtggt cctggacctg gag                               33

<210> SEQ ID NO 49
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 49
cgcgtctaga tcacctgtat ccaga                                       25

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 50
gtsctsgtsa agacscactt                                             20

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 51
sagsagsgcg ttgaasgtgt g                                           21

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 52
ctcgttggtg aaagtttccg tg                                          22

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 53
cgtccagttc atcgccggaa agga                                        24

<210> SEQ ID NO 54
<211> LENGTH: 27
<212> TYPE: DNA
<213> ORGANISM: Artificial Sequence
<220> FEATURE:
<223> OTHER INFORMATION: Description of Artificial Sequence: primer
```

<400> SEQUENCE: 54
tctggcaaca cgttctggag cacatcc					27

<210> SEQ ID NO 55
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 55
tgctggcgtt catcttcagg atg					23

<210> SEQ ID NO 56
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 56
catcctgaag atgaacgcca gca					23

<210> SEQ ID NO 57
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 57
aggttatcca cagggtcat gtgca					25

<210> SEQ ID NO 58
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 58
gtgtgtcata tgaacataac ggttcccaa					29

<210> SEQ ID NO 59
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 59
gcgcgaattc tcccttgtgg aaggcttag					29

<210> SEQ ID NO 60
<211> LENGTH: 13
<212> TYPE: PRT
<213> ORGANISM: Thermus thermophilus

<400> SEQUENCE: 60

Arg Val Glu Leu Asp Tyr Asp Ala Leu Thr Leu Asp Asp
 1               5                  10

```
<210> SEQ ID NO 61
<211> LENGTH: 14
<212> TYPE: PRT
<213> ORGANISM: Thermus thermophilus

<400> SEQUENCE: 61

Phe Phe Ile Glu Ile Gln Asn His Gly Leu Ser Glu Gln Lys
 1               5                  10

<210> SEQ ID NO 62
<211> LENGTH: 8
<212> TYPE: PRT
<213> ORGANISM: Thermus thermophilus

<400> SEQUENCE: 62

Phe Phe Ile Glu Ile Gln Asn His
 1               5

<210> SEQ ID NO 63
<211> LENGTH: 8
<212> TYPE: PRT
<213> ORGANISM: Thermus thermophilus

<400> SEQUENCE: 63

Tyr Asp Ala Leu Thr Leu Asp Asp
 1               5

<210> SEQ ID NO 64
<211> LENGTH: 6
<212> TYPE: PRT
<213> ORGANISM: Thermus thermophilus

<400> SEQUENCE: 64

Ala Met Gly Lys Lys Lys
 1               5

<210> SEQ ID NO 65
<211> LENGTH: 9
<212> TYPE: PRT
<213> ORGANISM: Thermus thermophilus

<400> SEQUENCE: 65

Phe Asn Lys Ser His Ser Ala Ala Tyr
 1               5

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: peptide
<220> FEATURE:
<221> NAME/KEY: PEPTIDE
<222> LOCATION: (3)
<223> OTHER INFORMATION: Xaa at position 3 is undefined
<220> FEATURE:
<221> NAME/KEY: PEPTIDE
<222> LOCATION: (5)
<223> OTHER INFORMATION: Xaa at position 5 is undefined

<400> SEQUENCE: 66

Val Val Xaa Asp Xaa Glu Thr Thr Gly
 1               5
```

```
<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence:  peptide
<220> FEATURE:
<221> NAME/KEY: PEPTIDE
<222> LOCATION: (4)
<223> OTHER INFORMATION: Xaa at position 4 is undefined
<220> FEATURE:
<221> NAME/KEY: PEPTIDE
<222> LOCATION: (7)
<223> OTHER INFORMATION: Xaa at position 7 is undefined

<400> SEQUENCE: 67

His Asn Ala Xaa Phe Asp Xaa Gly Phe
  1               5

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence:  peptide
<220> FEATURE:
<221> NAME/KEY: PEPTIDE
<222> LOCATION: (3)
<223> OTHER INFORMATION: Xaa at position 3 is undefined
<220> FEATURE:
<221> NAME/KEY: PEPTIDE
<222> LOCATION: (5)
<223> OTHER INFORMATION: Xaa at position 5 is undefined

<400> SEQUENCE: 68

Val Val Xaa Asp Xaa Glu Thr Thr Gly
  1               5

<210> SEQ ID NO 69
<211> LENGTH: 7
<212> TYPE: PRT
<213> ORGANISM: Thermus thermophilus

<400> SEQUENCE: 69

Val Leu Val Lys Thr His Leu
  1               5

<210> SEQ ID NO 70
<211> LENGTH: 6
<212> TYPE: PRT
<213> ORGANISM: Artificial Sequence
<220> FEATURE:
<223> OTHER INFORMATION: Description of Artificial Sequence:  peptide

<400> SEQUENCE: 70

His Arg Ala Leu Tyr Asp
  1               5

<210> SEQ ID NO 71
<211> LENGTH: 7
<212> TYPE: PRT
<213> ORGANISM: Thermus thermophilus

<400> SEQUENCE: 71

His Thr Phe Asn Ala Leu Leu
  1               5
```

```
<210> SEQ ID NO 72
<211> LENGTH: 34
<212> TYPE: PRT
<213> ORGANISM: Escherichia coli

<400> SEQUENCE: 72

Asp Arg Tyr Phe Leu Glu Leu Ile Arg Thr Gly Arg Pro Asp Glu Glu
 1               5                  10                  15

Ser Tyr Leu His Ala Ala Val Glu Leu Ala Glu Ala Arg Gly Leu Pro
            20                  25                  30

Val Val

<210> SEQ ID NO 73
<211> LENGTH: 34
<212> TYPE: PRT
<213> ORGANISM: Vibrio cholerae

<400> SEQUENCE: 73

Asp His Phe Tyr Leu Glu Leu Ile Arg Thr Gly Arg Ala Asp Glu Glu
 1               5                  10                  15

Ser Tyr Leu His Phe Ala Leu Asp Val Ala Glu Gln Tyr Asp Leu Pro
            20                  25                  30

Val Val

<210> SEQ ID NO 74
<211> LENGTH: 34
<212> TYPE: PRT
<213> ORGANISM: Haemophilus influenzae

<400> SEQUENCE: 74

Asp His Phe Tyr Leu Ala Leu Ser Arg Thr Gly Arg Pro Asn Glu Glu
 1               5                  10                  15

Arg Tyr Ile Gln Ala Ala Leu Lys Leu Ala Glu Arg Cys Asp Leu Pro
            20                  25                  30

Leu Val

<210> SEQ ID NO 75
<211> LENGTH: 34
<212> TYPE: PRT
<213> ORGANISM: Rickettsia prowazekii

<400> SEQUENCE: 75

Asp Arg Phe Tyr Phe Glu Ile Met Arg His Asp Leu Pro Glu Glu Gln
 1               5                  10                  15

Phe Ile Glu Asn Ser Tyr Ile Gln Ile Ala Ser Glu Leu Ser Ile Pro
            20                  25                  30

Ile Val

<210> SEQ ID NO 76
<211> LENGTH: 34
<212> TYPE: PRT
<213> ORGANISM: Helicobacter pylori

<400> SEQUENCE: 76

Asp Asp Phe Tyr Leu Glu Ile Met Arg His Gly Ile Leu Asp Gln Arg
 1               5                  10                  15

Phe Ile Asp Glu Gln Val Ile Lys Met Ser Leu Glu Thr Gly Leu Lys
            20                  25                  30

Ile Ile
```

-continued

<210> SEQ ID NO 77
<211> LENGTH: 34
<212> TYPE: PRT
<213> ORGANISM: Synechocystis sp.

<400> SEQUENCE: 77

Asp Asp Tyr Tyr Leu Glu Ile Gln Asp His Gly Ser Val Glu Asp Arg
 1               5                  10                  15

Leu Val Asn Ile Asn Leu Val Lys Ile Ala Gln Glu Leu Asp Ile Lys
            20                  25                  30

Ile Val

<210> SEQ ID NO 78
<211> LENGTH: 34
<212> TYPE: PRT
<213> ORGANISM: Mycobacterium tuberculosis

<400> SEQUENCE: 78

Asp Asn Tyr Phe Leu Glu Leu Met Asp His Gly Leu Thr Ile Glu Arg
 1               5                  10                  15

Arg Val Arg Asp Gly Leu Leu Glu Ile Gly Arg Ala Leu Asn Ile Pro
            20                  25                  30

Pro Leu

<210> SEQ ID NO 79
<211> LENGTH: 46
<212> TYPE: PRT
<213> ORGANISM: Escherichia coli

<400> SEQUENCE: 79

Asn Lys Arg Arg Ala Lys Asn Gly Glu Pro Pro Leu Asp Ile Ala Ala
 1               5                  10                  15

Ile Pro Leu Asp Asp Lys Lys Ser Phe Asp Met Leu Gln Arg Ser Glu
            20                  25                  30

Thr Thr Ala Val Phe Gln Leu Glu Ser Arg Gly Met Lys Asp
        35                  40                  45

<210> SEQ ID NO 80
<211> LENGTH: 46
<212> TYPE: PRT
<213> ORGANISM: Vibrio cholerae

<400> SEQUENCE: 80

Asn Pro Arg Leu Lys Lys Ala Gly Lys Pro Pro Val Arg Ile Glu Ala
 1               5                  10                  15

Ile Pro Leu Asp Asp Ala Arg Ser Phe Arg Asn Leu Gln Asp Ala Lys
            20                  25                  30

Thr Thr Ala Val Phe Gln Leu Glu Ser Arg Gly Met Lys Glu
        35                  40                  45

<210> SEQ ID NO 81
<211> LENGTH: 46
<212> TYPE: PRT
<213> ORGANISM: Haemophilus influenzae

<400> SEQUENCE: 81

Asn Val Arg Met Val Arg Glu Gly Lys Pro Arg Val Asp Ile Ala Ala
 1               5                  10                  15

Ile Pro Leu Asp Asp Pro Glu Ser Phe Glu Leu Leu Lys Arg Ser Glu
            20                  25                  30

```
Thr Thr Ala Val Phe Gln Leu Glu Ser Arg Gly Met Lys Asp
        35                  40                  45
```

<210> SEQ ID NO 82
<211> LENGTH: 46
<212> TYPE: PRT
<213> ORGANISM: Rickettsia prowazekii

<400> SEQUENCE: 82

```
Cys Lys Lys Leu Leu Lys Glu Gln Gly Ile Lys Ile Asp Phe Asp Asp
 1               5                  10                  15

Met Thr Phe Asp Asp Lys Lys Thr Tyr Gln Met Leu Cys Lys Gly Lys
            20                  25                  30

Gly Val Gly Val Phe Gln Phe Glu Ser Ile Gly Met Lys Asp
        35                  40                  45
```

<210> SEQ ID NO 83
<211> LENGTH: 45
<212> TYPE: PRT
<213> ORGANISM: Helicobacter pylori

<400> SEQUENCE: 83

```
Leu Lys Ile Ile Lys Thr Gln His Lys Ile Ser Val Asp Phe Leu Ser
 1               5                  10                  15

Leu Asp Met Asp Asp Pro Lys Val Tyr Lys Thr Ile Gln Ser Gly Asp
            20                  25                  30

Thr Val Gly Ile Phe Gln Ile Glu Ser Gly Met Phe Gln
        35                  40                  45
```

<210> SEQ ID NO 84
<211> LENGTH: 46
<212> TYPE: PRT
<213> ORGANISM: Synechocystis sp.

<400> SEQUENCE: 84

```
Gln Glu Arg Lys Ala Leu Gln Ile Arg Ala Arg Thr Gly Ser Lys Lys
 1               5                  10                  15

Leu Pro Asp Asp Val Lys Lys Thr His Lys Leu Leu Glu Ala Gly Asp
            20                  25                  30

Leu Glu Gly Ile Phe Gln Leu Glu Ser Gln Gly Met Lys Gln
        35                  40                  45
```

<210> SEQ ID NO 85
<211> LENGTH: 46
<212> TYPE: PRT
<213> ORGANISM: Mycobacterium tuberculosis

<400> SEQUENCE: 85

```
Ile Asp Asn Val Arg Ala Asn Arg Gly Ile Asp Leu Asp Leu Glu Ser
 1               5                  10                  15

Val Pro Leu Asp Asp Lys Ala Thr Tyr Glu Leu Leu Gly Arg Gly Asp
            20                  25                  30

Thr Leu Gly Val Phe Gln Leu Asp Gly Gly Pro Met Arg Asp
        35                  40                  45
```

<210> SEQ ID NO 86
<211> LENGTH: 1141
<212> TYPE: DNA
<213> ORGANISM: Thermus thermophilus -continued

```
<400> SEQUENCE: 86
atgggccggg agctccgctt cgcccacctc caccagcaca cccagttctc cctcctggac      60
ggggcgccga agctttccga cctcctcaag tgggtggagg agacgacccc cgaggacccc     120
gccttggcca tgaccgacca cggcaacctc ttcggggccg tagagttcta caagaaggcc     180
gccgaaatgg gcatcgagcc catcctgggt acgaggcctt acgtggcggc ggaaagcccg     240
tttgaccgca agcggggaaa gggcctagac ggggctact ttcacctcac cctcctcgcc      300
aaggacttca cggggtacca gaacctggtg cgcctggcga gccgggctta cctggagggg     360
ttttacgaaa agccccggat tgaccggag atcctgcgcg agcgccgagg cctcatcgc       420
ctctcggggt gcctcgggc ggagatcccc cagttcatcc tccaggaccg tctggacctg      480
gccgaggccc ggctcaacga ggacctctcc atcttcaagg accgcttctt cattcacatc     540
cagaaccacg gcctccccga gcagaaaaag gtcaacgagg tcctcaagga gttcgcccga     600
aagtacggcc tggggatggt ggccaccaac gacggccatt acgggaggaa ggaggcccgc     660
agcgcccacg aggttttcct cgccatccag tccaagagca ccctggacga ccccggggcc     720
gttggctttc ccctgcggga gttctacgtg aagacccccg aggagacgtg cgggccggtg     780
ttccccgagg aggagtgggg ggacgagccc tttgacaaca ccgtggagat cgcccgcatg     840
tgcaacgtgg agctgcccat cgggacaaga tggtctaccc gaatccccg cttccccctc      900
cccgagggac cggggaccga ggccaagtac ctaatggagc taaccttcaa ggggcccctc     960
cgccgttacc cggaccgaat caccgagggt ttctaccggg aggttttccg ccttttgggg    1020
aagcttcccc cccacgggca cggggaggcc ttggccgagg ccttggccca ggtggagcgg    1080
gaggcttggg agaggctcat gaagagcctc ccccccttg accggggtcc aaggagttcc    1140
a                                                                    1141

<210> SEQ ID NO 87
<211> LENGTH: 394
<212> TYPE: PRT
<213> ORGANISM: Thermus thermophilus

<400> SEQUENCE: 87

Met Gly Arg Glu Leu Arg Phe Ala His Leu His Gln His Thr Gln Phe
  1               5                  10                  15

Ser Leu Leu Asp Gly Ala Pro Lys Leu Ser Asp Leu Leu Lys Trp Val
             20                  25                  30

Glu Glu Thr Thr Pro Glu Asp Pro Ala Leu Ala Met Thr Asp His Gly
         35                  40                  45

Asn Leu Phe Gly Ala Val Glu Phe Tyr Lys Lys Ala Ala Glu Met Gly
     50                  55                  60

Ile Glu Pro Ile Leu Gly Thr Arg Pro Tyr Val Ala Ala Glu Ser Pro
 65                  70                  75                  80

Phe Asp Arg Lys Arg Gly Lys Gly Leu Asp Gly Gly Tyr Phe His Leu
                 85                  90                  95

Thr Leu Leu Ala Lys Asp Phe Thr Gly Tyr Gln Asn Leu Val Arg Leu
            100                 105                 110

Ala Ser Arg Ala Tyr Leu Glu Gly Phe Tyr Glu Lys Pro Arg Ile Asp
        115                 120                 125

Arg Glu Ile Leu Arg Glu Arg Gly Pro His Arg Leu Ser Gly Cys
    130                 135                 140

Leu Gly Ala Glu Ile Pro Gln Phe Ile Leu Gln Asp Arg Leu Asp Leu
145                 150                 155                 160
```

```
Phe Phe Ile Glu Ile Gln Asn His Gly Leu Ser Glu Gln Lys Ala Glu
            165                 170                 175

Ala Arg Leu Asn Glu Asp Leu Ser Ile Phe Lys Asp Arg Phe Phe Ile
        180                 185                 190

His Ile Gln Asn His Gly Leu Pro Glu Gln Lys Val Asn Glu Val
    195                 200                 205

Leu Lys Glu Phe Ala Arg Lys Tyr Gly Leu Gly Met Val Ala Thr Asn
210                 215                 220

Asp Gly His Tyr Gly Arg Lys Glu Ala Arg Ser Ala His Glu Val Phe
225                 230                 235                 240

Leu Ala Ile Gln Ser Lys Ser Thr Leu Asp Asp Pro Gly Ala Val Gly
                245                 250                 255

Phe Pro Leu Arg Glu Phe Tyr Val Lys Thr Pro Glu Glu Thr Cys Gly
            260                 265                 270

Pro Val Phe Pro Glu Glu Trp Gly Asp Glu Pro Phe Asp Asn Thr
        275                 280                 285

Val Glu Ile Ala Arg Met Cys Asn Val Glu Leu Pro Ile Gly Thr Arg
    290                 295                 300

Trp Ser Thr Arg Ile Pro Arg Phe Pro Leu Pro Glu Gly Pro Gly Thr
305                 310                 315                 320

Glu Ala Lys Tyr Leu Met Glu Leu Thr Phe Lys Gly Pro Leu Arg Arg
                325                 330                 335

Tyr Pro Asp Arg Ile Thr Glu Gly Phe Tyr Arg Glu Val Phe Arg Leu
            340                 345                 350

Leu Gly Lys Leu Pro Pro His Gly His Gly Glu Ala Leu Ala Glu Ala
        355                 360                 365

Leu Ala Gln Val Glu Arg Glu Ala Trp Glu Arg Leu Met Lys Ser Leu
    370                 375                 380

Pro Pro Phe Asp Arg Gly Pro Arg Ser Ser
385                 390

<210> SEQ ID NO 88
<211> LENGTH: 198
<212> TYPE: PRT
<213> ORGANISM: Thermus thermophilus

<400> SEQUENCE: 88

Val Glu Arg Val Val Arg Thr Leu Leu Asp Gly Arg Phe Leu Leu Glu
1               5                   10                  15

Glu Gly Val Gly Leu Trp Glu Trp Arg Tyr Pro Phe Pro Leu Glu Gly
            20                  25                  30

Glu Ala Val Val Leu Asp Leu Glu Thr Thr Gly Leu Ala Gly Leu
        35                  40                  45

Asp Glu Val Ile Glu Val Gly Leu Leu Arg Leu Glu Gly Gly Arg Arg
    50                  55                  60

Leu Pro Phe Gln Ser Leu Val Arg Pro Leu Pro Ala Glu Ala Arg
65                  70                  75                  80

Ser Trp Asn Leu Thr Gly Ile Pro Arg Glu Ala Leu Glu Glu Ala Pro
                85                  90                  95

Ser Leu Glu Glu Val Leu Glu Lys Ala Tyr Pro Leu Arg Gly Asp Ala
            100                 105                 110

Thr Leu Val Ile His Asn Ala Ala Phe Asp Leu Gly Phe Leu Arg Pro
        115                 120                 125

Ala Leu Glu Gly Leu Gly Tyr Arg Leu Glu Asn Pro Val Val Asp Ser
    130                 135                 140
```

```
Leu Arg Leu Ala Arg Arg Gly Leu Pro Gly Leu Arg Arg Tyr Gly Leu
145                 150                 155                 160

Asp Ala Leu Ser Glu Val Leu Glu Leu Pro Arg Arg Thr Cys His Arg
                165                 170                 175

Ala Leu Glu Asp Val Glu Arg Thr Leu Ala Val Val His Glu Val Tyr
            180                 185                 190

Tyr Met Leu Thr Ser Gly
        195

<210> SEQ ID NO 89
<211> LENGTH: 182
<212> TYPE: PRT
<213> ORGANISM: Deinococcus radiodurans
<220> FEATURE:
<221> NAME/KEY: PEPTIDE
<222> LOCATION: (79)
<223> OTHER INFORMATION: X at position 79 is undefined

<400> SEQUENCE: 89

Pro Trp Pro Gln Asp Val Val Phe Asp Leu Glu Thr Thr Gly Phe
1               5                   10                  15

Ser Pro Ala Ser Ala Ala Ile Val Glu Ile Gly Ala Val Arg Ile Val
                20                  25                  30

Gly Gly Gln Ile Asp Glu Thr Leu Lys Phe Glu Thr Leu Val Arg Pro
            35                  40                  45

Thr Arg Pro Asp Gly Ser Met Leu Ser Ile Pro Trp Gln Ala Gln Arg
        50                  55                  60

Val His Gly Ile Ser Asp Glu Met Val Arg Arg Ala Pro Ala Xaa Lys
65                  70                  75                  80

Asp Val Leu Pro Asp Phe Phe Asp Phe Val Asp Gly Ser Ala Val Val
                85                  90                  95

Ala His Asn Val Ser Phe Asp Gly Gly Phe Met Arg Ala Gly Ala Glu
            100                 105                 110

Arg Leu Gly Leu Ser Trp Ala Pro Glu Arg Glu Leu Cys Thr Met Gln
        115                 120                 125

Leu Ser Arg Arg Ala Phe Pro Arg Glu Arg Thr His Asn Leu Thr Val
130                 135                 140

Leu Ala Glu Arg Leu Gly Leu Glu Phe Ala Pro Gly Gly Arg His Arg
145                 150                 155                 160

Ser Tyr Gly Asp Val Gln Val Thr Ala Gln Ala Tyr Leu Arg Leu Leu
                165                 170                 175

Glu Leu Leu Gly Glu Arg
            180

<210> SEQ ID NO 90
<211> LENGTH: 201
<212> TYPE: PRT
<213> ORGANISM: Bacillus subtilis

<400> SEQUENCE: 90

His Gly Ile Lys Met Ile Tyr Gly Met Glu Ala Asn Leu Val Asp Asp
1               5                   10                  15

Gly Val Pro Ile Ala Tyr Asn Ala Ala His Arg Leu Leu Glu Glu Glu
                20                  25                  30

Thr Tyr Val Val Phe Asp Val Glu Thr Thr Gly Leu Ser Ala Val Tyr
            35                  40                  45

Asp Thr Ile Ile Glu Leu Ala Ala Val Lys Val Lys Gly Gly Glu Ile
        50                  55                  60
```

```
Ile Asp Lys Phe Glu Ala Phe Ala Asn Pro His Arg Pro Leu Ser Ala
 65                  70                  75                  80

Thr Ile Ile Glu Leu Thr Gly Ile Thr Asp Asp Met Leu Gln Asp Ala
                 85                  90                  95

Pro Asp Val Val Asp Val Ile Arg Asp Phe Arg Glu Trp Ile Gly Asp
            100                 105                 110

Asp Ile Leu Val Ala His Asn Ala Ser Phe Asp Met Gly Phe Leu Asn
        115                 120                 125

Val Ala Tyr Lys Lys Leu Leu Glu Val Glu Lys Ala Lys Asn Pro Val
    130                 135                 140

Ile Asp Thr Leu Glu Leu Gly Arg Phe Leu Tyr Pro Glu Phe Lys Asn
145                 150                 155                 160

His Arg Leu Asn Thr Leu Cys Lys Lys Phe Asp Ile Glu Leu Thr Gln
                165                 170                 175

His His Arg Ala Ile Tyr Asp Thr Glu Ala Thr Ala Tyr Leu Leu Leu
            180                 185                 190

Lys Met Leu Lys Asp Ala Ala Glu Lys
        195                 200

<210> SEQ ID NO 91
<211> LENGTH: 188
<212> TYPE: PRT
<213> ORGANISM: Haemophilus influenzae
<220> FEATURE:
<221> NAME/KEY: PEPTIDE
<222> LOCATION: (47)
<223> OTHER INFORMATION: X at position 47 is undefined
<220> FEATURE:
<221> NAME/KEY: PEPTIDE
<222> LOCATION: (57)
<223> OTHER INFORMATION: X at position 57 is undefined

<400> SEQUENCE: 91

Met Ile Asn Pro Asn Arg Gln Ile Val Leu Asp Thr Glu Thr Thr Gly
  1               5                  10                  15

Met Asn Gln Leu Gly Ala His Tyr Glu Gly His Cys Ile Ile Glu Ile
             20                  25                  30

Gly Ala Val Glu Leu Ile Asn Arg Arg Tyr Thr Gly Asn Asn Xaa His
         35                  40                  45

Ile Tyr Ile Lys Pro Asp Arg Pro Xaa Asp Pro Asp Ala Ile Lys Val
     50                  55                  60

His Gly Ile Thr Asp Glu Met Leu Ala Asp Lys Pro Glu Phe Lys Glu
 65                  70                  75                  80

Val Ala Gln Asp Phe Leu Asp Tyr Ile Asn Gly Ala Glu Leu Leu Ile
                 85                  90                  95

His Asn Ala Pro Phe Asp Val Gly Phe Met Asp Tyr Glu Phe Arg Lys
            100                 105                 110

Leu Asn Leu Asn Val Lys Thr Asp Asp Ile Cys Leu Val Thr Asp Thr
        115                 120                 125

Leu Gln Met Ala Arg Gln Met Tyr Pro Gly Lys Arg Asn Asn Leu Asp
    130                 135                 140

Ala Leu Cys Asp Arg Leu Gly Ile Asp Asn Ser Lys Arg Thr Leu His
145                 150                 155                 160

Gly Ala Leu Leu Asp Ala Glu Ile Leu Ala Asp Val Tyr Leu Met Met
                165                 170                 175

Thr Gly Gly Gln Thr Asn Leu Phe Asp Glu Glu Glu
            180                 185
```

```
<210> SEQ ID NO 92
<211> LENGTH: 189
<212> TYPE: PRT
<213> ORGANISM: Escherichia coli

<400> SEQUENCE: 92

Met Ser Thr Ala Ile Thr Arg Gln Ile Val Leu Asp Thr Glu Thr Thr
1               5                   10                  15

Gly Met Asn Gln Ile Gly Ala His Ser Glu Gly His Lys Ile Ile Glu
            20                  25                  30

Ile Gly Ala Val Glu Val Val Asn Arg Arg Leu Thr Gly Asn Asn Phe
        35                  40                  45

His Val Tyr Leu Lys Asp Arg Leu Val Asp Pro Glu Ala Phe Gly Val
    50                  55                  60

His Gly Ile Ala Val Asp Phe Leu Leu Asp Lys Pro Thr Phe Ala Glu
65                  70                  75                  80

Val Ala Val Glu Phe Met Asp Tyr Ile Arg Gly Ala Glu Leu Val Ile
                85                  90                  95

His Asn Ala Ala Phe Asp Ile Gly Phe Met Asp Tyr Glu Phe Ser Leu
            100                 105                 110

Leu Lys Arg Asp Ile Ala Lys Thr Asn Thr Phe Cys Lys Val Thr Asp
        115                 120                 125

Ser Leu Ala Val Ala Arg Lys Met Phe Pro Gly Lys Arg Asn Ser Leu
    130                 135                 140

Asp Ala Leu Cys Ala Arg Tyr Glu Ile Asp Asn Ser Lys Arg Thr Leu
145                 150                 155                 160

His Gly Ala Leu Leu Asp Ala Gln Ile Leu Ala Glu Val Tyr Leu Ala
                165                 170                 175

Met Thr Gly Gly Gln Thr Ser Met Ala Phe Ala Met Glu
            180                 185

<210> SEQ ID NO 93
<211> LENGTH: 201
<212> TYPE: PRT
<213> ORGANISM: Helicobacter pylori

<400> SEQUENCE: 93

Asn Leu Glu Tyr Leu Lys Ala Cys Gly Leu Asn Phe Ile Glu Thr Ser
1               5                   10                  15

Glu Asn Leu Ile Thr Leu Lys Asn Leu Lys Thr Pro Leu Lys Asp Glu
            20                  25                  30

Val Phe Ser Phe Ile Asp Leu Glu Thr Thr Gly Ser Cys Pro Ile Lys
        35                  40                  45

His Glu Ile Leu Glu Ile Gly Ala Val Gln Val Lys Gly Gly Glu Ile
    50                  55                  60

Ile Asn Arg Phe Glu Thr Leu Val Lys Val Lys Ser Val Pro Asp Tyr
65                  70                  75                  80

Ile Ala Glu Leu Thr Gly Ile Thr Tyr Glu Asp Thr Leu Asn Ala Pro
                85                  90                  95

Ser Ala His Glu Ala Leu Gln Glu Leu Arg Leu Phe Leu Gly Asn Ser
            100                 105                 110

Val Phe Val Ala His Asn Ala Asn Phe Asp Tyr Asn Phe Leu Gly Arg
        115                 120                 125

Tyr Phe Val Glu Lys Leu His Cys Pro Leu Leu Asn Leu Lys Leu Cys
    130                 135                 140
```

Thr Leu Asp Leu Ser Lys Arg Ala Ile Leu Ser Met Arg Tyr Ser Leu
145                 150                 155                 160

Ser Phe Leu Lys Glu Leu Leu Gly Phe Gly Ile Glu Val Ser His Arg
                165                 170                 175

Ala Tyr Ala Asp Ala Leu Ala Ser Tyr Lys Leu Phe Glu Ile Cys Leu
            180                 185                 190

Leu Asn Leu Pro Ser Tyr Ile Lys Thr
        195                 200

<210> SEQ ID NO 94
<211> LENGTH: 630
<212> TYPE: DNA
<213> ORGANISM: Thermus thermophilus

<400> SEQUENCE: 94
atggtggagc gggtggtgcg gaccettctg gacgggaggt tcctcctgga ggaggggtg      60 gggctttggg agtggcgcta ccccttcccc ctggaggggg aggcggtggt ggtcctggac    120
ctggagacca cggggcttgc cggcctggac gaggtgattg aggtgggcct cctccgcctg    180 gagggggggga ggcgcctccc cttccagagc ctcgtccggc ccctcccgcc cgccgaagcc    240
cgttcgtgga acctcaccgg catccccgg gaggccctgg aggagccccc ctccctggag    300
gaggttctgg agaaggccta ccccctccgc ggcgacgcca ccttggtgat ccacaacgcc    360
gcctttgacc tgggcttcct ccgccggcc ttggagggcc tgggctaccg cctggaaaac    420
cccgtggtgg actccctgcg cttggccaga cggggcttac caggcttag gcgctacggc    480 ctggacgccc tctccgaggt cctggagctt ccccgaagga cctgccaccg ggccctcgag    540
gacgtggagc gcaccctcgc cgtggtgcac gaggtatact atatgcttac gtccggccgt    600
ccccgcacgc tttgggaact cgggaggtag                                    630

<210> SEQ ID NO 95
<211> LENGTH: 210
<212> TYPE: PRT
<213> ORGANISM: Thermus thermophilus

<400> SEQUENCE: 95

Met Val Glu Arg Val Val Arg Thr Leu Leu Asp Gly Arg Phe Leu Leu
1               5                   10                  15

Glu Glu Gly Val Gly Leu Trp Glu Trp Arg Tyr Pro Phe Pro Leu Glu
                20                  25                  30

Gly Glu Ala Val Val Val Leu Asp Leu Glu Thr Thr Gly Leu Ala Gly
            35                  40                  45

Leu Asp Glu Val Ile Glu Val Gly Leu Arg Leu Glu Gly Gly Arg
    50                  55                  60

Arg Leu Pro Phe Gln Ser Leu Val Arg Pro Leu Pro Pro Ala Glu Ala
65                  70                  75                  80

Arg Ser Trp Asn Leu Thr Gly Ile Pro Arg Glu Ala Leu Glu Glu Ala
                85                  90                  95

Pro Ser Leu Glu Glu Val Leu Glu Lys Ala Tyr Pro Leu Arg Gly Asp
            100                 105                 110

Ala Thr Leu Val Ile His Asn Ala Ala Phe Asp Leu Gly Phe Leu Arg
        115                 120                 125

Pro Ala Leu Glu Gly Leu Gly Tyr Arg Leu Glu Asn Pro Val Val Asp
    130                 135                 140

Ser Leu Arg Leu Ala Arg Arg Gly Leu Pro Gly Leu Arg Arg Tyr Gly
145                 150                 155                 160

Leu Asp Ala Leu Ser Glu Val Leu Glu Leu Pro Arg Arg Thr Cys His
            165                 170                 175

Arg Ala Leu Glu Asp Val Glu Arg Thr Leu Ala Val Val His Glu Val
            180                 185                 190

Tyr Tyr Met Leu Thr Ser Gly Arg Pro Arg Thr Leu Trp Glu Leu Gly
            195                 200                 205

Arg Glx
    210

<210> SEQ ID NO 96
<211> LENGTH: 461
<212> TYPE: PRT
<213> ORGANISM: Pseudomonas marcesans

<400> SEQUENCE: 96

Met Leu Glu Ala Ser Trp Glu Lys Val Gln Ser Ser Leu Lys Gln Asn
  1               5                  10                  15

Leu Ser Lys Pro Ser Tyr Glu Thr Trp Ile Arg Pro Thr Glu Phe Ser
             20                  25                  30

Gly Phe Lys Asn Gly Glu Leu Thr Leu Ile Ala Pro Asn Ser Phe Ser
         35                  40                  45

Ser Ala Trp Leu Lys Asn Asn Tyr Ser Gln Thr Ile Gln Glu Thr Ala
     50                  55                  60

Glu Glu Ile Phe Gly Glu Pro Val Thr Val His Val Lys Val Lys Ala
 65                  70                  75                  80

Asn Ala Glu Ser Ser Asp Glu His Tyr Ser Ala Pro Ile Thr Pro
                 85                  90                  95

Pro Leu Glu Ala Ser Pro Gly Ser Val Asp Ser Ser Gly Ser Ser Leu
            100                 105                 110

Arg Leu Ser Lys Lys Thr Leu Pro Leu Leu Asn Leu Arg Tyr Val Phe
        115                 120                 125

Asn Arg Phe Val Val Gly Pro Asn Ser Arg Met Ala His Ala Ala
130                 135                 140

Met Ala Val Ala Glu Ser Pro Gly Arg Glu Phe Asn Pro Leu Phe Ile
145                 150                 155                 160

Cys Gly Gly Val Gly Leu Gly Lys Thr His Leu Met Gln Ala Ile Gly
                165                 170                 175

His Tyr Arg Leu Glu Ile Asp Pro Gly Ala Lys Val Ser Tyr Val Ser
            180                 185                 190

Thr Glu Thr Phe Thr Asn Asp Leu Ile Leu Ala Ile Arg Gln Asp Arg
        195                 200                 205

Met Gln Ala Phe Arg Asp Arg Tyr Arg Ala Ala Asp Leu Ile Leu Val
210                 215                 220

Asp Asp Ile Gln Phe Ile Glu Gly Lys Glu Tyr Thr Gln Glu Glu Phe
225                 230                 235                 240

Phe His Thr Phe Asn Ala Leu His Asp Ala Gly Ser Gln Ile Val Leu
                245                 250                 255

Ala Ser Asp Arg Pro Pro Ser Gln Ile Pro Arg Leu Gln Glu Arg Leu
            260                 265                 270

Met Ser Arg Phe Ser Met Gly Leu Ile Ala Asp Val Gln Ala Pro Asp
        275                 280                 285

Leu Glu Thr Arg Met Ala Ile Leu Gln Lys Lys Ala Glu His Glu Arg
290                 295                 300

Val Gly Leu Pro Arg Asp Leu Ile Gln Phe Ile Ala Gly Arg Phe Thr
305                 310                 315                 320

```
Ser Asn Ile Arg Glu Leu Glu Gly Ala Leu Thr Arg Ala Ile Ala Phe
                325                 330                 335

Ala Ser Ile Thr Gly Leu Pro Met Thr Val Asp Ser Ile Ala Pro Met
                340                 345                 350

Leu Asp Pro Asn Gly Gln Gly Val Glu Val Thr Pro Lys Gln Val Leu
                355                 360                 365

Asp Lys Val Ala Glu Val Phe Lys Val Thr Pro Asp Glu Met Arg Ser
370                 375                 380

Ala Ser Arg Arg Arg Pro Val Ser Gln Ala Arg Gln Val Gly Met Tyr
385                 390                 395                 400

Leu Met Arg Gln Gly Thr Asn Leu Ser Leu Pro Arg Ile Gly Asp Thr
                405                 410                 415

Phe Gly Gly Lys Asp His Thr Val Met Tyr Ala Ile Glu Gln Val
                420                 425                 430

Glu Lys Lys Leu Ser Ser Asp Pro Gln Ile Ala Ser Gln Val Gln Lys
                435                 440                 445

Ile Arg Asp Leu Leu Gln Ile Asp Ser Arg Arg Lys Arg
                450                 455                 460

<210> SEQ ID NO 97
<211> LENGTH: 447
<212> TYPE: PRT
<213> ORGANISM: Synechocystis sp.

<400> SEQUENCE: 97

Met Val Ser Cys Glu Asn Leu Trp Gln Gln Ala Leu Ala Ile Leu Ala
1               5                   10                  15

Thr Gln Leu Thr Lys Pro Ala Phe Asp Thr Trp Ile Lys Ala Ser Val
                20                  25                  30

Leu Ile Ser Leu Gly Asp Gly Val Ala Thr Ile Gln Val Glu Asn Gly
                35                  40                  45

Phe Val Leu Asn His Leu Gln Lys Ser Tyr Gly Pro Leu Leu Met Glu
            50                  55                  60

Val Leu Thr Asp Leu Thr Gly Gln Glu Ile Thr Val Lys Leu Ile Thr
65                  70                  75                  80

Asp Gly Leu Glu Pro His Ser Leu Ile Gly Gln Glu Ser Ser Leu Pro
                85                  90                  95

Met Glu Thr Thr Pro Lys Asn Ala Thr Ala Leu Asn Gly Lys Tyr Thr
                100                 105                 110

Phe Ser Arg Phe Val Val Gly Pro Thr Asn Arg Met Ala His Ala Ala
                115                 120                 125

Ser Leu Ala Val Ala Glu Ser Pro Gly Arg Glu Phe Asn Pro Leu Phe
            130                 135                 140

Leu Cys Gly Gly Val Gly Leu Gly Lys Thr His Leu Met Gln Ala Ile
145                 150                 155                 160

Ala His Tyr Arg Leu Glu Met Tyr Pro Asn Ala Lys Val Tyr Tyr Val
                165                 170                 175

Ser Thr Glu Arg Phe Thr Asn Asp Leu Ile Thr Ala Ile Arg Gln Asp
                180                 185                 190

Asn Met Glu Asp Phe Arg Ser Tyr Tyr Arg Ser Ala Asp Phe Leu Leu
                195                 200                 205

Ile Asp Asp Ile Gln Phe Ile Lys Gly Lys Glu Tyr Thr Gln Glu Glu
            210                 215                 220

Phe Phe His Thr Phe Asn Ser Leu His Glu Ala Gly Lys Gln Val Val
225                 230                 235                 240
```

```
Val Ala Ser Asp Arg Ala Pro Gln Arg Ile Pro Gly Leu Gln Asp Arg
                245                 250                 255

Leu Ile Ser Arg Phe Ser Met Gly Leu Ile Ala Asp Ile Gln Val Pro
                260                 265                 270

Asp Leu Glu Thr Arg Met Ala Ile Leu Gln Lys Lys Ala Glu Tyr Asp
                275                 280                 285

Arg Ile Arg Leu Pro Lys Glu Val Ile Glu Tyr Ile Ala Ser His Tyr
                290                 295                 300

Thr Ser Asn Ile Arg Glu Leu Glu Gly Ala Leu Ile Arg Ala Ile Ala
305                 310                 315                 320

Tyr Thr Ser Leu Ser Asn Val Ala Met Thr Val Glu Asn Ile Ala Pro
                325                 330                 335

Val Leu Asn Pro Pro Val Glu Lys Val Ala Ala Pro Glu Thr Ile
                340                 345                 350

Ile Thr Ile Val Ala Gln His Tyr Gln Leu Lys Val Glu Glu Leu Leu
                355                 360                 365

Ser Asn Ser Arg Arg Glu Val Ser Leu Ala Arg Gln Val Gly Met
370                 375                 380

Tyr Leu Met Arg Gln His Thr Asp Leu Ser Leu Pro Arg Ile Gly Glu
385                 390                 395                 400

Ala Phe Gly Gly Lys Asp His Thr Thr Val Met Tyr Ser Cys Asp Lys
                405                 410                 415

Ile Thr Gln Leu Gln Gln Lys Asp Trp Glu Thr Ser Gln Thr Leu Thr
                420                 425                 430

Ser Leu Ser His Arg Ile Asn Ile Ala Gly Gln Ala Pro Glu Ser
                435                 440                 445

<210> SEQ ID NO 98
<211> LENGTH: 446
<212> TYPE: PRT
<213> ORGANISM: Bacillus subtilis

<400> SEQUENCE: 98

Met Glu Asn Ile Leu Asp Leu Trp Asn Gln Ala Leu Ala Gln Ile Glu
1               5                   10                  15

Lys Lys Leu Ser Lys Pro Ser Phe Glu Thr Trp Met Lys Ser Thr Lys
                20                  25                  30

Ala His Ser Leu Gln Gly Asp Thr Leu Thr Ile Thr Ala Pro Asn Glu
                35                  40                  45

Phe Ala Arg Asp Trp Leu Glu Ser Arg Tyr Leu His Leu Ile Ala Asp
            50                  55                  60

Thr Ile Tyr Glu Leu Thr Gly Glu Glu Leu Ser Ile Lys Phe Val Ile
65                  70                  75                  80

Pro Gln Asn Gln Asp Val Glu Asp Phe Met Pro Lys Pro Gln Val Lys
                85                  90                  95

Lys Ala Val Lys Glu Asp Thr Ser Asp Phe Pro Gln Asn Met Leu Asn
                100                 105                 110

Pro Lys Tyr Thr Phe Asp Thr Phe Val Ile Gly Ser Gly Asn Arg Phe
            115                 120                 125

Ala His Ala Ala Ser Leu Ala Val Ala Glu Ala Pro Ala Lys Ala Tyr
130                 135                 140

Asn Pro Leu Phe Ile Tyr Gly Gly Val Gly Leu Gly Lys Thr His Leu
145                 150                 155                 160

Met His Ala Ile Gly His Tyr Val Ile Asp His Asn Pro Ser Ala Lys
                165                 170                 175
```

```
Val Val Tyr Leu Ser Ser Glu Lys Phe Thr Asn Glu Phe Ile Asn Ser
            180                 185                 190

Ile Arg Asp Asn Lys Ala Val Asp Phe Arg Asn Arg Tyr Arg Asn Val
            195                 200                 205

Asp Val Leu Leu Ile Asp Ile Gln Phe Leu Ala Gly Lys Glu Gln
            210                 215                 220

Thr Gln Glu Glu Phe Phe His Thr Phe Asn Thr Leu His Glu Glu Ser
225                 230                 235                 240

Lys Gln Ile Val Ile Ser Ser Asp Arg Pro Pro Lys Glu Ile Pro Thr
                245                 250                 255

Leu Glu Asp Arg Leu Arg Ser Arg Phe Glu Trp Gly Leu Ile Thr Asp
                260                 265                 270

Ile Thr Pro Pro Asp Leu Glu Thr Arg Ile Ala Ile Leu Arg Lys Lys
                275                 280                 285

Ala Lys Ala Glu Gly Leu Asp Ile Pro Asn Glu Val Met Leu Tyr Ile
            290                 295                 300

Ala Asn Gln Ile Asp Ser Asn Ile Arg Glu Leu Glu Gly Ala Leu Ile
305                 310                 315                 320

Arg Val Val Ala Tyr Ser Ser Leu Ile Asn Lys Asp Ile Asn Ala Asp
                325                 330                 335

Leu Ala Ala Glu Ala Leu Lys Asp Ile Ile Pro Ser Ser Lys Pro Lys
                340                 345                 350

Val Ile Thr Ile Lys Glu Ile Gln Arg Val Val Gly Gln Gln Phe Asn
                355                 360                 365

Ile Lys Leu Glu Asp Phe Lys Ala Lys Lys Arg Thr Lys Ser Val Ala
            370                 375                 380

Phe Pro Arg Gln Ile Ala Met Tyr Leu Ser Arg Glu Met Thr Asp Ser
385                 390                 395                 400

Ser Leu Pro Lys Ile Gly Glu Glu Phe Gly Gly Arg Asp His Thr Thr
                405                 410                 415

Val Ile His Ala His Glu Lys Ile Ser Lys Leu Leu Ala Asp Asp Glu
                420                 425                 430

Gln Leu Gln Gln His Val Lys Glu Ile Lys Glu Gln Leu Lys
            435                 440                 445

<210> SEQ ID NO 99
<211> LENGTH: 507
<212> TYPE: PRT
<213> ORGANISM: Mycobacterium tuberculosis

<400> SEQUENCE: 99

Met Thr Asp Asp Pro Gly Ser Gly Phe Thr Thr Val Trp Asn Ala Val
1               5                   10                  15

Val Ser Glu Leu Asn Gly Asp Pro Lys Val Asp Asp Gly Pro Ser Ser
                20                  25                  30

Asp Ala Asn Leu Ser Ala Pro Leu Thr Pro Gln Gln Arg Ala Trp Leu
            35                  40                  45

Asn Leu Val Gln Pro Leu Thr Ile Val Glu Gly Phe Ala Leu Leu Ser
        50                  55                  60

Val Pro Ser Ser Phe Val Gln Asn Glu Ile Glu Arg His Leu Arg Ala
65              70                  75                  80

Pro Ile Thr Asp Ala Leu Ser Arg Arg Leu Gly His Gln Ile Gln Leu
                85                  90                  95

Gly Val Arg Ile Ala Pro Pro Ala Thr Asp Glu Ala Asp Asp Thr Thr
                100                 105                 110
```

-continued

```
Val Pro Pro Ser Glu Asn Pro Ala Thr Thr Ser Pro Asp Thr Thr Thr
        115                 120                 125

Asp Asn Asp Glu Ile Asp Ser Ala Ala Arg Gly Asp Asn Gln
130                 135                 140

His Ser Trp Pro Ser Tyr Phe Thr Glu Arg Pro His Asn Thr Asp Ser
145                 150                 155                 160

Ala Thr Ala Gly Val Thr Ser Leu Asn Arg Arg Tyr Thr Phe Asp Thr
                165                 170                 175

Phe Val Ile Gly Ala Ser Asn Arg Phe Ala His Ala Ala Ala Leu Ala
            180                 185                 190

Ile Ala Glu Ala Pro Ala Arg Ala Tyr Asn Pro Leu Phe Ile Trp Gly
        195                 200                 205

Glu Ser Gly Leu Gly Lys Thr His Leu Leu His Ala Ala Gly Asn Tyr
        210                 215                 220

Ala Gln Arg Leu Phe Pro Gly Met Arg Val Lys Tyr Val Ser Thr Glu
225                 230                 235                 240

Glu Phe Thr Asn Asp Phe Ile Asn Ser Leu Arg Asp Asp Arg Lys Val
                245                 250                 255

Ala Phe Lys Arg Ser Tyr Arg Asp Val Asp Val Leu Leu Val Asp Asp
            260                 265                 270

Ile Gln Phe Ile Glu Gly Lys Glu Gly Ile Gln Glu Glu Phe Phe His
        275                 280                 285

Thr Phe Asn Thr Leu His Asn Ala Asn Lys Gln Ile Val Ile Ser Ser
290                 295                 300

Asp Arg Pro Pro Lys Gln Leu Ala Thr Leu Glu Asp Arg Leu Arg Thr
305                 310                 315                 320

Arg Phe Glu Trp Gly Leu Ile Thr Asp Val Gln Pro Pro Glu Leu Glu
                325                 330                 335

Thr Arg Ile Ala Ile Leu Arg Lys Lys Ala Gln Met Glu Arg Leu Ala
            340                 345                 350

Val Pro Asp Asp Val Leu Glu Leu Ile Ala Ser Ser Ile Glu Arg Asn
        355                 360                 365

Ile Arg Glu Leu Glu Gly Ala Leu Ile Arg Val Thr Ala Phe Ala Ser
370                 375                 380

Leu Asn Lys Thr Pro Ile Asp Lys Ala Leu Ala Glu Ile Val Leu Arg
385                 390                 395                 400

Asp Leu Ile Ala Asp Ala Asn Thr Met Gln Ile Ser Ala Ala Thr Ile
                405                 410                 415

Met Ala Ala Thr Ala Glu Tyr Phe Asp Thr Thr Val Glu Glu Leu Arg
            420                 425                 430

Gly Pro Gly Lys Thr Arg Ala Leu Ala Gln Ser Arg Gln Ile Ala Met
        435                 440                 445

Tyr Leu Cys Arg Glu Leu Thr Asp Leu Ser Leu Pro Lys Ile Gly Gln
450                 455                 460

Ala Phe Gly Arg Asp His Thr Thr Val Met Tyr Ala Gln Arg Lys Ile
465                 470                 475                 480

Leu Ser Glu Met Ala Glu Arg Arg Glu Val Phe Asp His Val Lys Glu
                485                 490                 495

Leu Thr Thr Arg Ile Arg Gln Arg Ser Lys Arg
            500                 505
```

<210> SEQ ID NO 100
<211> LENGTH: 446
<212> TYPE: PRT
<213> ORGANISM: Thermus thermophilus

<400> SEQUENCE: 100

| Met | Ser | His | Glu | Ala | Val | Trp | Gln | His | Val | Leu | Glu | His | Ile | Arg | Arg |
|---|---|---|---|---|---|---|---|---|---|---|---|---|---|---|---|
| 1 | | | | 5 | | | | | 10 | | | | | 15 | |

| Ser | Ile | Thr | Glu | Val | Glu | Phe | His | Thr | Trp | Phe | Glu | Arg | Ile | Arg | Pro |
| | | | 20 | | | | | 25 | | | | | 30 | | |

| Leu | Gly | Ile | Arg | Asp | Gly | Val | Leu | Glu | Leu | Ala | Val | Pro | Thr | Ser | Phe |
| | | 35 | | | | | 40 | | | | | 45 | | | |

| Ala | Leu | Asp | Trp | Ile | Arg | Arg | His | Tyr | Ala | Gly | Leu | Ile | Gln | Glu | Gly |
| | 50 | | | | | 55 | | | | | 60 | | | | |

| Pro | Arg | Leu | Leu | Gly | Ala | Gln | Ala | Pro | Arg | Phe | Glu | Leu | Arg | Val | Val |
| 65 | | | | | 70 | | | | | 75 | | | | | 80 |

| Pro | Gly | Val | Val | Gln | Glu | Asp | Ile | Phe | Gln | Pro | Pro | Ser | Pro |
| | | | | 85 | | | | | 90 | | | | 95 |

| Pro | Ala | Gln | Ala | Gln | Pro | Glu | Asp | Thr | Phe | Lys | Thr | Ser | Trp | Trp | Gly |
| | | | 100 | | | | | 105 | | | | | 110 | | |

| Pro | Thr | Thr | Pro | Trp | Pro | His | Gly | Gly | Ala | Val | Ala | Val | Ala | Glu | Ser |
| | | 115 | | | | | 120 | | | | | 125 | | | |

| Pro | Gly | Arg | Ala | Tyr | Asn | Pro | Leu | Phe | Ile | Tyr | Gly | Gly | Arg | Gly | Leu |
| | 130 | | | | | 135 | | | | | 140 | | | | |

| Gly | Lys | Thr | Tyr | Leu | Met | His | Ala | Val | Gly | Pro | Leu | Arg | Ala | Lys | Arg |
| 145 | | | | | 150 | | | | | 155 | | | | | 160 |

| Phe | Pro | His | Met | Arg | Leu | Glu | Tyr | Val | Ser | Thr | Glu | Thr | Phe | Thr | Asn |
| | | | | 165 | | | | | 170 | | | | | 175 | |

| Glu | Leu | Ile | Asn | Arg | Pro | Ser | Ala | Arg | Asp | Arg | Met | Thr | Glu | Phe | Arg |
| | | | 180 | | | | | 185 | | | | | 190 | | |

| Glu | Arg | Tyr | Arg | Ser | Val | Asp | Leu | Leu | Val | Asp | Asp | Val | Gln | Phe |
| | | | 195 | | | | | 200 | | | | | 205 | |

| Ile | Ala | Gly | Lys | Glu | Arg | Thr | Gln | Glu | Glu | Phe | Phe | His | Thr | Phe | Asn |
| | 210 | | | | | 215 | | | | | 220 | | | | |

| Ala | Leu | Tyr | Glu | Ala | His | Lys | Gln | Ile | Ile | Leu | Ser | Ser | Asp | Arg | Pro |
| 225 | | | | | 230 | | | | | 235 | | | | | 240 |

| Pro | Lys | Asp | Ile | Leu | Thr | Leu | Glu | Ala | Arg | Leu | Arg | Ser | Arg | Phe | Glu |
| | | | | 245 | | | | | 250 | | | | | 255 | |

| Trp | Gly | Leu | Ile | Thr | Asp | Asn | Pro | Ala | Pro | Asp | Leu | Glu | Thr | Arg | Ile |
| | | | 260 | | | | | 265 | | | | | 270 | | |

| Ala | Ile | Leu | Lys | Met | Asn | Ala | Ser | Ser | Gly | Pro | Glu | Asp | Pro | Glu | Asp |
| | 275 | | | | | 280 | | | | | 285 | | | | |

| Ala | Leu | Glu | Tyr | Ile | Ala | Arg | Gln | Val | Thr | Ser | Asn | Ile | Arg | Glu | Trp |
| | 290 | | | | | 295 | | | | | 300 | | | | |

| Glu | Gly | Ala | Leu | Met | Arg | Ala | Ser | Pro | Phe | Ala | Ser | Leu | Asn | Gly | Val |
| 305 | | | | | 310 | | | | | 315 | | | | | 320 |

| Glu | Leu | Thr | Arg | Ala | Val | Ala | Ala | Lys | Ala | Leu | Arg | His | Leu | Arg | Pro |
| | | | | 325 | | | | | 330 | | | | | 335 | |

| Arg | Glu | Leu | Glu | Ala | Asp | Pro | Leu | Glu | Ile | Ile | Arg | Lys | Ala | Ala | Gly |
| | | | 340 | | | | | 345 | | | | | 350 | | |

| Pro | Val | Arg | Pro | Glu | Thr | Pro | Gly | Gly | Ala | His | Gly | Glu | Arg | Arg | Lys |
| | | 355 | | | | | 360 | | | | | 365 | | | |

| Lys | Glu | Val | Val | Leu | Pro | Arg | Gln | Leu | Ala | Met | Tyr | Leu | Val | Arg | Glu |
| | 370 | | | | | 375 | | | | | 380 | | | | |

Leu Thr Pro Ala Ser Leu Pro Glu Ile Gly Gln Leu Phe Gly Gly Arg
385                 390                 395                 400

Asp His Thr Thr Val Arg Tyr Ala Ile Gln Lys Val Gln Glu Leu Ala
            405                 410                 415

Gly Lys Pro Asp Arg Glu Val Gln Gly Leu Leu Arg Thr Leu Arg Glu
            420                 425                 430

Ala Cys Thr Asp Pro Val Asp Asn Leu Trp Ile Thr Cys Gly
        435                 440                 445

<210> SEQ ID NO 101
<211> LENGTH: 467
<212> TYPE: PRT
<213> ORGANISM: Escherichia coli

<400> SEQUENCE: 101

Met Ser Leu Ser Leu Trp Gln Gln Cys Leu Ala Arg Leu Gln Asp Glu
1               5                   10                  15

Leu Pro Ala Thr Glu Phe Ser Met Trp Ile Arg Pro Leu Gln Ala Glu
            20                  25                  30

Leu Ser Asp Asn Thr Leu Ala Leu Tyr Ala Pro Asn Arg Phe Val Leu
        35                  40                  45

Asp Trp Val Arg Asp Lys Tyr Leu Asn Asn Ile Asn Gly Leu Leu Thr
    50                  55                  60

Ser Phe Cys Gly Ala Asp Ala Pro Gln Leu Arg Phe Glu Val Gly Thr
65                  70                  75                  80

Lys Pro Val Thr Gln Thr Pro Gln Ala Ala Val Thr Ser Asn Val Ala
                85                  90                  95

Ala Pro Ala Gln Val Ala Gln Thr Gln Pro Gln Arg Ala Ala Pro Ser
            100                 105                 110

Thr Arg Ser Gly Trp Asp Asn Val Pro Ala Pro Ala Glu Pro Thr Tyr
        115                 120                 125

Arg Ser Asn Val Asn Val Lys His Thr Phe Asp Asn Phe Val Glu Gly
    130                 135                 140

Lys Ser Asn Gln Leu Ala Arg Ala Ala Ala Arg Gln Val Ala Asp Asn
145                 150                 155                 160

Pro Gly Gly Ala Tyr Asn Pro Leu Phe Leu Tyr Gly Gly Thr Gly Leu
                165                 170                 175

Gly Lys Thr His Leu Leu His Ala Val Gly Asn Gly Ile Met Ala Arg
            180                 185                 190

Lys Pro Asn Ala Lys Val Val Tyr Met His Ser Glu Arg Phe Val Gln
        195                 200                 205

Asp Met Val Lys Ala Leu Gln Asn Asn Ala Ile Glu Glu Phe Lys Arg
    210                 215                 220

Tyr Tyr Arg Ser Val Asp Ala Leu Leu Ile Asp Asp Ile Gln Phe Phe
225                 230                 235                 240

Ala Asn Lys Glu Arg Ser Gln Glu Glu Phe Phe His Thr Phe Asn Ala
                245                 250                 255

Leu Leu Glu Gly Asn Gln Gln Ile Ile Leu Thr Ser Asp Arg Tyr Pro
            260                 265                 270

Lys Glu Ile Asn Gly Val Glu Asp Arg Leu Lys Ser Arg Phe Gly Trp
        275                 280                 285

Gly Leu Thr Val Ala Ile Glu Pro Pro Glu Leu Glu Thr Arg Val Ala
    290                 295                 300

Ile Leu Met Lys Lys Ala Asp Glu Asn Asp Ile Arg Leu Pro Gly Glu
305                 310                 315                 320

```
Val Ala Phe Phe Ile Ala Lys Arg Leu Arg Ser Asn Val Arg Glu Leu
                325                 330                 335

Glu Gly Ala Leu Asn Arg Val Ile Ala Asn Ala Asn Phe Thr Gly Arg
            340                 345                 350

Ala Ile Thr Ile Asp Phe Val Arg Glu Ala Leu Arg Asp Leu Leu Ala
            355                 360                 365

Leu Gln Glu Lys Leu Val Thr Ile Asp Asn Ile Gln Lys Thr Val Ala
370                 375                 380

Glu Tyr Tyr Lys Ile Lys Val Ala Asp Leu Leu Ser Lys Arg Arg Ser
385                 390                 395                 400

Arg Ser Val Ala Arg Pro Arg Gln Met Ala Met Ala Leu Ala Lys Glu
                405                 410                 415

Leu Thr Asn His Ser Leu Pro Glu Ile Gly Asp Ala Phe Gly Gly Arg
                420                 425                 430

Asp His Thr Thr Val Leu His Ala Cys Arg Lys Ile Glu Gln Leu Arg
            435                 440                 445

Glu Glu Ser His Asp Ile Lys Glu Asp Phe Ser Asn Leu Ile Arg Thr
        450                 455                 460

Leu Ser Ser
465

<210> SEQ ID NO 102
<211> LENGTH: 440
<212> TYPE: PRT
<213> ORGANISM: Thermatoga maritima

<400> SEQUENCE: 102

Met Lys Glu Arg Ile Leu Gln Glu Ile Lys Thr Arg Val Asn Arg Lys
1               5                   10                  15

Ser Trp Glu Leu Trp Phe Ser Ser Phe Asp Val Lys Ser Ile Glu Gly
            20                  25                  30

Asn Lys Val Val Phe Ser Val Gly Asn Leu Phe Ile Lys Glu Trp Leu
        35                  40                  45

Glu Lys Lys Tyr Tyr Ser Val Leu Ser Lys Ala Val Lys Val Val Leu
    50                  55                  60

Gly Asn Asp Ala Thr Phe Glu Ile Thr Tyr Glu Ala Phe Glu Pro His
65                  70                  75                  80

Ser Ser Tyr Ser Glu Pro Leu Val Lys Arg Ala Val Leu Leu Thr
                85                  90                  95

Pro Leu Asn Pro Asp Tyr Thr Phe Glu Asn Phe Val Val Gly Pro Gly
            100                 105                 110

Asn Ser Phe Ala Tyr His Ala Ala Leu Glu Val Ala Lys His Pro Gly
        115                 120                 125

Arg Tyr Asn Pro Leu Phe Ile Tyr Gly Gly Val Gly Leu Gly Lys Thr
    130                 135                 140

His Leu Leu Gln Ser Ile Gly Asn Tyr Val Val Gln Asn Glu Pro Asp
145                 150                 155                 160

Leu Arg Val Met Tyr Ile Thr Ser Glu Lys Phe Leu Asn Asp Leu Val
                165                 170                 175

Asp Ser Met Lys Glu Gly Lys Leu Asn Glu Phe Arg Glu Lys Tyr Arg
            180                 185                 190

Lys Lys Val Asp Ile Leu Leu Ile Asp Asp Val Gln Phe Leu Ile Gly
        195                 200                 205

Lys Thr Gly Val Gln Thr Glu Leu Phe His Thr Phe Asn Glu Leu His
    210                 215                 220
```

```
Asp Ser Gly Lys Gln Ile Val Ile Cys Ser Asp Arg Glu Pro Gln Lys
225                 230                 235                 240

Leu Ser Glu Phe Gln Asp Arg Leu Val Ser Arg Phe Gln Met Gly Leu
            245                 250                 255

Val Ala Lys Leu Glu Pro Pro Asp Glu Thr Arg Lys Ser Ile Ala
        260                 265                 270

Arg Lys Met Leu Glu Ile Glu His Gly Glu Leu Pro Glu Glu Val Leu
        275                 280                 285

Asn Phe Val Ala Glu Asn Val Asp Asp Asn Leu Arg Arg Leu Arg Gly
        290                 295                 300

Ala Ile Ile Lys Leu Leu Val Tyr Lys Glu Thr Thr Gly Lys Glu Val
305                 310                 315                 320

Asp Leu Lys Glu Ala Ile Leu Leu Lys Asp Phe Ile Lys Pro Asn
        325                 330                 335

Arg Val Lys Ala Met Asp Pro Ile Asp Glu Leu Ile Glu Ile Val Ala
        340                 345                 350

Lys Val Thr Gly Val Pro Arg Glu Glu Ile Leu Ser Asn Ser Arg Asn
        355                 360                 365

Val Lys Ala Leu Thr Ala Arg Arg Ile Gly Met Tyr Val Ala Lys Asn
        370                 375                 380

Tyr Leu Lys Ser Ser Leu Arg Thr Ile Ala Glu Lys Phe Asn Arg Ser
385                 390                 395                 400

His Pro Val Val Val Asp Ser Val Lys Val Lys Asp Ser Leu Leu
        405                 410                 415

Lys Gly Asn Lys Gln Leu Lys Ala Leu Ile Asp Glu Val Ile Gly Glu
        420                 425                 430

Ile Ser Arg Arg Ala Leu Ser Gly
        435                 440

<210> SEQ ID NO 103
<211> LENGTH: 457
<212> TYPE: PRT
<213> ORGANISM: Helicobacter pylori

<400> SEQUENCE: 103

Met Asp Thr Asn Asn Asn Ile Glu Lys Glu Ile Leu Ala Leu Val Lys
1               5                   10                  15

Gln Asn Pro Lys Val Ser Leu Ile Glu Tyr Glu Asn Tyr Phe Ser Gln
            20                  25                  30

Leu Lys Tyr Asn Pro Asn Ala Ser Lys Ser Asp Ile Ala Phe Phe Tyr
        35                  40                  45

Ala Pro Asn Gln Val Leu Cys Thr Thr Ile Thr Ala Lys Tyr Gly Ala
    50                  55                  60

Leu Leu Lys Glu Ile Leu Ser Gln Asn Lys Val Gly Met His Leu Ala
65                  70                  75                  80

His Ser Val Asp Val Arg Ile Glu Val Ala Pro Lys Ile Gln Ile Asn
                85                  90                  95

Ala Gln Ser Asn Ile Asn Tyr Lys Ala Ile Lys Thr Ser Val Lys Asp
            100                 105                 110

Ser Tyr Thr Phe Glu Asn Phe Val Val Gly Ser Cys Asn Asn Thr Val
        115                 120                 125

Tyr Glu Ile Ala Lys Lys Val Ala Gln Ser Asp Thr Pro Tyr Asn
    130                 135                 140

Pro Val Leu Phe Tyr Gly Gly Thr Gly Leu Gly Lys Thr His Ile Leu
145                 150                 155                 160
```

```
Asn Ala Ile Gly Asn His Ala Leu Glu Lys His Lys Lys Val Val Leu
                165                 170                 175

Val Thr Ser Glu Asp Phe Leu Thr Asp Phe Leu Lys His Leu Asp Asn
            180                 185                 190

Lys Thr Met Asp Ser Phe Lys Ala Lys Tyr Arg His Cys Asp Phe Phe
        195                 200                 205

Leu Leu Asp Asp Ala Gln Phe Leu Gln Gly Lys Pro Lys Leu Glu Glu
    210                 215                 220

Glu Phe Phe His Thr Phe Asn Glu Leu His Ala Asn Ser Lys Gln Ile
225                 230                 235                 240

Val Leu Ile Ser Asp Arg Ser Pro Lys Asn Ile Ala Gly Leu Glu Asp
                245                 250                 255

Arg Leu Lys Ser Arg Phe Glu Trp Gly Ile Thr Ala Lys Val Met Pro
            260                 265                 270

Pro Asp Leu Glu Thr Lys Leu Ser Ile Val Lys Gln Lys Cys Gln Leu
        275                 280                 285

Asn Gln Ile Thr Leu Pro Glu Glu Val Met Glu Tyr Ile Ala Gln His
    290                 295                 300

Ile Ser Asp Asn Ile Arg Gln Met Glu Gly Ala Ile Ile Lys Ile Ser
305                 310                 315                 320

Val Asn Ala Asn Leu Met Asn Ala Ser Ile Asp Leu Asn Leu Ala Lys
                325                 330                 335

Thr Val Leu Glu Asp Leu Gln Lys Asp His Ala Glu Gly Ser Ser Leu
            340                 345                 350

Glu Asn Ile Leu Leu Ala Val Ala Gln Ser Leu Asn Leu Lys Ser Ser
        355                 360                 365

Glu Ile Lys Val Ser Ser Arg Gln Lys Asn Val Ala Leu Ala Arg Lys
    370                 375                 380

Leu Val Val Tyr Phe Ala Arg Leu Tyr Thr Pro Asn Pro Thr Leu Ser
385                 390                 395                 400

Leu Ala Gln Phe Leu Asp Leu Lys Asp His Ser Ser Ile Ser Lys Met
                405                 410                 415

Tyr Ser Gly Val Lys Lys Met Leu Glu Glu Lys Ser Pro Phe Val
            420                 425                 430

Leu Ser Leu Arg Glu Glu Ile Lys Asn Arg Leu Asn Glu Leu Asn Asp
        435                 440                 445

Lys Lys Thr Ala Phe Asn Ser Ser Glu
    450                 455

<210> SEQ ID NO 104
<211> LENGTH: 1305
<212> TYPE: DNA
<213> ORGANISM: Thermus thermophilus

<400> SEQUENCE: 104
gtgtcgcacg aggccgtctg gcaacacgtt ctggagcaca tccgccgcag catcaccgag    60
gtggagttcc acacctggtt tgaaaggatc cgccccttgg ggatccggga cggggtgctg   120
gagctcgccg tgcccacctc ctttgccctg actggatccg gcgccactac gccggcctc    180 atccaggagg gccctcggct cctcggggcc caggcgcccc ggtttgagct ccgggtggtg   240
ccgggggtcg tagtccagga ggacatcttc cagccccgc cgagcccccc ggcccaagct    300
caacccgaag ataccttaa aacttcgtgg tgggccccaa caactccatg gccccacggc    360
ggcgccgtgg ccgtggccga gtccccccggc cgggcctaca ccccctctct catctacggg   420
```

```
ggccgtggcc tgggaaagac ctacctgatg cacgccgtgg gcccactccg tgcgaagcgc    480
ttcccccaca tgagattaga gtacgtttcc acggaaactt tcaccaacga gctcatcaac    540
cggccatccg cgagggaccg gatgacggag ttccgggagc ggtaccgctc cgtggacctc    600
ctgctggtgg acgacgtcca gttcatcgcc ggaaaggagc gcacccagga ggagtttttc    660
cacaccttca cgcccttta cgaggccac aagcagatca tcctctcctc cgaccggccg      720
cccaaggaca tcctcaccct ggaggcgcgc tgcgggagcc gctttgagtg gggcctgatc    780
accgacaatc cagcccccga cctggaaacc cggatcgcca tcctgaagat gaacgccagc    840
agcgggcctg aggatcccga ggacgccctg gagtacatcg cccggcaggt cacctccaac    900
atccgggagt gggaaggggc cctcatgcgg gcatcgcctt cgcctccct caacggcgtt     960 gagctgaccc cgccgtggc ggccaaggct ctccgacatc ttcgcccag ggagctggag     1020 gcggacccct tggagatcat ccgcaaagcg gcgggaccag ttcggcctga aaccccggga   1080
ggagctcacg gggagcgccg caagaaggag gtggtcctcc cccggcagct cgccatgtac   1140
ctggtgcggg agctcacccc ggcctccctg cccgagatcg accagctcaa cgacgaccgg   1200
gaccacacca cggtcctcta cgccatccag aaggtccagg agctcgcgga aagcgaccgg   1260
gaggtgcagg gcctcctccg caccctccgg gaggcgtgca catga                   1305
```

<210> SEQ ID NO 105
<211> LENGTH: 434
<212> TYPE: PRT
<213> ORGANISM: Thermus thermophilus

<400> SEQUENCE: 105

```
Val Ser His Glu Ala Val Trp Gln His Val Leu Glu His Ile Arg Arg
  1               5                  10                  15

Ser Ile Thr Glu Val Glu Phe His Thr Trp Phe Glu Arg Ile Arg Pro
             20                  25                  30

Leu Gly Ile Arg Asp Gly Val Leu Glu Leu Ala Val Pro Thr Ser Phe
         35                  40                  45

Ala Leu Asp Trp Ile Arg Arg His Tyr Ala Gly Leu Ile Gln Glu Gly
     50                  55                  60

Pro Arg Leu Leu Gly Ala Gln Ala Pro Arg Phe Glu Leu Arg Val Val
 65                  70                  75                  80

Pro Gly Val Val Val Gln Glu Asp Ile Phe Gln Pro Pro Ser Pro
                 85                  90                  95

Pro Ala Gln Ala Gln Pro Glu Asp Thr Phe Lys Thr Ser Trp Trp Gly
            100                 105                 110

Pro Thr Thr Pro Trp Pro His Gly Gly Ala Val Ala Val Ala Glu Ser
        115                 120                 125

Pro Gly Arg Ala Tyr Asn Pro Leu Phe Ile Tyr Gly Gly Arg Gly Leu
    130                 135                 140

Gly Lys Thr Tyr Leu Met His Ala Val Gly Pro Leu Arg Ala Lys Arg
145                 150                 155                 160

Phe Pro His Met Arg Leu Glu Tyr Val Ser Thr Glu Thr Phe Thr Asn
                165                 170                 175

Glu Leu Ile Asn Arg Pro Ser Ala Arg Asp Arg Met Thr Glu Phe Arg
            180                 185                 190

Glu Arg Tyr Arg Ser Val Asp Leu Leu Leu Val Asp Asp Val Gln Phe
        195                 200                 205

Ile Ala Gly Lys Glu Arg Thr Gln Glu Glu Phe Phe His Thr Phe Asn
    210                 215                 220
```

```
Ala Leu Tyr Glu Ala His Lys Gln Ile Ile Leu Ser Ser Asp Arg Pro
225                 230                 235                 240

Pro Lys Asp Ile Leu Thr Leu Glu Ala Arg Leu Arg Ser Arg Phe Glu
                245                 250                 255

Trp Gly Leu Ile Thr Asp Asn Pro Ala Pro Asp Leu Glu Thr Arg Ile
            260                 265                 270

Ala Ile Leu Lys Met Asn Ala Ser Ser Gly Pro Glu Asp Pro Glu Asp
        275                 280                 285

Ala Leu Glu Tyr Ile Ala Arg Gln Val Thr Ser Asn Ile Arg Glu Trp
    290                 295                 300

Glu Gly Ala Leu Met Arg Ala Ser Pro Phe Ala Ser Leu Asn Gly Val
305                 310                 315                 320

Glu Leu Thr Arg Ala Val Ala Ala Lys Ala Leu Arg His Leu Arg Pro
                325                 330                 335

Arg Glu Leu Glu Ala Asp Pro Leu Glu Ile Ile Arg Lys Ala Ala Gly
            340                 345                 350

Pro Val Arg Pro Glu Thr Pro Gly Gly Ala His Gly Glu Arg Arg Lys
        355                 360                 365

Lys Glu Val Val Leu Pro Arg Gln Leu Ala Met Tyr Leu Val Arg Glu
    370                 375                 380

Leu Thr Pro Ala Ser Leu Pro Glu Ile Asp Gln Leu Asn Asp Asp Arg
385                 390                 395                 400

Asp His Thr Thr Val Leu Tyr Ala Ile Gln Lys Val Gln Glu Leu Ala
                405                 410                 415

Glu Ser Asp Arg Glu Val Gln Gly Leu Leu Arg Thr Leu Arg Glu Ala
            420                 425                 430

Cys Thr

<210> SEQ ID NO 106
<211> LENGTH: 1128
<212> TYPE: DNA
<213> ORGANISM: Thermus thermophilus

<400> SEQUENCE: 106
atgaacataa cggttcccaa aaaactcctc tcggaccagc tttccctcct ggagcgcatc      60
gtcccctcta gaagcgccaa ccccctctac acctacctgg ggctttacgc cgaggaaggg     120
gccttgatcc tcttcgggac caacggggag gtggacctcg aggtccgcct ccccgccgag     180
gcccaaagcc ttccccgggt gctcgtcccc gcccagccct tcttccagct ggtgcggagc     240
cttcctgggg acctcgtggc cctcggcctc gcctcggagc cgggccaggg ggggcagctg     300
gagctctcct ccgggcgttt ccgcacccgg ctcagcctgg ccctgccga gggctacccc     360 gagcttctgg tgcccgaggg ggaggacaag ggggccttcc ccctccggac gcggatgccc     420
tccggggagc tcgtcaaggc cttgacccac gtgcgctacg ccgcgagcaa cgaggagtac     480
cgggccatct ccgcggggt gcagctggag ttctcccccc agggcttccg gcggtggcc     540 tccgacgggt accgcctcgc cctctacgac ctgcccctgc ccaagggtt ccaggccaag     600 gccgtggtcc ccgccggag cgtggacgag atggtgcggg tcctgaaggg gcggacggg     660 gccgaggccg tcctcgccct gggcgagggg gtgttggccc tgcccctcga gggcggaagc     720
ggggtccgga tgcccctccg cctcatggaa ggggagttcc ccgactacca gagggtcatc     780
ccccaggagt cgccctcaa ggtccaggtg gaggggagg ccctcaggga ggcggtgcgc     840
cgggtgagcg tcctctccga ccggcagaac accgggtgg acctcctttt ggaggaaggc     900
```

```
cggatcctcc tctccgccga gggggactac ggcaaggggc aggaggaggt gcccgcccag    960 gtggagggc  cggacatggc cgtggcctac aacgcccgct acctcctcga ggccctcgcc   1020
cccgtggggg accggcccca cctgggcatc tccgggccca cgagcccgag cctcatctgg   1080
ggggacgggg aggggtaccg ggcggtggtg gtgcccctca gggtctag              1128
```

<210> SEQ ID NO 107
<211> LENGTH: 376
<212> TYPE: PRT
<213> ORGANISM: Thermus thermophilus

<400> SEQUENCE: 107

```
Met Asn Ile Thr Val Pro Lys Lys Leu Leu Ser Asp Gln Leu Ser Leu
 1               5                  10                  15

Leu Glu Arg Ile Val Pro Ser Arg Ser Ala Asn Pro Leu Tyr Thr Tyr
                20                  25                  30

Leu Gly Leu Tyr Ala Glu Glu Gly Ala Leu Ile Leu Phe Gly Thr Asn
            35                  40                  45

Gly Glu Val Asp Leu Glu Val Arg Leu Pro Ala Glu Ala Gln Ser Leu
    50                  55                  60

Pro Arg Val Leu Val Pro Ala Gln Pro Phe Phe Gln Leu Val Arg Ser
65                  70                  75                  80

Leu Pro Gly Asp Leu Val Ala Leu Gly Leu Ala Ser Glu Pro Gly Gln
                85                  90                  95

Gly Gly Gln Leu Glu Leu Ser Ser Gly Arg Phe Arg Thr Arg Leu Ser
            100                 105                 110

Leu Ala Pro Ala Glu Gly Tyr Pro Glu Leu Leu Val Pro Glu Gly Glu
        115                 120                 125

Asp Lys Gly Ala Phe Pro Leu Arg Thr Arg Met Pro Ser Gly Glu Leu
    130                 135                 140

Val Lys Ala Leu Thr His Val Arg Tyr Ala Ala Ser Asn Glu Glu Tyr
145                 150                 155                 160

Arg Ala Ile Phe Arg Gly Val Gln Leu Glu Phe Ser Pro Gln Gly Phe
                165                 170                 175

Arg Ala Val Ala Ser Asp Gly Tyr Arg Leu Ala Leu Tyr Asp Leu Pro
            180                 185                 190

Leu Pro Gln Gly Phe Gln Ala Lys Ala Val Val Pro Ala Arg Ser Val
        195                 200                 205

Asp Glu Met Val Arg Val Leu Lys Gly Ala Asp Gly Ala Glu Ala Val
    210                 215                 220

Leu Ala Leu Gly Glu Gly Val Leu Ala Leu Ala Leu Glu Gly Gly Ser
225                 230                 235                 240

Gly Val Arg Met Ala Leu Arg Leu Met Glu Gly Phe Pro Asp Tyr
                245                 250                 255

Gln Arg Val Ile Pro Gln Glu Phe Ala Leu Lys Val Gln Val Glu Gly
            260                 265                 270

Glu Ala Leu Arg Glu Ala Val Arg Arg Val Ser Val Leu Ser Asp Arg
        275                 280                 285

Gln Asn His Arg Val Asp Leu Leu Leu Glu Glu Gly Arg Ile Leu Leu
    290                 295                 300

Ser Ala Glu Gly Asp Tyr Gly Lys Gly Gln Glu Glu Val Pro Ala Gln
305                 310                 315                 320

Val Glu Gly Pro Asp Met Ala Val Ala Tyr Asn Ala Arg Tyr Leu Leu
                325                 330                 335
```

```
Glu Ala Leu Ala Pro Val Gly Asp Arg Ala His Leu Gly Ile Ser Gly
            340                 345                 350

Pro Thr Ser Pro Ser Leu Ile Trp Gly Asp Gly Gly Tyr Arg Ala
        355                 360                 365

Val Val Val Pro Leu Arg Val Glx
    370                 375

<210> SEQ ID NO 108
<211> LENGTH: 376
<212> TYPE: PRT
<213> ORGANISM: Thermus thermophilus

<400> SEQUENCE: 108

Met Asn Ile Thr Val Pro Lys Lys Leu Leu Ser Asp Gln Leu Ser Leu
  1               5                  10                  15

Leu Glu Arg Ile Val Pro Ser Arg Ser Ala Asn Pro Leu Tyr Thr Tyr
                 20                  25                  30

Leu Gly Leu Tyr Ala Glu Gly Ala Leu Ile Leu Phe Gly Thr Asn
             35                  40                  45

Gly Glu Val Asp Leu Glu Val Arg Leu Pro Ala Glu Ala Gln Ser Leu
 50                  55                  60

Pro Arg Val Leu Val Pro Ala Gln Pro Phe Phe Gln Leu Val Arg Ser
 65                  70                  75                  80

Leu Pro Gly Asp Leu Val Ala Leu Gly Leu Ala Ser Glu Pro Gly Gln
                 85                  90                  95

Gly Gly Gln Leu Glu Leu Ser Ser Gly Arg Phe Arg Thr Arg Leu Ser
            100                 105                 110

Leu Ala Pro Ala Glu Gly Tyr Pro Glu Leu Leu Val Pro Glu Gly Glu
            115                 120                 125

Asp Lys Gly Ala Phe Pro Leu Arg Thr Arg Met Pro Ser Gly Glu Leu
130                 135                 140

Val Lys Ala Leu Thr His Val Arg Tyr Ala Ala Ser Asn Glu Glu Tyr
145                 150                 155                 160

Arg Ala Ile Phe Arg Gly Val Gln Leu Glu Phe Ser Pro Gln Gly Phe
                165                 170                 175

Arg Ala Val Ala Ser Asp Gly Tyr Arg Leu Ala Leu Tyr Asp Leu Pro
            180                 185                 190

Leu Pro Gln Gly Phe Gln Ala Lys Ala Val Val Pro Ala Arg Ser Val
            195                 200                 205

Asp Glu Met Val Arg Val Leu Lys Gly Ala Asp Gly Ala Glu Ala Val
210                 215                 220

Leu Ala Leu Gly Glu Gly Val Leu Ala Leu Ala Leu Glu Gly Gly Ser
225                 230                 235                 240

Gly Val Arg Met Ala Leu Arg Leu Met Glu Gly Glu Phe Pro Asp Tyr
                245                 250                 255

Gln Arg Val Ile Pro Gln Glu Phe Ala Leu Lys Val Gln Val Glu Gly
            260                 265                 270

Glu Ala Leu Arg Glu Ala Val Arg Arg Val Ser Val Leu Ser Asp Arg
            275                 280                 285

Gln Asn His Arg Val Asp Leu Leu Glu Glu Gly Arg Ile Leu Leu
290                 295                 300

Ser Ala Glu Gly Asp Tyr Gly Lys Gly Gln Glu Glu Val Pro Ala Gln
305                 310                 315                 320

Val Glu Gly Pro Asp Met Ala Val Ala Tyr Asn Ala Arg Tyr Leu Leu
                325                 330                 335
```

```
Glu Ala Leu Ala Pro Val Gly Asp Arg Ala His Leu Gly Ile Ser Gly
            340                 345                 350

Pro Thr Ser Pro Ser Leu Ile Trp Gly Asp Gly Gly Tyr Arg Ala
            355                 360                 365

Val Val Val Pro Leu Arg Val Glx
            370             375

<210> SEQ ID NO 109
<211> LENGTH: 367
<212> TYPE: PRT
<213> ORGANISM: Escherichia coli

<400> SEQUENCE: 109

Met Lys Phe Thr Val Glu Arg Glu His Leu Leu Lys Pro Leu Gln Gln
  1               5                  10                  15

Val Ser Gly Pro Leu Gly Gly Arg Pro Thr Leu Pro Ile Leu Gly Asn
                 20                  25                  30

Leu Leu Leu Gln Val Ala Asp Gly Thr Leu Ser Leu Thr Gly Thr Asp
             35                  40                  45

Leu Glu Met Glu Met Val Ala Arg Val Ala Leu Val Gln Pro His Glu
         50                  55                  60

Pro Gly Ala Thr Thr Val Pro Ala Arg Lys Phe Phe Asp Ile Cys Arg
 65                  70                  75                  80

Gly Leu Pro Glu Gly Ala Glu Ile Ala Val Gln Leu Glu Gly Glu Arg
                 85                  90                  95

Met Leu Val Arg Ser Gly Arg Ser Arg Phe Ser Leu Ser Thr Leu Pro
            100                 105                 110

Ala Ala Asp Phe Pro Asn Leu Asp Asp Trp Gln Ser Glu Val Glu Phe
        115                 120                 125

Thr Leu Pro Gln Ala Thr Met Lys Arg Leu Ile Glu Ala Thr Gln Phe
    130                 135                 140

Ser Met Ala His Gln Asp Val Arg Tyr Tyr Leu Asn Gly Met Leu Phe
145                 150                 155                 160

Glu Thr Glu Gly Glu Glu Leu Arg Thr Val Ala Thr Asp Gly His Arg
                165                 170                 175

Leu Ala Val Cys Ser Met Pro Ile Gly Gln Ser Leu Pro Ser His Ser
            180                 185                 190

Val Ile Val Pro Arg Lys Gly Val Ile Glu Leu Met Arg Met Leu Asp
        195                 200                 205

Gly Gly Asp Asn Pro Leu Arg Val Gln Ile Gly Ser Asn Asn Ile Arg
    210                 215                 220

Ala His Val Gly Asp Phe Ile Phe Thr Ser Lys Leu Val Asp Gly Arg
225                 230                 235                 240

Phe Pro Asp Tyr Arg Arg Val Leu Pro Lys Asn Pro Asp Lys His Leu
                245                 250                 255

Glu Ala Gly Cys Asp Leu Leu Lys Gln Ala Phe Ala Arg Ala Ala Ile
            260                 265                 270

Leu Ser Asn Glu Lys Phe Arg Gly Val Arg Leu Tyr Val Ser Glu Asn
        275                 280                 285

Gln Leu Lys Ile Thr Ala Asn Asn Pro Glu Gln Glu Glu Ala Glu Glu
    290                 295                 300

Ile Leu Asp Val Thr Tyr Ser Gly Ala Glu Met Glu Ile Gly Phe Asn
305                 310                 315                 320

Val Ser Tyr Val Leu Asp Val Leu Asn Ala Leu Lys Cys Glu Asn Val
                325                 330                 335
```

```
Arg Met Met Leu Thr Asp Ser Val Ser Ser Val Gln Ile Glu Asp Ala
                340                 345                 350

Ala Ser Gln Ser Ala Ala Tyr Val Val Met Pro Met Arg Leu Glx
            355                 360                 365

<210> SEQ ID NO 110
<211> LENGTH: 367
<212> TYPE: PRT
<213> ORGANISM: Proteus mirabilis

<400> SEQUENCE: 110

Met Lys Phe Ile Ile Glu Arg Glu Gln Leu Leu Lys Pro Leu Gln Gln
 1               5                  10                  15

Val Ser Gly Pro Leu Gly Gly Arg Pro Thr Leu Pro Ile Leu Gly Asn
                20                  25                  30

Leu Leu Leu Lys Val Thr Glu Asn Thr Leu Ser Leu Thr Gly Thr Asp
            35                  40                  45

Leu Glu Met Glu Met Met Ala Arg Val Ser Leu Ser Gln Ser His Glu
        50                  55                  60

Ile Gly Ala Thr Thr Val Pro Ala Arg Lys Phe Phe Asp Ile Trp Arg
 65                  70                  75                  80

Gly Leu Pro Glu Gly Ala Glu Ile Ser Val Glu Leu Asp Gly Asp Arg
                85                  90                  95

Leu Leu Val Arg Ser Gly Arg Ser Arg Phe Ser Leu Ser Thr Leu Pro
               100                 105                 110

Ala Ser Asp Phe Pro Asn Leu Asp Asp Trp Gln Ser Glu Val Glu Phe
            115                 120                 125

Thr Leu Pro Gln Ala Thr Leu Lys Arg Leu Ile Glu Ser Thr Gln Phe
        130                 135                 140

Ser Met Ala His Gln Asp Val Arg Tyr Tyr Leu Asn Gly Met Leu Phe
145                 150                 155                 160

Glu Thr Glu Asn Thr Glu Leu Arg Thr Val Ala Thr Asp Gly His Arg
                165                 170                 175

Leu Ala Val Cys Ala Met Asp Ile Gly Gln Ser Leu Pro Gly His Ser
            180                 185                 190

Val Ile Val Pro Arg Lys Gly Val Ile Glu Leu Met Arg Leu Leu Asp
        195                 200                 205

Gly Ser Gly Glu Ser Leu Leu Gln Leu Gln Ile Gly Ser Asn Asn Leu
    210                 215                 220

Arg Ala His Val Gly Asp Phe Ile Phe Thr Ser Lys Leu Val Asp Gly
225                 230                 235                 240

Arg Phe Pro Asp Tyr Arg Arg Val Leu Pro Lys Asn Pro Thr Lys Thr
                245                 250                 255

Val Ile Ala Gly Cys Asp Ile Leu Lys Gln Ala Phe Ser Arg Ala Ala
            260                 265                 270

Ile Leu Ser Asn Glu Lys Phe Arg Gly Val Arg Ile Asn Leu Thr Asn
        275                 280                 285

Gly Gln Leu Lys Ile Thr Ala Asn Asn Pro Glu Gln Glu Glu Ala Glu
    290                 295                 300

Glu Ile Val Asp Val Gln Tyr Gln Gly Glu Glu Met Glu Ile Gly Phe
305                 310                 315                 320

Asn Val Ser Tyr Leu Leu Asp Val Leu Asn Thr Leu Lys Cys Glu Glu
                325                 330                 335
```

```
Val Lys Leu Leu Leu Thr Asp Ala Val Ser Ser Val Gln Val Glu Asn
                340                 345                 350

Val Ala Ser Ala Ala Ala Ala Tyr Val Val Met Pro Met Arg Leu
            355                 360                 365

<210> SEQ ID NO 111
<211> LENGTH: 366
<212> TYPE: PRT
<213> ORGANISM: Haemophilus influenzae

<400> SEQUENCE: 111

Met Gln Phe Ser Ile Ser Arg Glu Asn Leu Leu Lys Pro Leu Gln Gln
  1               5                  10                  15

Val Cys Gly Val Leu Ser Asn Arg Pro Asn Ile Pro Val Leu Asn Asn
                 20                  25                  30

Val Leu Leu Gln Ile Glu Asp Tyr Arg Leu Thr Ile Thr Gly Thr Asp
             35                  40                  45

Leu Glu Val Glu Leu Ser Ser Gln Thr Gln Leu Ser Ser Ser Ser Glu
 50                  55                  60

Asn Gly Thr Phe Thr Ile Pro Ala Lys Lys Phe Leu Asp Ile Cys Arg
 65                  70                  75                  80

Thr Leu Ser Asp Asp Ser Glu Ile Thr Val Thr Phe Glu Gln Asp Arg
                 85                  90                  95

Ala Leu Val Gln Ser Gly Arg Ser Arg Phe Thr Leu Ala Thr Gln Pro
            100                 105                 110

Ala Glu Glu Tyr Pro Asn Leu Thr Asp Trp Gln Ser Glu Val Asp Phe
        115                 120                 125

Glu Leu Pro Gln Asn Thr Leu Arg Arg Leu Ile Glu Ala Thr Gln Phe
130                 135                 140

Ser Met Ala Asn Gln Asp Ala Arg Tyr Phe Leu Asn Gly Met Lys Phe
145                 150                 155                 160

Glu Thr Glu Gly Asn Leu Leu Arg Thr Val Ala Thr Asp Gly His Arg
                165                 170                 175

Leu Ala Val Cys Thr Ile Ser Leu Glu Gln Glu Leu Gln Asn His Ser
            180                 185                 190

Val Ile Leu Pro Arg Lys Gly Val Leu Glu Leu Val Arg Leu Leu Glu
        195                 200                 205

Thr Asn Asp Glu Pro Ala Arg Leu Gln Ile Gly Thr Asn Asn Leu Arg
    210                 215                 220

Val His Leu Lys Asn Thr Val Phe Thr Ser Lys Leu Ile Asp Gly Arg
225                 230                 235                 240

Phe Pro Asp Tyr Arg Arg Val Leu Pro Arg Asn Ala Thr Lys Ile Val
                245                 250                 255

Glu Gly Asn Trp Glu Met Leu Lys Gln Ala Phe Ala Arg Ala Ser Ile
            260                 265                 270

Leu Ser Asn Glu Arg Ala Arg Ser Val Arg Leu Ser Leu Lys Glu Asn
        275                 280                 285

Gln Leu Lys Ile Thr Ala Ser Asn Thr Glu His Glu Glu Ala Glu Glu
    290                 295                 300

Ile Val Asp Val Asn Tyr Asn Gly Glu Glu Leu Glu Val Gly Phe Asn
305                 310                 315                 320

Val Thr Tyr Ile Leu Asp Val Leu Asn Ala Leu Lys Cys Asn Gln Val
                325                 330                 335
```

```
Arg Met Cys Leu Thr Asp Ala Phe Ser Ser Cys Leu Ile Glu Asn Cys
            340                 345                 350

Glu Asp Ser Ser Cys Glu Tyr Val Ile Met Pro Met Arg Leu
            355                 360                 365

<210> SEQ ID NO 112
<211> LENGTH: 367
<212> TYPE: PRT
<213> ORGANISM: Pseudomonas putida

<400> SEQUENCE: 112

Met His Phe Thr Ile Gln Arg Glu Ala Leu Leu Lys Pro Leu Gln Leu
  1               5                  10                  15

Val Ala Gly Val Val Glu Arg Arg Gln Thr Leu Pro Val Leu Ser Asn
             20                  25                  30

Val Leu Leu Val Val Gln Gly Gln Leu Ser Leu Thr Gly Thr Asp
         35                  40                  45

Leu Glu Val Glu Leu Val Gly Arg Val Gln Leu Glu Glu Pro Ala Glu
 50                  55                  60

Pro Gly Glu Ile Thr Val Pro Ala Arg Lys Leu Met Asp Ile Cys Lys
 65                  70                  75                  80

Ser Leu Pro Asn Asp Ala Leu Ile Asp Ile Lys Val Asp Glu Gln Lys
             85                  90                  95

Leu Leu Val Lys Ala Gly Arg Ser Arg Phe Thr Leu Ser Thr Leu Pro
            100                 105                 110

Ala Asn Asp Phe Pro Thr Val Glu Glu Gly Pro Gly Ser Leu Thr Cys
            115                 120                 125

Asn Leu Glu Gln Ser Lys Leu Arg Arg Leu Ile Glu Arg Thr Ser Phe
130                 135                 140

Ala Met Ala Gln Gln Asp Val Arg Tyr Tyr Leu Asn Gly Met Leu Leu
145                 150                 155                 160

Glu Val Ser Arg Asn Thr Leu Arg Ala Val Ser Thr Asp Gly His Arg
                165                 170                 175

Leu Ala Leu Cys Ser Met Ser Ala Pro Ile Glu Gln Glu Asp Arg His
            180                 185                 190

Gln Val Ile Val Pro Arg Lys Gly Ile Leu Glu Leu Ala Arg Leu Leu
        195                 200                 205

Thr Asp Pro Glu Gly Met Val Ser Ile Val Leu Gly Gln His His Ile
210                 215                 220

Arg Ala Thr Thr Gly Glu Phe Thr Phe Thr Ser Lys Leu Val Asp Gly
225                 230                 235                 240

Lys Phe Pro Asp Tyr Glu Arg Val Leu Pro Lys Gly Gly Asp Lys Leu
                245                 250                 255

Val Val Gly Asp Arg Gln Ala Leu Arg Glu Ala Phe Ser Arg Thr Ala
            260                 265                 270

Ile Leu Ser Asn Glu Lys Tyr Arg Gly Ile Arg Leu Gln Leu Ala Ala
            275                 280                 285

Gly Gln Leu Lys Ile Gln Ala Asn Asn Pro Glu Gln Glu Glu Ala Glu
        290                 295                 300

Glu Glu Ile Ser Val Asp Tyr Glu Gly Ser Ser Leu Glu Ile Gly Phe
305                 310                 315                 320

Asn Val Ser Tyr Leu Leu Asp Val Leu Gly Val Met Thr Thr Glu Gln
                325                 330                 335
```

```
Val Arg Leu Ile Leu Ser Asp Ser Asn Ser Ser Ala Leu Leu Gln Glu
            340                 345                 350

Ala Gly Asn Asp Asp Ser Ser Tyr Val Val Met Pro Met Arg Leu
            355                 360                 365

<210> SEQ ID NO 113
<211> LENGTH: 366
<212> TYPE: PRT
<213> ORGANISM: Buchnera aphidicola

<400> SEQUENCE: 113

Met Lys Phe Thr Ile Gln Asn Asp Ile Leu Thr Lys Asn Leu Lys Lys
  1               5                  10                  15

Ile Thr Arg Val Leu Val Lys Asn Ile Ser Phe Pro Ile Leu Glu Asn
             20                  25                  30

Ile Leu Ile Gln Val Glu Asp Gly Thr Leu Ser Leu Thr Thr Thr Asn
             35                  40                  45

Leu Glu Ile Glu Leu Ile Ser Lys Ile Glu Ile Ile Thr Lys Tyr Ile
 50                  55                  60

Pro Gly Lys Thr Thr Ile Ser Gly Arg Lys Ile Leu Asn Ile Cys Arg
 65                  70                  75                  80

Thr Leu Ser Glu Lys Ser Lys Ile Lys Met Gln Leu Lys Asn Lys Lys
                 85                  90                  95

Met Tyr Ile Ser Ser Glu Asn Ser Asn Tyr Ile Leu Ser Thr Leu Ser
            100                 105                 110

Ala Asp Thr Phe Pro Asn His Gln Asn Phe Asp Tyr Ile Ser Lys Phe
            115                 120                 125

Asp Ile Ser Ser Asn Ile Leu Lys Glu Met Ile Glu Lys Thr Glu Phe
130                 135                 140

Ser Met Gly Lys Gln Asp Val Arg Tyr Tyr Leu Asn Gly Met Leu Leu
145                 150                 155                 160

Glu Lys Lys Asp Lys Phe Leu Arg Ser Val Ala Thr Asp Gly Tyr Arg
                165                 170                 175

Leu Ala Ile Ser Tyr Thr Gln Leu Lys Lys Asp Ile Asn Phe Phe Ser
            180                 185                 190

Ile Ile Ile Pro Asn Lys Ala Val Met Glu Leu Leu Lys Leu Leu Asn
            195                 200                 205

Thr Gln Pro Gln Leu Leu Asn Ile Leu Ile Gly Ser Asn Ser Ile Arg
210                 215                 220

Ile Tyr Thr Lys Asn Leu Ile Phe Thr Thr Gln Leu Ile Glu Gly Glu
225                 230                 235                 240

Tyr Pro Asp Tyr Lys Ser Val Leu Phe Lys Glu Lys Asn Pro Ile
                245                 250                 255

Ile Thr Asn Ser Ile Leu Leu Lys Lys Ser Leu Leu Arg Val Ala Ile
            260                 265                 270

Leu Ala His Glu Lys Phe Cys Gly Ile Glu Ile Lys Ile Glu Asn Gly
            275                 280                 285

Lys Phe Lys Val Leu Ser Asp Asn Gln Glu Glu Thr Ala Glu Asp
290                 295                 300

Leu Phe Glu Ile Asp Tyr Phe Gly Glu Lys Ile Glu Ile Ser Ile Asn
305                 310                 315                 320

Val Tyr Tyr Leu Leu Asp Val Ile Asn Asn Ile Lys Ser Glu Asn Ile
                325                 330                 335
```

```
Ala Leu Phe Leu Asn Lys Ser Lys Ser Ser Ile Gln Ile Glu Ala Glu
            340                 345                 350

Asn Asn Ser Ser Asn Ala Tyr Val Val Met Leu Leu Lys Arg
            355                 360                 365

<210> SEQ ID NO 114
<211> LENGTH: 39
<212> TYPE: DNA
<213> ORGANISM: Artificial Sequence
<220> FEATURE:
<223> OTHER INFORMATION: Description of Artificial Sequence:  primer

<400> SEQUENCE: 114
gtgtggatcc tcgtccccct catgcgcgac caggaaggg                              39

<210> SEQ ID NO 115
<211> LENGTH: 27
<212> TYPE: DNA
<213> ORGANISM: Artificial Sequence
<220> FEATURE:
<223> OTHER INFORMATION: Description of Artificial Sequence:  primer

<400> SEQUENCE: 115
gtgtggatcc gtggtgacct tagccac                                           27

<210> SEQ ID NO 116
<211> LENGTH: 30
<212> TYPE: DNA
<213> ORGANISM: Artificial Sequence
<220> FEATURE:
<223> OTHER INFORMATION: Description of Artificial Sequence:  primer

<400> SEQUENCE: 116
ttcgtgtccg aggaccttgt ggtccacaac                                        30

<210> SEQ ID NO 117
<211> LENGTH: 7
<212> TYPE: PRT
<213> ORGANISM: Artificial Sequence
<220> FEATURE:
<223> OTHER INFORMATION: Description of Artificial Sequence:  Peptide

<400> SEQUENCE: 117

His Gly Leu Ser Glu Gln Lys
  1               5
```

ENZYME DERIVED FROM THERMOPHILIC ORGANISMS THAT FUNCTIONS AS A CHROMOSOMAL REPLICASE, AND PREPARATION AND USES THEREOF

This Application is a Continuation of application Ser. No. 09/057,416, filed Apr. 8, 1998 now abandoned.

FIELD OF THE INVENTION

The present invention relates to thermostable DNA polymerases, and more particularly to such polymerases as can serve as chromosomal replicases and are derived from thermophilic bacteria. More particularly, the invention extends to DNA polymerase III-type enzymes from thermophilic bacteria, including recombinant subunits thereof, to isolated DNA coding for such polymerases which hybridizes to DNA probes prepared from the DNA sequence coding for *T. thermophilus* and its subunits, to DNA and antibody probes employed in isolation of said DNA, as well as to related methods for isolating said DNA and methods to express and purify the DNA and its subunits from the respective genes such as dnaX, dnaA, dnaN, dnaQ, dnaE and the like. The invention also relates to the purification and use of *T. thermophilus* Pol III-type enzymes in efficient replication of a long natural template.

BACKGROUND OF THE INVENTION

Thermostable DNA polymerases have been disclosed previously as set forth in U.S. Pat. No. 5,192,674 to Oshima et al., U.S. Pat. Nos. 5,322,785 and 5,352,778 to Comb et al., and U.S. Pat. No. 5,545,552, and others. All of the noted references recite the use of polymerases as important catalytic tools in the practice of molecular cloning techniques such as polymerase chain reaction (PCR). Each of the references states that a drawback of the extant polymerases are their limited thermostability, and consequent useful life in the participation in PCR. Such limitations also manifest themselves in the inability to obtain extended lengths of nucleotides, and in the instance of Taq polymerase, the lack of 3' to 5' exonuclease activity, and the drawback of the inability to excise misinserted nucleotides (Tindall, et al. (1990) *Biochemistry* 29:5226-5231).

More generally, such polymerases, including those disclosed in the referenced patents, are of the Polymerase I variety as they have are approximately 90-95 kDa in size and may have 5' to 3' exonuclease activity. They define a single subunit with concomitant limits on their ability to hasten the amplification process and to promote the rapid preparation of longer strands of DNA.

Chromosomal replicases are composed of several subunits in all organisms (Kornberg and Baker, 1992). In keeping with the need to replicate long chromosomes, replicases are rapid and highly processive multiprotein machines. All cellular replicases examined to date derive their processivity from one subunit that is shaped like a ring and completely encircles DNA (Kuriyan and O'Donnell, 1993; Kelman and O'Donnell, 1994). This "sliding clamp" subunit acts as a mobile tether for the polymerase machine (Stukenberg et. al., 1991). The sliding clamp does not assemble onto the DNA by itself, but requires a complex of several proteins, called a "clamp loader" which couples ATP hydrolysis to the assembly of sliding clamps onto DNA (O'Donnell et. al. 1992). Hence, cellular replicases are classically comprised of three components: a clamp, a clamp loader, and the DNA polymerase, and for purposes of the present invention, the foregoing components also serve as a broad definition of a "Pol III-type enzyme".

DNA polymerase III holoenzyme (Pol III holoenzyme) is the multi-subunit replicase of the *E. coli* chromosome. Pol III holoenzyme is distinguished from Pol I type DNA polymerases by its high processivity (>50 kbp) and rapid rate of synthesis (750 nts/s) (reviewed in Kornberg and Baker, 1991; Kelman and O'Donnell, 1995). The high processivity and speed is rooted in a ring shaped subunit, called $\beta$, that encircles DNA and slides along it while tethering the Pol III holoenzyme to the template (Stukenberg et. al., 1991; Kong et. al., 1992). The ring shaped $\beta$ clamp is assembled around DNA by the multisubunit clamp loader, called $\gamma$ complex. The $\gamma$ complex couples the energy of ATP hydrolysis to the assembly of the $\beta$ clamp onto DNA. This $\gamma$ complex clamp loader is an integral component of the Pol III holoenzyme particle. A brief overview of the organization of subunits within the holoenzyme and their function follows.

Pol III holoenzyme consists of 10 different subunits, some of which are present in multiple copies for a total of 18 polypeptide chains (Onrust et. al., 1995b). The organization of these subunits in the holoenzyme particle is illustrated in FIG. 1. As depicted in the diagram, the subunits of the holoenzyme can be grouped functionally into three components: 1) the DNA polymerase III core is the catalytic unit and consists of the $\alpha$ (DNA polymerase), $\epsilon$ (3'-5' exonuclease) and $\theta$ subunits (McHenry and Crow, 1979), 2) the $\beta$ "sliding clamp" is the ring shaped protein that secures the core-polymerase to DNA for processivity (Kong et. al., 1992), and 3) the 5 protein $\gamma$ complex ($\gamma\delta\delta'\chi\psi$) is the "clamp loader" that couples ATP hydrolysis to assembly of $\beta$ clamps around DNA (O'Donnell, 1987; Maki and Kornberg, 1988). A dimer of the $\tau$ subunit acts as a "macromolecular organizer" holding together two molecules of core and one molecule of $\gamma$ complex forming the Pol III* subassembly (Onrust et. al., 1995b). This organizing role of $\tau$ to form Pol III* is indicated in the center of FIG. 1. Two $\beta$ dimers associate with the two cores within Pol III* to form the holoenzyme capable of replicating both strands of duplex DNA simultaneously (Maki et. al., 1998).

The DNA polymerase III holoenzyme assembles onto a primed template in two distinct steps. In the first step, the $\gamma$ complex assembles the $\beta$ clamp onto the DNA. The $\gamma$ complex and the core polymerase utilize the same surface of the $\beta$ ring and they cannot both utilize it at the same time (Naktinis et. al., 1996). Hence, in the second step the $\gamma$ complex moves away from $\beta$ thus allowing access of the core polymerase to the $\beta$ clamp for processive DNA synthesis. The $\gamma$ complex and core remain attached to each other during this switching process by the $\tau$ subunit organizer.

The $\gamma$ complex consists of 5 different subunits ($\gamma_{2-4} \delta_1 \delta'_1 \chi_1 \psi_1$). An overview of the mechanism of the clamp loading process follows. The $\delta$ subunit is the major touch point to the $\beta$ clamp and leads to ring opening, but $\delta$ is buried within $\gamma$ complex such that contact with $\beta$ is prevented (Naktinis et. al., 1995). The $\gamma$ subunit is the ATP interactive protein but is not an ATPase by itself (Tsuchihashi and Kornberg, 1989). The $\delta'$ subunit bridges the $\delta$ and $\gamma$ subunits resulting in a $\gamma\delta\delta'$ complex that exhibits DNA dependent ATPase activity and is competent to assemble clamps on DNA (Onrust et. al., 1991). Upon binding of ATP to $\gamma$, a change in the conformation of the complex exposes $\delta$ for interaction with $\beta$ (Naktinis et. al., 1995). The function of the smaller subunits, $\chi$ and $\psi$, is to contact SSB (through $\chi$) thus promoting clamp assembly and high processivity during replication (Kelman and O'Donnell, 1995).

The three component Pol III-type enzyme in eukaryotes contains a clamp that has the same shape as *E. coli* β, but instead of a homodimer it is a heterotrimer. This hetertrimeric ring, called PCNA (proliferating cell nuclear antigen), has 6 domains like β, but instead of each PCNA monomer being composed of 3 domains and dimerizing to form a 6 domain ring (e.g. like β), the PCNA monomer has 2 domains and it trimerizes to form a 6 domain ring (Krishna et. al., 1994; Kuriyan and O'Donnell, 1993). The chain fold of the domains are the same in prokaryotes (β) and eukaryotes (PCNA) and thus the rings have the same overall 6-domain ring shape. The clamp loader of the eukaryotic Pol III-type replicase is called RFC (Replication factor C) and it consists of subunits having homolgy to the γ and δ' subunits of the *E. coli* γ complex. The eukaryotic DNA polymerase III-type enzyme contains either of two DNA polymerases, DNA polymerase δ and DNA polymerase ε. It is entirely conceivable that yet other types of DNA polymerases can function with either a PCNA or β clamp to form a Pol III-type enzyme (for example, DNA polymerase II of *E. coli* functions with the β subunit placed onto DNA by the γ complex clamp loader). The bacteriophage T4 also utilizes a Pol III-type 3-component replicase. The clamp is a homotrimer like PCNA, called gene 45 protein. The gene 45 protein forms the same 6-domain ring structure as β and PCNA. The clamp loader is a complex of two subunits called the gene 44/62 protein complex. The DNA polymerase is the gene 43 protein and it is stimulated by the gene 45 sliding clamp when it is assembled onto DNA by the 44/62 protein clamp loader. The Pol III-type enzyme may be either bound together into one particle (e.g., *E. coli* Pol III holoenzyme), or its three components may not be assembled together into a stable particle in solution (like the eukaryotic Pot III-type replicases).

There is an early report on separation of three DNA polymerases from *T.th.* cells, however each polymerase form was reminiscent of the preexisting types of DNA polymerase isolated from thermophiles in that each polymerase was in the 110,000-120,000 range and lacked 3'-5' exonuclease activity (Ruttimann et. Al., 1985). These are well below the molecular weight of Pot III-type complexes that contain in addition to the DNA polymerase subunit, other subunits such as γ and τ. Although the three polymerases displayed some differences in activity (column elution behavior, and optimum divalent cation, template, and temperatures) it seems likely that these three forms were either different repair type polymerases or derivatives of one repair enzyme (e.g. Pol I) that was modified into three forms by post translational modification(s) that altered their properties (e.g. phosphorylation, methylation, slight proteolytic clipping of residues that alter activity, or association with different ligands such as a small protein or contaminating DNA). Despite this previous work, it remained to be demonstrated that thermophiles harbor a Pot III-type enzyme that contain multiple subunits such as γ and/or τ, functioned with a sliding clamp accessory protein, or could extend a primer over a long stretch of ssDNA. Ruttimann, C., Cotoras, M., Zaldivar, J., and Vicuna, R. (1986) DNA polymerases from the extremely thermophilic bacterium *Thermus thermophilus* HB-8. European J., of Biochem. 149, 41-46.

Previously it was not known how thermophilic bacteria replicated—only Pol I's have been reported. By distinction, chromsomal replicases such as Polymerase III identified in *E. coli*, if available in a thermostable bacterium, with all its accessory subunits, could provide a great improvement over the Polymerase I's, in that they are generally much more efficient—about 5 times faster and much more highly processive. Hence, one may expect faster and longer chain production in PCR, and higher quality of DNA sequencing ladders. Clearly the ability to practice such synthetic techniques as PCR would be enhanced by these methods disclosed for how to obtain genes and subunits of DNA polymerase III holoenzyme from thermophilic sources.

SUMMARY OF THE INVENTION

In accordance with the present invention, DNA Polymerase III-type enzymes as defined herein are disclosed that may be isolated and purified from a thermophilic bacterial source, that can function as a chromosomal replicase, and that possesses all of the structural and processive advantages sought and recited above. More particularly, the invention extends to the Polymerase III-type enzymes derived from thermostable thermophilic bacteria that exhibit the ability to extend a primer over a long stretch of ssDNA at elevated temperature, the ability to be stimulated by a cognate sliding clamp of the type that is assembled on DNA by a 'clamp' loader (e.g. γ complex), have clamp loading sub-units that show DNA stimulated ATPase activity at elevated temperature and/or ionic strength, and have a DNA polymerase-associated 3'-5' exonuclease activity (e.g. ε subunit). Representative thermophiles include polymerases isolated from the thermophilic bacteria *Thermus thermophilus* (*T.th.* polymerase), *Thermococcus litoralis* (Tli or VENT™ polymerase), *Pyrococcus furiosus* (Pfu or DEEPVENT polymerase), *Pyrococcus woosii* (Pwo polymerase) and other *Pyrococcus* species, *Bacillus sterothermophilus* (Bst polymerase), *sulfolobus acidocaldarius* (Sac polymerase), *thermoplasma acidophilum* (Tac polymerase), *Thermus favus* (Tfl/Tub polymerase), *Thermus ruber* (Tru polymerase), *Thermus brockianus* (DYNAZYME™ polymerase), *Thermotoga neapolitana* (Tne polymerase; See WO 96/10640), *Thermotoga maritima* (Tma polymerase; See U.S. Pat. No. 5,374,553) and other species of the *Thermotoga* genus (Tsp polymerase) and *Methanobacterium thermoautotrophicum* (Mth polymerase). In a preferred embodiment, the thermophilic comprise those of the *Thermus* and *Thermotoga* species, and particularly *T.th.*, and Tne and Tma.

A particular Polymerase III-type enzyme in accordance with the invention may include at least one of the following sub-units:
  A. a γ subunit having an amino acid sequence selected from the formula set forth in SEQ ID NOS:4 and 5;
  B. a τ subunit having an amino acid sequence corresponding to the formula set forth in SEQ ID NO:2;
  C. a ε subunit having an amino acid sequence corresponding to the formula set forth in SEQ ID NO:95;
  D. a α subunit including an amino acid sequence corresponding to the formula set forth in SEQ ID NO:87;
  E. a β subunit having an amino acid sequence corresponding to the formula set forth in SEQ ID NO:107; and
  variants, including allelic variants, muteins. analogs and fragments of any of subparts (A) through (E), and combinations thereof, capable of functioning in DNA amplification and sequencing.

The invention also extends to the genes that correspond to and can code on expression for the subunits set forth above, and accordingly includes the following: dnaX, dnaQ, dnaE and dnaN, and conserved variants and active fragments thereof.

Accordingly, the Polymerase III-type enzyme of the present invention comprises at least one gene encoding a subunit thereof, which gene is selected from the group consisting of dnaX, dnaQ, dnaE and dnaN, and combinations thereof. More particularly, the invention extends to the nucleic acid molecule encoding the γ and τ subunits, and includes the dnaX gene which has a nucleotide sequence as set forth in SEQ ID NO. 3, as well as conserved variants, active fragments and analogs thereof. Likewise, the nucleotide sequences encoding the α subunit (the dnaE gene), the ε subunit (dnaQ gene) and the β subunit (dnaN gene) each comprise the nucleotide sequences as set forth respectively, in SEQ ID NO'S: 94; 86 and 106, as well as conserved variants, active fragments and analogs thereof.

The invention also provides methods and products for identifying, isolating and cloning DNA molecules which encode such accessory subunits encoded by the recited genes of the DNA polymerase III-type enzyme hereof.

Yet further, the invention extends to Polymerase III-type enzymes prepared by the purification of an extract taken from e.g. the particular thermophile under examination, treated with appropriate solvents and then subjected to chromatographic separation on e.g. an anion exchange column, followed by analysis of long chain synthetic ability or Western analysis of the respective peaks against antibody to at least one of the anticipated enzyme subunits to confirm presence of Pol III, and thereafter, peptide sequencing of subunits that co purify and amplification to obtain the putative gene and its encoded enzyme.

The present invention also relates to recombinant γ, τ, ε, α and β subunits from thermophiles. In the instance of the γ and τ subunits, the invention includes the characterization of a frameshifting sequence that is internal to the gene and specifies relative abundance of the γ and τ gene products of dnaX. From this characterization it is obvious how to increase expression of either one of the subunits at the expense of the other (i.e. mutant frameshift could make all τ, simple reckoning at the end of the frameshift could make exclusively γ and no τ).

In a further aspect of the present invention, DNA probes can be constructed from the DNA sequences coding for, eg the *T.th*. dnaX, dnaQ, dnaE, dnaA and dnaN genes, conserved variants and active fragments thereof, all as defined herein, and may be used to identify and isolate the corresponding genes coding for the subunits of DNA polymerase III holoenzyme from other thermophiles, such as those listed earlier herein. Accordingly, all chromosomal replicases (DNA Polymerase III-type) from thermophilic sources are contemplated and included herein.

The invention also extends to methods for identifying Polymerase III-type enzymes by use of the techniques of long-chain extension and elucidation of subuits with antibodies, as described herein and with reference to the examples.

The invention further extends to the isolated and purified DNA Polymerase III, the amino acid sequences of the γ, τ, ε, α and β subunits, as set forth in SEQ ID NOS:4, 5, 2, 95, 87, and 107, and the nucleotide sequences of the corresponding genes from *T.th*. set forth, e.g. in SEQ ID NOS:3 (dnaX), 94 (dnaQ), 86 (dnaE) and 106 (dnaN), as well as to active fragments thereof, oligonucleotides and probes prepared or derived therefrom and the transformed cells that may be likewise prepared. Accordingly, the invention comprises the individual subunits enumerated above and hereinafter, corresponding isolated polynucleotides and respective amino acid sequences for each of the γ, τ, ε, α and β subunits, and to conserved variants, fragments, and the like, as well as to methods of their preparation and use in DNA amplification and sequencing. In a particular embodiment, the invention extends to vectors for the expression of the sub-unit genes of the present invention, and more specifically to the vectors pET16dnaX and pET24dnaN.

The invention also includes methods for the preparation of the DNA Polymerase III-type enzymes and the corresponding subunit genes of the present invention, and to the use of the enzymes and constructs having active fragments thereof, in the preparation, reconstitution of modification of like enzymes, as well as in amplification and sequencing of DNA by methods such as PCR, and like protocols, and to the DNA molecules amplified and sequenced by such methods. In this regard, a Pol III-type enzyme that is reconstituted in the absence of ε, or using a mutated ε with less 3'-5' exonuclease activity, may be a superior enzyme in either PCR or DNA sequencing applications, (e.g. Tabor and Richardson, 1995.)

The invention is directed to methods for amplifying and sequencing a DNA molecule, particularly via the polymerase chain reaction (PCR), using the present DNA polymerase III-type enzymes or complexes. In particular, the invention extends to methods of amplifying and sequencing of DNA using thermostable pol III-type enzyme complexes isolated from thermophilic bacteria such as *Thermotoga* and *Thermus* species, or recombinant thermostable enzymes. The invention also provides amplified DNA molecules made by the methods of the invention, and kits for amplifying or sequencing a DNA molecule by the methods of the invention.

In this connection, the invention extends to methods for amplification of DNA that can achieve long chain extension of primed DNA, as by the application and use of Polymerase III-type enzymes of the present invention. An illustration of such methods is presented in Examples 13 and 14, infra.

Likewise, kits for amplification and sequencing of such DNA molecules are included, which kits contain the enzymes of the present invention, including subunits thereof, together with other necessary or desirable reagents and materials, and directions for use. The details of the practice of the invention as set forth above and later on herein, and with reference to the patents and literature cited herein, are all expressly incorporated herein by reference and made a part hereof.

As stated, and in accordance with a principal object of the present invention, Polymerase III-type enzymes and their sub-units are provided that are derived from thermophiles and that are adapted to participate in improved DNA amplification and sequencing techniques, and the consequent ability to prepare larger DNA strands more rapidly and accurately.

It is a further object of the present invention to provide DNA molecules that are amplified and sequenced using the Polymerase III-type enzymes hereof.

It is a still further object of the present invention to provide enzymes and corresponding methods for amplification and sequencing of DNA that can be practiced without the participation of the clamp-loading component of the enzyme.

It is a still further object of the present invention to provide kits and other assemblies of materials for the practice of the methods of amplification and sequencing as aforesaid, that include and use the DNA polymerase III-type enzymes herein as part thereof.

Other objects and advantages will become apparent from a review of the ensuing description which proceeds with reference to the following illustrative drawings.

DESCRIPTION OF THE DRAWINGS

FIG. 2. Alignment of the N-terminal regions of *E. coli* (SEQ ID NO: 19) and *B. subtilis* (SEQ ID NO: 20) dnaX gene product—Asterisks indicate identities. The ATP binding consensus sequence is indicated. The two regions used for PCR primer design are shown in bold.

FIGS. 4A and 4B depict the full sequence of the dnaX gene of *T. thermophilus*-DNA sequence (upper case, and corresponding to SEQ ID NO:1) and predicted amino acid sequence (lower case, and corresponding to SEQ ID NO:2) yields a 529 amino acid protein (τ) of 58.0 kDa. A putative frameshifting sequence containing several A residues 1478-1486 (underlined) may produce a smaller protein (γ) of 49.8 kDa. The potential Shine-Dalgarno (S.D.) signal is bold and underlined. The start codon is in bold, and the stop codon for τ is marked by an asterisk. The potential stop codon for γ is shown in bold after the frameshift site, and two potential Shine-Dalgarno sequences upstream of the frameshift site are indicated. Sequences of the primers used for PCR are shown in italics above the nucleotide sequence of dnaX. The ATP binding site is indicated, and the asterisks above the four Cys residues near the ATP site indicate the putative Zn++ finger. The proline rich area is indicated above the sequence. Numbering of the nucleotide sequence is presented to the right. Numbering of the amino acid sequence of τ is shown in parenthesis to the right.

FIG. 4C depicts the isolated DNA coding sequence for the dnaX gene (also present in FIGS. 4A and 4B) in accordance with the invention, and corresponds to SEQ ID NO:3.

FIG. 4D depicts the polypeptide sequence of the γ subunit of the Polymerase III of the present invention, and corresponds to SEQ ID NO:4.

FIG. 4E depicts the polypeptide sequence of the γ subunit of the Polymerase III of the present invention defined by a −1 frameshift, and corresponds to SEQ ID NO:4.

FIG. 4F depicts the polypeptide sequence of the γ subunit of the Polymerase III of the present invention defined by a −2 frameshift, and corresponds to SEQ ID NO:5.

FIG. 5. Alignment of the γ/τ ATP binding domains for different bacteria—Dots indicated those residues that are identical to the *E. coli* dnaX sequence. The ATP consensus site is underlined, and the conserved cysteine residues that form the zinc finger are indicated with asterisks. *E. coli, Escherichia coli* (SEQ ID NO: 21); *H. inf, Haemophilus influenzae* (SEQ ID NO: 22); *B. sub., Bacillus subtilis* (SEQ ID NO:23); *C. cres., Caulobacter crescentus* (SEQ ID NO: 24); *M. gen., Mycoplasma genitalium* (SEQ ID NO: 25); *T.th., Thermus theromophilus* (SEQ ID NO: 26). Alignments were produced using Clustal.

FIG. 15 shows the alignments of the peptides obtained from T.th. α subunit, TTH1 (shown in Panel A) and TTH2 (shown in Panel B) with the amino acid sequences of the α subunits of other organisms. The amino acid number of these regions within each respective protein sequence are shown to the right. The abbreviations of the organisms are as follows. E. coli—Escherichia coli (Panel A, SEQ ID NO: 72; Panel B, SEQ ID NO: 79), V. chol.—Vibrio cholerae (Panel A, SEQ ID NO: 73; Panel B, SEQ ID NO: 80) H. inf.—Haemophilus influenzae (Panel A, SEQ ID NO: 74; Panel B, SEQ ID NO: 81), R. prow.—Rickesttsia prowazekii (Panel A, SEQ ID NO: 75; Panel B. SEQ ID NO: 82), H. pyl.—Helicobacter pylori (Panel A, SEQ ID NO: 76; Panel B, SEQ ID NO: 83), S. sp.—Synechocystis sp. (Panel A, SEQ ID NO: 77; Panel B, SEQ ID NO: 84), M. tub.—Mycobacterium tuberculosis (Panel A, SEQ ID NO: 78; Panel B. SEQ ID NO: 85), T.th—Thermus thermophilus (Panel A, SEQ ID NO: 61; Panel B, SEQ ID NO: 60).

FIG. 16 shows a partial nucleotide (Panel A, SEQ ID NO: 86) and amino acid (Panel B, SEQ ID NO: 87) sequence of the dnaE gene encoding the α subunit of DNA polymerase III holoenzyme. The peptide sequence in bold was obtained by microsequencing of the α subunit isolated from T.th. cells.

FIG. 17 shows an alignment of the amino acid sequence of ε subunits encoded by dnaQ of several organisms. The amino acid sequence of the Thermus thermophilus ε subunit of dnaQ is also shown. T.th., Thermus thermophilus (SEQ ID NO: 88); D. rad., Deinococcus radiodurans (SEQ ID NO: 89); Bac. sub., Bacillus subtilis (SEQ ID NO: 90); H. inf, Haemophilus influenzae (SEQ ID NO: 91); E. c., Escherichia coli (SEQ ID NO: 92); H. pyl., Helicobacter pylori (SEQ ID NO: 93). The regions used to obtain the inner part of the dnaQ gene are shown in bold. The starts used for expression of the T.th. ε subunit are marked.

FIG. 18 shows the nucleotide (Panel A, SEQ ID NO: 94) and amino acid (Panel B, SEQ ID NO: 95) sequence of the dnaQ gene encoding the ε subunit of DNA polymerase III holoenzyme.

FIG. 19 shows an alignment of the DnaA protein of several organisms. The amino acid sequence of the Thermus thermophilus DnaA protein is also shown. P. mar, Pseudomonas marcesans (SEQ ID NO: 96); Syn. sp., Synechocystis sp. (SEQ ID NO: 97); Bac. sub., Bacillus subtilies (SEQ ID NO: 98); M. tub., Mycobacterium tuberculosis (SEQ ID NO: 99); T. th., Thermus thermophilus (SEQ ID NO: 100); E. c., Escherichia coli (SEQ ID NO: 101); T. mar., Thermotoga maratima (SEQ ID NO: 102); H. pyl., Helicobacter pylori (SEQ ID NO: 103).

FIG. 20 shows the nucleotide (Panel A, SEQ ID NO: 104) and amino acid (Panel B, SEQ ID NO: 105) sequence of the dnaA gene of Thermus thermophilus.

FIG. 21 shows the nucleotide (Panel A, SEQ ID NO: 106) and amino acid (Panel B, SEQ ID NO: 107) sequence of the dnaN gene encoding the β subunit of DNA polymerase III holoenzyme.

FIG. 22 shows an alignment of the β subunit of T.th. to the β subunits of other organisms. T.th. Thermus thermophilus; E. coli, Escherichia coli; P. put., Pseudomonas putiida; P. mirab, Proteus mirabilis; H. infl, Haemophilus influenzae; B. cap., Buchnera aphidicola.

FIG. 24 shows the induction of T.th. β in E. coli cells harboring the T.th. β expression vector. Panel A is the cell induction. The first lane shows melecular weight markers (MW). The second lane shows uninduced E. coli cells, and the third lane shows induced E. coli. The induced T.th. β is indicated by the arrow shown to the left. Induced cells were lysed then treated with heat and the soluble portion was chromatographed on MonoQ. Panel B shows the results of MonoQ purification of T.th. β.

DETAILED DESCRIPTION OF THE INVENTION

Figure 1:
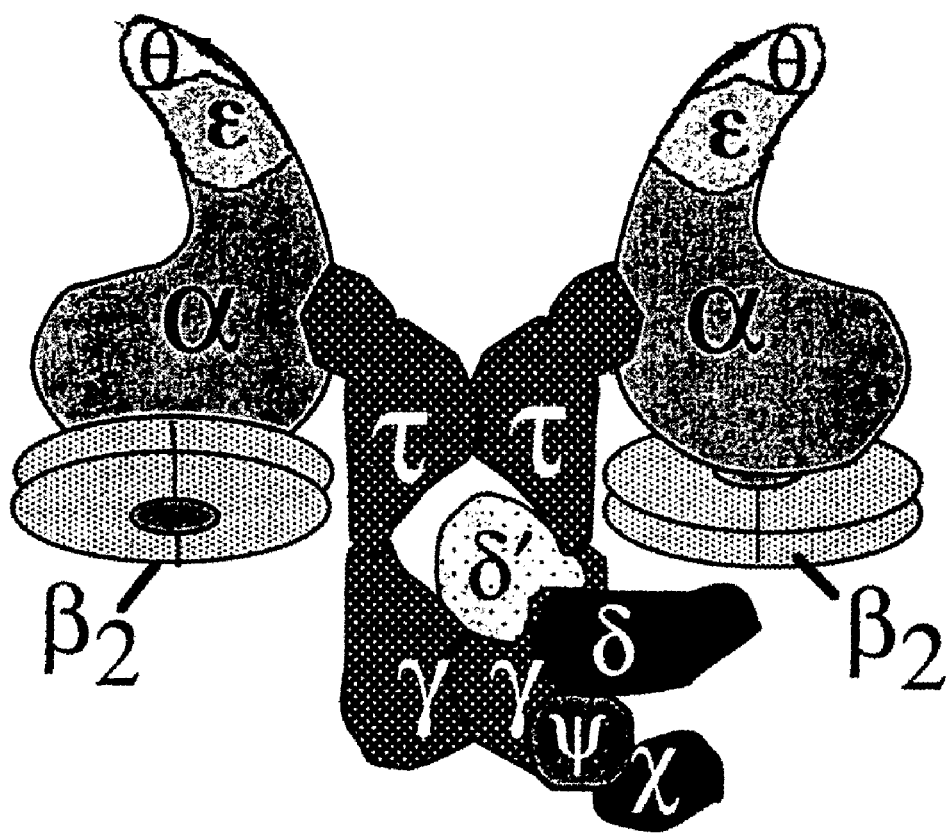
FIG. 1 is a schematic depiction of the structure and components of enzymes of the general family to which the enzymes of the present invention belong.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M. ed. (1994)]; "Cell Biology: A Laboratory Handbook" Volumes I-III [J. E. Celis. ed. (1994)]; "Current Protocols in Immunology" Volumes I-III [Coligan, J. E., ed. (1994)]; "Oligonucleotide Synthesis" (M. J. Gait ed. 1984): "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984). Therefore, if appearing herein, the following terms shall have the definitions set out below.

The terms "DNA Polymerase III," "Polymerase III-type enzyme(s)", "Polymerase III enzyme complex(s)". "*T.th.* DNA Polymerase III", "clamp loader" and any variants not specifically listed, may be used herein interchangeably, as are β subunit and sliding clamp and clamp as are also γ complex, clamp loader and RFC, as used throughout the present application and claims refer to proteinaceous material including single or multiple proteins, and extends to those proteins having the amino acid sequence data described herein and presented in the Figures and corresponding Sequence Listing entries, and the corresponding profile of activities set forth herein and in the Claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "DNA Polymerase III," "*T.th.* DNA Polymerase III," and "γ and τ subunits" "β subunit", "α subunit", "ε subunit", "sliding clamp" and "clamp loader" are intended to include within their scope proteins specifically recited herein as well as all substantially homologous analogs and allelic variations.

Also as used herein, the term "thermolabile enzyme" refers to a DNA polymerase which is not resistant to inactivation by heat. For example, T5 DNA polymerase, the activity of which is totally inactivated by exposing the enzyme to a temperature of 90° C. for 30 seconds, is considered to be a thermolabile DNA polymerase. As used herein, a thermolabile DNA polymerase is less resistant to heat inactivation than in a thermostable DNA polymerase. A thermolabile DNA polymerase typically will also have a lower optimum temperature than a thermostable DNA polymerase. Thermolabile DNA polymerases are typically isolated from mesophilic organisms, for example mesophilic bacteria or eukaryotes, including certain animals.

As used herein, the term "thermostable enzyme" refers to an enzyme which is stable to heat and is heat resistant and catalyzes (facilitates) combination of the nucleotides in the proper manner to form the primer extension products that are complementary to each nucleic acid strand. Generally, the synthesis will be initiated at the 3' end of each primer and will proceed in the 5' direction along the template strand, until synthesis terminates, producing molecules of different lengths.

The thermostable enzyme herein must satisfy a single criterion to be effective for the amplification reaction, i.e., the enzyme must not become irreversibly denatured (inactivated) when subjected to the elevated temperatures for the time necessary to effect denaturation of double-stranded nucleic acids. Irreversible denaturation for purposes herein refers to permanent and complete loss of enzymatic activity. The heating conditions necessary for denaturation will depend, e.g., on the buffer salt concentration and the length and nucleotide composition of the nucleic acids being denatured, but typically range from about 90° to about 96° C. for a time depending mainly on the temperature and the nucleic acid length, typically about 0.5 to four minutes. Higher temperatures may be tolerated as the buffer salt concentration and/or GC composition of the nucleic acid is increased. Preferably, the enzyme will not become irreversibly denatured at about 90°-100° C.

The thermostable enzymes herein preferably have an optimum temperature at which they function that is higher than about 40° C., which is the temperature below which hybridization of primer to template is promoted, although, depending on (1) magnesium and salt concentrations and (2) composition and length of primer, hybridization can occur at higher temperature (e.g. 45'-70° C.). The higher the temperature optimum for the enzyme, the greater the specificity and/or selectivity of the primer-directed extension process. However, enzymes that are active below 40° C., e.g., at 37° C., are also within the scope of this invention provided they are heat-stable. Preferably, the optimum temperature ranges from about 50° to 90° C., more preferably 60'-80° C. In this connection, the term "elevated temperature" as used herein is intended to cover sustained temperatures of operation of the enzyme that are equal to or higher than about 60° C.

The term "template" as used herein refers to a double-stranded or single-stranded DNA molecule which is to be amplified, synthesized or sequenced. In the case of a double-stranded DNA molecule, denaturation of its strands to form a first and a second strand is performed before these molecules may be amplified, synthesized or sequenced. A primer, complementary to a portion of a DNA template is hybridized under appropriate conditions and the DNA polymerase of the invention may then synthesize a DNA molecule complementary to said template or a portion thereof. The newly synthesized DNA molecule, according to the invention, may be equal or shorter in length than the original DNA template. Mismatch incorporation during the synthesis or extension of the newly synthesized DNA molecule may result in one or a number of mismatched base pairs. Thus, the synthesized DNA molecule need not be exactly complementary to the DNA template.

The term "incorporating" as used herein means becoming a part of a DNA molecule or primer.

As used herein "amplification" refers to any in vitro method for increasing the number of copies of a nucleotide sequence, or its complimentary sequence, with the use of a DNA polymerase. Nucleic acid amplification results in the incorporation of nucleotides into a DNA molecule or primer thereby forming a new DNA molecule complementary to a DNA template. The formed DNA molecule and its template can be used as templates to synthesize additional DNA molecules. As used herein, one amplification reaction may consist of many rounds of DNA replication. DNA amplification reactions include, for example, polymerase chain reactions (PCR). One PCR reaction may consist of 30 to 100 "cycles" of denaturation and synthesis of a DNA molecule. In this connection, the use of the term "long stretches of DNA" as it refers to the extension of primer along DNA is intended to cover such extensions of an average length exceeding 7 kilobases. Naturally, such length will vary, and all such variations are considered to be included within the scope of the invention.

As used herein, the term "holoenzyme" refers to a multi-subunit DNA polymerase activity comprising and resulting from various subunits which each may have distinct activities but which when contained in an enzyme reaction operate to carry out the function of the polymerase (typically DNA synthesis) and enhance its activity over use of the DNA polymerase subunit alone. For example, *E. coli* DNA polymerase III is a holoenzyme comprising three components of one or more subunits each: (1) a core component consisting of a heterotrimer of α, ε and θ subunits; (2) a β component consisting of a β subunit dimer; and (3) a γ clex component consisting of a heteropentamer of γ, δ, δ', χ and Ψ subunits (see Studwell, P. S., and O'Donnell, M., *J. Biol. Chem.* 265 (2):1171-1178 (1990), for review). These three components, and the various subunits of which they consist, are linked non-covalently to form the DNA polymerase III holoenzyme complex.

As used herein, "enzyme complex" refers to a protein structure consisting essentially of two or more subunits of a holoenzyme, which may or may not be identical, noncovalently linked to each other to form a multi-subunit structure. An enzyme complex according to this definition ideally will have a particular enzymatic activity, up to and including the activity of the holoenzyme. For example, a "DNA pot III enzyme complex" as used herein means a multi-subunit protein activity comprising two or more of the subunits of the DNA pol III holoenzyme as defined above, and having DNA polymerizing or synthesizing activity. Thus, this term encompasses the native holoenzyme, as well as an enzyme complex lacking one or more of the subunits of the holoenzyme (e.g., DNA pol III exo-, which lacks the ε subunit).

The amino acid residues described herein are preferred to be in the "L" isomeric form. However, residues in the "D" isomeric form can be substituted for any L-amino acid residue, as long as the desired fuctional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552-59 (1969), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g. mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used generally herein, such as in referring to probes prepared and used in the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e. in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

It should be appreciated that also within the scope of the present invention are DNA sequences encoding T.th. DNA Polymerase III which code for a T.th. DNA Polymerase III having the same amino acid sequence as SEQ ID NO:2, but which are degenerate to SEQ ID NO:2. By "degenerate to" is meant that a different three-letter codon is used to specify a particular amino acid. It is well known in the art that the following codons can be used interchangeably to code for each specific amino acid:

| | |
|---|---|
| Phenylalanine (Phe or F) | UUU or UUC |
| Leucine (Leu or L) | UUA or UUG or CUU or CUC or CUA or CUG |
| Isoleucine (Ile or I) | AUU or AUC or AUA |
| Methionine (Met or M) | AUG |
| Valine (Val or V) | GUU or GUC of GUA or GUG |
| Serine (Ser or S) | UCU or UCC or UCA or UCG or AGU or AGC |
| Proline (Pro or P) | CCU or CCC or CCA or CCG |
| Threonine (Thr or T) | ACU or ACC or ACA or ACG |
| Alanine (Ala or A) | GCU or GCG or GCA or GCG |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU or CGC or CGA or CGG or AGA or AGG |
| Glycine (Gly or G) | GGU or GGC or GGA or GGG |
| Tryptophan (Trp or W) | UGG |
| Termination codon | UAA (ochre) or UAG (amber) or UGA (opal) |

It should be understood that the codons specified above are for RNA sequences. The corresponding codons for DNA have a T substituted for U.

Mutations can be made, e.g. in SEQ ID NO:1, or any of the nucleic acids set forth herein, such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

The following is one example of various groupings of amino acids:

Amino Acids with Nonpolar R Groups
    Alanine
    Valine
    Leucine
    Isoleucine
    Proline
    Phenylalanine
    Tryptophan
    Methionine Amino Acids with Uncharged Polar R Groups
  Glycine
  Serine
  Threonine
  Cysteine
  Tyrosine
  Asparagine
  Glutamine Amino Acids with Charged Polar R Groups (Negatively Charged at ph 6.0)
  Aspartic acid
  Glutamic acid Basic Amino Acids (Positively Charged at pH 6.0)
  Lysine
  Arginine
  Histidine (at pH 6.0)

Another grouping may be those amino acids with phenyl groups:
  Phenylalanine
  Tryptophan
  Tyrosine Another grouping may be according to molecular weight (i.e., size of R groups):

| | |
|---|---|
| Glycine | 75 |
| Alanine | 89 |
| Serine | 105 |
| Proline | 115 |
| Valine | 117 |
| Threonine | 119 |
| Cysteine | 121 |
| Leucine | 131 |
| Isoleucine | 131 |
| Asparagine | 132 |
| Aspartic acid | 133 |
| Glutamine | 146 |
| Lysine | 146 |
| Glutamic acid | 147 |
| Methionine | 149 |
| Histidine (at pH 6.0) | 155 |
| Phenylalanine | 165 |
| Arginine | 174 |
| Tyrosine | 181 |
| Tryptophan | 204 |

Particularly preferred substitutions are:
Lys for Arg and vice versa such that a positive charge may be maintained;
Glu for Asp and vice versa such that a negative charge may be maintained;
Ser for Thr such that a free —OH can be maintained; and
Gln for Asn such that a free $NH_2$ can be maintained.

Amino acid substitutions may also be introduced to substitute an amino acid with a particularly preferable property. For example, a Cys may be introduced into a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

Two amino acid sequences are "substantially homologous" when at least about 70% of the amino acid residues (preferably at least about 80%, and most preferably at least about 90 or 95%) are identical, or represent conservative substitutions.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816.567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example. U.S. Pat. No. 4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20° C. below the predicted or determined $T_m$ with washes of higher stringency, if desired.

In its primary aspect, the present invention concerns the identification of a class of DNA Polymerase III-type enzymes or complexes found in thermophilic bacteria such as *Thermus thermophilus* (*T.th.*), and other eubacteria such as Thermatoga, which exhibit the following characteristics, among their properties: the ability to extend a primer over a long stretch of ssDNA at elevated temperature, stimulation by its cognate sliding clamp of the type that is assembled on DNA by a clamp loader (e.g. γ complex), accessory subunits that exhibit DNA-stimulated ATPase activity at elevated temperature and/or ionic strength, and an associated 3'-5' exonuclease activity. In a particular aspect, the invention extends to Polymerase III-type enzymes derived from a broad class of thermophilic bacteria that include polymerases isolated from the thermophilic bacteria *Thermus thermophilus* (*T.th.* polymerase), *Thermococcus litoralis* (Tli or VENT™ polymerase), *Pyrococcus furiosus* (Pfu or DEEPVENT polymerase), *Pyrococcus woosii* (Pwo polymerase) and other *Pyrococcus* species, *Bacillus sterothermophilus* (Bst polymerase), *sulfolobus acidocaldarius* (Sac polymerase), *thermoplasma acidophilum* (Tac polymerase), *Thermus favus* (Tfl/Tub polymerase), *Thermus ruber* (Tru polymerase). *Thermus brockianus* (DYNAZYME™ polymerase), *Thermotoga neapolitana* (Tne polymerase; See WO 96/10640). *Thermotoga maritima* (Tma polymerase; See U.S. Pat. No. 5,374,553) and other species of the *Thermotoga* genus (Tsp polymerase) and *Methanobacterium thermoautotrophicum* (Mth polymerase). The particular polymerase discussed herein by way of illustration and not limitation, is the enzyme derived from *T.th.*

Polymerase III-type enzymes covered by the invention include those that may be prepared by purification from cellular material, as described in detail in Example 9 herein, as well as enzyme assemblies or complexes that comprise the combination of individually prepared enzyme subunits or components. Accordingly, the entire enzyme may be prepared by purification from cellular material, or may be constructed by the preparation of the individual components and their assembly into the functional enzyme. A representative and non-limitative protocol for the preparation of an enzyme by this latter route is set forth in U.S. Pat. No. 5,583,026, issued Dec. 10, 1996, to one of the inventors herein, and the disclosure thereof is incorporated herein in its entirety for such purpose.

Likewise, individual subunits may be modified, e.g. as by incorporation therein of single residue substitutions to create active sites therein, for the purpose of imparting new or enhanced properties to enzymes containing the modified subunits. See, for example, Tabor, S. et al. (1995) *Proc. Natl. Acad. Sci. USA*, 92(14):6339-6343, the disclosure of which is also incorporated herein in its entirety. Likewise, individual subunits prepared in accordance with the invention, may be used individually and for example, may be substituted for their counterparts in other enzymes, to improve or particularize the properties of the resultant modified enzyme. Such modifications are within the skill of the art and are considered to be included within the scope of the present invention.

Accordingly, the invention includes the various subunits that may comprise the enzymes, and accordingly extends to the genes and corresponding proteins that may be encoded thereby, such as the α, β, γ, ε, τ, δ and δ' subunits, respectively. More particularly, the α subunit corresponds to dnaE, the β subunit corresponds to dnaN, the ε subunit corresponds to dnaQ, and the γ and τ subunits correspond to dnaX.

Accordingly, the Polymerase III-type enzyme of the present invention comprises at least one gene encoding a subunit thereof, which gene is selected from the group consisting of dnaX, dnaQ, dnaE, dnaN, and combinations thereof. More particularly, the invention extends to the nucleic acid molecule encoding them and their subunits, and includes the dnaX gene which has a nucleotide sequence as set forth in SEQ ID NO. 3, as well as conserved variants, active fragments and analogs thereof. Likewise, the nucleotide sequences encoding the α subunit (dnaE gene). The ε subunit (dnaQ gene) and the β subunit (dnaN gene) each comprise the nucleotide sequences as set forth respectively, in SEQ ID NOS: 94, 86, and 106, as well as conserved variants, active fragments and analogs thereof.

A particular Polymerase III-type enzyme in accordance with the invention may include at least one of the following sub-units:

A. a γ subunit having an amino acid sequence selected from the formula set forth in SEQ ID NOS:4 and 5;
B. a τ subunit having an amino acid sequence corresponding to the formula set forth in SEQ ID NO:2;
C. a ε subunit having an amino acid sequence corresponding to the formula set forth in SEQ ID NO:95;
D. a α Subunit including an amino acid sequence corresponding to the formula set forth in SEQ ID NO:87;
E. a β subunit having an amino acid sequence corresponding to the formula set forth in SEQ ID NO:107; and
F. combinations of the above.

The invention also includes and extends to the use and application of the enzyme and/or one or more of its components for DNA molecule amplification and sequencing by the methods set forth hereinabove, and in greater detail later on herein.

One of the subunits of the invention is the γ/τ subunit encoded by a dnaX gene, which frameshifts as much as −2 with high efficiency, and that, upon frameshifting, leads to the addition of more than one extra amino acid residue to the C-terminus (to form the γ subunit). Further, the invention likewise extends to a dnaX gene derived from a thermophile such as *T.th.*, that possesses the frameshift defined herein and that codes for expression of the γ and τ subunits of DNA Polymerase III.

The present invention provides methods for amplifying or sequencing a nucleic acid molecule comprising contacting the nucleic acid molecule with a composition comprising a DNA polymerase III enzyme (DNA pol III) complex, preferably a DNA pol III complex that is substantially reduced in 3'-5' exonuclease activity. DNA pol III complexes used in the methods of the present invention are thermostable.

The invention also provides DNA molecules amplified by the present methods, methods of preparing a recombinant vector comprising inserting a DNA molecule amplified by the present methods into a vector, which is preferably an expression vector, and recombinant vectors prepared by these methods.

The invention also provides methods of preparing a recombinant host cell comprising inserting a DNA molecule amplified by the present methods into a host cell, which preferably a bacterial cell, most preferably an *Escherichia coli* cell; a yeast cell; or an animal cell, most preferably an insect cell, a nematode cell or a mammalian cell. The invention also provides and recombinant host cells prepared by these methods.

In additional preferred embodiments, the present invention provides kits for amplifying or sequencing a nucleic acid molecule. DNA amplification kits according to the invention comprise a carrier means having in close confinement therein two or more container means, wherein a first container means contains a DNA polymerase III enzyme complex and a second container means contains a deoxynucleoside triphosphate. DNA sequencing kits according to the present invention comprise a multi-protein Pol III-type enzyme complex and a second container means contains a dideoxynucleoside triphosphate. The DNA pol III contained in the container means of such kits is preferably substantially reduced in 5'-3' exonuclease activity, may be thermostable, and may be isolated from the thermophilic cellular sources described above. Most preferably, the DNA pot III contained in the container means of such kits is a DNA polymerase III-type complex of a thermophile which lacks the ϵ subunit.

DNA pol III-type enzyme complexes for use in the present invention may be isolated from any organism that produced the DNA pol III-type enzyme complexes naturally or recombinantly. Such enzyme complexes may be thermostable, isolated from a variety of thermophilic organisms.

The thermostable DNA polymerase III-type enzymes or complexes that are an important aspect of this invention, may be isolated from a variety of thermophilic bacteria that are available commercially (for example, from American Type Culture Collection, Rockville Md.). Suitable for use as sources of thermostable enzymes are the thermophilic bacteria *Thermus aquaticus, Thermus thermophilus, Thermococcus litortalis, Pyrococcus furiosus, Pyrococcus woosii* and other species of the *Pyrococcus* genus. *Bacillus stearothermophilus, Sulfolobus acidocaldarius, Thermoplasma aciclophilum, Thermus flavus, Thermzs ruber, Thermus brockianus, Thermotoga neapolitana, Thermotoga maritima* and other species of the *Thermotoga* genus, and *Methanobacterium thermoautotrophicum*, and mutants of each of these species. It will be understood by one of ordinary skill in the art, however, that any thermophilic microorganism might be used as a source of thermostable DNA pol III-type enzymes and polypeptides for use in the methods of the present invention. Bacterial cells may be grown according to standard microbiological techniques, using culture media and incubation conditions suitable for growing active cultures of the particular thermophilic species that are well-known to one of ordinary skill in the art (see, e.g., Brock, T. D., and Freeze, H., *J. Bacteriol.* 98(1):289-297 (1969); Oshima, T., and Imahori, K. *Int. J. Syst. Bacteriol.* 24(1):102-112(1974)). Thermostable DNA pol III complexes may then be isolated from such thermophilic cellular sources as described for thermolabile complexes above.

As stated above and in accordance with the present invention, nucleic acid molecules may be amplified according to any of the literature-described manual or automated amplification methods. Such methods includes, but are not limited to, PCR (U.S. Pat. Nos. 4,683,195 and 4,683,202), Strand Displacement Amplification (SDA; U.S. Pat. No. 5,455,166; EP 0 684 315), and Nucleic Acid Sequence-Based Amplification (NASBA; U.S. Pat. No. 5,409,818; EP 0 329 822). Most preferably, nucleic acid molecules are amplified by the methods of the present invention using PCR-based amplification techniques.

In the initial steps of each of these amplification methods, the nucleic acid molecule to be amplified is contacted with a composition comprising a DNA polymerase belonging to the evolutionary "family A" class (e.g. Taq DNA pol I or *E. coli* pol I) or the "family "B" class (e.g. Vent and Pfu DNA polymerases—see Ito, J., and Braithwaite, D., *Nucl. Acids Res.* 19(15):4045-4057 (1991)). All of these DNA polymerases are present as single subunits and are primarily involved in DNA repair. In contrast, the DNA pot III-type enzymes are multisubunit complexes that mainly function in the replication of the chromosome, and the subunit containing the DNA polymerase activity is in the "family C" class.

Thus, in amplifying a nucleic acid molecule according to the methods of the present invention, the nucleic acid molecule is contacted with a composition comprising a thermostable DNA pol III-type enzyme complex. The DNA pot III-type complexes used in the present methods are preferably substantially reduced in 3'-5' exonuclease activity (i.e., they are "exo-").

Once the nucleic acid molecule to be amplified is contacted with the DNA pol III-type complex, the amplification reaction may proceed according to standard protocols for each of the above-described techniques. Since most of these techniques comprise a high-temperature denaturation step, if a thermolabile DNA pot III-type enzyme complex (such as *E. coli* DNA pol III exo-) is used in nucleic acid amplification by any of these techniques the enzyme would need to be added at the start of each amplification cycle, since it would be heat-inactivated at the denaturation step. However, a thermostable DNA pol III-type complex used in these methods need only be added once at the start of the amplification (as for Taq DNA polymerase in traditional PCR amplifications), as its activity will be unaffected by the high temperature of the denaturation step. It should be noted, however, that because DNA pol III-type enzymes have a much more rapid rate of nucleotide incorporation than the polymerases commonly used in these amplification techniques, the cycle times may need to be adjusted to shorter intervals than would be standard.

In an alternative preferred embodiment, the invention provides methods of extending primers for several kilobases, a reaction that is central to amplifying large nucleic acid molecules, by a technique commonly referred to as "long PCR" (Barnes, W. M., *Proc. Natl. Acad. Sci.* USA 91:2216-2220 (1994); Cheng. S. et al., *Proc. Natl. Acad. Sci.* USA 91:5659-5699 (1994)).

In such a method the target primed DNA can contain a single strand stretch of DNA to be copied into the double strand form of several or tens of kilobases. The reaction is performed in a suitable buffer, preferably Tris, at a pH of between 5.5-9.5, preferably 7.5. The reaction also contains $MgCl_2$ in the range 1 mM to 10 mM, preferably 8 mM, and may contain a suitable salt such as NaCl, KCl or sodium or potassium acetate. The reaction also contains ATP in the range of 20 uM to 1 mM, preferably 0.5 mM, that is needed for the clamp loader to assemble the clamp onto the primed template, and a sufficient concentration of deoxynucleoside triphosphates in the range of 50 µM to 0.5 mM. preferably 60 µM for chain extension. The reaction contains a sliding clamp, such as the β subunit, in the range of 20 ng to 200 ng, preferably 100 ng, for action as a clamp to stimulate the DNA polymerase. The chain extension reaction contains a DNA polymerase and a clamp loader, that could be added either separately or as a single Pol III*-like particle, preferably as a Pot III* like particle that contains the DNA polymerase and clamp loading activities. The Pol III-type enzyme is added preferably at a concentrations of about 0.0002-200 units per milliliter, about 0.002-100 units per milliliter, about 0.2-50 units per milliliter, and most preferably about 2-50 units per milliliter. The reaction is incubated at elevated temperature, preferably 60° C. or more, and could include other proteins to enhance activity such as a single strand DNA binding protein.

In another preferred embodiment, the invention provides methods of extending primers on linear templates in the absence of the clamp loader. In this reaction, the primers are annealed to the linear DNA, preferably at the ends such as in standard PCR applications. The reaction is performed in a suitable buffer, preferably Tris, at a pH of between 5.5-9.5, preferably 7.5. The reaction also contains $MgCl_2$ in the range of 1 mM to 10 mM. preferably 8 mM, and may contain a suitable salt such as NaCl, KCl or sodium or potassium acetate. The reaction also contains a sufficient concentration of deoxynucleoside triphosphates in the range of 50 μM to 0.5 mM, preferably 60 μM for chain extension. The reaction contains a sliding clamp, such as the 1 subunit, in the range of 20 ng to 20 μg, preferably 7 μg, for ability to slide on the end of the DNA and associate with the polymerase for action as a clamp to stimulate the DNA polymerase. The chain extension reaction also contains a Pol III-type polymerase subunit such as α, core, or a Pol III*-like particle. The Pol III-type enzyme is added preferably at a concentrations of about 0.0002-200 units per milliliter, about 0.002-100 units per milliliter, about 0.2-50 units per milliliter, and most preferably about 2-50 units per milliliter. The reaction is incubated at elevated temperature, preferably 60° C. or more, and could include other proteins to enhance activity such as a single strand DNA binding protein.

The methods of the present invention thus will provide high-fidelity amplified copies of a nucleic acid molecule in a more rapid fashion than traditional amplification methods using the repair-type enzymes.

These amplified nucleic acid molecules may then be manipulated according to standard recombinant DNA techniques. For example, a nucleic acid molecule amplified according to the present methods may be inserted into a vector, which is preferably an expression vector, to produce a recombinant vector comprising the amplified nucleic acid molecule. This vector may then be inserted into a host cell, where it may, for example, direct the host cell to produce a recombinant polypeptide encoded by the amplified nucleic acid molecule. Methods for inserting nucleic acid molecules into vectors, and inserting these vectors into host cells, are well-known to one of ordinary skill in the art (see, e.g., Maniatis, T., et al., *Molecular Cloning, A Laboratory Manual*. Boca Raton, Fla.: CRC Press (1992)).

Alternatively, the amplified nucleic acid molecules may be directly inserted into a host cell, where it may be incorporated into the host cell genome or may exist as an extrachromosomal nucleic acid molecule, thereby producing a recombinant host cell. Methods for introduction of a nucleic acid molecule into a host cell, including calcium phosphate transfection. DEAE-dextran mediated transfection, cationic lipid-mediated transfection, electroporation, transduction, infection or other methods, are described in many standard laboratory manuals (see e.g., Davis et al., *Basic Methods In Molecular Biology* (1986)).

For each of the above techniques wherein an amplified nucleic acid molecule is introduced into a host cell via a vector or via direct introduction, preferred host cells include but are not limited to a bacterial cell, a yeast cell, or an animal cell. Bacterial host cells preferred in the present invention are *E. coli, Bacillus* spp., *Streptomyces* spp., *Erwinia* spp., *Klebsiella* spp. and *Salmonella typhimurium*. Preferred as a host cell is *E. coli*, and particularly preferred are *E. coli* strians DH10B and Stb12, which are available commercially (Life Technologies, Inc. Gaitherburg, Md.). Preferred animal host cells are insect cells, nematode cells and mammalian cells. Insect host cells preferred in the present invention are *Drosophila* spp. cells, *Spodoptera* Sf9 and St21 cells, and *Trichoplusa* High-Five cells, each of which is available commercially (e.g., from Invitrogen; San Diego, Calif.). Preferred nematode host cells are those derived from *C. elegans*, and preferred mammalian host cells are those derived from rodents, particularly rats, mice or hamsters, and primates, particularly monkeys and humans. Particularly preferred as mammalian host cells are CHO cells, COS cells and VERO cells.

By the present invention, nucleic acid molecules may be sequenced according to any of the literature-described manual or automated sequencing methods. Such methods include, but are not limited to, dideoxy sequencing methods ("Sanger sequencing"; Sanger, F., and Coulson, A. R., *J. Mol. Biol.* 94:444-448 (1975); Sanger, F., et al., *Proc. Natl. Acad. Sci.* USA 74:5463-5467 (1977); U.S. Pat. Nos. 4,962,022 and 5,498,523), as well as more complex PCR-based nucleic acid fingerprinting techniques such as Random Amplified Polymorphic DNA 9RAPD) analysis (Williams, J. G. K. et al., *Nuc. Acids Res.* 18(22):6531-6535, 1990). Arbitrarily Primed PCR (AP-PCR; Welsh, J., and McClelland. M., *Nucl. Acids Res.* 18(24):7213-7218, 1990), DNA Amplification Fingerprinting (DAF; Caetano-Anolles et al., Bio/Technology 9:553-557, 1991), microsatellite PCR or Directed Amplification of Minisatellite-region DNA (DAMD; Heath, D. D., et al., *Nucl. Acids Res.* 21(24):5782-5785, 1993), and Amplification Fragment Length Polymorphism (AFLP) analysis (EP 0 534 858; Vos. P. et al., *Nucl. Acids Res.* 23(21):4407-4414, 1995; Lin, J. J., and Kuo, J. FOCUS 17(2):66-70, 1995).

As described above for amplification methods, the nucleic acid molecule to be sequenced by these methods is typically contacted with a composition comprising a type A or type B DNA polymerase. By contrast, in sequencing a nucleic acid molecule according to the methods of the present invention, the nucleic acid molecule is contacted with a composition comprising a thermostable DNA pol III-type enzyme complex instead of necessarily using a DNA polymerase of the family A or B classes. As for amplification methods, the DNA pol III-type complexes used in the nucleic acid sequencing methods of the present invention are preferably substantially reduced in 5'-3' exonuclease activity; most preferable for use in the present methods is a DNA polymerase III-type complex which lacks the ε subunit. DNA pot III-type complexes used for nucleic acid sequencing according to the present methods are used at the same preferred concentration ranges described above for long chain extension of primers.

Once the nucleic acid molecule to be sequenced is contacted with the DNA pol III complex, the sequencing reactions may proceed according to the protocols disclosed in the above-referenced techniques.

As discussed above, the invention extends to kits for use in nucleic acid amplification or sequencing utilizing DNA polymerase III-type enzymes according to the present methods. A DNA amplification kit according to the present invention may comprise a carrier means, such as vials, tubes, bottles and the like. A first such container means may contain a DNA polymerase III-type enzyme complex, and a second such container means may contain a deoxynucleoside triphosphate. The amplification kit encompassed by this aspect of the present invention may further comprise additional reagents and compounds necessary for carrying out standard nucleic amplification protocols (See U.S. Pat. Nos. 4,683,195 and 4,683,202, which are directed to methods of DNA amplification by PCR).

Similarly, a DNA sequencing kit according to the present invention comprises a carrier means having in close confinement therein two or more container means, such as vials, tubes, bottles and the like. A first such container means may contain a DNA polymerase III-type enzyme complex, and a second such container means may contain a dideoxynucleoside triphosphate. The sequencing kit may further comprise additional reagents and compounds necessary for carrying out standard nucleic sequencing protocols, such as pyrophosphatase, agarose or polyacrylamide media for formulating sequencing gels, and other components necessary for detection of sequenced nucleic acids (See U.S. Pat. Nos. 4,962,020 and 5,498,523, which are directed to methods of DNA sequencing.

The DNA polymerase III-type complex contained in the first container means of the amplification and sequencing kits provided by the invention is preferably a thermostable DNA polymerase III-type enzyme complex and more preferably a DNA polymerase III-type enzyme complex that is substantially reduced in 3-5' exonuelease activity. Naturally, the foregoing methods and kits are presented as illustrative and not restrictive of the use and application of the enzymes of the invention for DNA molecule amplification and sequencing. Likewise, the applications of specific embodiments of the enzymes, including conserved variants and active fragments thereof are considered to be disclosed and included within the scope of the invention.

As discussed earlier, individual subunits could be modified to customize enzyme construction and corresponding use and activity. For example, the region of a that interacts with β could be subcloned onto another DNA polymerase, thereby causing β to enhance the activity of the recombinant polymerase. Alternatively, the β clamp could be modified to function with another protein or enzyme thereby enhancing its activity or acting to localize its action to a particular targeted DNA. Finally, the polymerase active site could be modified to enhance its action, sor example changing Tyrosine enabling more equal site stoppage with the four ddNTPs (Tabor et al. 1995). This represents a particular non-limiting illustration of the scope and practice of the present invention with reference to the utility of individual subunits hereof.

Accordingly and as stated above, the present invention also relates to a recombinant DNA molecule or cloned gene, or a degenerate variant thereof, which encodes any one or all of the subunits of the DNA Polymerase III-type enzymes of the present invention, or active fragments thereof. In the instance of the τ subunit, a predicted molecular weight of about 58 kD and an amino acid sequence set forth in SEQ ID NOS:4 or 5 is comprehended; preferably a nucleic acid molecule, in particular a recombinant DNA molecule or cloned gene, encoding the 58 kD subunit of the Polymerase III of the invention, that has a nucleotide sequence or is complementary to a DNA sequence shown in FIGS. 4A and 4B (SEQ ID NO:1), and the coding region for dnaX set forth in FIG. 4C (SEQ ID NO:3). The γ subunit is smaller, and is approximately 50 kD, depending upon the extent of the frameshift that occurs. More particularly, and as set forth in FIG. 4E (SEQ ID NO:4), the γ subunit defined by a −1 frameshift possesses a molecular weight of 50.8 kD, while the γ subunit defined by a −2 frameshift, set forth in FIG. 4F (SEQ ID NO:5), possesses a molecular weight of 49.8 kD.

As discussed above, the invention also extends to the genes including dnaX, dnaQ, dnaE and dnaN, that have been isolated and purified from *Thermus thermophilus*, to corresponding vectors for the genes, and particularly, to the vectors pETdnaX and pETdnaN, and to host cells including such vectors. In this connection, probes have been prepared which hybridize to the DNA polymerase III-type enzymes of the present invention, and which are selected from the group consisting of the oligonucleotide defined in SEQ ID NO:6; the oligonucleotide defined in SEQ ID NO:8; the oligonucleotide defined in SEQ ID NO:10; the oligonucleotide defined in SEQ ID NO:11; the oligonucleotide defined in SEQ ID NO:12; the oligonucleotide defined in SEQ ID NO:13; the oligonucleotide defined in SEQ ID NO:14; the oligonucleotide defined in SEQ ID NO:15, and the oligonucleotide defined in SEQ ID NO:16.

The methods of the invention include a method for producing a recombinant themmiostable DNA polymerase III-type enzyme from a thermophilic bacterium such as *Thermus thermophilus* which comprises culturing a host cell transformed with a vector of the invention under conditions suitable for the expression of the present DNA polymerase III. Another method includes a method for isolating a target DNA fragment consisting essentially of a DNA coding for a thermostable DNA polymerase III-type enzyme from a thermophilic bacterium comprising the steps of:

(a) forming a genomic library from the bacterium;
(b) transforming or transfecting an appropriate host cell with the library of step (a);
(c) contacting DNA from the transformed or transfected host cell with a DNA probe which hybridizes to a DNA fragment selected from the group consisting of the DNA fragments defined in SEQ ID NO:6 and the DNA fragments defined in SEQ ID NO:8 or the oligonucleotides set forth above; wherein hybridization is conduction under the following conditions:
  i) hybridization: 1% crystalline BSA (fraction V) (Sigma), 1 mM EDTA, 0.5 M NaHPO$_4$ (pH 7.2), 7% SDS at 65° C. for 12 hours and;
  ii) wash: 5×20 minutes with wash buffer consisting of 0.5% BSA, fraction V), 1 mM Na2EDTA, 40 mM NaHPO4 (pH 7.2), and 5% SDS;
(d) assaying the transformed or transfected cell of step (c) which hybridizes to the DNA probe for DNA polymerase III-type activity; and
(e) isolating a target DNA fragment which codes for the thermostable DNA polymerase III-type enzyme.

Also, antibodies including both polyclonal and monoclonal antibodies, and the DNA Polymerase III-like enzyme complex and/or their γ and τ subunits or α subunit may be used in the preparation of the enzymes of the present invention as well as other enzymes of similar thermophilic origin. For example, the DNA Polymerase III-type complex or its subunits may be used to produce both polyclonal and monoclonal antibodies to themselves in a variety of cellular media, by known techniques such as the hybridoma technique utilizing, for example, fused mouse spleen lymphocytes and myeloma cells.

The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al. "Monoclonal Antibodies" (1980); see also U.S. Pat. Nos. 4,341,761; 4,399,121; 4,427,783; 4,444,887; 4,451,570; 4,466,917; 4,472,500; 4,491,632: 4,493,890.

Methods for producing polyclonal anti-polypeptide antibodies are well-known in the art. See U.S. Pat. No. 4,493,795 to Nestor et al. A monoclonal antibody, typically containing Fab and/or F(ab')$_2$ portions of useful antibody molecules, can be prepared using the hybridoma technology described in *Antibodies—A Laboratory Manual*, Harlow and Lane, eds., Cold Spring Harbor Laboratory, New York (1988), which is incorporated herein by reference. Briefly, to form the hybridoma from which the monoclonal antibody composition is produced, a myeloma or other self-perpetuating cell line is fused with lymphocytes obtained from the spleen of a mammal hyperimmunized with an elastin-binding portion thereof.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Media useful for the preparation of these compositions are both well-known in the art and commercially available and include synthetic culture media, inbred mice and the like. An exemplary synthetic medium is Dulbecco's minimal essential medium (DMEM; Dulbecco et al., *Virol.* 8:396 (1959)) supplemented with 4.5 gm/l glucose, 20 mm glutamine, and 20% fetal calf serum. An exemplary inbred mouse strain is the Balb/c.

Another feature of this invention is the expression of the DNA sequences disclosed herein. As is well known in the art, DNA sequences may be expressed by operatively linking them to an expression control sequence in an appropriate expression vector and employing that expression vector to transform an appropriate unicellular host.

Such operative linking of a DNA sequence of this invention to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. Coli* plasmids col E1, pCR1, pBR322, pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast α-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of *E. coli, Pseudomonas, Bacillus, Streptomyces,* fungi such as yeasts, and animal cells, such as CHO, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly with regard to potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors a person skilled in the art will be able to construct a variety of vector/expression control sequence/host combinations that will express the DNA sequences of this invention on fermentation or in large scale animal culture.

It is further intended that analogs may be prepared from nucleotide sequences of the protein complex/subunit derived within the scope of the present invention. Analogs, such as fragments, may be produced, for example, by pepsin digestion of bacterial material. Other analogs, such as muteins, can be produced by standard site-directed mutagenesis of dnaX, dnaE, dnaQ or dnaN coding sequences. Especially useful may be a mutation in dnaE that provides the polymerase with the ability to incorporate all four ddNTPs with equal efficiency thereby producing an even binding pattern in sequencing gels, as discussed above and with reference to Tabor et al. 1995, supra. As mentioned above, a DNA sequence corresponding to dnaX, dnaQ, dnaE or dnaN, or encoding the subunits of the DNA Polymerase III of the invention can be prepared synthetically rather than cloned. The DNA sequence can be designed with the appropriate codons for the amino acid sequence of the subunit(s) of interest. In general, one will select preferred codons for the intended host if the sequence will be used for expression. The complete sequence is assembled from overlapping oligonucleotides prepared by standard methods and assembled into a complete coding sequence. See, e.g. Edge, *Nature,* 292:756 (1981); Nambair et al., *Science,* 223:1299 (1984); Jay et al., *J. Biol. Chem.,* 259:6311 (1984).

Synthetic DNA sequences allow convenient construction of genes which will express DNA Polymerase III analogs or "muteins". Alternatively, DNA encoding muteins can be made by site-directed mutagenesis of native dnaX, dnaQ, dnaE or dnaN genes or their corresponding cDNAs, and muteins can be made directly using conventional polypeptide synthesis.

A general method for site-specific incorporation of unnatural amino acids into proteins is described in Christopher J. Noren, Spencer J. Anthony-Cahill, Michael C. Griffith, Peter G. Schultz, *Science.* 244:182-188 (April 1989). This method may be used to create analogs with unnatural amino acids.

GENERAL DESCRIPTION

As discussed above, the present invention has as one of its characterizing features, that a Polymerase III-type enzyme as defined hereinabove, has been discovered in a thermophile, that has the structure and function of a chromosomal replicase. This structure and function confers significant benefit when the enzyme is employed in procedures such as PCR where speed and accuracy of DNA reconstruction is crucial. Chromosomal replicases are composed of several subunits in all organisms (Kornberg and Baker, 1992). In keeping with the need to replicate long chromosomes, replicases are rapid and highly processive multiprotein machines. All cellular replicases examined to date derive their processivity from one subunit that is shaped like a ring and completely encircles DNA (Kuriyan and O'Donnell, 1993; Kelman and O'Donnell. 1994). This "sliding clamp" subunit acts as a mobile tether for the polymerase machine (Stukenberg et. al., 1991). The sliding clamp does not assemble onto the DNA by itself, but requires a complex of several proteins, called a "clamp loader" which couples ATP hydrolysis to the assembly of sliding clamps onto DNA (O'Donnell et. al., 1992). Hence, Pol III-type cellular replicases are comprised of three components: a clamp, a clamp loader, and the DNA polymerase.

An overall goal is to identify and isolate all of the genes encoding the replicase subunits from a thermophile for expression and purification in large quantity. Following this, the replication apparatus can be reassembled from individual subunit components for use in kits, PCR, sequencing and diagnostic applications (Onrust et. al., 1995).

As a beginning to identify and characterize the replicase of a thermophile, we started by looking for a homologue to the prokaryotic dnaX gene which encode subunits (γ and τ) of the replicase. The dnaX gene has another homologue, holB, which encodes yet another subunit (δ') of the replicase. The amino acid sequence of δ' (encoded by holA) and τ/γ subunits (encoded by dnaX) are particularly highly conserved in evolution from prokaryotes to eukaryotes (Chen et. al., 1992; O'Donnell et. al., 1993; Onrust et. al., 1993; Carter et. al., 1993; Cullman et. al., 1995).

The organism chosen for study and exposition herein is the exemplary extreme thermophile, *Thermus thermophilus* (*T.th.*). It is understood that other members of the class such as the *eubacterium* Thermotoga are expected to be analogous in both structure and function. Thus, the investigation of *T.th.* proceeded and initially, a *T.th.* homologue of dnaX was identified. The gene encodes a full length protein of 529 amino acids. The amino terminal third of the sequence shares over 50% homology to dnaX genes as divergent as *E. coli* (gram negative) and *B. subtilis* (gram positive). The *T.th.* dnaX gene contains a DNA sequence that provides a translational frameshift signal for production of two proteins from the same gene. Such frameshifting has been documented only in the case of *E. coli* (Tsuchihashi and Komberg, 1990; Flower and McHenry, 1990; Blinkowa and Walker, 1990). No frameshifting has been documented to occur in the dnaX homologues (RFC subunit genes) of yeast and humans (Eukaryotic kingdom).

The presence of a dnaX gene that produces two subunits implies that *T.th.* has a clamp loader (γ) and is organized by τ into a three component Pol III-type replicase. The three components of its replicase may be organized into a holoenzyme particle like the replicative DNA polymerase of *Escherichia coli*, DNA polymerase III holoenzyme. The *E. coli* DNA polymerase III holoenzyme contains 10 different subunits, some in copies of two or more for a total composition of 18 polypeptide chains (Baker and Kornberg, 1992; Onrust et. al., 1995). The holoenzyme is composed of three major activities: the 3-subunit DNA polymerase core (αεθ), the β subunit DNA sliding clamp, and the 5-subunit γ complex clamp loader (γδδ'χψ). This 3 component strategy generalizes to eukaryotes which utilize a clamp (PCNA) and a 5-subunit RFC clamp loader (RFC) which provide processivity to DNA polymerase δ (reviewed in Kelman and O'Donnell, 1994).

In *E. coli*, the three components are organized into one holoenzyme particle by the τ subunit, that acts as a "glue" protein (Onrust and O'Donnell, 1995). One dimer of τ holds together two core polymerases into one particle which are utilized for the coordinated and simultaneous replication of both strands of duplex DNA (McHenry, 1982; Maki et. al., 1988; Yuzhakov et. al., 1996). The "glue" protein τ subunit also binds one clamp loader (called γ complex) thereby acting as a scaffold for a large superstructure assembly called DNA polymerase III holoenzyme. The gene encoding τ, called dnaX, also encodes the γ subunit of DNA polymerase III. The β subunit then associates with Pol III to form the DNA polymerase III holoenzyme. The γ subunit is approximately ⅔ the length of τ. γ shares the N-terminus of τ, but is truncated by a translational frameshifting mechanism that, after the shift, encounters a stop codon within two amino acids (Tsuchihashi and Komberg, 1990; Flower and McHenry, 1990; Blinkowa and Walker, 1990). Hence, γ is the N-terminal 453 amino acids of τ, but contains one unique residue at the C-terminus (the penultimate codon encodes a Lys residue which is the same sequence as if the frameshift did not take place). This frameshift is highly efficient and occurs approximately 50% of the time.

The sequence of the γ and τ subunits encoded by the dnaX gene are homologous to the clamp loading subunits in all other organisms extending from gram negative bacteria through gram positive bacteria, the Archeae Kingdom and the Eukaryotic Kingdom from yeast to humans (O'Donnell et al., 1993). All of these organisms utilize a three component replicase (DNA polymerase, clamp and clamp loader) and in these cases the 3 components appear to behave as independent units in solution rather than forming a large holoenzyme superstructure. For example, in eukaryotes from yeast to humans, the clamp loader is the five subunit RFC, the clamp is PCNA and the polymerases δ and ε are all stimulated by the PCNA clamp assembled onto primed DNA by RFC (reviewed in Kelman et. al., 1994).

The discovery of a dnaX gene in *T.th.* provided confidence that thermophilic bacteria would contain a three component Pol III-type enzyme. Hence, we proceeded to identify the dnaQ and dnaN genes encoding, respectively, the proofreading 3'-5' exonuclease, and the β DNA sliding clamp subunits of a Pol III-type enzyme. Following this, we purified from extracts of *T.th.* cells, a Pol III-type enzyme. This enzyme preparation had the unique property of extending a single primer around a long 7.2 kb single strand DNA genome of M13mp18 bacteriophage. Such a primer extension assay serves as a tool to detect and identify the Pol III-type of enzyme in cell extracts. The enzyme was confirmed to be a Pol III-type enzyme based on its reactivity with antibody directed against the E. coli α subunit (the DNA polymerase subunit) and antibody directed against E. coli γ subunit. Proteins corresponding to α, τ, γ, δ and δ' were easily visible and will lend themselves to identification of the genes through use of peptide microsequencing followed by primer design for PCR amplification. From this DNA pol III-type preparation we obtained peptide sequence of the α subunit enabling us to obtain the dnaE gene encoding the α subunit (DNA polymerase) of the Pol III-type enzyme.

These methods should be widely applicable to other thermophilic bacteria. Additional antibody reaents against other Pol III-type enzyme components, such as RFC subunits, DNA polymerase delta, epsilon or beta, and the PCNA clamp from known organisms can be made quite easily as polyclonal or monoclonal antibody preparations using as antigen either naturally purified sequence, recombinant sequence, or synthetic peptide sequence. Examples of known sequences of these Pol III-type enzymes are to be found in: 1) DNA polymerases (Braithwaite and Ito, 1993), RFC clamp loaders (Cullman et. Al., 1995), and PCNA (letman and O'Donnell, 1995).

Braithwaite, D. K. and Ito, J. (1993) Compilation, alignment, and phylogenetic relationships of DNA polymerases. Nuc. Acids Res. 21, 787-802.

Cullman G., Fein, K., Kobayashi, R., and Stillman. B. (1995) Characterization of the five replication factor C genes of Saccharomyces cerevisiae. Mol. Cell. Biol. 15, 4661-4671.

Kelman, Z., and O'Donnell, M. (1995) Structural and functional similarities of prokaryotic and eukaryotic DNA polymerase sliding clamps. Nucl Acids Res. 23, 3613-3620.

The remaining genes of Pol III needed for efficient extension of primed templates should be easy to obtain from the T.th. Pol III by similar methods as those described herein. These genes will provide the subunit preparations through use of standard recombinant techniques and protein purification protocols. The protein subunits can then be used to reconstitue the enzyme complexes as they exist in the cell. This type of reconstitution of Pol III has been demonstrated using the protein subunits of DNA polymerase III holoenzyme from E. coli to assemble the entire particle. See e.g., U.S. Pat. No. 5,583,026, issued December. 1996, O'Donnell, M. E.; and U.S. Pat. No. 5,668,004, issued September. 1997, both to one of the inventors herein, and Onrust et. al. 1995b. The disclosures of these references are incorporated herein in their entireties.

The following experiments illustrate the identification and characterization of the enzymes and constructs of the present invention. Accordingly, in Examples 1-8 below, the identification and expression of the γ and τ is presented, as the first step in the elucidation of the Polymerase III reflective of the present invention. Examples 9-13 which follow set forth the protocol for the purification of the remainder of the sub-units of the enzyme that represent substantial entirety of the functional replicative machinery of the enzyme.

EXAMPLE 1

Experimental Procedures

Materials—DNA modification enzymes were from New England Biolabs. Labelled nucleotides were from Amersham, and unlabeled nucleotides were from New England Biolabs The Alter-1 vector was from Promega. pET plasmids and E. coli strains, BL21(DE3) and BL21(DE3)pLysS, were from Novagen. Oligonucleotides were from Operon. Buffer A is 20 mM Tris-HCl (pH 7.5), 0.1 mM EDTA, 5 mMDTT, and 10% glycerol.

Genomic DNA

Thermus thermophilus (strain HB8) was obtained from the American Type Tissue Collection. Genomic DNA was prepared from cells grown in 0.1l of (Thermus medium N697 (ATCC: 4 γ yeast extract, 8.0 g polypeptone (BBL 11910), 2.0 g NaCl, 30.0 g agar, 1.0 L distilled water) at 75° C. overnight. Cells were collected by centrifugation at 4° C. and the cell pellet was resuspended in 25 ml of 100 mM Tris-HCl (pH 8.0), 0.05 M EDTA, 2 mg/ml lysozyme and incubated at room temperature for 10 min. Then 25 ml 0.10 M EDTA (pH 8.0), 6% SDS was added and mixed followed by 60 ml of phenol. The mixture was shaken for 40 min. followed by centrifugation at 10.000×G for 10 min. at room temperature. The upper phase (50 ml) was removed and mixed with 50 ml of phenol: chloroform (50:50 v/v) for 30 min. followed by centrifugation for 10 min. at room temperature. The upper phase was decanted and the DNA was precipitated upon addition of 1/10th volume 3 M sodium acetate (pH 6.5) and 1 volume ethanol. The precipitate was collected by centrifugation and washed twice with 2 ml of 80% ethanol, dried and resuspended in 1 ml T.E. buffer (10 mM Tris Hcl (pH 7.5), 1 mM EDTA).

Cloning of dnaX—DNA oligonucleotides for amplification of T.th. genomic DNA were as follows. The upstream 32mer (5'-CGC AAGCTTCACGCSTACCTSTTCTCCGGSAC-3') (SEQ ID NO: 6) (S indicates a mixture of G and C) consists of a Hind III site within the first 9 nucleotides (underlined) followed by codons (SEQ ID NO: 29) encoding the following sequence (HAYLFSGT) (SEQ ID NO: 7). The downstream 34 mer (5'-CGC GAATTCGTGCTCSGGSGGCTCCTCSAGSGTC-3') (SEQ ID NO: 8) consists of an EcoRI site (underlined) followed by codons encoding the sequence KTLEEPPEH (SEQ ID NO: 9) on the complementary strand. The amplification reactions contained 10 ng T.th. genomic DNA, 0.5 mM of each primer, in a volume of 100 μl of Vent polymerase reaction mixture according to the manufacturers instructions (10 μl ThermoPol Buffer, 0.5 mM each dNTP and 0.5 mM MgSO$_4$). Amplification was performed using the following cycling scheme: 5 cycles of: 30 s at 95.5° C., 30 s at 40° C., 2 min. at 72° C.; 5 cycles of: 30 s at 95.5° C., 30 s at 45° C., and 2 min. at 72° C.; and 30 cycles of: 30 s at 95.5° C., 30 s at 50° C., and 30 s at 72° C. Products were visualized in a 1.5% native agarose gel.

Genomic DNA was digested with either XhoI, XbaI, Stul, PstI, NcoI, MluI, KpnI, HindIII, EcoRI, EagI, BglI, or BamHI, followed by Southern analysis in a native agarose gel (Maniatis et. al., 1982). Approximately 0.5 μg of digest was analyzed in each lane of a 0.8% native agarose gel followed by transfer to an MSI filter (Micron Separations Inc.). The transfer included the following steps:

1. The agarose gel was soaked in 500 ml of 1% HCl with gentle shaking for 10 min.

2. Then the gel was soaked in 500 ml of 0.5 M NaOH+1.5 M NaCl for 40 min.

3. After that the gel was soaked in 500 ml of 1 M ammonium acetate for 1 h.

4. The DNA was transferred to the MSI filter with the use of blotting paper for 4 h.

5. The filter was kept at 80° C. for 15 min. in the oven.

6. The pre-hybridization step was run in 10 ml of Hybridization solution (1% crystalline BSA (fraction V) (Sigma). 1 mM EDTA. 0.5 M NaHPO4 (pH 7.2), 7% SDS) at 65° C. for 30 min.

7. The probe, radiolabelled by the random priming method (see below), was added to the pre-hybridization solution and kept at 65° C. for 12 h.

8. The filter was washed with low stringency with 200 ml of the wash buffer (0.5% BSA, fractionV), 1 mM Na2EDTA, 40 mM NaHPO4 (pH 7.2), 5% SDS with gentle shaking for 20 min. This step was repeated 5 times, followed by exposure to X-ray film (XAR-5, Kodak).

As a probe, the PCR product was radiolabelled by random as follows.

1. 14 ml of the mixture containing 0.2 μg of PCR product DNA, 1 μg of the pd(N6) (Promega) and 2.5 ml of the 10× Klenow reaction buffer (100 mM Tris-HCl (pH 7.5), 50 mM $MgCl_2$, 75 mM dithiothreitol) were boiled for 10 min. and then kept at 4° C.

2. The reaction volume was increased up to 25 μl, containing in addition 33 μM of each dNTP, except dATP, 10 μCi [$\alpha$-$^{32}$P] dATP (800 Ci/mM), and 2 units of Klenow enzyme. The reaction mixture was incubated 1.5 h.

3. 2 mg of sonicated herring sperm DNA (GibcoBRL) was added to the reaction and the volume was increased to 2 ml using hybridization solution. The sample was then boiled for 10 min.

A genomic library of XbaI digested DNA was prepared upon treating 1 μg genomic $T.th$. DNA with 10 units of XbaI in 100 μl of NEBuffer N2 (50 mM NaCl, 10 mM Tris-HCl (pH 7.9). 10 mM $MgCl_2$, 1 mM DTT) for 2 h at 37° C. The digested DNA was purified by phenol chloroform extraction and ethanol precipitation. The Alter-1 vector (0.5 μg) (Promega) was digested with 1 unit of XbaI in NEBuffer N2 and then purified by phenol/chloroform extraction and ethanol precipitation. One microgram of genomic digest was incubated with 0.05 μg of digested Alter-1 and 20 U of T4 ligase in 30 μl of ligase buffer (50 mM Tris-HCl (pH 7.8), 10 mM $MgCl_2$, 10 mM DTT and 1 mM ATP) at 15° C. for 12 h. The ligation reaction was transformed into the DH5α strain of $E. coli$ and transformants were plated on LB plates containing ampicillin and screened for the dnaX insert using the radiolabelled PCR probe as follows:

1. The colonies tested were lifted onto MSI filters, approximately 100 colonies to each filter.

2. The filters, removed from the LB/Tc plates, were placed side up on a sheet of Whatman 3 mM paper soaked with 0.5 M NaOH for 5 min.

3. The filters were transferred to a sheet of paper soaked with 1 M Tris-HCl (pH 7.5) for 5 min.

4. The filters were placed on a sheet of paper soaked in 0.5 M Tris-HCl (pH 7.5), 1.25 M NaCl for 5 min.

5. After drying by air, the filters were heated in the oven 80° C. for 15 min. and then were analyzed by Southern hybridization.

Plasmid DNA was prepared from 20 positive colonies; of these 6 contained the expected 4 kb insert when digested with XbaI. Sequencing of the insert was performed by the Sanger method using the Vent polymerase sequencing kit according to the manufacturers instructions (New England Biolabs).

Identification of the dnaX Gene

Figure 3:
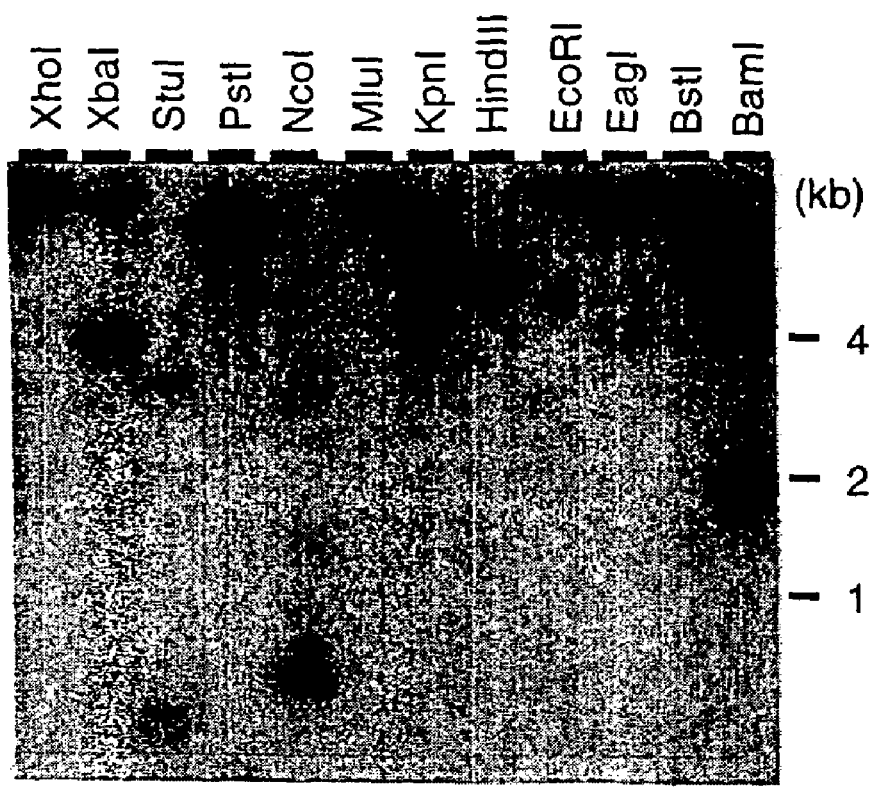
FIG. 3. Southern analysis of *T. thermophilus* genomic DNA—Genomic DNA was analyzed for presence of the DnaZ gene using the PCR radiolabelled probe. Enzymes used for digestion are shown above each lane. The numbering to the right corresponds to the length of DNA fragments (kb).
Figure 6:
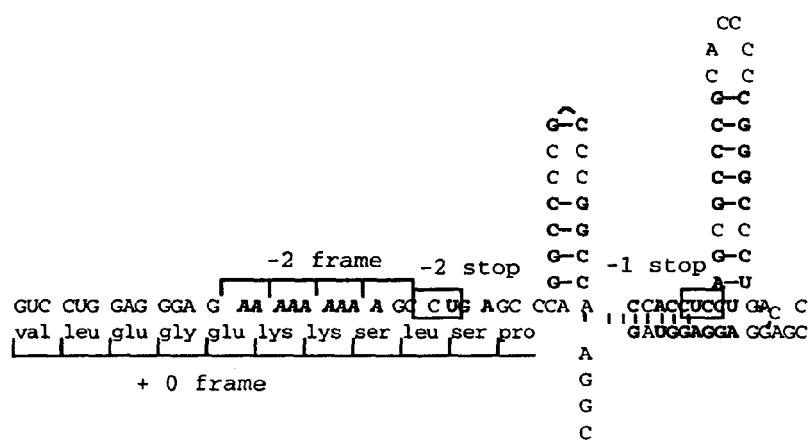
FIG. 6. Signal for ribosomal frameshifting in *T.th*. dnaX—The diagram shows part of the sequence of the RNA (SEQ ID NO: 27) around the frameshifting site (SEQ ID NO: 28), including the suspected slippery sequence A9 (bold italic). The stop codon in the −2 reading frame is indicated. Also indicated are potential step loop structures and the nearest stop codons in the −1 reading frame.

The dnaX genes of the gram negative, $E. coli$, and the gram positive $B. subtilis$, share more than 50% identity in amino acid sequence within the N-terminal 180 residues containing the ATP-binding domain (FIG. 2). Two highly conserved regions (shown in bold in FIG. 2) were used to design oligonucleotide primers for application of the polymerase chain reaction to $T.th$. genomic DNA. The expected PCR product, including the restriction sites (i.e. before cutting) is 345 nucleotides. Use of these primers with genomic $T.th$. DNA resulted in a product of the expected size. The PCR product was then radiolabelled and used to probe genomic DNA in a Southern analysis (FIG. 3). Genomic DNA was digested with several different restriction endonucleases, electrophoresed in a native agarose gel and then probed with the PCR fragment. The Southern analysis showed an XbaI fragment of approximately 4 kb, more than sufficient length to encode the dnaX gene. Other restriction nucleases produced fragments that were significantly longer, or produced two or more fragments indicating presence of a site within the coding sequence of dnaX.

To obtain full length dnaX, genomic DNA was digested with XbaI and ligated into XbaI digested Alter-1 vector. Ligated DNA was transformed into DH5 alpha cells, and colonies were screened with the labeled PCR probe. Plasmid DNA was prepared from 20 positive colonies and analyzed for the appropriate sized insert using XbaI. Six of the twenty clones contained the expected 4 kb XbaI fragment as an insert, the sequence of which is shown in FIGS. 4A and 4B.

The Frameshift Site

The dnaX gene of $E. coli$ produces two proteins, the γ and τ subunits, by a −1 frameshift (Tsuchihashi and Kornberg, 1990; Flower and McHenry, 1990; Blinkowa and Walker, 1990). The full length product yields τ, and the frameshift results in addition of one amino acid before encountering a stop codon to produce γ. The −1 frameshift site in the $E. coli$ dnaX gene contains the sequence, A AAA AAG, which follows the XXXYYYZ rule found in retroviral genes (Jacks et. al. 1988). This "slippery sequence" preserves the initial two residues of the tRNAs in the aminoacyl and peptidyl sites both before and after the frameshift. Mutagenesis of the $E. coli$ dnaX frameshifting site has shown that the first three residues can be nucleotides other than A, but that A's in the second set of three nucleotides is important to frameshifting (Tsuchihashi and Brown, 1992).

Immediately downstream of the stop codon is a potential stem-loop structure which enhances frameshifting, presumably by causing the ribosome to pause. Further, the AAG codon lacks a cognate tRNA in $E. coli$ and thus the G residue may facilitate the pause, and has been shown to aid the vigorous frameshifting observed in the $E. coli$ dnaX gene (Tsuchihashi and Brown, 1992). A fourth component of frameshifting in the $E. coli$ dnaX gene is presence of an upstream Shine-Dalgarno sequence which is thought to pair with the 16S rRNA to increase the frequency of frameshifting still further (Larsen et. al. 1994).

Examination of the $T.th$. dnaX sequence reveals a single site that fulfills the X XXY YYZ rule in which positions 4-7 are A residues. The site is unique from that in $E. coli$ as all seven residues are A, and the heptanucleotide sequence is flanked by another A residue on each side (i.e. A9). Surprisingly, the stop codon immediately downstream of this site is in the −2 frame, although there is a stop codon in the −1 frame 28 nucleotides downstream of the −2 stop codon. Indeed, a −2 frameshift would fulfill the requirement that the first two nucleotides of each codon in the peptidyl and aminoacyl sites be conserved during either a −1 or a −2 frameshift. As with the case of $E. coli$ dnaX, there are secondary structure step loop structures immediately downstream. Finally, there is a Shine-Dalgarno sequence immediately adjacent to the frameshift site, as well as another Shine-Dalgarno sequence 22 nucleotides upstream of the frameshift site.

Figure 8:
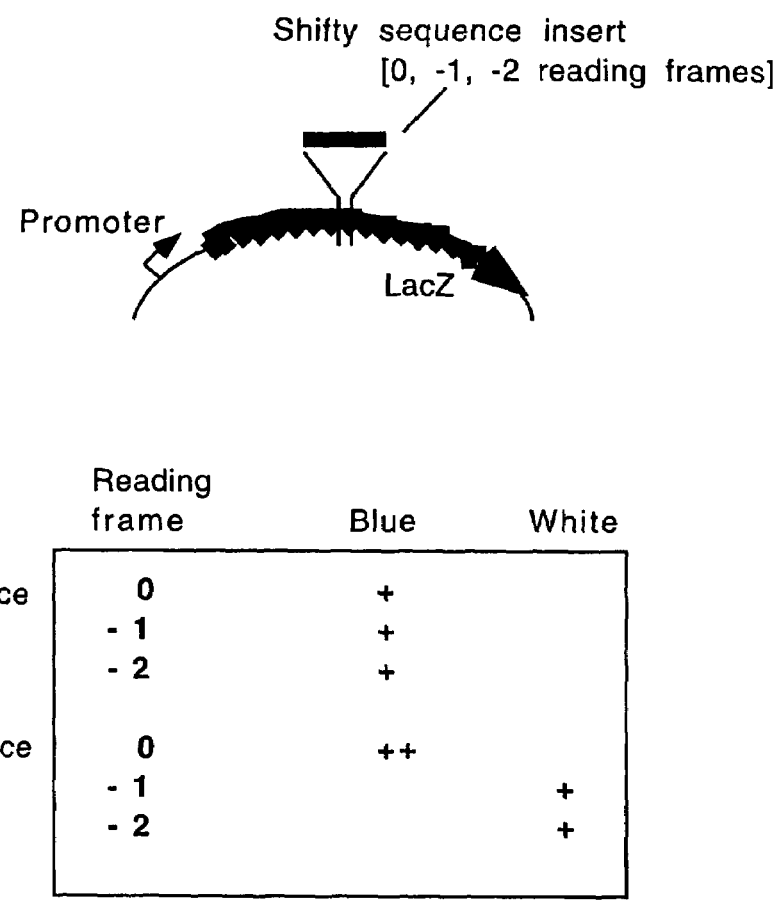
FIG. 8. The frameshift sequence in *T.th*. dnaX promotes −1 and −2 frameshifts in *E. coli*—The region of the dnaX gene slippery sequence was cloned into the lacZ gene of pUC19 in three reading frames, then transformed into *E. coli* cells and plated on LB plates containing X-gal. The slippery sequence was also mutated by inserting two G residues into the A9 sequence and then cloned into pUC19 in all three reading frames. Color of colonies observed are indicated by the plus signs. The picture shows the colonies, the type of frameshift required for readthrough (blue color) is indicted next to the sector.

Assuming the first stop codon is utilized (i.e. −2 frameshift), the predicted size of the γ subunit in *T.th.* is 454 amino acids for a mass of 49.8 kDa, over 2 kDa larger than the 431 residue γ subunit (47.5 kDa) of *E. coli*. This would result in 2 residues after the −2 frameshift (i.e. after the GluLysLys, the residues LysAla would be added) to be compared to the result of the −1 frameshift in *E. coli* which also results in 2 residues (LysGlu). In the event that a −1 frameshift were utilized in the *T.th.* dnaX gene, then an additional 12 residues would be added following the frameshift for a molecular mass of 50.8 kDa (i.e. after the GluLysLys, the residues LysProAsp-ProLysAlaProProGlyProThrSer (SEQ ID NO: 18) would be added). As explained later, this nucleotide sequence was found to promote both −1 and −2 frameshifting in *E. coli* (FIG. 8). But first, we examined *T.th.* cells by Western analysis for the presence of two subunits homologous to *E. coli* γ and τ.

EXAMPLE 2

Frameshifting Analysis of the *T.th.* dnaX Gene

Frameshifting was analyzed by inserting the frameshift site into lacZ in the three different reading frames, followed by plating on X-gal and scoring for blue or white colony formation (Weiss et. al., 1987). The frameshifting region within *T.th* dnaX was subcloned into the EcoRI/BamHI sites of pUC19. These sites are within the polylinker inside of the β-galactosidase gene. Three constructs were produced such that the insert was either in frame with the downstream coding sequence of β-galactosidase, or were out of frame (either −1 or −2). An additional three constructs were designed by mutating the frameshift sequence and then placing this insert into the three reading frames of the β-galactosidase gene. These six plasmids were constructed as described below.

The upstream primer for the shifty sequences was 5'-gcg cgg atc cgg agg gag aaa aaa aaa gcc tca gcc ca-3' (SEQ ID NO: 10). The BamHI site for cloning into pUC is underlined. Also, the stop codon, tga, has been mutated to tca (also underlined). The upstream primer for the mutant shifty sequence was: 5'-gcg cgg atc cgg agg gag aga aga aaa gcc tca gcc ca-3' (SEQ ID NO: 11). The mutant sequence contains two substitutions of a G for an A residue in the polyA stretch (underlined). Three downstream primers were utilized with each upstream primer to create two sets of three inserts in the 0 frame, −1 frame and −2 frame. The sequence of these primers, and the length of insert (after cutting with EcoRI and BanHI and inserting into pUC19) are as follows: 5'-gaa tta aat tcg cgc ttc ggg agg tgg g-3' (SEQ ID NO: 12) (0 frameshift, total 58 nucleotide insert); 5'-gcg cga att cgc gct tcg gga ggt ggg-3' (SEQ ID NO: 13(−1 frame, 54mer insert); and 5'-gcg cga att cgg gcg ctt cag gag gtg gg-3' (SEQ ID NO: 14) (−2 frame, 56mer insert). The downstream primers have an EcoRI site (underlined); the EcoRI site of the 0 frame insert was blunt ended to produce the greater length insert (converting the EcoRI site to an aattaatt sequence). Also, the tcg sequence, which produces the tga stop codon (underlined) was mutated to tca in the −2 downstream primer so that readthrough would be allowed after the frameshift occurred.

In summary, a region surrounding the frameshift site and ending at least 5 nucleotides past the −1 frameshift stop codon was inserted into the β galactosidase gene of pUC19 in the three different reading frames (stop codons were mutated to prevent stoppage following a frameshift). These three plasmids were introduced into *E. coli* and plated with X-gal. The results, in FIG. 8, show that blue colonies were observed after 24 h incubation with all three plasmids and therefore both −1 and −2 frameshifting had occurred.

To further these results, two γ residues were introduced into the polyA tract which should disrupt the ability of this sequence to direct frameshifts. The mutated slippery sequence was inserted into pUC19 followed by transformation into *E. coli* and plating on X-gal. The results showed that both −1 and −2 frameshifting was prevented, further supporting the fact that frameshifting requires the polyA tract as expected (FIG. 8).

EXAMPLE 3

Expression Vector for *T.th.* γ and τ

Figure 9:
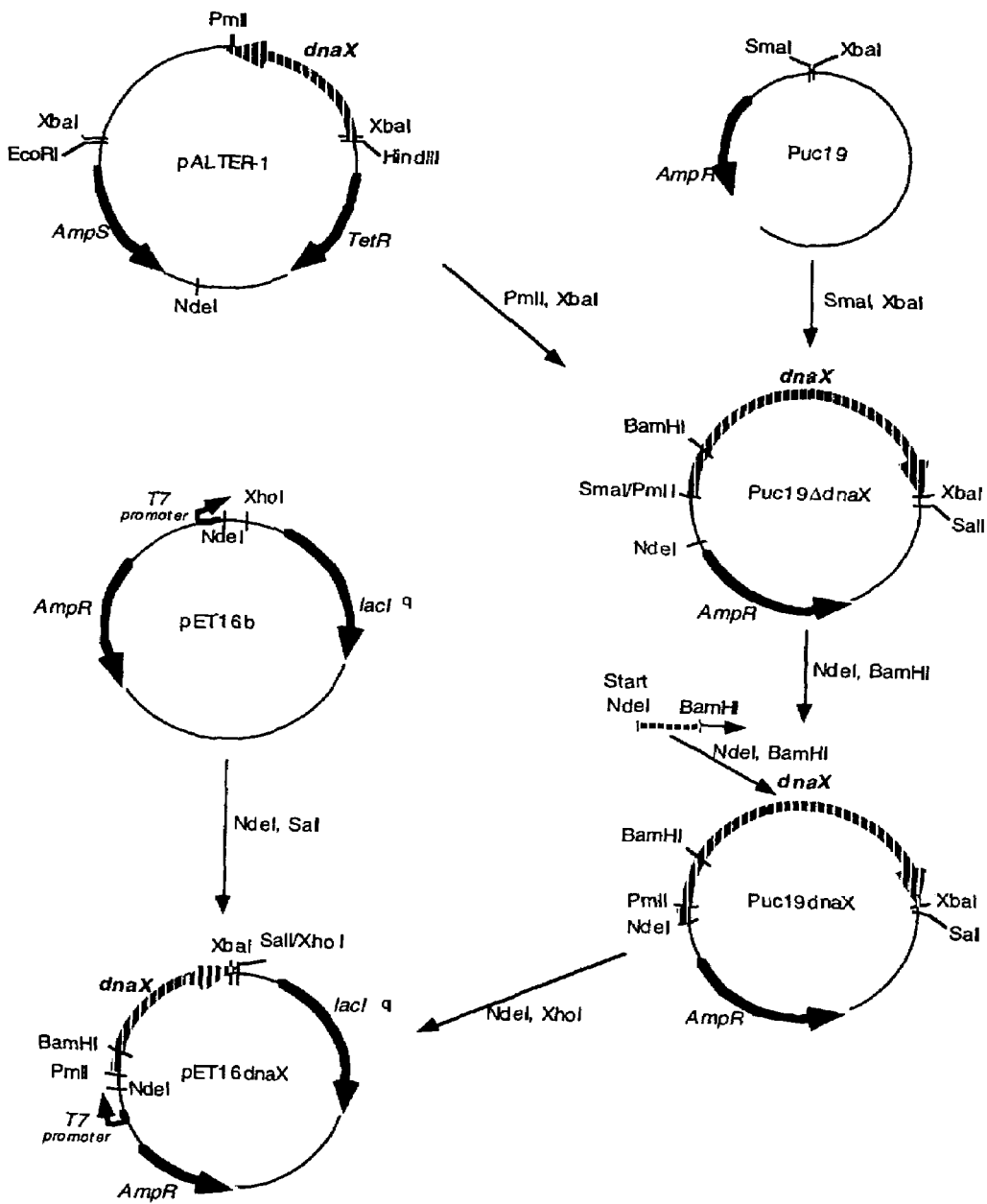
FIG. 9. Construction of the *T.th*. γ/τ expression vector—A genomic fragment containing a partial sequence of dnaX was cloned into pALTER-1. This fragment was subcloned into pUC19 (pUC19_dnaX). Then the N-terminal section of dnaX was amplified such that the fragment was flanked by NdeI (at the initiating codon) and the internal BamHI site. This fragment was inserted to form the entire coding sequence of the dnaX gene in pUC19 (pUC19dnaX). The dnaX gene was then cloned behind the polyhistidine leader in the T7 based expression vector pET16 to give pET16dnaX. Details are in "Experimental Procedures".

The dnaX gene was cloned into the pET16 expression vector in the steps shown in FIG. 9. First, the bulk of the gene was cloned into pET16 by removing the PmlI/XbaI fragment from pAlterdnaX, and placing it into SmaI/XbaI digested Puc19 to yield Puc19dnaXCterm. The N-terminal sequence of the dnaX gene was then reconstructed to position an NdeI site at the N-terminus. This was performed by amplifying the 5' region encoding the N-terminal section of γ/τ using an upstream primer containing an NdeI site that hybridizes to the dnaX gene at the initiating gtg codon (i.e. to encode Met where the Met is created by the PCR primer, and the Val is the initiating gtg start codon of dnaX). The primer sequence for this 5' end was: 5'-gtggtgcatatg gtg agc gcc ctc tac cgc c-3' (SEQ ID NO: 15)(where the NdeI site is underlined, and the coding sequence of dnaX follows). The downstream primer hybridizes past the PmlI site at nucleotide positions 987-1004 downstream of the initiating gtg (primer sequence: 5'-gtggtg-gtcgac cca gga ggg cca cct cca g-3' (SEQ ID NO: 16) where the initial 12 nucleotides contain a SalGI restriction site, followed by the sequence from the region downstream the stop codon). The 1.1 kb nucleotide PCR product was digested with PmlI/NdeI and the PmlI/NdeI fragment was ligated into NdeI/PmlI digested Puc19dnaXCterm to form Puc19dnaX. The Puc19dnaX plasmid was then digested with NdeI and SalI and the 1.9 kb fragment containing the dnaX gene was purified using the Sephaglas B and Prep Kit (Pharmacia-LKB). pET16b was digested with NdeI and XhoI. Then the full length dnaX gene was ligated into the digested pET16b to form pETdnaX.

EXAMPLE 4

Expression of *T.th.* γ and τ

Figure 10:
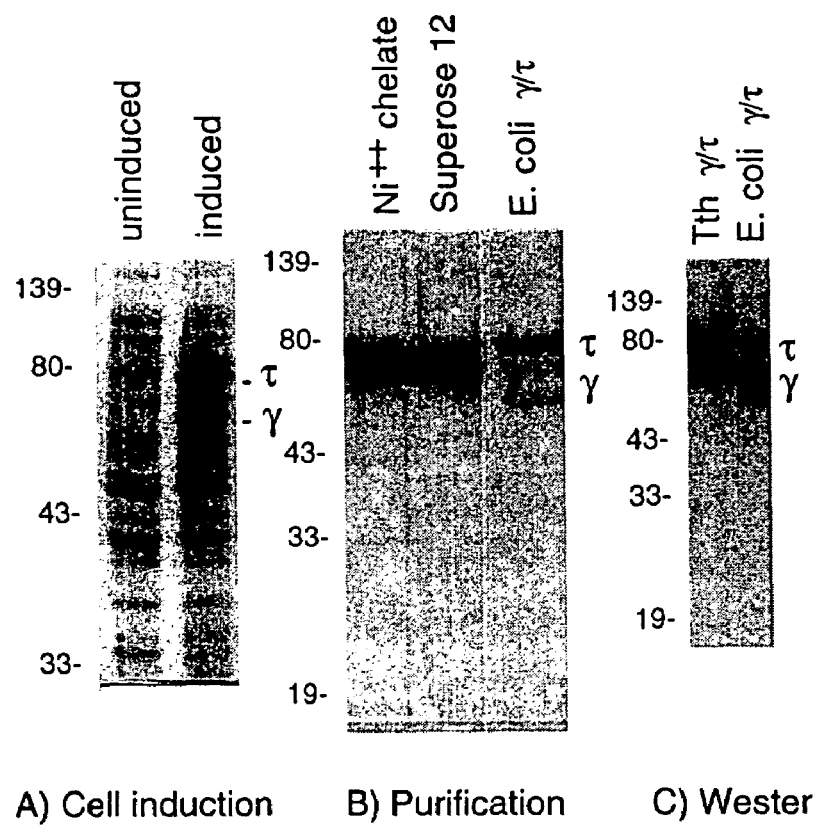
FIG. 10. Purification of recombinant *T.th*. γ and τ subunits—*T.th*. γ and τ subunits were expressed in *E. coli* harboring pET16dnaX. Molecular size markers are shown to the left of the gels, and the two induced proteins are labelled as g and t to the right of the gel. Panel A) 10% SDS gel of *E. coli* whole cell lysates before and after induction with IPTG. Panel B) 8% SDS gel of the purification two steps after cell lysis. First lane: the lysate was applied to a HiTrap Nickel chromatography column. Second lane: the *T.th*. γ/τ subunits were further purified on a Superose 12 gel filtration column. Third lane, the *E. coli* γ and τ subunits. Panel C) Western analysis of the pure *T.th*. γ and τ subunits (first lane) and *E. coli* γ and τ subunits (second lane).

As discussed in the previous example, the dnaX gene was engineered into the T7 based IPTG inducible pET16 vector such that the initiation codon was placed precisely following the Met residue N-terminal leader sequence (FIG. 9). This should produce a protein containing the entire sequence of γ and τ, along with a 21 residue leader containing 10 contiguous His residues (tagged-τ=60.6 kDa; tagged-γ=52.4 kDa for −2 frameshift). The pETdnaX plasmid was introduced into BL21(DE3)pLysS cells harboring the gene encoding T7 RNA polymerase under control of the lac repressor. Log phase cells were induced with IPTG and analyzed before and after induction in an SDS polyacrylamide gel (FIG. 10, lanes 1 and 2). The result shows that upon induction, two new proteins are expressed with the approximate sizes expected of the *T.th.* γ and τ subunits (larger than *E. coli* γ, and smaller than *E. coli* τ). The two proteins are produced in nearly equal amounts, similar to the case of the *E. coli* γ and τ subunits. Western analysis using antibodies against the *E. coli* γ and τ subunits cross reacted with the induced proteins further supporting their identity as *T.th.* γ and τ (data not shown, but repeated with the pure subunits shown in FIG. 10, lane 6).

EXAMPLE 5

Purification of *T.th.* γ and τ

The His-tagged *T.th.* γ and τ proteins were purified from 6 L of induced *E. coli* cells containing the pETdnaX plasmid. Cells were lysed, clarified from cell debris by centrifugation and the supernatant was applied to a HiTrap chelate affinity column. Elution of the chelate affinity column yielded approximately 35 mg of protein in which the two predominant bands migrated in a region consistent with the molecular weight predicted from the dnaX gene (FIG. 10, lane 3), and produced a positive signal by Western analysis using polyclonal antibody directed against the *E. coli* γ and τ subunits (lane 4). The γ and τ subunits are present in nearly equal amounts consistent with the nearly equal expression of these proteins in *E. coli* cells harboring the pETdnaX plasmid.

Figure 11:
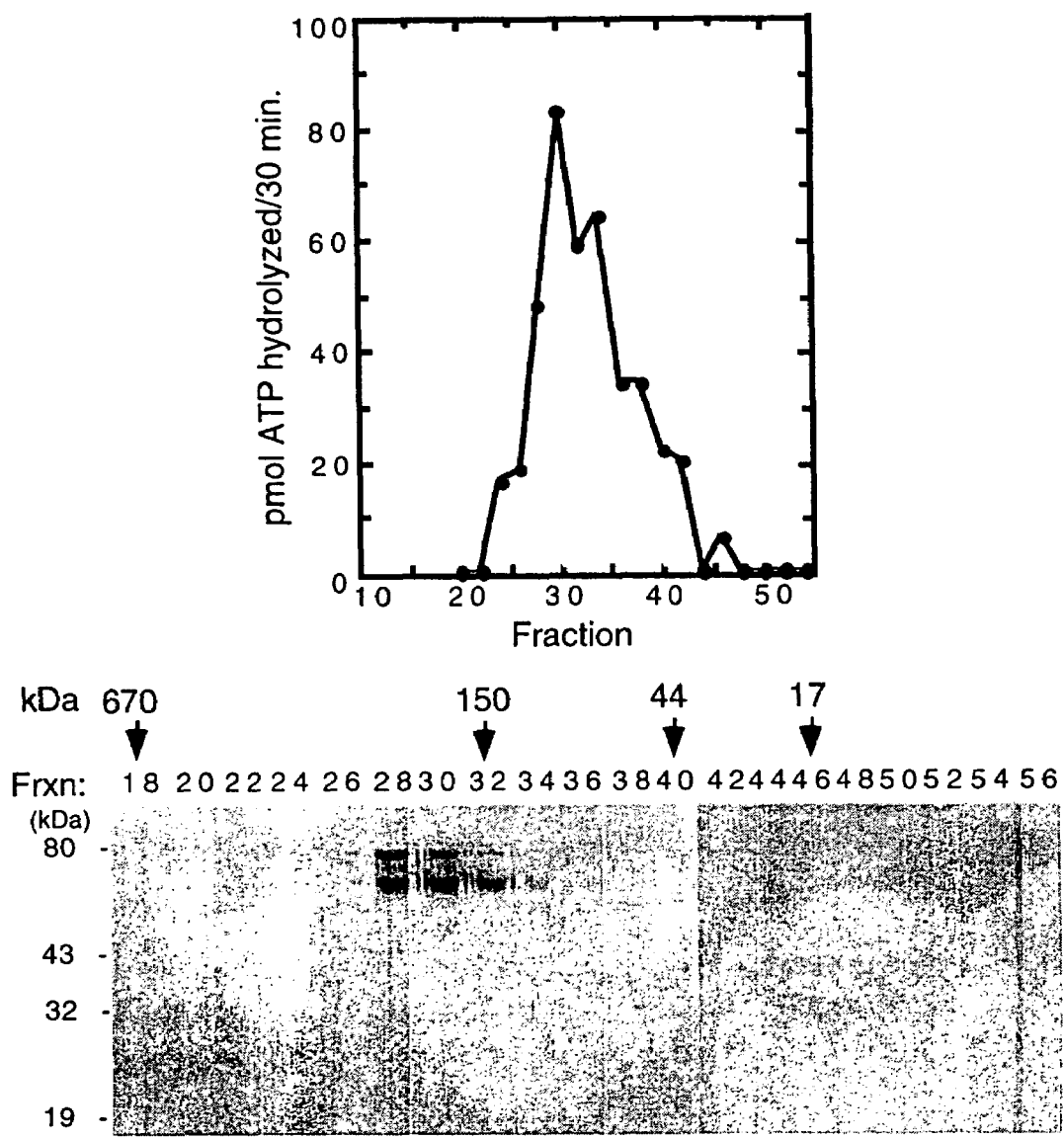
FIG. 11. Gel filtration of *T.th*. γ and τ-*T.th*. γ and τ were gel filtered on a q Superose 12 column. Column fractions were analyzed for ATPase activity and in a Coomassie Blue stained 10% SDS polyacrylamide gel. Positions of molecular weight markers are shown to the left of the gel. The elution position of size standards analyzed in a parallel Superose 12 column under identical conditions are indicated above the gel. Thyroglobin (670 kDa), bovine gamma globin (150 kDa), chicken ovalbumin (44 kDa). equine myoglobin (17 kDa).

The γ and τ subunits were further purified by gel filtration on a Superose 12 column (FIG. 10, lane 4; FIG. 11). Recovery of *T.th.* γ and τ subunits through gel filtration was 81%. The *E. coli* γ and τ subunits, when separated from one another, elute during gel filtration as tetramers. A mixture of *E. coli* γ/τ results in a mixed tetramer of γ2τ2 along with τ4 and γ4 tetramers (Onrust et. al., 1995). The mixture of *T.th.* γ/τ elutes ahead of the 150 kDa marker, and thus is consistent with the expected mass of a γ2τ2 tetramer (225 kDa) and τ4 and γ4 tetramers.

As described earlier, the dnaX frameshifting sequence could produce either a −1 or −2 framehift to yield a His-tagged γ subunit of mass either 53.3 kDa or 52.4 kDa, respectively. The difference in these two possible products is too close to determine from migration in SDS gels. It also remains possible that two γ products are present and do not resolve under the conditions used. The exact protocol for this purification is described below.

Six liters of BL21(DE3)pLysSpETdnaX cells were grown in LB media containing 50 μg/ml ampicillin and 25 μg/ml chloramphenicol at 37° C. to an O.D. of 0.8 and then IPTG was added to a concentration of 2 mM. After a further 2 h at 37° C., cells were harvested by centrifugation and stored at −70° C. The following steps were performed at 4° C. Cells (15 g wet weight) were thawed and resuspended in 45 ml 1× binding buffer (5 mM imidizole, 0.5 M NaCl, 20 mM Tris HCl (final pH 7.5)) using a dounce homogenizer to complete cell lysis and 450 ml of 5% polyamine P (Sigma) was added. Cell debris was removed by centrifugation at 18,000 rpm for 30 min. in a Sorvall SS24 rotor at 4° C. The supernatant (Fraction I, 40 ml, 376 mg protein) was applied to a 5 ml HiTrap Chelating Separose column (Pharmacia-LKB). The column was washed with 25 ml of binding buffer, then with 30 ml of binding buffer containing 60 mM imidizole, and then eluted with 30 ml of 0.5 M imidizole, 0.5 M NaCl, 20 mM Tris-HCl (pH 7.5). Fractions of 1 ml were collected and analyzed on an 8% Coomassie Blue stained SDS polyacrylamide gel. Fractions containing subunits migrating at the *T.th* γ and τ positions, and exhibiting cross reactivity with antibody to *E. coli* γ and τ in a Western analysis, were pooled and dialyzed against buffer A (20 mM Tris-HCl (pH 7.5), 0.1 mM EDTA, 5 mM DTT and 10% glycerol) containing 0.5 M NaCl (Fraction II, 36 mg in 7 ml). Fraction II was diluted 2-fold with buffer A and passed through a 2 ml ATP agarose column equilibrated in buffer A containing 0.2 M NaCl to remove any *E. coli* γ complex contaminant. Then 0.18 mg (300 ml) Fraction II was gel filtered on a 24 ml Superose 12 column (Pharmacia-LKB) in buffer A containing 0.5 M NaCl. After the first 216 drops, fractions of 200 μl were collected (Fraction III) and analyzed by Western analysis (by procedures similar to those described in Example 6), by ATPase assays and by Coomassie Blue staining of an 8% Coomassie Blue stained SDS polyacrylamide gel. The Coomassie stained gels and Western analysis of recombinant *T.th.* gamma and tau for these purification steps are summarized in FIG. 10.

EXAMPLE 6

Western Analysis of *T.th.* Cells for Presence of γ and τ Subunits

Polyclonal antibody to *E. coli* γ/τ—*E. coli* γ subunit was prepared as described (Studwell-Vaughan and O'Donnell, 1991). Pure γ subunit (100 μg) was brought up in Freund's adjuvant and injected subcutaneously into a New Zealand Rabbit (Poccono Rabbit Farms). After two weeks, a booster consisting of 50 μg γ in Freund's adjuvant was administered, followed after two weeks by a third injection (50 μg).

Figure 7:
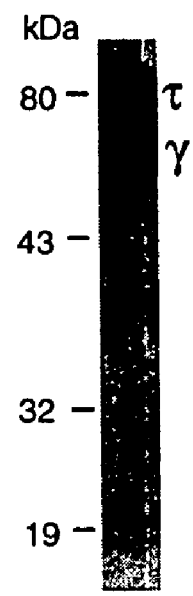
FIG. 7. Analysis of γ and τ in *T.th*. cells by Western—Whole cells were lysed in SDS and electrophoresed on a 10% SDS polyacrylamide gel then transferred to a membrane and probed with polyclonal antibody against *E. coli* γ/τ as described in Experimental Procedures. Positions of molecular weight size markers are shown to the left. Putative *T.th.* γ and τ are indicated to the right.

The homology between the amino terminal regions of *T.th.* and *E. coli* γ/τ subunits suggested that there may be some epitopes in common between them. Hence, polyclonal antibody directed against the *E. coli* γ/τ subunits was raised in rabbits for use in probing *T.th.* cells by Western analysis. FIG. 7 shows the results of a Western analysis of whole *T.th.* cells lysed in SDS. The results show that in *T.th.* cells, the antibody is rather specific for two high molecular proteins which migrate in the vicinity of the molecular masses of *E. coli* γ and τ subunits.

Procedure for Western Analysis

Samples were analyzed in duplicate 10% SDS polyacrylamide gels by the Western method (Towbin et. al. 1979). One gel was Coomassie stained to evaluate the pattern of proteins present, and the other gel was then electroblotted onto a nitrocellulose membrane (Schleicher and Schuell). For molecular size markers, the kaliedoscope molecular weight markers (Bio-Rad) were used to verify by visualization that transfer of proteins onto the blotted membrane had occurred. The gel used in electroblotting was also stained after electroblotting to confirm that efficient transfer of protein had occurred. Membranes were blocked using 5% non-fat milk, washed with 0.05% Tween in TBS (TBS-T) and then incubated for over 1 h with a 1/5000 dilution of rabbit polyclonal antibody directed against *E. coli* γ and τ in 1% gelatin in TBS-T at room temperature. Membranes were washed using TBS-T buffer and then antibody was detected on X-ray film (Kodak) by using the ECL kit from (Amersham) and the manufactures reccommended procedures.

Samples included: 1) a mixture of *E. coli* γ (15 ng) and τ (15 ng) subunits; 2) *T.th.* whole cells (100 μl) suspended in cracking buffer; and 3) purified *T.th.* γ and τ fraction II (0.6 μg as a mixture).

EXAMPLE 7

Characterization of the ATPase Activity of γ/τ—

The *E. coli* τ subunit is a DNA dependent ATPase (Lee and Walker, 1987; Tsuchihashi and Kornberg, 1989). The γ subunit binds ATP but does not hydrolyze it even in the presence of DNA unless other subunits of the DNA polymerase III holoenzyme are also present (Onrust et. al., 1991). Next we examined the *T.th.* γ/τ subunits for DNA dependent ATPase activity. The γ/τ preparation was, in fact, a DNA stimulated ATPase (FIG. 11, top panel). The specific activity of the T.th. γ/τ was 11.5 mol ATP hydrolyzed/mol γ/τ (as monomer and assuming an equal mixture of the two). Furthermore, analysis of the gel filtration column fractions shows that the ATPase activity coelutes with the T.th. g/t subunits, supporting evidence that the weak ATPase activity is intrinsic to the γ/τ subunits (FIG. 11). The specific activity of the γ/τ preparation before gel filtration was the same as after gel filtration (within 10%), further indicating that the DNA stimulated ATPase is an inherent activity of the γ/τ subunits. Presumably, only the τ subunit contains ATPase activity, as in the case of E. coli. Assuming only T.th. τ contains ATPase activity, its specific activity is twice the observed rate (after factoring out the weight of γ). This rate is still only one-fifth that of E. coli τ.

The T.th. γ/τ ATPase activity is lower at 37° C. than at 65° C. (middle panel), consistent with the expected behavior of protein activity from a thermophilic source. However, there is no apparent increase in activity in proceeding from 50° C. to 65° C. (the rapid breakdown of ATP above 65° C. precluded measurement of ATPase activity at temperatures above 65° C.). In contrast, the E. coli τ subunit lost most of its ATPase activity upon elevating the temperature to 50° C. (middle panel). These reactions contain no stabalizers such as a non-ionic detergent or gelatin, nor did they include substrates such as ATP, DNA or magnesium.

Figure 12:
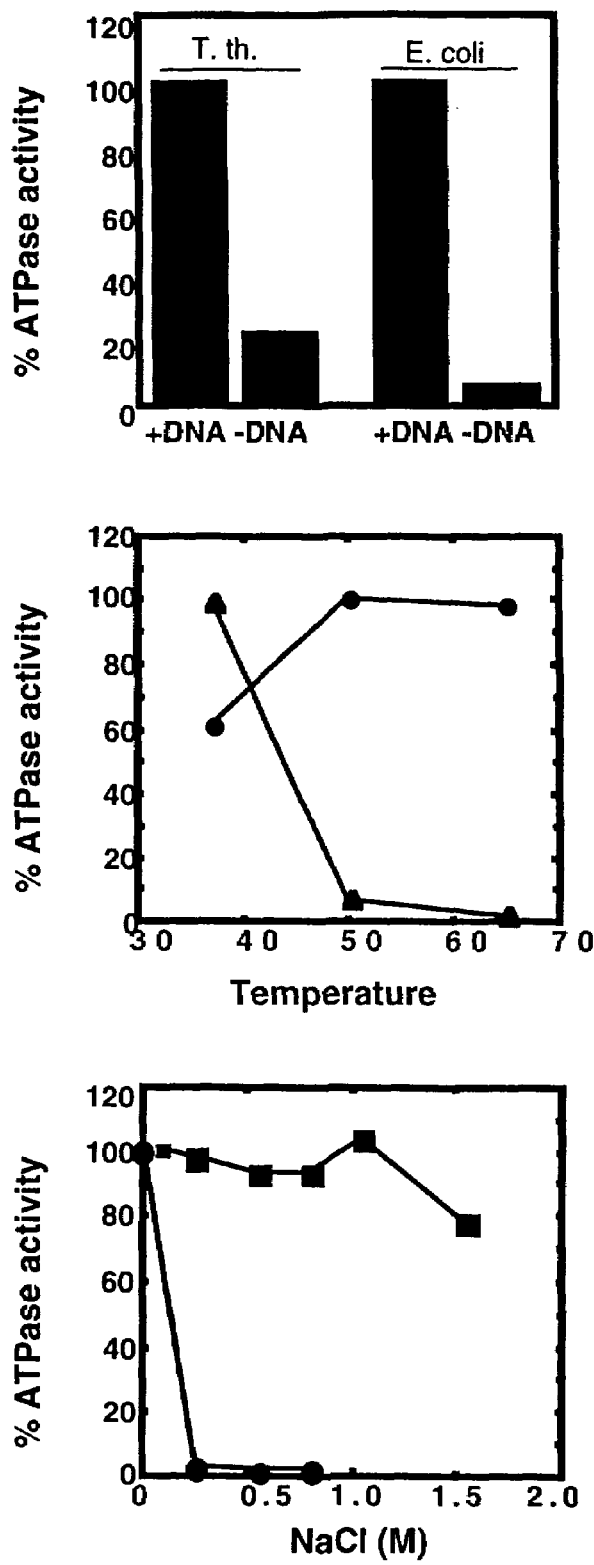
FIG. 12. Characterization of the *T.th*. γ and τ ATPase activity—The *T.th*. γ/τ and *E. coli* τ subunits are compared in their ATPase activity characteristics. Due to the greater activity of *E. Coli* τ, the values are plotted as percent for ease of comparison. Actual specific activities for 100% values are given below as pmol ATP hydrolyzed/30 min./pmol *T.th*. γ/τ (or pmol *E. coli* τ). Panel A) *T.th*. γ and τ ATPase is stimulated by the presence of ssDNA. *T.th*. γ/τ was incubated at 65° C. Specific activity was: 11.5 (+DNA); 2.5 (−DNA); *E. coli* τ was assayed at 37° C. Specific activity values were: 112.5 (+DNA); (7.3-DNA). Panel B) Temperature stability of DNA stimulated ATPase activity. *T.th*. γ/τ, 11.3 (65° C.); *E. coli* τ, 97.5 (37° C.). Panel C) Stability of *T.th*. γ/τ ATPase to NaCl. *T.th*. γ/τ, 8.1 (100 mM added NaCl and 65° C.); *E. coli* τ, 52.7 (0 M added NaCl and 37° C.).

Last, the relative stability of T.th. γ/τ and E. coli γ/τ to addition of NaCl (FIG. 12, bottom panel) was examined. Whereas the E. coli τ subunit rapidly lost activity at even 0.2 M NaCl. the T.th. γ/τ retained full activity in 1.0 M NaCl and was still 80% active in 1.5 M NaCl. The detailed procedure for the ATPase activity assay is described below.

ATPase assays: ATPase assays were performed in 20 μl of 20 mM Tris-HCl (pH 7.5), 8 mM MgCl$_2$ containing 0.72 μg of M13mp18 ssDNA (where indicated), 100 mM [γ-$^{32}$P]-ATP (specific activity of 2000-4000 cpm/pmol), and the indicated protein. Some reactions contained additional NaCl where indicated. Reactions were incubated at the temperatures indicated in the figure legends for 30 min. and then were quenched with an equal volume of 25 mM EDTA (final). The aliquots were analyzed by spotting them (1 μl each) onto thin layer chromatography (TLC) sheets coated with Cel-300 polyethyleneimine (Brinkmann Instruments Co.). TLC sheets were developed in 0.5 M lithium chloride, 1 M formic acid. An autoradiogram of the TLC chromatogram was used to visualize Pi at the solvent front and ATP near the origin which were then cut from the TLC sheet and quantitated by liquid scintillation. The extent of ATP hydrolyzed was used to calculate the mol of Pi released per mol of protein per min. One mol of E. coli τ was calculated assuming a mass of 71 kDa per monomer. The T.th. γ and τ preparation was treated as an equal mixture and thus one mole of protein as monomer was the average of the predicted masses of the γ and τ subunits (54 kDa).

EXAMPLE 7

Western Analysis of T.th. Cells for Presence of γ and τ Subunits—The homology between the amino terminal regions of T.th. and E. coli γ/τ subunits suggested that there may be some epitopes in common between them. Hence, polyclonal antibody directed against the E. coli γ/τ subunits was raised in rabbits for use in probing T.th. cells by Western analysis. FIG. 7 shows the results of a Western analysis of whole T.th. cells lysed in SDS. The results show that in T.th. cells, the antibody is rather specific for two high molecular proteins which migrate in the vicinity of the molecular masses of E. coli γ and τ subunits.

EXAMPLE 8

Homolog of T.th. γ/τ to dnaX Gene Products of Other Organism

The XbaI insert encoded an open reading frame, starting with a GTG codon, of 529 amino acids in length (58.0 kDa), closer to the predicted length of the B. subtilis τ subunit (563 amino acids, 62.7 kDa mass)(Alonso et. al., 1986) than the E. coli τ subunit (71.1 kDa)(Yin et. al., 1986). dnaX encoding the γ/τ subunits of E. coli DNA polymerase III holoenzyme is homologous to the holB gene encoding the 5' subunit of the γ complex clamp loader, and this homology extends to all 5 subunits of the eukaryotic RFC clamp loader as well as the bacteriophage gene protein 44 of the gp44/62 clamp loading complex (O'Donnell et. al., 1993). These gene products show greatest homology over the N-terminal 166 amino acid residues (of E. coli dnaX); the C-terminal regions are more divergent. FIG. 4 shows an alignment of the amino acid sequence of the N-terminal regions of the Tth dnaX gene product to those of several other bacteria. The consensus GXXGXGKT (SEQ ID NO: 17) motif for nucleotide binding, is conserved in all these protein products. Further, the E. coli δ' crystal structure reveals one atom of zinc coordinated to four Cys residues (Guenther, 1996). These four Cys residues are conserved in the E. coli dnaX gene, and the γ and τ subunits encoded by E. coli dnaX bind one atom of zinc (J. Turner and M. O'Donnell, unpublished). These Cys residues are also conserved in Tth dnaX (shown in FIG. 4). Overall, the level of amino acid identity relative to E. coli dnaX in the N-terminal 165 residues of Tth dnaX is 53%. The Tth dnaX gene is just as homologous to the B. subtilis dnaX (53% identity) gene relative to E. coli dnaX. After this region of homology, the C-terminal region of Tth dnaX shares 26% and 20% identity to E. coli and B. subtilis dnaX, respectively. A proline rich region, downstream of the conserved region, is also present in Tth dnaX (residues 346-375), but not in the B. subtilis dnaX (see FIGS. 3A and 3B). The overall identity between E. coli dnaX and Tth dnaX over the entire gene is 34%. Identity of Tth. dnaX to B. subtilis dnaX over the entire gene is 28%.

Comparison of dnaX Genes from T.th. and E. coli

The above identifies a homologue of the dnaX gene of E. coli in Thermus thermophilus. Like the E. coli gene, T.th. dnaX encodes two related proteins through use of a highly efficient translational frameshift. The T.th. γ/τ subunits are tetramers, or mixed tetramers, similar to the γ and τ subunits of E. coli. Further, the γ/τ subunit is a DNA stimulated ATPase like its E. coli counterpart. As expected for proteins from a thermophile, the T.th. γ/τ ATPase activity is thermostabile and resistant to added salt.

In E. coli, γ is a component of the clamp loader, and the τ subunit serves the function of holding the clamp loading apparatus together with two DNA polymerases for coordinated replication of duplex DNA. The presence of γ in T.th. suggests it has a clamp loading apparatus and thus a clamp as well. The presence of the τ subunit T.th. implies that T.th. contains a replicative polymerase with a structure similar to that of E. coli DNA polymerase III holoenzyme.

A significant difference between E. coli and T.th. dnaX genes is in the translational frameshift sequence. In E. coli, the heptamer frameshift site contains six A residues followed by a G residue in the context A AAA AAG. This sequence satisfies the X XXY YYZ rule for −1 frameshifting. The frameshift is made more efficient by the absence of the AAG tRNA for Lys which presumably leads to stalling of the ribosome at the frameshift site and increases the efficiency of frameshifting (Tsuchihashi and Brown, 1992). Two additional aids to frameshifting include a downstream hairpin, and an upstream Shine-Dalgarno sequence (Tsuchihashi and Kornberg, 1990; Larsen et. al., 1994). The −1 frameshift leads to incorporation of one unique residue at the C-terminus of *E. coli* γ before encounter with a stop codon.

In *T.th.*, the dnaX frameshifting heptamer is A AAA AAA, and it is flanked by two other A residues, one on each side. There is also a downstream region of secondary structure. The nearest downstream stop codon is positioned such that gamma would contain only one unique amino acid, as in *E. coli*. However, the *T.th.* stop codon is in the −2 reading frame thus requires a −2 frameshift. No precedent exists in nature for −2 frameshifting, although −2 frameshifting has been shown to occur in test cases (Weiss et. al., 1987). In vivo analysis of the *T.th.* frameshift sequence shows that this natural sequence promotes both −1 and −2 frameshifting in *E. coli*. Whereas the −2 frameshift results in only one unique C-terminal residue, a −1 frameshift would result in an extension of 12 C-terminal residues. At present, the results do not discriminate which path occurs in *T.th.*, a −1 or −2 frameshift, or a combination of the two.

There are two Shine-Dalgarno sequences just upstream of the frameshift site in *T.th.* dnaX. In two cases of frameshifting in *E. coli*, an upstream Shine-Dalgarno sequence has been shown to stimulate frameshifting (reviewed in Weiss et. al., 1897). In release factor 2 (RF2), the Shine-Dalgarno is 3 nucleotides upstream of the shift site, and it stimulates a +1 frameshift event. In the case of *E. coli* dnaX, a Shine-Dalgarno sequence 10 nucleotides upstream of the shift sequence stimulates the −1 frameshift. One of the *T.th.* dnaX Shine-Dalgarno sequences is immediately adjacent to the frameshift sequence with no extra space, the other is 22 residues upstream of the frameshift site. Which of these Shine-Dalgarno sequences plays a role in *T.th.* dnaX frameshifting, if any, will require future study.

In *E. coli*, efficient separation of the two polypeptides, γ and τ, is achieved by mutation of the frameshift site such that only one polypeptide is produced from the gene (Tsuchihashi and Kornberg, 1990). Substitution of G-to-A in two positions of the heptamer of *T.th.* dnaX eliminates frameshifting and thus should be a source to obtain τ subunit free of γ. To produce pure γ subunit free of τ, the frameshifting site and sequence immediately downstream of it can be substituted for an in frame sequence with a stop codon.

Examination of the *B. subtilis* dnaX gene shows no frameshift sequence that satisfies the X XXY YYZ rule. Hence, it would appear that dnaX does not make two proteins in this gram positive organism.

Rapid thermal motions associated with high temperature may make coordination of complicated processes more difficult. It seems possible that organizing the components of the replication apparatus may become yet more important at higher temperature. Hence, production of a τ subunit that could be used to crosslink two polymerases and a clamp loader into one organized particle may be most useful at elevated temperature.

As stated above, the following examples describe the continued isolation and purification of the substantial entirety of the Polymerase III from the extreme thermophile *Thermus thermophilus*. It is to be understood that the following exposition is reflective of the protocol and characteristics, both morphological and functional, of the Polymerase III-type enzymes that are the focus of the present invention, and that the invention is hereby illustrated and comprehends the entire class of enzymes of thermophilic origin.

EXAMPLE 9

Purification of the *Thermus thermophilus* DNA Polymerase III

All steps in the purification assay were performed at 4° C. The following assay was used in the purification of DNA polymerase from *T.th.* cell extracts. Assays contained 2.5 mg activated calf thymus DNA (Sigma Chemical Company) in a final volume of 25 ml of 20 mM Tris-Cl (pH 7.5), 8 mM $MgCl_2$, 5 mM DTT, 0.5 mM EDTA, 40 mg/ml BSA, 4% glycerol, 0.5 mM ATP. 3 mM each dCTP; dGTP, dATP, and 20 mM [α-$^{32}$P]dTTP. An aliquot of the fraction to be assayed was added to the assay mixture on ice followed by incubation at 60° C. for 5 min. DNA synthesis was quantitated using DE81 paper followed by washing off unincorporated nucleotide. Incorporated nucleotide was determined by scintillation counting of the filters.

*Thermus thermophilus* cell extracts were prepared by suspending 35 grams of cell paste in 200 ml of 50 mM TRIS-HCl, pH=7.5, 30 mM spermidine, 100 mM NaCl, 0.5 mM EDTA, 5 mM DTT, 5% glycerol, followed by disruption by passage through a French pressure cell (15,000 PSI). Cell debris was removed by centrifugation (12,000 RPM, 60 min). DNA polymerase III in the clarified supernatant was precipitated by treatment with ammonium sulphate (0.226 gm/liter) and recovered by centrifugation. This fraction was then backwashed with the same buffer (but lacking spermidine) containing 0.20 gm/l ammonium sulfate. The pellet was then resuspended in buffer A and dialyzed overnight against 2 liters of buffer A; a precipitate which formed during dialysis was removed by centrifugation (17,000 RPM, 20 min).

Figure 13:
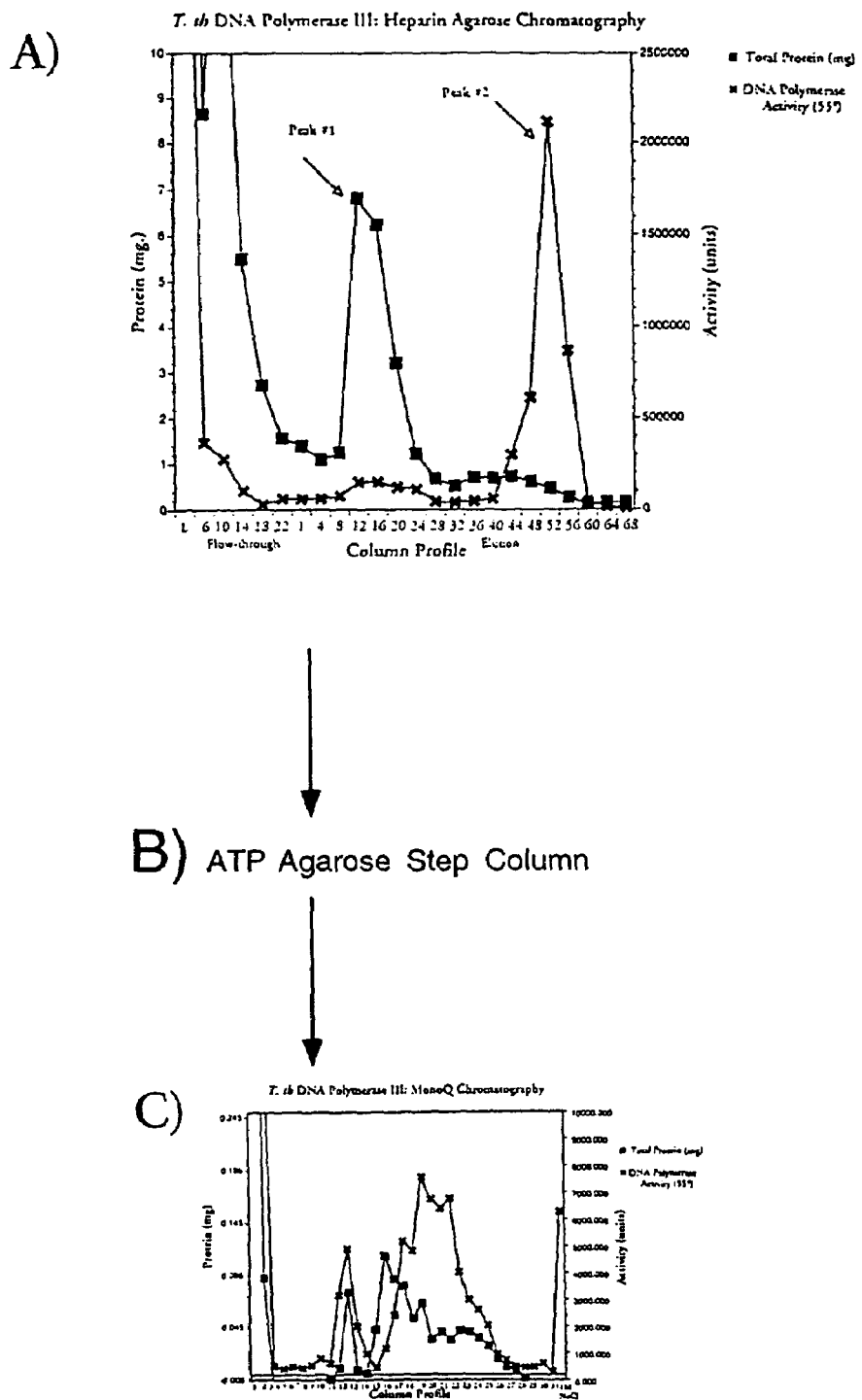
FIGS. 13A-13C are graphs that summarize the purification of the DNA polymerase III from *T.th*. extracts. A) shows the activity and total protein in column fractions from the Heparin Agarose column. Peak 1 fractions were chromatographed on ATP agarose, and Panel B) depicts the ATP-agarose column step, and Panel C) shows the total protein and DNA polymerase activity eluted from the MonoQ column.

The clarified dialysis supernatant, containing approximately 336 mg of protein, was applied onto a 60 ml heparin agarose column equilibrated in buffer A which was washed with the same buffer until A280 reached baseline. The column was developed with a 500 ml linear gradient of buffer A from 0 to 500 mM NaCl. More tightly adhered proteins were washed off the column by treatment with buffer A (20 mM Tris Hcl, pH=7.5, 0.1 mM EDTA, 5 mM DTT, and 10% glycerol) and 1M NaCl. Some DNA polymerase activity flowed through the column. Two peaks (HEP.P1 and HEP.P2) of DNA polymerase activity eluted from the heparin agarose column containing 20 mg and 2 mg of total protein respectively (FIG. 13A). These were kept separate throughout the remainder of the purification protocol.

The Pol III resided in HEP.P1 as indicated by the following criteria: 1) Western analysis using antibody directed against the α subunit of *E. coli* Pol III indicated presence of Pol III in HEP.P1, 2) Only the HEP.P1 fraction was capable of extending a single primer around an M13 mp18 7.2 kb ssDNA circle (explained later in Example 14). This type of long primer extension is a characteristic of Pol III type enzymes. 3) Only the HEP.P1 provided DNA polymerase activity that was retained on an ATP-agarose affinity column. This is indicative of a Pol III-type DNA polymerase since the γ and τ subunits are ATP interactive proteins.

The first peak of the heparin agarose column (HEP.P1: 20 mg in 127.5 ml) was dialyzed against buffer A and applied onto a 2 ml N6-linkage ATP agarose column pre-equilibrated in the same buffer. Bound protein was eluted by a slow (0.05 ml/min) wash with buffer A+2M NaCl and collected into 200 µl fractions. Chromatography of peak HEP.P1 yielded a flow-through (HEP.P1-ATP-FT) and a bound fraction (HEP.P1-

ATP-Bound) (FIG. 13B). Binding of peak HEP.P2 to the ATP column could not be detected, though DNA polymerase activity was recovered in the flow-through.

Figure 14:
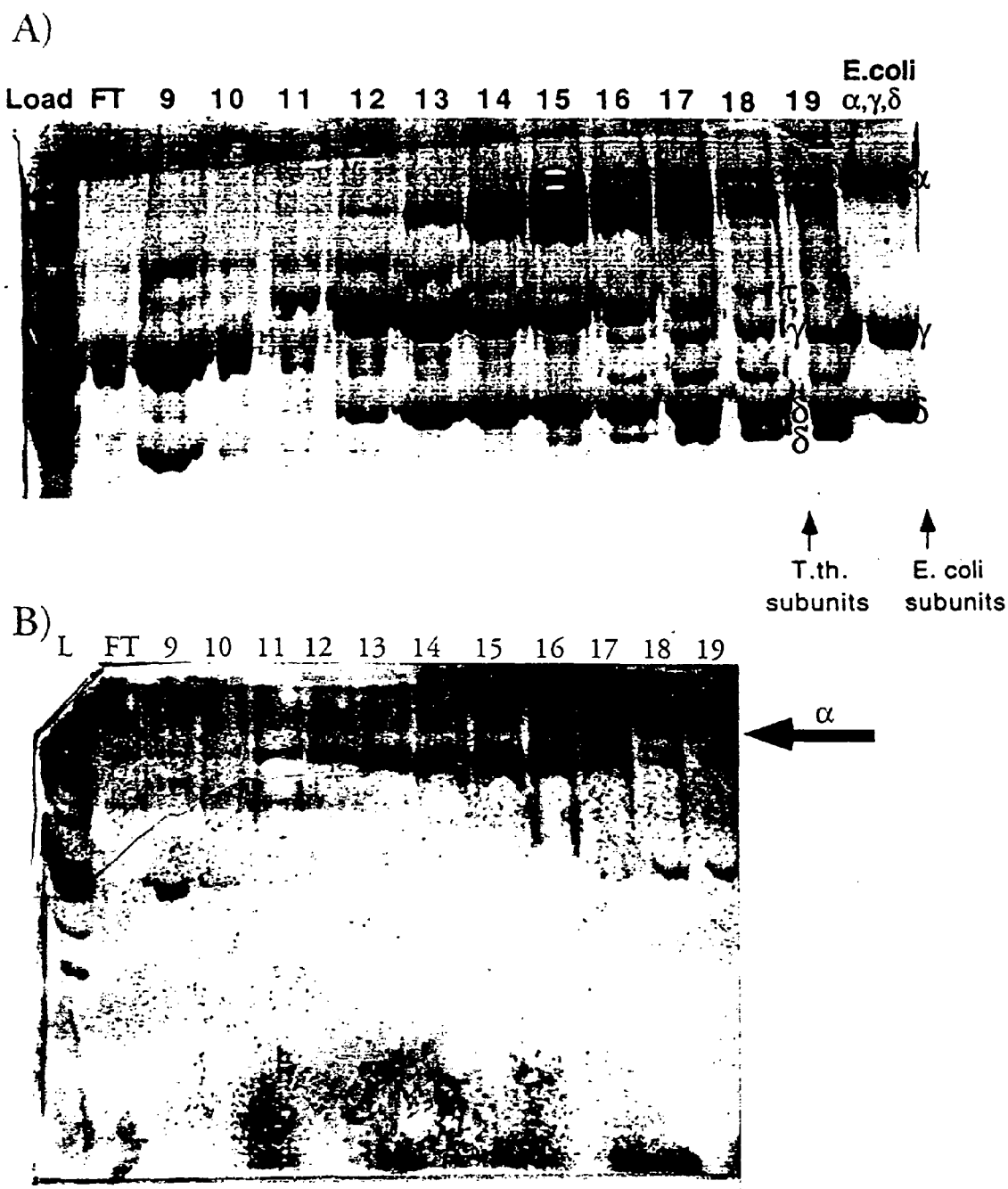
FIG. 14 is a 12% SDS polyacrylamide gel stained with Coomassie Blue (Panel A) of the MonoQ column. Loud stands for the material loaded onto the column (ATP agarose bound fractions). FT stands for protein that flowed through the MonoQ column. Fractions are indicated above the gel. *T.th*. subunits α, τ, γ, δ, δ' in fractions 17-19 are indicated by the labels placed between fractions 18 and 19. Additional small subunits may be present but difficult to visualize, or may have run off the gel. E. Coli, γ, δ shows a mixture of the α, γ and δ subunits of DNA polymerase III holoenzyme (they are labelled to the right in the figure). Panel B shows the Western results of an SDS gel of the MonoQ fractions probed with rabbit antiserum raised against the E. coli α subunit. L and FT are as described in Panel A. Fraction numbers are shown above the gel. The band that comigrates with E. coli α, and the band in the Coomassie Blue stained gel in Panel A, is marked with an arrow. This band was analyzed for microsequence and the results are shown in FIG. 15.

The HEP.P1-ATP-Bound fractions from the ATP agarose chromatographic step were further purified by anion exchange over monoQ. The HEP.P1-ATP-Bound fractions were diluted with buffer A to approximately the conductivity of buffer A plus 25 mM NaCl and applied to a 1 ml monoQ column equilibrated in Buffer A. DNA polymerase activity eluted in the flow-through and in two resolved chromatographic peaks (MONOQ peak1 and peak2) (FIG. 13C). Peak 2 was by far the major source of DNA polymerase activity. Western analysis using rabbit antibody directed against the *E. coli* α subunit confirmed presence of the α subunit in the second peak (see the Western analysis in FIG. 14B). Antibody against the *E. coli* γ subunit also confirmed the presence of the γ subunit in the second peak (not shown). Some reaction against α and γ was also present in the minor peak (first peak). The Coomassie Blue SDS polyacrylamide gel of the MonoQ fractions (FIG. 14A) showed a band that co-migrated with *E. coli* α and was in the same postion as the antibody reactive material (antibody against *E. coli* α). Also present are bands corresponding to τ, δ and δ'. These subunits, along with β, are all that is necessary for rapid and processive synthesis and primer extension over a long (>7 kb) stretch of ssDNA in the case of *E. coli* DNA Polymerase III holoenzyme.

The Pol III-type enzyme purified from *T.th*. may be a Pol III*-like enzyme that contains the DNA polymerase and clamp loader subuits (i.e. like the Pol III* of *E. coli*). The evidence for this is: 1) the presence of dnaX and dnaE gene products in the same column fractions as indicated by Western analysis (see above); 2) the ability of this enzyme to extend a primer around a 7.2 kb circular ssDNA upon adding only β (see Example 14); 3) stimulation of Pol III by adding β on linear DNA, indicating β subunit is not present in saturating amounts (see Example 13); and 4) the presence of τ in *T.th*. which may glue the polymerase and clamp loader into a Pol III* as in *E. coli*; and 5) the comigration of α with subunits γ, δ and δ' of the clamp loader in the column fractions of the last chromatographic step (MonoQ, FIG. 14A).

Micro-Sequencing of *T.th* DNA Polymerase III α Subunit

The α Subunit from the Purified *T.th* DNA Polymerase III (HEP.P1.ATP-Bound.MONOQ peak2) was blotted onto PVDF membrane and was cut out of the SDS-PAGE gel and submitted to the Protein-Nucleic Acid Facility at Rockefeller University for N-terminal sequencing and proteolytic digestion, purification and microsequencing of the resultant peptides. Analysis of the a candidate band (Mw≈130 kD) yielded four peptides, two of which (TTH1, TTH2) showed sequence similarity to a subunits from various bacterial sources (see FIG. 15).

EXAMPLE 10

Identification of the *Thermus thermophilus* dnaE Gene Encoding the α subunit of DNA Polymerase III Holoenzyme Cloning of the dnaE gene was started with the sequence of the TTH1 peptide from the purified α subunit (FFIEIQNH-GLSEQK) (SEQ ID NO: 61). The fragment was aligned to a region at approximately 180 amino acids downstream of the N-termini of several other known a subunits as shown in FIG. 15. The upstream 33mer (5'-GTG GGATCCGTGGTTCTGGATCTCGATGAAGAA-3') (SEQ ID NO: 31) consists of a BamHI site within the first 9 nucleotides (underlined) and the sequence coding for the following peptide HGLSEQK (SEQ ID NO.: 117) on the complementary strand. The downstream 29mer (5'-GTG GGATCCACGGSCTSTCSGAGCAGAAG-3') (SEQ ID NO: 32) consists of a BamHI site within the first 9 nucleotides (underlined) and the following sequence coding for the peptide FFIEIQNH (SEQ ID NO: 62).

These two primers were directed away from each other for the purpose of performing inverse PCR (also called circular PCR). The amplification reactions contained 10 ng *T.th*. genomic DNA (that had been cut and religated with XmaI), 0.5 mM of each primer, in a volume of 100 μl of Vent polymerase reaction mixture containing 10 μl ThermoPol Buffer, 0.5 mM of each dNTP and 0.25 mM MgSO₄. Amplification was performed using the following cycling scheme:
1. 4 cycles of: 95.5° C.-30", 45° C.-30". 75° C.-8'
2. 6 cycles of: 95.5° C.-30", 50° C.-30". 75° C.-6'
3. 30 cycles of: 95.5° C.-30", 52.5° C.-30", 75° C.-5'

A 1.4 kb fragment was obtained and cloned into pBS-SK: BamHI (i.e. pBS-SK (Stratragene) was cut pith BamHI). This sequence was bracketted by the 29mer primer on both sides and contained the sequence coding for the N-terminal part of the α subunit up to the peptide used for primer design.

To obtain further dnaE gene sequence, the TTH2 peptide was used. It was aligned to a region about 600 amino acids from the N-termini of the other known a subunits (FIG. 15B). The upstream 34mer (5'-GCG GGATCCTCAACGAGGACCTCTCCATCTTCAA-3') (SEQ ID NO: 33) consists of a BamHI site within the first 9 nucleotides (underlined) and the sequence from the end of the fragment previously obtained. The downstream 35mer (5'-GCG GGATCCTTGTCGTCSAGSGTSAGSGCGTCGTA-3') (SEQ ID NO: 34) consists of a BamHI site within the first 9 nucleotides (underlined) and the following sequence coding for the peptide YDALTLDD on the complementary strand. The amplification reactions contained 10 ng *T.th*. genomic DNA, 0.5 mM of each primer, in a volume of 100 μl of Vent polymerase reaction mixture containing 10 μl ThermoPol Buffer, 0.5 mM of each dNTP and 0.25 mM Mg SO₄. Amplification was performed using the following cycling scheme:
1.4 cycles of: 95.5° C.-30", 45° C.-30", 75° C.-8'
2. 6 cycles of: 95.5° C.-30", 50° C.-30", 75° C.-6'
3. 30 cycles of: 95.5° C.-30", 55° C.-30", 75° C.-5'

A 1.2 kb PCR fragment was obtained and cloned into pUC19:BamHI. The fragment was bracketted by the downstream primer on both sides and contained the region overlapping in 56 bp with the fragment previously cloned.

To obtain yet more dnaE sequence, the following primers were used. The upstream 39mer (3'-GTGTGGATCC TCGTCCCCCTCATGCGCGACCAGGAAGGG-5') (SEQ ID NO: 114) consists of a BamHI site within the first 10 nucleotides (underlined) and the sequence from the end of the fragment previously obtained. The downstream 27mer (5'-GTGTGGATCCTTCTTCTTSCCCATSGC-3') (SEQ ID NO: 36) consists of a BamHI site within the first 10 nucleotides (underlined), and the sequence coding for the peptide AMGKKK (SEQ ID NO: 64) (at position approximately 800 residues from the N terminus) on the complementary strand. The AMGKKK (SEQ ID NO: 64) sequence was chosen for primer design as it is highly conserved among the known gram-negative α subunits. The amplification reactions contained 10 ng *T.th*. genomic DNA, 0.5 mM of each primer, in a volume of 100 μl of Taq polymerase reaction mixture containing 10 μl PCR Buffer, 0.5 mM of each dNTP and 2.5 mM MgCl₂. Amplification was performed using the following cycling scheme:

1. 3 cycles of: 95.5° C.-30", 45° C.-30", 72° C.-8'
2. 6 cycles of: 94.5° C.-30", 55° C.-30", 72° C.-6'
3. 32 cycles of: 94.5° C.-30", 50° C.-30", 72° C.-5'

A 2.3 kb PCR fragment was obtained instead of the expected 0.6 kb fragment. BamHI digestion of the PCR product resulted in three fragments of 1.1 kb, 0.7 kb and 0.5 kb. The 1.1 kb fragment was cloned into pUC19:BamHI. It turned out to be the one adjacent to the fragment previously obtained and contained the dnaE sequence right up to the region coding for the AMGKKK (SEQ ID NO: 64) peptide, but was disrupted by an intein just upstream of this region.

The sequence that follows this was amplified from the 2.3 kb original PCR product using the same conditions and cycling scheme as for the 2.3 kb fragment. The downstream primer was the same as in the previous step. The upstream 27mer (3'-GTGTGGATCCGTGGTGACCTTAGCCAC-5') (SEQ ID NO: 115) consisted of a BamHI site within the first 9 nucleotides (underlined) and the sequence from the end of the 1.1 kb fragment previously described.

The expected 1.2 kb PCR fragment was obtained and cloned into pUC19:SmaI. This fragment coded for the rest of the intein and the end of it was used to obtain the next sequence of dnaE downstream of this region. The upstream 30mer (3'-TTCGTGTCCGAGGACCTTGTGGTCCA-CAAC-5') (SEQ ID NO: 116) was a sequence from the end of the intein. The downstream 23mer (5'-CCAGAATCGTCT-GCTGGTCGTAG-3') (SEQ ID NO: 39) was the sequence from the end of the dnaE gene of D.rad. (coding on the complementary strand for the region slightly homologous in the distantly related α subunits and possibly highly homologous between T.th. and D.rad. α subunits). The amplification reactions contained 10 ng T.th. genomic DNA, 0.5 mM of each primer, in a volume of 100 µl of Vent polymerase reaction mixture containing 10 µl ThermoPol Buffer, 0.5 mM of each dNTP and 0.1 mM Mg SO$_4$. Amplification was performed using the following cycling scheme:

1. 3 cycles of: 95.5° C.-30", 55° C.-30", 75° C.-8'
2. 32 cycles of: 94.5° C.-30", 50° C.-30", 75° C.-5'

A 2.5 kb PCR fragment was obtained and cloned into pUC19:SmaI. This fragment contained the dnaE sequence coding for the 300 amino acids next to the AMGKKK (SEQ ID NO: 64) region disrupted by yet a second intein inside another sequence that is conserved among the known a subunits (FNKSHSAAY) (SEQ ID NO: 65).

To obtain the rest of the dnaE gene the upstream 19mer (5'-AGCACCCTGGAGGAGCTTC-3') (SEQ ID NO: 40) from the end of the known dnaE sequence was used. The downstream primer was: 5'-CATGTCGTACTGGGTGTAC-3' (SEQ ID NO: 41). The amplification reactions contained 10 ng T.th. genomic DNA, 0.5 mM of each primer, in a volume of 100 µl of Vent polymerase reaction mixture containing 10 µl ThermoPol Buffer, 0.5 mM of each dNTP and 0.1 mM Mg SO$_4$. Amplification was performed using the following cycling scheme:

1. 3 cycles of: 95.5° C.-30", 55° C.-30", 75° C.-8'
2. 32 cycles of: 94.5° C.-30", 50° C.-30", 75° C.-5'

A 1.0 kb fragment bracketed by this upstream primer was obtained. It contained the 3' end of the dnaE gene.

EXAMPLE 11

Cloning and Expression of the *Thermus thermophilus* dnaQ gene encoding the ε subunit of DNA polymerase III Holoenzyme Cloning of dnaQ—The DnaQ gene of *E. coli* and the corresponding region of PolC of *B. subtilis*, evolutionary divergent organisms, share approximately 30% identity. Comparison of the predicted amino acid sequences encoded by DnaQ of *E. coli* and PolC of *B. subtilis* revealed two highly conserved regions positions (FIG. 17). Within each of these regions, a nine amino acid sequence was used to design two oligonucleotide primers for use in the polymerase chain reaction.

The regions highly conservative among Pol III exonucleases were chosen to design the degenerate primers for the amplification of a T.th. dnaQ internal fragment (see FIG. 17). DNA oligonucleotides for amplification of T.th. genomic DNA were as follows. The upstream 27mer (5'-GTS-GTSNNSGACNNSGAGACSACSGGG-3') (SEQ ID NO: 42) encodes the following sequence (VVXDXETTG) (SEQ ID NO: 66). The downstream 27mer (5'-GAASCCSNNGTC-GAASNNGGCGTTGTG-3') (SEQ ID NO: 43) encodes the sequence HNAXFDXGF (SEQ ID NO: 67) on the complementary strand. The amplification reactions contained 10.ng T.th. genomic DNA, 0.5 mM of each primer, in a volume of 100 µl of Vent polymerase reaction mixture containing 10 µl ThermoPol Buffer, 0.5 mM of each dNTP and 0.5 mM MgSO$_4$. Amplification was performed using the following cycling scheme:

1. 5 cycles of: 95.5° C.-30", 40° C.-30", 72° C.-2'
2. 5 cycles of: 95.5° C.-30", 45° C.-30", 72° C.-2'
3. 30 cycles of: 95.5° C.-30", 50° C.-30", 72° C.-30"

Products were visualized in a 1.5% native agarose gel. A fragment of the expected size of 270 bp was cloned into the SmaI site of pUC19 and sequenced with the CircumVent Thermal Cycle DNA sequencing kit according to the manufacturer's instructions (New England Biolabs).

To obtain further sequence of the dnaQ gene, genomic DNA was digested with either mhoI, BamHI, KpnI or NcoI. These restriction enzymes were chosen because the cut T.th. genomic DNA frequently. 0.1 µg of DNA for each digest was ligated by T4 DNA ligase in 50 µl of ligation buffer (50 mM Tris-HCl (pH 7.8), 10 mM MgCl$_2$, 10 mM dithiothreitol, 1 mM ATP, 25 mg/ml bovine serum albumin) overnight at 20° C. The ligation mixtures were used for cicular PCR.

DNA oligonucleotides for amplification of T.th. genomic DNA were the following. The upstream 27mer (5'-CGG GGATCCACCTCAATCACCTCGTGG-3') (SEQ ID NO: 44) consists of a BamHI site within the first 9 nucleotides (underlined) and the sequence complementary to 42-61 bp region of the previously cloned dnaQ fragment. The downstream 30mer (5'-CGG GGATCCGCCACCTTGCGGCTCCGGGTG-3') (SEQ ID NO: 45) consists of a BamHI site within the first 9 nucleotides (underlined) and the sequence corresponding to 240-261 bp region of the dnaQ fragment (see FIG. 17).

The amplification reactions contained 1 ng T.th. genomic DNA (that had been cut with NcoI and religated into circular DNA for circular PCR), 0.4 mM of each primer, in a volume of 100 µl of Vent polymerase reaction mixture containing 10 µl ThermoPol Buffer. 0.5 mM of each dNTP, 0.5 mM MgSO$_4$, and 10% DMSO. Circular amplification was performed using the following cycling scheme:

1. 5 cycles of: 95.5° C.-30", 50° C.-30", 72° C.-8'
2. 35 cycles of: 95.5° C.-30", 55° C.-30", 72° C.-6'
3. 72° C.-10'

A 1.5 kb fragment was obtained and cloned into the BamHI site of the pUC19 vector. Partial sequencing of the fragment reveiled that it contained the dnaQ regions adjacent to sequences corresponding to the PCR primers and hence contained the sequences both upstream and downstream of the previously cloned dnaQ fragment. One of NcoI sites turned out to be approximately 300 bp downstream of the end of the first cloned dnaQ sequence and hence did not include the 3' end of dnaQ. To obtain the 3' end, another inverse PCR reaction was performed. Since an ApaI restriction site was recognized within this newly sequenced dnaQ fragment, the circular PCR procedure was performed using as template an ApaI digest of *T.th.* genomic DNA that was ligated (circularized) under the same conditions as described above.

DNA oligonucleotides for amplification of the ApaI/religated *T.th.* genomic DNA were as follows. The upstream 31 mer (5'-GCGC TCTAGACGAGTTCCCAAAGCGTGCGGT-3') (SEQ ID NO: 46) consists of a mbaI site within the first 10 nucleotides (underlined) and the sequence complementary to the region downstream of the ApaI restriction site in the newly sequenced dnaQ fragment. The downstream 25mer (5'-CGCGTCTAGATCACCTGTATCCAGA-3') (SEQ ID NO: 47) consists of a XbaI site within the first 10 nucleotides (underlined) and the sequence corresponding to another region downstream of the ApaI restriction site in the newly sequenced dnaQ fragment. The 1.7 kb PCR fragment was cloned into the XbaI site of the pUC19 vector and partially sequenced. The sequence of dnaQ, and the protein sequence of the ε subunit encoded by it, is shown in FIG. 18.

The dnaQ gene is encoded by an open reading frame of 209 (or 190 depending on which Val is used as the initiating residue) amino acids in length (23598.5 kDa—or 21383.8 kDa for shorter version), similar to the length of the *E. coli* ε subunit (243 amino acids. 27099.1 kDa mass) (see FIG. 17).

The entire amino acid sequence of the E subunit predicted from the *T.th.* dnaQ gene aligns with the predicted amino acid sequence of the dnaQ genes of other organisms with only a few gaps and insertions (the first two amino acids, and four positions downstream) (FIG. 17). The consensus motifs (VVXDXETTG (SEQ ID NOS: 66 and 68). HNAXFDXGF (SEQ ID NO: 67) and HRALYD (SEQ ID NO: 70)), characteristic for exonucleases, are conserved. Overall, the level of amino acid identity relative to most of the known ε subunits, or corresponding proofreading exonuclease domains of gram positive PolC genes is approximately 30%. Upstream of start 1 (FIG. 17) there were stop codons in all three reading frames.

Expression of DnaQ—The DnaQ gene was cloned gene into the pET24-a expression vector in two steps. First, the PCR fragment encoding the N-terminal part of the gene was cloned into the pUC19 plasmid, containing the ApaI inverse PCR fragment into NdeI/ApaI sites. DNA oligonucleotides for amplification of *T.th.* genomic DNA were as follows. The upstream 33mer (5'-GCGGCG CATATGGTGGTGGTCCTGGACCTGGAG-3') (SEQ ID NO: 48) consists of an NdeI site within the first 12 nucleotides (underlined) and the beginning of the dnaQ gene. The downstream 25mer (5'-CGCG TCTAGATCACCTGTATCCAGA-3') (SEQ ID NO: 49), already used for ApaI circular PCR, consists of an XbaI site within the first 10 nucleotides (underlined) and the sequence corresponding to the region downstream of the ApaI restriction site. The 2.2 kb NdeI/SalI fragment was then cloned into the NdeI/XhoI sites of the pET16 vector to produce pET24-a:dnaQ. The ε subunit was expressed in the BL21/LysS strain transformed by the pET24-a:dnaQ plasmid.

EXAMPLE 12

The *Thermus thermophilus* dnaN Gene Encoding the β Subunit of DNA Polymerase III Holoenzyme Strategy of Cloning DnaN by use of DnaA—DnaN proteins are highly divergent in bacteria making it difficult to clone them by homology. The level of identity between DnaN representatives from *E. coli* and *B. subtilis* is as low as 18%. These 18% of identical amino acid residues are dispersed through the proteins rather then clustering together in conservative regions, further complicating use of homology to design PCR primers. However, one feature of dnaN genes among widely different bacteria is their location in the chromosome. They appear to be near the origin, and immediately adjacent to the dnaA gene. DnaA genes show good homology among different bacteria and thus we first cloned dnaA in order to obtain a DNA probe that is likely near dnaN.

Identification of dnaA and dnaN—The DnaA genes of *E. coli* and *B. subtilis* share 58% identity at the amino acid sequence level within the ATP-binding domain (or among the representatives of gram-positive and gram-negative bacteria, evolutionary divergent organisms). Comparison of the predicted amino acid sequences encoded by dnaa of *E. coli* and *B. subtilis* revealed two highly conserved regions (FIG. 19). Within each of these regions, a seven amino acid sequence was used to design two oligonucleotide primers for use in the polymerase chain reaction. The DNA oligonucleotides for amplification of *T.th.* genomic DNA were as follows. The upstream 20mer (5'-GTSCTSGTSAAGACSCACTT-3') (SEQ ID NO: 50) encodes the following sequence: VLVK-THL (SEQ ID NO: 69). The downstream 21mer (5'-SAG-SAGSGCGTTGAASGTGTG-3') (SEQ ID NO: 51) encodes the sequence: HTFNALL (SEQ ID NO: 71), on the complementary strand. The amplification reactions contained 10 ng *T.th.* genomic DNA, 0.5 mM of each primer, in a volume of 100 μl of Vent polymerase reaction mixture containing 10 μl ThermoPol Buffer, 0.5 mM of each dNTP and 0.5 mM $MgSO_4$. Amplification was performed using the following cycling scheme:

1. 5 cycles of: 95.5° C.-30", 45° C.-30", 75° C.-2'
2. 5 cycles of: 95.5° C.-30", 50° C.-30", 75° C.-2'
3. 30 cycles of: 95.5° C.-30", 52° C.-30", 75° C.-30"

Products were visualized in a 1.5% native agarose gel. A fragment of the expected size of 300 bp was cloned into the SmaI site of pUC19 and sequenced with the CircumVent Thermal Cycle DNA sequencing kit (New England Biolabs).

To obtain a larger section of the *T.th.* Linda gene, genomic DNA was digested with either HaeII. HindIII. KasI, KpnI, MluI, NcoI. NgoMI, NheI, NsiI, PaeR7I, PstI, SacI. SalI, SpeI, SphI, StuI, or XhoI, followed by Southern analysis in a native agarose gel. The filter was probed with the 300 bp PCR product radiolabeled by random priming. Four different restriction digests showed a single fragment of reasonable size for further cloning. These were. KasI, NgoMI, and StuI which produced fragments of about 3 kb, and NcoI that produced a 2 kb fragment. Also, a KpnI digest resulted in two fragments of about 1.5 kb and 10 kb.

Genomic DNA digests using either NgoMI and StuI were used to obtain the dnaA gene by inverse PCR (also referred to as circular PCR). In this procedure, 0.1 μg of DNA from each digest was treated separately with T4 DNA ligase in 50 μl of ligation buffer (50 mM Tris-HCl (pH 7.8), 10 mM $MgCl_2$, 10 mM dithiothreitol, 1 mM ATP, 25 mg/ml bovine serum albumin) overnight at 20° C. This results in circularizing the genomic DNA fragments. The ligation mixtures were used as substrate in inverse PCR.

DNA oligonucleotides for amplification of recirculized *T.th.* genomic DNA were as follows. The upstream 22mer was 5'-CTCGTTGGTGAAAGTTTCCGTG-3' (SEQ ID NO: 52) and the downstream 24mer was 5'-CGTCCAGTTCATCGC-CGGAAAGGA-3' (SEQ ID NO: 53). The amplification reactions contained 5 ng *T.th.* genomic DNA, 0.5 μM of each primer, in a volume of 100 μl of Taq polymerase reaction mixture containing 10 µl PCR Buffer, 0.5 mM of each dNTP and 2.5 mM MgCl$_2$. Amplification was performed using the following cycling scheme:
1. 5 cycles of: 95.0° C.-30", 55° C.-30", 72° C.-10'
2. 35 cycles of: 95.5° C.-30", 50° C.-30", 72° C.-8'

The PCR fragments of the expected length for NgoMI and StuI treated and then ligated chromosomal DNA were digested with either BamHI or Sau3a and cloned into pUC19: BamHI and pUC19:(BamHI+SmaI) and sequenced with CircumVent Thermal Cycle DNA sequencing kit. The 1.6 kb (BamHI+BamH) fragment from the NgoMI PCR product contained a sequence coding for the N-terminal part of DnaN, followed by the gene for enolase. The 1 kb (Sau3a+Sau3a) fragment from the same PCR product included the start of dnaN gene and sequence characteristic of the origin of replication (i.e. 9mer DnaA-binding site sequences). The 0.6 kb (BamHI+BamHI) fragment from the StuI PCR reaction contained starts for dnaA and gidA genes in inverse orientation to each other. The 0.4 kb (Sau3a+Sau3a) fragment from the same PCR product contained the 3' end of the dnaA gene and DNA sequence characteristic for the origin of replication.

This sequence information provided the beginning and end of both the dnaA and the dnaN genes. Hence, these genes were easily cloned from this information. Further, the DnaN gene was readily cloned and expressed in a pET24-a vector. These steps are described below.

Cloning and sequence of the dnaA gene—The dnaA gene was cloned for sequencing in two parts: from the potential start of the gene up to its middle and from the middle up to the end. For the N-terminal part the upstream 27mer (5'-TCTG-GCAACACGTTCTGGAGCACATCC-3') (SEQ ID NO: 54) was 20 bp downsteam of the potential start codon of the gene. The downstream 23mer (5'-TGCTGGCGTTCATCTTCAG-GATG-3') (SEQ ID NO: 55) was approximately from the middle of the dnaA gene. For the C-terminal part the upstream 23mer (5'-CATCCTGAAGATGAACGCCAGCA-3') (SEQ ID NO: 56) was complementary to the previous primer. The downstream 25mer (5'-AGGTTATCCA-CAGGGGTCATGTGCA-3') (SEQ ID NO: 57) was 20 bp upstream the potential stop codon for the dnaA gene. The amplification reactions contained 10 ng *T.th*. genomic DNA, 0.5 µM of each primer, in a volume of 100 µl of Vent polymerase reaction mixture containing 10 µl ThermoPol Buffer, 0.5 mM of each dNTP and 0.5 mM MgSO$_4$. Amplification was performed using the following cycling scheme:
1.5 cycles of: 95.5° C.-30", 55° C.-30", 75° C.-3'
2. 30 cycles of: 95.5° C.-30", 50° C.-30", 75° C.-2'

Products were visualized in a 1.0% native agarose gel. Fragments of the expected sizes of 750 bp and 650 bp were produced, and were sequenced using CircumVent Thermal Cycle DNA sequencing method (New England Biolabs). The nucleotide and amino acid sequences of dnaA and its protein product are shown in FIG. 20. The DnaA protein is homologous to the DnaA proteins of several other bacteria as shown in FIG. 19.

Cloning and expression of dnaN—The full length dnaN gene was obtained by PCR from *T.th*. total DNA. DNA oligonucleotides for amplification of *T.th*. dnaN were the following: the upstream 29mer (5'-GTGTGT CATATGAACATAACGGTTCCCAA-3') (SEQ ID NO: 58) consists of an NdeI site within first 11 nucleotides (underlined), followed by the sequence for the start of the dnaN gene; the downstream 29mer (5'-GCGC GAATTCTCCCTTGTGGAAGGCTTAG-3') (SEQ ID NO: 59) consists of an EcoRI site within the first 10 nucleotides (underlined), followed by the sequence complementary to a section just downstream of the dnaN stop codon. The amplification reactions contained 10 ng *T.th*. genomic DNA, 0.5 µM of each primer, in a volume of 100 µl of Vent polymerase reaction mixture containing 10 µl Thermopol Buffer, 0.5 mM of each dNTP and 0.2 mM Mg SO$_4$. Amplification was performed using the following cycling scheme:
1. 5 cycles of: 95.0° C.-30", 55° C.-30", 75° C.-5',
2. 35 cycles of: 95.5° C.-30", 50° C.-30", 75° C.-4'.

The nucleotide and amino acid sequences of dnaN and the β subunit, respectively, are shown in FIG. 21. The *T.th*. β subunit shows limited homology to the β subunit sequences of several other bacteria over its entire length (FIG. 22).

Figure 23:
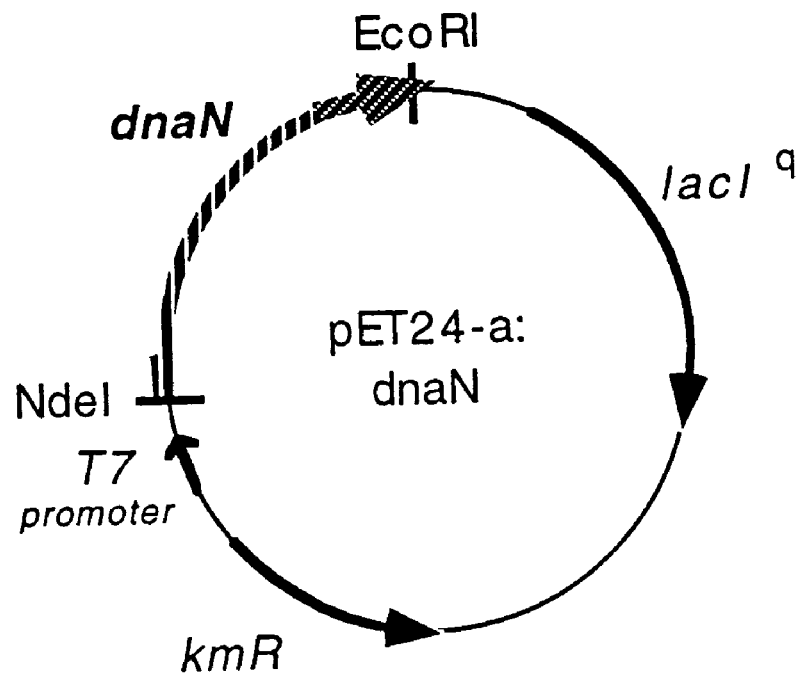
FIG. 23 is a map of the pET24:dnaN plasmid. The functional regions of the plasmid are indicated by arrows and italic, restriction sites are marked with bars and symbols. The hatched parts in the plasmid correspond to T.th. dnaN.

The approximately 1 kb dnaN gene was cloned into the pET24-a expression vector using the NdeI and EcoRI restriction sites both in the dnaN containing PCR product and in pEt24-a (FIG. 23). Expression of *T.th*. β subunit was obtained under the following conditions: a fresh colony of B121(DE3) *E. coli* strain was transformed by the pET24-a:dnaN plasmid, and then was grown in LB broth containing 50 mg/ml kanamycin at 37° C. until the cell density reached 0.4 OD$_{600}$. The cell culture was then induced for dnaN expression upon addition of 2 mM IPTG. Cells were harvested after 4 additional hours of growth under 37° C. The induction of the *T.th*. 13 subunit is shown in FIG. 24.

Two liters of BL21(DE3)pETdnaNcells were grown in LB media containing 50 mg/ml ampicillin at 37° C. to an O.D. of 0.8 and then IPTG was added to a concentration of 2 mM. After a further 2 h at 37° C. cells were harvested by centrifugation and stored at −70° C. The following steps were performed at 4° C. Cells were thawed and resuspended in 40 ml of 5 mM Tris-HCl (pH 8.0), 1% sucrose, 1M NaCl, 5 mM DTT, and 30 mM spermidine. Cells were lysed using a French Pressure cell at 20,000 psi. The lysate was allowed to sit at 4° C. for 30 min. and then cell debris was removed by centrifugation (Sorvall SS-34 rotor, 45 min. 18,000 rpm). The supernatant was incubated at 65° C. for 20 minutes with occasional stirring. The resulting protein precipitate was removed by centrifugation as described above. The supernatant was dialyzed against 4 liters of buffer A containing 50 mM NaCl overnight. The dialyzed supernatant was clarified by centrifugation (35 ml, 150 mg total) and then loaded onto an 8 ml MonoQ column equilibrated in buffer A containing 50 mM NaCl. The column was washed with 5 column volumes of the same buffer and then eluted with a 120 ml gradient of buffer A plus 50 mM NaCl to buffer A plus 500 mM NaCl. Fractions of 2 ml were collected. Over 50 mg of *T.th*. β was recovered in fractions 5-21.

EXAMPLE 13

Alternate Synthetic Path in Absence of Clamp Loader Activity

As discussed earlier, the Pol III-type enzyme of the present invention is capable of application and use in a variety of contexts, including a method wherein the clamp loader component that is traditionally involved in the initiation of enzyme activity, is not required. The clamp loader generally functions to increase the efficiency of ring assembly onto circular primed DNA because both the ring and the DNA are circles and one must be broken transiently for them to become interlocked rings. In such a reaction, the clamp loader increases the efficiency of opening the ring.

The procedure described below illustrates the instance where the clamp loader need not be present. For example, the β clamp can be assembled onto DNA in the absence of the clamp loader. Particularly, the bulk of primed templates in PCR reactions are linear ssDNA fragments that are primed at the ends. On linear primed DNA, the ring need not open at all. Instead, the ring can simply thread onto the end of the linear primed template (Bauer and Burgers. 1988; Tan et. al, 1986; O'Day et. al., 1992; Burgers and Yoder. 1993). Hence, on linear primed templates, such as those generated in PCR, the beta clamp can simply slide over the DNA end. After the ring slides onto the end, the DNA polymerase can associate with the ring for enhanced DNA synthesis.

Such "end assembly" is common among Pol III-type enzymes and has been demonstrated in the yeast and human systems. Rings assembling onto linear DNA for use by their respective DNA polymerases are shown in the following example demonstrated in the *E. coli* bacterial system, in the human system, and in the *T.th.* system.

The bulk of the primed templates in PCR reactions are linear ssDNA fragments that are primed at their ends. However, these end primed linear fragments are not generated until after the first step of PCR has already been performed. In the very first step, PCR primers generally anneal at internal sites in a heat denatured ssDNA template. Primed linear templates are then generated in subsequent steps enabling use of this alternate path. For this first step, the clamp may be assembled onto an internal site in the absence of the clamp loader using special conditions that allow clamp assembly in the absence of a clamp loader.

For example, a set of conditions that lead to assembly of the clamp onto circular DNA (i.e. internal primed sites) have been described in the protocol for the use of the bacteriophage T4 ring shaped clamp (gene 45 protein) without the clamp loader (Reddy et. al., 1993). In this case, polyethylene glycol leads to "macromolecular crowding" such that the clamp and DNA are pushed together in close proximity leading to the ring self assembling onto internal primed sites on circular DNA. Other possible conditions that may lead to assembly of rings onto internal sites include use of a high concentration of beta such that use of heat or denaturant to break the dimeric ring into two half rings (crescents) followed by lowering the heat (or dilution or removal of denaturant) leading to rings assembling around the DNA.

The ring shaped sliding clamps of *E. Coli* and human slide over the end of linear DNA to activate their respective DNA polymerase in the absence of the clamp loader. This clamp loader independent assay is performed in the bacterial system in FIG. 25A. For this assay, the linear template is polydA primed with oligodT. The polydA is of average length 4500 nucleotides and was purchased from SuperTecs. OligodT35 was synthesized by Oligos etc. The template was prepared using 145 μl of 5.2 mM (as nucleotide) polydA and 22μ; of 1.75 mM (as nucleotide) oligodT. The mixture was incubated in a final volume of 2100μ: T.E. buffer (ratio as nucleotide was 21:1 polydA to oligodT). The mixture was heated to boiling in a 1 ml Eppendorf tube, then removed and allowed to cool to room temperature. Assays were performed in a final volume of 25 μl 20 mM Tris-Cl (pH 7.5), 8 mM $MgCl_2$, 5 mM DTT, 0.5 mM EDTA, 40 mg/ml BSA. 4% glycerol, containing 20 μM [$\alpha$-$^{32}$P]dTTP, 0.1 μg polydA-oligodT, 25 no Pol III and, where present, 5 ug of β subunit. Proteins were added to the reaction on ice, then shifted to 37° C. for 5 min. DNA synthesis was quantitated using DE81 paper as described (Rowen and Kornberg, 1979).

In the linear template assay, no ATP or dATP is provided and therefore, a clamp loader, even if present, is not active. Thus, the clamp (e.g. B) can only stimulate the DNA polymerase provided the clamp threads onto the DNA (see diagram in FIG. 25). Hence, threading of the clamp is shown by a stimulation of the DNA polymerase. In lane 1 of FIG. 25A, the DNA polymerase is incubated with the linear DNA in the absence of the clamp and lane 2 shows the result of adding the clamp. The results show that the clamp is able to thread onto the DNA ends and stimulate the DNA polymerase in the absence of ATP and thus, in the absence of clamp loading as well.

Figure 25:
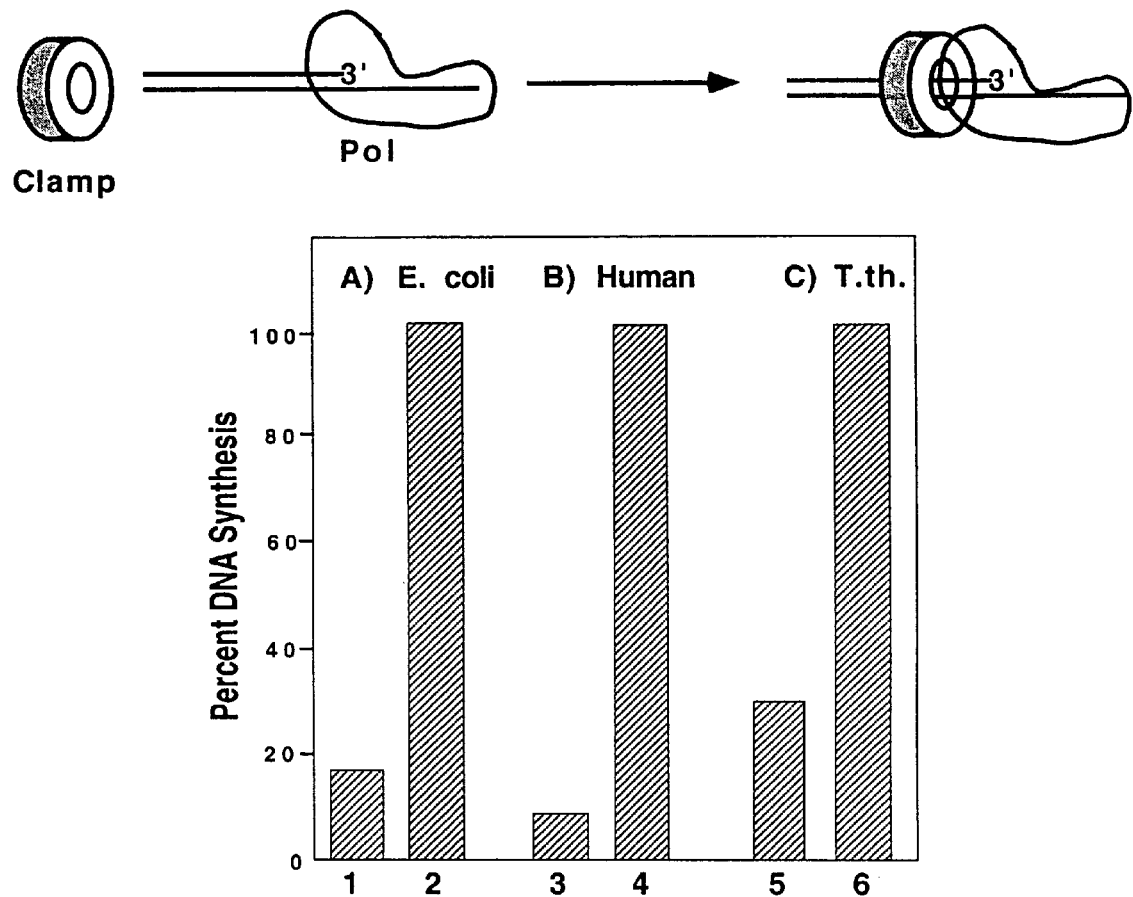
FIG. 25A is a schematic depiction of the use of the use of the enzymes of the present invention in accordance with an alternate embodiment hereof. In this scheme the clamp (β or PCNA) slides over the end of linear DNA to enhance the polymerase (Pol III-type such as Pol III, Polβ or Polδ) In this fashion the clamp loader activity is not needed.
FIG. 25B graphically demonstrates the results of the practice of the alternate embodiment of the invention described and set forth in Example 13, infra. Lane 1, E. coli Pol III without β; Lane 2, E. coli with β; Lane 3), human Polδ without PCNA; Lane 4, human Polδ with PCNA; Lane 5, T.th. Pol III heparin Peak 1 without T.th. β; Lane 6, T.th. Pol III with T.th. β. The respective pmol synthesis in lanes 1-6 are: 6, 35, 2, 24, 0.6 and 1.9.

This clamp loader independent assay is performed in the human system in FIG. 25B. The assay reaction (25 μl) contains 50 mM Tris-HCl (pH=7.8), 8 mM MgCl2, 1 mM DTT, 1 mM creatine phosphate, 40 μg/ml bovine serum albumin, 0.55 μg human SSB, 100 ng PCNA (where present), 7 units DNA polymerase delta (1 unit incorporates 1 pmol dTMP in 60 min.), 40 mM [$\alpha$-$^{32}$P]dTTP and 0.1 μg polydA-oligodT. Proteins were added to the reaction on ice, then shifted to 37° C. for 60 min. DNA synthesis was quantitated using DE81 paper as described (Rowen and Kornberg, 1979). In lane 3, (FIG. 25) the DNA polymerase δ is incubated with the linear DNA in the absence of the clamp, and lane 4 showes the result of adding the PCNA clamp. The results demonstrate that the clamp is able to thread onto the DNA ends and stimulate the DNA polymerase in the absence of ATP and thus, the absence of clamp loading.

This clamp loader independent assay is performed in the *T.th.* system in FIG. 25C. The assay reaction is exactly as described above for use of the *E. coli* Pol III and beta system except the temperature is 60° C. and here the Pol III is HEP.P1 *T.th.* Pol III (0.5 μl, providing 0.1 units where one unit is equal to 1 pmol of dTTP incorporated in 1 minute under these conditions and in the absence of beta), and the beta subunit is 7 μg *T.th.* B (from the MonoQ column). Proteins were added to the reaction on ice, then shifted to 37° C. for 60 min. DNA synthesis was quantitated using DE81 paper as described (Rowen and Kornberg, 1979). In lane 3 (FIG. 25C), the T.Th. Pol III is incubated with the linear DNA in the absence of the clamp, and lane 4 shows the result of adding the *T.th.* β clamp. The results demonstrate that the clamp is able to thread onto the DNA ends and stimulate the DNA polymerase in the absence of clamp loader activity.

EXAMPLE 14

Use of *T.th.* Pol III in Long Chain Primer Extension

A characteristic of Pol III-type enzymes is their ability to extend a single primer for several kilobases around a long (e.g. 7 kb) circular single stranded DNA genome of a bacteriophage. This reaction uses the circular β clamp protein. For the circular β to be assembled onto a circular DNA genome, the circular β must be opened, positioned around the DNA, then closed. This assembly of the circular beta around DNA requires the action of the clamp loader, which uses ATP to open and close the ring around DNA. In this example we use as a template the 7.2 kb circular single strand DNA genome of bacteriophage M13 mp18. This template was primed with a single DNA 57mer oligonucleotide and the Pol III enzyme was tested for conversion of this template to a double strand circular form (RFII). The reaction was supplemented with recombinant *T.th.* β produced in *E. coli*. This assay is summarized in the scheme at the top of FIG. 26. M13mp18 ssDNA was phenol extracted from phage purified as described (Turner and O'Donnell, 1995). M13 mp18 ssDNA was primed with a 57mer DNA oligomer synthesized by Oligos etc. The replication assays contained 73 ng singly primed M13 mp18 ssDNA and 100 ng *T.th.* β subunit in a 25 μl reaction containing 20 mM Tris-HCl (pH 7.5), 8 mM $MgCl_2$, 40 μg/ml BSA, 0.1 mM EDTA, 4% glycerol. 0.5 mM ATP, 60 μM each of dCTP, dGTP, dATP and 20 μM $\alpha$-$^{32}$P-TTp (specific activity 2.000-4,000 cpm/pmol). Either *T.th.*

Pol III from the Heparin, peak 1 (HEP.P1: 5 μl. 0.21 units where 1 unit equals 1 pmol nucleotide incorporated in 1 min.) or a non-Pol III from the Heparin peak 2 (HEP.P2; 5 μl, 2.6 units) were added to the reaction. Reactions were shifted to 60° C. for 5 min., and then DNA synthesis was quenched upon adding 25 μl of 1% SDS, 40 mM EDTA. One half of the reaction was analyzed in a 0.8% native agarose gel, and the other half was quantitated using DE81 paper as described (Studwell and O'Donnell, 1990).

Figure 26:
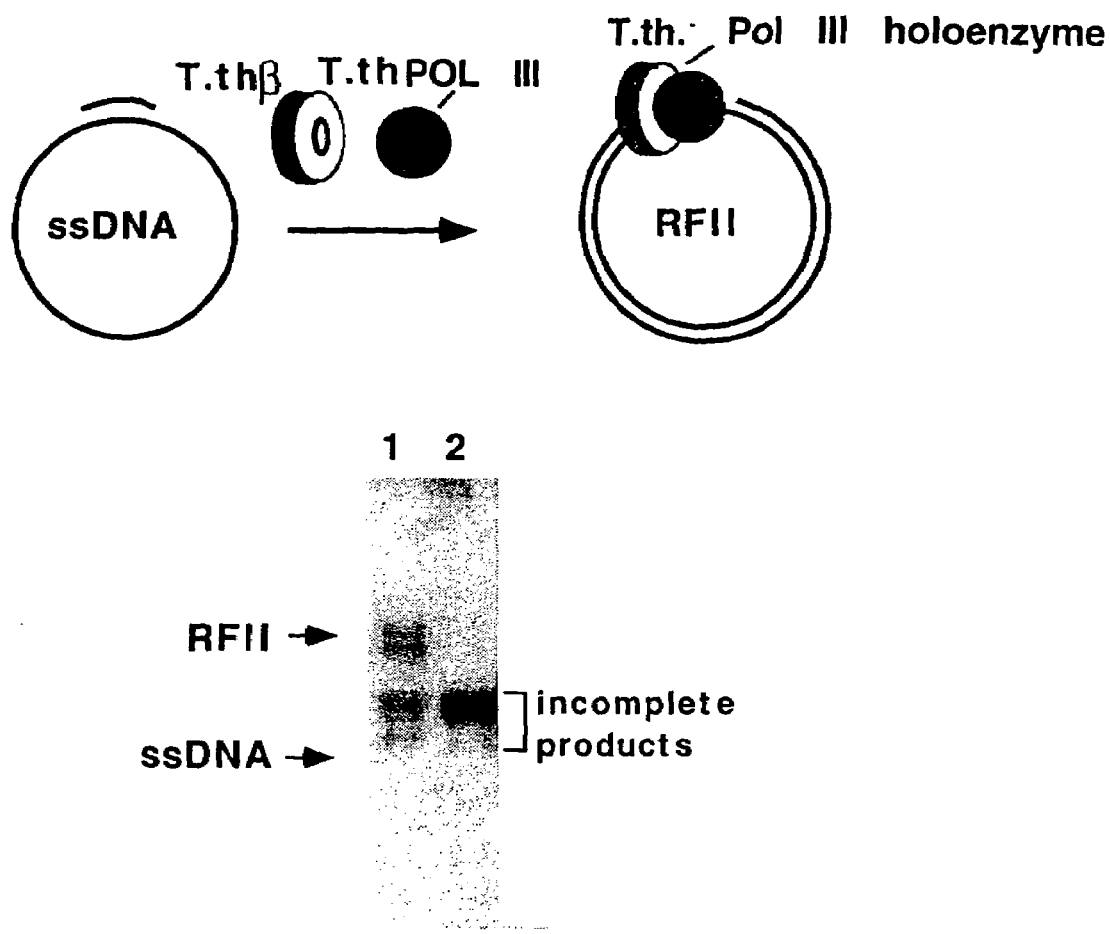
FIG. 26 shows the use of T.th. Pol III in extending singly primed M13 mp18 to an RFII form. The scheme at the top shows the primed template in which a DNA 57mer was annealled to the M13 mp18 ssDNA circle. Then T.th. β subunit (produced recombinantly) and T.th. Pol III were added to the DNA in the presence of radioactive nucleoside triphosphates. In panel B, the products of the reaction were analyzed in a 0.8% native agarose gel. The position of ssDNA starting material, the PFII product, and of intermediate species, are shown to the sides of the gel. Lane 1, use of Pol III from the Heparin Agarose peak 1. Lane 2, use of the non-Pol III DNA polymerase contained in the peak 2 of the T.th. Heparin Agarose column.

The results of the assay are shown in FIG. 26. Lane 1 is the result obtained using the *T.th*. Pol III (HEP.P1) which was capable of extending the primer around the ssDNA circle to form RFII. Lane 2 shows the result of using the non-Pol III (HEP.P2) which was not capable of this extension and produced only incomplete DNA products (the result shown included 0.8 μg *E. coli* SSB which did not increase the chain length of the product. In the absence of SSB, the same product was observed, although the band contained more counts. The greater amount of total synthesis observed in lane 2 is due to the build up of immature products in a small region of the gel. The presence of immature products in lane 1 is likely due to a contaminating polymerase in the preparation that can not convert the single primer to the full length RFII form. Alternatively, the presence of incomplete products in lane 1 (Pol III type enzyme) is due to secondary structure in the DNA which causes the Pol III to pause. In this case it may be presumed that performing the reaction at higher temperature could remove the secondary structure barrier. Alternatively, SSB (single strand binding protein) could be added to the assay (although *T.th*. SSB would be needed since addition of *E. coli* SSB was tried and did not alter the quality of the product profile). Generally, SSB is needed to remove secondary structure elements from ssDNA at 37° C. for complete extension of primers by mesophilic Pol III-type enzymes.

The assay described above was performed at 60° C. The *T.th*. Pol III HEP.P1 gained activity as the temperature was increased from 37° C. to 60° C., as expected for an enzyme from a thermophilic source. The *E. coli* Pol III lost activity at 60° C. compared to 37° C. as expected for an enzyme from a mesophilic source.

The following is a list of documents related to the above disclosure and particularly to the experimental procedures and discussions. The documents should be considered as incorporated by reference in their entirety.

Alonso, J. C. Shirahige, K., and Ogasawara, N. (1990) Molecular cloning, genetic characterization and DNA sequence analysis of the recM region of *Bacillus subtilis*. *Nuc. Acids Res.* 18:6771-6777.

Carter, J. R., Franden. M. A., Aebersold. R., and McHenry, C. S. (1993) Identification, isolation, and characterization of the structural gene encoding the δ' subunit of *E. coli* DNA polymerase III holoenzyme. *J. Bacteriol.* 175:3812-3822.

Chen, M., Pan, Z.-Q., and Hurwitz, J. (1992) Studies of the cloned 37-kDa subunit of activator 1 (replication factor C) of HeLa cells. *Proc. Natl. Acad. Sci. USA* 5211-5215.

Cullman, G., Fien. K. Kobayashi, R., and Stillman. B. (1995) Characterization of the five replication factor C genes of *Saccharomyces* cerevesiae. *Mol. and Cell. Biol.* 15 0:4661-4671.

Flower, A. M. and NicHenrv. C. S. (1990) The γ subunit of DNA polymerase III holoenzyme of *Escherichia coli* is produced by ribosomal frameshifting. *Proc. Natl. Acad. Sci. USA* 87:3713-3717.

Guenther, B. D. (1996) Structural studies on the DNA replication apparatus: X-ray crystal structure of the δ' subunit of *Escherichia coli* DNA Pot III. Ph.D. Thesis, Rockefeller University.

Guibus, J. M., Kelman, Z., Hurwitz, J., O'Donnell, M., and Kuriyan, J. (1996) Structure of the C-terminal region of p21 waf1/cip1 complexed with human PCNA. *Cell* 87:297-306.

Jacks, T., Madhami. H. D., Masiarz, F. R., and Varmus, H. E. (1988) Signals for ribosomal frameshifting in the Rous sarcoma virus gag-pol region. *Cell* 55:447-458.

Kelman, Z., and O'Donnell. M. (1994) DNA replication: enzymology and mechanisms. Current Opinion is *Genetics and Development* 4:185-195.

Kong, X.-P., Onrust. R., O'Donnell, M., and Kuriyan, J. (1992). Three dimensional structure of the β subunit of *Escherichia coli* DNA polymerase III holoenzyme: a sliding DNA clamp. *Cell* 69:425-437.

Kornberg, A., and Baker, T. (1992). DNA Replication, second edition. (New York: W. H. Freeman and Company), pp. 165-194.

Krishna, T. S., Kong, X.-P., Gary, S., Burgers, P. M., and Kuriyan, J. (1994) Crystal structure of the eukaryotic DNA polymerase processivity factor PCNA. Cell 79 (7), 1233-1243.

Kuriyan, J. and O'Donnell, M. (1993) Sliding clamps of DNA polymerases. *J. Mol. Biol.* 234:915-925.

Larsen, B., Wills, N., Gesteland, R. F. and Atkins. J. F. (1994) rRNA-mRNA base pairing stimulates a programmed −1 ribosomal frameshift. *J. Bact.* 176: 6842-6851.

Lee. S. H. and Walker. J. R. (1987) *Escherichia coli* dnaX product, the τ subunit of DNA polymerase III, is a multi-functional protein with single-stranded DNA-dependent ATPase activity. *Proc. Natl. Acad. Sci. USA* 84:2713-2717.

Maki, H., Maki, S, and Kornberg, A. (1988) DNA polymerase III holoenzyme of *Escherichia coli* IV. The holoenzyme is an asymmetric dimer with twin active sites. *J. Biol. Chem.* 263:6570-6578.

Maniatis, T., Fritsch. E. F., and Sambrook, J. (1982) Molecular Cloning: A Laboratory Manual. pp. 76-85 and 382-367, Cold Spring Harbor Laboratory, Cold Spring Harbor, N.Y.

McHenry, C. S. (1982) Purification and characterization of DNA polymerase III'. Identification of τ as a subunit of the DNA polymerase III holoenzyme. *J. Biol. Chem.* 257: 2657-2663.

O'Donnell, M., Kurivan, J., Kong, X-P., Stukenberg, P. T. and Onrust, R. (1992) The sliding clamp of DNA polymerase III holoenzyme encircles DNA. *Molec. Biol. Cell* 3:953-957.

O'Donnell, M., Onrust, R., Dean, F. B., Chen, M., and Hurwitz, J. (1993) Homology in accessory proteins of replicative polymerases-*E. coli* to humans. *Nucl. Acids Res.* 21:1-3.

Onrust, R. Finkelstein. J., Turner, J., Naktinis, V., and O'Donnell, M. (1995b) Assembly of a chromosomal replication machine: two DNA polymerases, a clamp loader and sliding clamps in one holoenzyme particle. III. Interface between two polymerases and the clamp loader. *J. Biol. Chem.* 270:13366-13377.

Onrust, R. and O'Donnell, M. (1993) DNA polymerase III accessory proteins. I. holA and holB encoding δ and δ'. *J. Biol. Chem.* 268:11758-11765.

Onrust, R., Stukenberg, P. T., and O'Donnell, M. (1991) Analysis of the ATPase subassembly which initiates processive DNA synthesis by DNA polymerase III holoenzyme. *J. Biol. Chem.* 266:21681-21686.

Rowen, L. and Kornberg, A. (1979) Primase, the DnaG protein of *Escherichia coli*. An enzyme which starts DNA chains. *J. Biol. Chem.* 253:758-764.

Studwell-Vaughan. P. S. and O'Donnell. M. (1991) Constitution of the twin polymerase of DNA polymerase III holoenzyme. *J. Biol. Chem.* 266:19833-19841.

Stukenberg, P. T., Studwell-Vaughan, P. S., and O'Donnell, M. (1991). Mechanism of the sliding β-clamp of DNA polymerase III holoenzyme. *J. Biol. Chem.* 266:11328-11334.

Tsuchihashi, Z. and Komberg, A. (1990) Translational frameshifting generates the γ subunit of DNA polymerase III holoenzyme. *Proc. Natl. Acad. Sci. USA* 87:2516-2520.

Tsuchihashi, Z., and Brown, P. O. (1992) Sequence requirements for efficient translational frameshifting in the *Escherichia coli* dnaX gene and the role of an unstable interaction between tRNALys and an AAG lysine codon. *Genes and Dev.* 6:511-519.

Tsuchihashi. Z. and Komberg. A. (1989) ATP interactions of the τ and γ subunits of DNA polymerase III holoenzyme of *Escherichia coli. J. Biol. Chem.* 264:17790-17795.

Weiss, R. B. Dunn. D. M., Atkins, J. F. and Gesteland, R. F., (1987) Slippery runs, shifty stops, backward steps, and forward hops: −2, −1, +2, +5 and +6 ribosomal frameshifting, in Cold Spring Harbor Symposia on Quantitative Biology 52: 687-693.

Yin, K-C., Blinkowa. A., and Walker, J. R. (1986) Nucleotide sequence of the *Escherichia* replication gene dnaZX. *Nuc. Acids. Res.* 14:6541-6549.

Yuzhakov, A., Turner. J. and O'Donnell, M. (1996) Replisome assembly reveals the basis for asymmetric function in leading and lagging strand replication. *Cell* 86:877-886.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

What is claimed is:

1. An isolated polynucleotide encoding a τ subunit or a γ subunit of a DNA polymerase III-type enzyme of a thermophilic bacterium, wherein the polynucleotide comprises a nucleotide sequence that encodes the amino acid sequence of SEQ ID NO: 2, the amino acid sequence of SEQ ID NO: 4, or the amino acid sequence of SEQ ID NO: 5.

2. The polynucleotide according to claim 1, wherein the polynucleotide comprises a nucleotide sequence that encodes the amino acid sequence of SEQ ID NO: 2.

3. The polynucleotide according to claim 1, wherein the polynucleotide comprises a nucleotide sequence that encodes the amino acid sequence of SEQ ID NO: 4.

4. The polynucleotide according to claim 1, wherein the polynucleotide comprises a nucleotide sequence that encodes the amino acid sequence of SEQ ID NO: 5.

5. The polynucleotide according to claim 1, wherein the polynucleotide comprises the nucleotide sequence of SEQ ID NO: 3.

6. A vector comprising the polynucleotide according to claim 1.

7. A host cell comprising the vector according to claim 6.

8. The host cell according to claim 7, wherein the host cell is a prokaryotic cell.

* * * * *